United States Patent
Silos-Santiago et al.

(10) Patent No.: US 7,169,751 B2
(45) Date of Patent: Jan. 30, 2007

(54) METHOD OF IDENTIFYING A COMPOUND CAPABLE OF TREATING A PAIN OR A PAINFUL DISORDER

(75) Inventors: Inmaculada Silos-Santiago, Del Mar, CA (US); Venkateswarlu Karicheti, Chapel Hill, NC (US); Scott D. Eliasof, Lexington, MA (US)

(73) Assignee: Bayer Healthcare AG, Leverkusen (DE)

( * ) Notice: Subject to any disclaimer, the term of this patent is extended or adjusted under 35 U.S.C. 154(b) by 135 days.

(21) Appl. No.: 10/768,158

(22) Filed: Jan. 30, 2004

(65) Prior Publication Data

US 2004/0204359 A1   Oct. 14, 2004

Related U.S. Application Data

(60) Provisional application No. 60/491,048, filed on Jul. 30, 2003, provisional application No. 60/478,805, filed on Jun. 16, 2003, provisional application No. 60/454,540, filed on Mar. 13, 2003, provisional application No. 60/452,291, filed on Mar. 5, 2003, provisional application No. 60/444,781, filed on Feb. 4, 2003.

(51) Int. Cl.
*G01N 33/15* (2006.01)
*G01N 33/483* (2006.01)
*A61K 38/16* (2006.01)

(52) U.S. Cl. .................. 514/2; 435/7.1; 435/7.9; 530/350

(58) Field of Classification Search .............. 514/2; 435/7.1, 7.9; 530/350
See application file for complete search history.

(56) References Cited

FOREIGN PATENT DOCUMENTS

WO   WO 00/14251 A2   3/2000
WO   WO 02/18541 A2   3/2002

OTHER PUBLICATIONS

Nakamura et al. (2003) Steroid sulfatase and estrogen sulfotransferase in the atherosclerotic human aorta. Am. J. Pathol. vol. 163, No. 4, pp. 1329-1339.*
Nagata et al. (2000) Pharmacogenetics of sulfotransferase. Annu. Rev. Pharmacol. Toxicol. vol. 40, pp. 159-176.*
Oliveras et al. (1996) Picrotoxin produces a "central" pain-like syndrome when microinjected into the somato-motor cortex of the rat.. Physiol. Behav. vol. 60, No. 6, pp. 1425-1434.*
Majewska et al. (1990) The neurosteroid dehydroepiandrosterone sulfate is an allosteric antagonist of the GABAA receptor. Brain Res. vol. 526, No. 1, pp. 143-146.*
Baek, et al., "Overexpression of Arylsulfate Sulfotransferase as Fusion Protein with Glutathione S-Transferase", Protein Expression and Purification 11:257-262 (Dec. 1997).
Alam, et al., "Platelet sulphotransferase activity, plasma sulphate levels and sulphation capacity in patients with migraine and tension headache", Cephalalgia 17:761-764 (Nov. 1997).

* cited by examiner

*Primary Examiner*—Jon Weber
*Assistant Examiner*—Samuel W. Liu
(74) *Attorney, Agent, or Firm*—Banner & Witcoff, Ltd.

(57) ABSTRACT

We claim a methods for identifying a compound capable of treating a pain or a painful disorder state comprising combining the test compound with the polypeptide of SEQ ID NO:2, and detecting binding of said test compound to said polypeptide thereby identifying a compound that binds to said polypeptide.

7 Claims, No Drawings

SEQUENCE LISTING

<160> NUMBER OF SEQ ID NOS: 46

<210> SEQ ID NO 1
<211> LENGTH: 2419
<212> TYPE: DNA
<213> ORGANISM: Homo Sapiens
<220> FEATURE:
<221> NAME/KEY: CDS
<222> LOCATION: (21)...(875)

<400> SEQUENCE: 1

```
gcgacggcga cggcggcggc atg gcg gag agc gag gcc gag acc ccc agc acc      53
                      Met Ala Glu Ser Glu Ala Glu Thr Pro Ser Thr
                       1               5                  10 ccg ggg gag ttc gag agc aag tac ttc gag ttc cat ggc gtg cgg ctg       101
Pro Gly Glu Phe Glu Ser Lys Tyr Phe Glu Phe His Gly Val Arg Leu
             15                  20                  25 ccg ccc ttc tgc cgc ggg aag atg gag gag atc gcc aac ttc ccg gtg       149
Pro Pro Phe Cys Arg Gly Lys Met Glu Glu Ile Ala Asn Phe Pro Val
         30                  35                  40 cgg ccc agc gac gtg tgg atc gtc acc tac ccc aag tcc ggc acc agc       197
Arg Pro Ser Asp Val Trp Ile Val Thr Tyr Pro Lys Ser Gly Thr Ser
     45                  50                  55 ttg ctg cag gag gtg gtc tac ttg gtg agc cag ggc gct gac ccc gat       245
Leu Leu Gln Glu Val Val Tyr Leu Val Ser Gln Gly Ala Asp Pro Asp
 60                  65                  70                  75
```

-continued

| | | |
|---|---|---|
| gag atc ggc ttg atg aac atc gac gag cag ctc ccg gtc ctg gag tac<br>Glu Ile Gly Leu Met Asn Ile Asp Glu Gln Leu Pro Val Leu Glu Tyr<br>               80                       85                    90 | 293 |
| cca cag ccg ggc ctg gac atc atc aag gaa ctg acc tct ccc cgc ctc<br>Pro Gln Pro Gly Leu Asp Ile Ile Lys Glu Leu Thr Ser Pro Arg Leu<br>               95                     100                 105 | 341 |
| atc aag agc cac ctg ccc tac cgc ttt ctg ccc tct gac ctc cac aat<br>Ile Lys Ser His Leu Pro Tyr Arg Phe Leu Pro Ser Asp Leu His Asn<br>          110                   115                 120 | 389 |
| gga gac tcc aag gtc atc tat atg gct cgc aac ccc aag gat ctg gtg<br>Gly Asp Ser Lys Val Ile Tyr Met Ala Arg Asn Pro Lys Asp Leu Val<br>125                   130                 135 | 437 |
| gtg tct tat tat cag ttc cac cgc tct ctg cgg acc atg agc tac cga<br>Val Ser Tyr Tyr Gln Phe His Arg Ser Leu Arg Thr Met Ser Tyr Arg<br>140                 145                150               155 | 485 |
| ggc acc ttt caa gaa ttc tgc cgg agg ttt atg aat gat aag ctg ggc<br>Gly Thr Phe Gln Glu Phe Cys Arg Arg Phe Met Asn Asp Lys Leu Gly<br>               160                  165               170 | 533 |
| tac ggc tcc tgg ttt gag cac gtg cag gag ttc tgg gag cac cgc atg<br>Tyr Gly Ser Trp Phe Glu His Val Gln Glu Phe Trp Glu His Arg Met<br>          175                   180                 185 | 581 |
| gac tcg aac gtg ctt ttt ctc aag tat gaa gac atg cat cgg gac ctg<br>Asp Ser Asn Val Leu Phe Leu Lys Tyr Glu Asp Met His Arg Asp Leu<br>               190                  195               200 | 629 |
| gtg acg atg gtg gag cag ctg gcc aga ttc ctg ggg gtg tcc tgt gac<br>Val Thr Met Val Glu Gln Leu Ala Arg Phe Leu Gly Val Ser Cys Asp<br>          205                   210                 215 | 677 |
| aag gcc cag ctg gaa gcc ctg acg gag cac tgc cac cag ctg gtg gac<br>Lys Ala Gln Leu Glu Ala Leu Thr Glu His Cys His Gln Leu Val Asp<br>220                   225                 230               235 | 725 |
| cag tgc tgc aac gct gag gcc ctg ccc gtg ggc cgg gga aga gtt ggg<br>Gln Cys Cys Asn Ala Glu Ala Leu Pro Val Gly Arg Gly Arg Val Gly<br>               240                  245               250 | 773 |
| ctg tgg aag gac atc ttc acc gtc tcc atg aat gag aag ttt gac ttg<br>Leu Trp Lys Asp Ile Phe Thr Val Ser Met Asn Glu Lys Phe Asp Leu<br>          255                   260                 265 | 821 |
| gtg tat aaa cag aag atg gga aag tgt gac ctc acg ttt gac ttt tat<br>Val Tyr Lys Gln Lys Met Gly Lys Cys Asp Leu Thr Phe Asp Phe Tyr<br>270                   275                 280 | 869 |
| tta taa taacagaaac aacaacctgc atgctcacaa tacccagaca gtctactagc<br>Leu  * | 925 |
| caaaagtcct gtatgcattc atttattcct tgctggacaa actctggaag cagcgtgtga | 985 |
| aacagcgggg gaagggaaga gcggcgtgag cggagggagt gtgatgattc ccaaccgaag | 1045 |
| cagctgtctc gcctttagaa cgtgcagcct ctccatgtct gattacaaac agtctccaca | 1105 |
| ttgcagttcc aatggcctgg accgtaagga taaagcctgt aatatatgca actagaatgt | 1165 |
| ctgccttttc aacccgtat tattgtattt tatagagctt ttcactggaa atctacataa | 1225 |
| atgtcagtaa accaaataaa agttcatttc caaggggaat caggagcgag ccacacccga | 1285 |
| atggtagaaa gatctcaggg ttaactcttt attttgtag ttttattatc taaggcacag | 1345 |
| ccattctgtt ctcacttggt tctgagatag tggtgagaac agaggatgag ttgggtctgt | 1405 |
| tgggggggaat ctggacactt gtttattctg acggagttca cttcttcaga accttcctga | 1465 |
| aatgagcaga aattgttcac taggtcttca gaatggacgt ccttctgcca gagacttcca | 1525 |
| gcgggcggct ccaaaggccc aatgcagagg agcccgcgga gcatgtgctg agggaagtct | 1585 |
| gcctggtgag gctggcaggt gggagtctaa tgcagtcagg agcatttgca tgcagtgggt | 1645 |

```
ggagagtcgg ccaccaaagg accgagttgc gctcggaatt tgagctgaat tccacagcct    1705
tactttgttt cctgaagtga tagcctacta atgctggcaa gcagatgctt aatagtaaat    1765
ttctaaaatc cccgggtctt tatcattcag tttgttctgt gcacctgagg cgctcagccg    1825
tgggaggacc attttgcgag tgtagccctg tttcactcgg atcaggttgg cacggccgcc    1885
tgcgtgtctg tccacctcat ccctccgtgt atctgaggga gtaaaggtga ggtctttatt    1945
gcttcactgc ctaattttct cacccacatt cgctgaagcg atggagagtc gggggccagt    2005
agccagccaa ccccgtgggg accggggttg tctgtcattt atgtggctgg aaagcaccca    2065
aagtggtggt caggagggtc gctgctgtgg aagggggtctc cgttcttggt gctgtatttg    2125
aaacgggtgt agagagaagc ttgtgttttt gtttgtaatg gggagaagcg tggccaggca    2185
ggtggcacgt ggcatcgcat ggtgggctcg cagcaccctt gcctgtgttt ctgtgaggga    2245
ggctgctttc tgtgaaattt catttatatt tttctatttt tagtactgta tggatgttac    2305
tgagcactac acatgatcct tctgtgcttg cttgcatctt taataaagac atgttcccgg    2365
cgttgcaaaa aaaaaaaaaa aaaaaaaaaa aaaaaaaaaa aaaaaaaaaa aaaa         2419
```

```
<210> SEQ ID NO 2
<211> LENGTH: 284
<212> TYPE: PRT
<213> ORGANISM: Homo Sapiens

<400> SEQUENCE: 2

Met Ala Glu Ser Glu Ala Glu Thr Pro Ser Thr Pro Gly Glu Phe Glu
 1               5                  10                  15

Ser Lys Tyr Phe Glu Phe His Gly Val Arg Leu Pro Pro Phe Cys Arg
                20                  25                  30

Gly Lys Met Glu Glu Ile Ala Asn Phe Pro Val Arg Pro Ser Asp Val
            35                  40                  45

Trp Ile Val Thr Tyr Pro Lys Ser Gly Thr Ser Leu Leu Gln Glu Val
        50                  55                  60

Val Tyr Leu Val Ser Gln Gly Ala Asp Pro Asp Glu Ile Gly Leu Met
65                  70                  75                  80

Asn Ile Asp Glu Gln Leu Pro Val Leu Glu Tyr Pro Gln Pro Gly Leu
                85                  90                  95

Asp Ile Ile Lys Glu Leu Thr Ser Pro Arg Leu Ile Lys Ser His Leu
            100                 105                 110

Pro Tyr Arg Phe Leu Pro Ser Asp Leu His Asn Gly Asp Ser Lys Val
        115                 120                 125

Ile Tyr Met Ala Arg Asn Pro Lys Asp Leu Val Val Ser Tyr Tyr Gln
    130                 135                 140

Phe His Arg Ser Leu Arg Thr Met Ser Tyr Arg Gly Thr Phe Gln Glu
145                 150                 155                 160

Phe Cys Arg Arg Phe Met Asn Asp Lys Leu Gly Tyr Gly Ser Trp Phe
                165                 170                 175

Glu His Val Gln Glu Phe Trp Glu His Arg Met Asp Ser Asn Val Leu
            180                 185                 190

Phe Leu Lys Tyr Glu Asp Met His Arg Asp Leu Val Thr Met Val Glu
        195                 200                 205

Gln Leu Ala Arg Phe Leu Gly Val Ser Cys Asp Lys Ala Gln Leu Glu
    210                 215                 220

Ala Leu Thr Glu His Cys His Gln Leu Val Asp Gln Cys Cys Asn Ala
225                 230                 235                 240
```

-continued

```
Glu Ala Leu Pro Val Gly Arg Gly Arg Val Gly Leu Trp Lys Asp Ile
                245                 250                 255
Phe Thr Val Ser Met Asn Glu Lys Phe Asp Leu Val Tyr Lys Gln Lys
            260                 265                 270
Met Gly Lys Cys Asp Leu Thr Phe Asp Phe Tyr Leu
        275                 280

<210> SEQ ID NO 3
<211> LENGTH: 2877
<212> TYPE: DNA
<213> ORGANISM: Homo Sapiens
<220> FEATURE:
<221> NAME/KEY: CDS
<222> LOCATION: (387)...(1457)

<400> SEQUENCE: 3
```

| | |
|---|---|
| cggccggata ggcgcgaggg ggccgcgtga ggcggtgccg gcgttctggc ccccaaagcc | 60 |
| ggtctagcgc gccgggcgtc ttccttactt ccgctgccgc cgccgccaca tcccgggacc | 120 |
| cgacgggccg cggcgcggag gcctcgggcg aaggtggggc gggcctcccg agctcccagg | 180 |
| accccgcgcg cttcgcccac aggcccggcg aagcccgacc cgcgcggcgc ccccagggcc | 240 |
| aggggaggag cctaaggacc cggacgagcg ccgctccagt aggtgacaag aggaaacaag | 300 |
| aacctcagtt caggggaaac acagcaagga aatgtgagcc ccaggctgca gaaggaagag | 360 |

```
tcagtgaatg gctgcggtgt gacaac atg cac cac cag tgg ctt ctg ctg gcc      413
                              Met His His Gln Trp Leu Leu Leu Ala
                               1               5 gca tgc ttt tgg gtg att ttc atg ttc atg gtg gct agc aag ttc atc       461
Ala Cys Phe Trp Val Ile Phe Met Phe Met Val Ala Ser Lys Phe Ile
 10              15                  20                  25 acg ttg acc ttt aaa gac cca gat gtg tac agt gcc aaa cag gag ttt       509
Thr Leu Thr Phe Lys Asp Pro Asp Val Tyr Ser Ala Lys Gln Glu Phe
            30                  35                  40 ctg ttc ctg aca acc atg ccg gaa gtg agg aag ttg cca gaa gag aag       557
Leu Phe Leu Thr Thr Met Pro Glu Val Arg Lys Leu Pro Glu Glu Lys
        45                  50                  55 cac att cct gag gaa ctg aag cca act ggg aag gag ctt cca gac agc       605
His Ile Pro Glu Glu Leu Lys Pro Thr Gly Lys Glu Leu Pro Asp Ser
    60                  65                  70 cag ctc gtt cag ccc ctg gtc tac atg gag cgc ctg gaa ctc atc aga       653
Gln Leu Val Gln Pro Leu Val Tyr Met Glu Arg Leu Glu Leu Ile Arg
75                  80                  85 aac gtc tgc agg gat gat gcc ctg aag aat ctc tcg cac act cct gtc       701
Asn Val Cys Arg Asp Asp Ala Leu Lys Asn Leu Ser His Thr Pro Val
 90                  95                 100                 105 tcc aag ttt gtc ctg gac cga ata ttt gtc tgt gac aag cac aag att       749
Ser Lys Phe Val Leu Asp Arg Ile Phe Val Cys Asp Lys His Lys Ile
                110                 115                 120 ctt ttc tgc cag act ccc aaa gtg ggc aac acc cag tgg aag aaa gtg       797
Leu Phe Cys Gln Thr Pro Lys Val Gly Asn Thr Gln Trp Lys Lys Val
            125                 130                 135 ctg att gtt cta aat gga gca ttt tct tcc att gag gag atc ccc gaa       845
Leu Ile Val Leu Asn Gly Ala Phe Ser Ser Ile Glu Glu Ile Pro Glu
        140                 145                 150 aac gtg gtg cac gac cac gag aag aac ggc ctt cct cgg ctc tct tcc       893
Asn Val Val His Asp His Glu Lys Asn Gly Leu Pro Arg Leu Ser Ser
    155                 160                 165 ttc agt gat gca gaa att cag aag cga ttg aaa aca tac ttc aag ttt       941
Phe Ser Asp Ala Glu Ile Gln Lys Arg Leu Lys Thr Tyr Phe Lys Phe
170                 175                 180                 185
```

```
ttt att gta aga gat ccc ttc gaa aga ctt att tct gca ttt aag gat     989
Phe Ile Val Arg Asp Pro Phe Glu Arg Leu Ile Ser Ala Phe Lys Asp
            190                 195                 200 aaa ttt gtt cac aat ccc cgg ttt gag cct tgg tac agg cat gag att    1037
Lys Phe Val His Asn Pro Arg Phe Glu Pro Trp Tyr Arg His Glu Ile
                205                 210                 215 gct cct ggc atc atc aga aaa tac agg agg aac cgg aca gag acg cgg    1085
Ala Pro Gly Ile Ile Arg Lys Tyr Arg Arg Asn Arg Thr Glu Thr Arg
            220                 225                 230 ggg atc cag ttt gaa gat ttc gtg cgc tac ctc ggc gat ccg aac cac    1133
Gly Ile Gln Phe Glu Asp Phe Val Arg Tyr Leu Gly Asp Pro Asn His
        235                 240                 245 aga tgg cta gac ctt cag ttt ggg gac cac atc att cac tgg gtg acg    1181
Arg Trp Leu Asp Leu Gln Phe Gly Asp His Ile Ile His Trp Val Thr
250                 255                 260                 265 tat gta gag ctc tgt gct ccc tgt gag ata atg tac agt gtg att gga    1229
Tyr Val Glu Leu Cys Ala Pro Cys Glu Ile Met Tyr Ser Val Ile Gly
                270                 275                 280 cac cac gag acc ctg gag gac gat gcc cca tac atc tta aaa gag gct    1277
His His Glu Thr Leu Glu Asp Asp Ala Pro Tyr Ile Leu Lys Glu Ala
            285                 290                 295 ggc att gac cac ctg gtg tca tac ccg act atc cct ccg ggc att acc    1325
Gly Ile Asp His Leu Val Ser Tyr Pro Thr Ile Pro Pro Gly Ile Thr
            300                 305                 310 gtg tat aac aga acc aag gtg gag cac tat ttc ctg ggc atc agc aaa    1373
Val Tyr Asn Arg Thr Lys Val Glu His Tyr Phe Leu Gly Ile Ser Lys
        315                 320                 325 cga gac atc cga cgc ctg tat gcc cgt ttc gaa ggg gac ttt aag ctc    1421
Arg Asp Ile Arg Arg Leu Tyr Ala Arg Phe Glu Gly Asp Phe Lys Leu
330                 335                 340                 345 ttt ggg tac cag aaa cca gac ttt ttg cta aac taa tgcataagac         1467
Phe Gly Tyr Gln Lys Pro Asp Phe Leu Leu Asn  *
                350                 355 ctatgaattc aaatatcttt attagacctg ggctaacca ggtgaagatc tgagcccaga   1527
aatgacccct tcctccaccac acccctcctt tgaggatgcc cggggtctcc cacaggcctg 1587 tgagttgcct cggcatatga cgcagaaccc caactgttac aacttagttt ggatgtaaga  1647
tgctctgagg accctgccca cacccctgcg tgcattagga gtcgctggc ctttgctcac   1707 ctcagagggg agaaaaggct aaagatttgc agtttgacag cccagcaggg aggaagcatc  1767
acacagcgtt aggagccgtt tccttcaggt gttaaggaag gggatgcccc tgaggttctc  1827
ctggctagtc ggggtggctt cacccatcac tggtgggttg caggaacagc acccaggact  1887
ctgaggaggg acagagaagc aaggggggctg ctgaaatcgc agagactttt gcagcatcag  1947
atctgaggag taaaacggca cctctggcct tcatcttggt gctgcgacaa ttgtggaggc   2007
aaagcattct ttctgtgact attttgttcc tgtagacagt cagcgatggc cagagggtgg   2067
tgtggtgtcc agggtccat ctttccagaa tccatgcctg tgtaatgctg gtccatgctt    2127
ctgaacctgt gtctgccaag cgcctatttc attcagcaca agacatacga ttttagaagg   2187 tgagggggagg ggaggcttttt tctacctgag aaggggagtg tctttgaggg ccttaaaagg   2247
accatggccc aggaatgggg gcgctggttg ggcttggagc tcaggctgct gtggatcccg    2307
gcgcatcagt tctgacttgc cttacctggg tggacagcag tgaatctcca cctgtcttct    2367
ccagggagct cccatgttgg ggctgaagac gagcagggc aacctgccag catcacagaa     2427
ttcagtgtag tttatacatt tcgattcctt tcatctcagc aaaatgggca ctgccagagc    2487
catttctgat cacaccacca tcctggacca tgtgactgga aggtgggtaa ccaagttcac    2547
```

-continued

```
cagcaataaa acccagcgcc caggtagcct ccagcagtgc ggcttcctgg caacaaggta    2607
ggccctggtg cagggcaagc cgcagcgacc atttcagata ccgtccacag ccaggaccgc    2667
tgagaactgg gacagtttcc tgggatgagt gccagcctga gcctgcatgg tgccgccgag    2727
cccggggtgg aggagggagc caggcttcgc ttcaaggcgg cctctacctt ttctcagaat    2787
ggtttcctga ttgtgtcaat gtgaaagtta aataaatttt atgtgccaaa aaaaaaaaa     2847 aaaaaaaaaa aaaaaaaaaa aaaaaaaaaa                                     2877
```

<210> SEQ ID NO 4
<211> LENGTH: 356
<212> TYPE: PRT
<213> ORGANISM: Homo Sapiens

<400> SEQUENCE: 4

```
Met His His Gln Trp Leu Leu Ala Ala Cys Phe Trp Val Ile Phe
1               5                   10                  15

Met Phe Met Val Ala Ser Lys Phe Ile Thr Leu Thr Phe Lys Asp Pro
            20                  25                  30

Asp Val Tyr Ser Ala Lys Gln Glu Phe Leu Phe Leu Thr Thr Met Pro
        35                  40                  45

Glu Val Arg Lys Leu Pro Glu Glu Lys His Ile Pro Glu Glu Leu Lys
    50                  55                  60

Pro Thr Gly Lys Glu Leu Pro Asp Ser Gln Leu Val Gln Pro Leu Val
65                  70                  75                  80

Tyr Met Glu Arg Leu Glu Leu Ile Arg Asn Val Cys Arg Asp Asp Ala
                85                  90                  95

Leu Lys Asn Leu Ser His Thr Pro Val Ser Lys Phe Val Leu Asp Arg
            100                 105                 110

Ile Phe Val Cys Asp Lys His Lys Ile Leu Phe Cys Gln Thr Pro Lys
        115                 120                 125

Val Gly Asn Thr Gln Trp Lys Lys Val Leu Ile Val Leu Asn Gly Ala
    130                 135                 140

Phe Ser Ser Ile Glu Glu Ile Pro Glu Asn Val Val His Asp His Glu
145                 150                 155                 160

Lys Asn Gly Leu Pro Arg Leu Ser Ser Phe Ser Asp Ala Glu Ile Gln
                165                 170                 175

Lys Arg Leu Lys Thr Tyr Phe Lys Phe Phe Ile Val Arg Asp Pro Phe
            180                 185                 190

Glu Arg Leu Ile Ser Ala Phe Lys Asp Lys Phe Val His Asn Pro Arg
        195                 200                 205

Phe Glu Pro Trp Tyr Arg His Glu Ile Ala Pro Gly Ile Ile Arg Lys
    210                 215                 220

Tyr Arg Arg Asn Arg Thr Glu Thr Arg Gly Ile Gln Phe Glu Asp Phe
225                 230                 235                 240

Val Arg Tyr Leu Gly Asp Pro Asn His Arg Trp Leu Asp Leu Gln Phe
                245                 250                 255

Gly Asp His Ile Ile His Trp Val Thr Tyr Val Glu Leu Cys Ala Pro
            260                 265                 270

Cys Glu Ile Met Tyr Ser Val Ile Gly His His Glu Thr Leu Glu Asp
        275                 280                 285

Asp Ala Pro Tyr Ile Leu Lys Glu Ala Gly Ile Asp His Leu Val Ser
    290                 295                 300

Tyr Pro Thr Ile Pro Pro Gly Ile Thr Val Tyr Asn Arg Thr Lys Val
305                 310                 315                 320
```

```
                    Glu His Tyr Phe Leu Gly Ile Ser Lys Arg Asp Ile Arg Arg Leu Tyr
                                    325                 330                 335

Ala Arg Phe Glu Gly Asp Phe Lys Leu Phe Gly Tyr Gln Lys Pro Asp
                                340                 345                 350

Phe Leu Leu Asn
                                355

<210> SEQ ID NO 5
<211> LENGTH: 3931
<212> TYPE: DNA
<213> ORGANISM: Homo Sapiens
<220> FEATURE:
<221> NAME/KEY: CDS
<222> LOCATION: (298)...(1446)

<400> SEQUENCE: 5
ccggctttct tccgtcctgc cgtccccggg cccctagccc ccagtcccct ctcccccctc        60
cacctcttgt ccctcggcct ccgcgcctcc cctcccccga ctctctggcc tcccattcat       120
tccgtccgct ccctcccatt tcctcttttc cgctcgggcc ctctcccccag agcctccccg      180 cgcggacccc gctgcagtct cggggttctc agcacattta tggaagttta gggcctggac      240
agtggccccg agtccggcct gagagcgcag cctgggctgc tggcagggaa gaggaag atg     300
                                                                  Met
                                                                   1 tct gtg ctc agg cgg atg atg cgg gtt tcc aat cgc tct ctc ctc gcc       348
Ser Val Leu Arg Arg Met Met Arg Val Ser Asn Arg Ser Leu Leu Ala
         5                  10                  15 ttc atc ttc ttc ttc tcc ctc tct tcg tcc tgt ctg tac ttc atc tat       396
Phe Ile Phe Phe Phe Ser Leu Ser Ser Ser Cys Leu Tyr Phe Ile Tyr
             20                  25                  30 gtg gcc cca ggc atc gcc aac aca tat ctc ttt atg gta caa gct cga       444
Val Ala Pro Gly Ile Ala Asn Thr Tyr Leu Phe Met Val Gln Ala Arg
 35                  40                  45 ggt ata atg ttg aga gaa aat gtg aaa aca ata ggt cat atg atc agg       492
Gly Ile Met Leu Arg Glu Asn Val Lys Thr Ile Gly His Met Ile Arg
 50                  55                  60                  65 ctg tac aca aat aaa aac agt acg ctc aac ggt aca gat tat ccc gaa       540
Leu Tyr Thr Asn Lys Asn Ser Thr Leu Asn Gly Thr Asp Tyr Pro Glu
             70                  75                  80 ggc aat aat tca agt gat tat ctt gtt caa aca aca acg tat ctc ccg       588
Gly Asn Asn Ser Ser Asp Tyr Leu Val Gln Thr Thr Thr Tyr Leu Pro
             85                  90                  95 gaa aac ttc aca tac tca cca tac ctc ccc tgt cca gaa aag ctg cct       636
Glu Asn Phe Thr Tyr Ser Pro Tyr Leu Pro Cys Pro Glu Lys Leu Pro
            100                 105                 110 tat atg cga gga ttc ctc aat gtc aat gta agc gaa gtc agt ttt gat       684
Tyr Met Arg Gly Phe Leu Asn Val Asn Val Ser Glu Val Ser Phe Asp
115                 120                 125 gaa att cat caa ctc ttc tcc aag gat tta gat att gag cca ggg ggt       732
Glu Ile His Gln Leu Phe Ser Lys Asp Leu Asp Ile Glu Pro Gly Gly
130                 135                 140                 145 cat tgg agg cca aaa gac tgt aaa ccc aga tgg aag gtg gca gtt ctc       780
His Trp Arg Pro Lys Asp Cys Lys Pro Arg Trp Lys Val Ala Val Leu
                150                 155                 160 att cct ttc cgt aat cgc cat gaa cat ctt cca att ttt ttc tta cat       828
Ile Pro Phe Arg Asn Arg His Glu His Leu Pro Ile Phe Phe Leu His
            165                 170                 175 ctg att cca atg ctc cag aag cag cgg ctg gaa ttt gcg ttt tat gtc       876
Leu Ile Pro Met Leu Gln Lys Gln Arg Leu Glu Phe Ala Phe Tyr Val
            180                 185                 190
```

```
att gaa cag act ggc aca caa cct ttt aac cgt gcg atg ctt ttc aat    924
Ile Glu Gln Thr Gly Thr Gln Pro Phe Asn Arg Ala Met Leu Phe Asn
    195                 200                 205 gtg ggc ttc aaa gag gcc atg aaa gac agt gtc tgg gac tgt gta atc    972
Val Gly Phe Lys Glu Ala Met Lys Asp Ser Val Trp Asp Cys Val Ile
210                 215                 220                 225 ttc cac gat gtg gat cat cta cct gaa aat gac cgg aac tat tac gga   1020
Phe His Asp Val Asp His Leu Pro Glu Asn Asp Arg Asn Tyr Tyr Gly
                230                 235                 240 tgt gga gaa atg cca cgt cat ttt gct gca aag ctg gat aaa tac atg   1068
Cys Gly Glu Met Pro Arg His Phe Ala Ala Lys Leu Asp Lys Tyr Met
            245                 250                 255 tat att ctt cca tat aaa gaa ttt ttt ggt ggt gta agt ggg ctg aca   1116
Tyr Ile Leu Pro Tyr Lys Glu Phe Phe Gly Gly Val Ser Gly Leu Thr
        260                 265                 270 gtg gaa caa ttt aga aag atc aat ggt ttt cct aat gcc ttc tgg gga   1164
Val Glu Gln Phe Arg Lys Ile Asn Gly Phe Pro Asn Ala Phe Trp Gly
    275                 280                 285 tgg gga gga gaa gat gat gac ctt tgg aac aga gtt cac tat gct gga   1212
Trp Gly Gly Glu Asp Asp Asp Leu Trp Asn Arg Val His Tyr Ala Gly
290                 295                 300                 305 tat aat gta acc aga cca gag gga gac tta gga aaa tac aag tca att   1260
Tyr Asn Val Thr Arg Pro Glu Gly Asp Leu Gly Lys Tyr Lys Ser Ile
                310                 315                 320 cct cat cac cat aga ggt gaa gtc cag ttt tta gga cgg tat aaa tta   1308
Pro His His His Arg Gly Glu Val Gln Phe Leu Gly Arg Tyr Lys Leu
            325                 330                 335 cta agg tat tcc aag gag cgt cag tac atc gat gga ctg aac aat tta   1356
Leu Arg Tyr Ser Lys Glu Arg Gln Tyr Ile Asp Gly Leu Asn Asn Leu
        340                 345                 350 ata tat agg cca aaa ata ctg gtt gat agg ttg tat aca aac ata tct   1404
Ile Tyr Arg Pro Lys Ile Leu Val Asp Arg Leu Tyr Thr Asn Ile Ser
    355                 360                 365 gta aac ctc atg cca gag tta gct cca atc gaa gac tat taa           1446
Val Asn Leu Met Pro Glu Leu Ala Pro Ile Glu Asp Tyr *
370                 375                 380 aagaagtggc tgtcgtggca aggtagacca caatgctgga tcataaactt ggagcgcgct   1506
cttagtggag gtcagtgatt ggctgtgtca cagtgcccct ttctctgaga agagccagca   1566
gtccacagtg tttacagagt gggactatat acagtcaccc ttctctcacc cgtcctccct   1626
gctctgagac acaccctgt  ggcgagcacc gcagaaatgg gaagccacta cttaagatcg   1686
gaagttaaga gagctccctc cgaagagaaa attttatac  taaaatctat aatttaattc   1746
aagagaatgc ttttatttcc gtttaaacat attttgtata tatgtgatat aaattaatgt   1806
gtgcaaattg tttaaaaatt agatgtgttg cagttttgca tgtaatcggt tataccttta   1866
ttggactttt atagacattt tttatttgca tgaaaaaaac tcactaaatt tacatcacta   1926
aacaaaggtt aaccctttgtg tgaaatgaag gaactgtcaa taattgacag ccaactaata   1986
cagtaaactg ttatactagt tttgagcttt agacctcagc cttttgtgtg aagaagtca    2046
cagctttctt aggcttttaaa ggaaagaag  gaaggactta aatagctttt cttcctaccg   2106
ggattaccta tgttttcct  tgcttgcaat ctcatctgat tttgctagaa atcacaacca   2166
tattgtttat gcatattgca tgagtattac caagaaaaat cttaaaagtt gtgatgtgac   2226
atgatataaa ggatctcttt atgttaaatg tctttccatg tacctctggt gtgtcaggga   2286
ttttgtgcct caaaaaatgt ttccaaggtt gtgtgtttat actgtgtatt ttttttaaat   2346
tcacggtgaa cagcactttt attatttcca gttcagaaga gccaaaaaaa agtatcttca   2406
```

```
                                -continued tttaaaaaga aatcaagtca gttttttaa aagaatgatc tatggaagaa aacccaatag      2466
tacttataat atacaaatga attatactat tagataagaa ttaaatattc tatttttata      2526
aagataaata cttagtagat aaaaacaaat tttaagttta gttttcagac atagaatttc      2586
acttttggag gggacccttg aatgttagtt tcattcaaac tatattttgt ttttttcact      2646
tttaagagat tatatctctg gtgttaatta ctaaaatttt ctttctaaaa gtataattta      2706
atagaattat cttaaaatac atgatcagta ttcagtgcgc tgatattata atgtcttcta      2766
tatgtagtat ctaaaagcat aatttaatag cattgtctta aaatacatga tgagttattt      2826
ggtgcactga tgccataatg tcttctatat gtaatatctt acatgtttgc atgagtgtca      2886
gggctttgtc cagttatctt catatgactg ttctctgaga aaggtctta ctacctgata       2946 tcaagtacat atcttaattt tggatgaatt tttccacagt aaagccgaac agtattcttt      3006
tttgaaaatt agcaattata aagattgttt aaaatatctt gatattttca caattttaa       3066 acaaaaaatt aaatatctat aaagtgaatg ttcaacaaca atgatgagca atagaaatct      3126
atatatgaga aacgtttgga taatatttgc ctcaaggatt gtttacctaa aacagaacta      3186
tggttattta tctcagattg taagtttat tttgaagtgt cattttatg gcaatattga        3246 taacacaaat gaccacaaac taaatcataa ataattgaa tccttactt gagaaaatgg        3306 atagcttctg tgttatgata ccaaacaaaa tattttcata tttatttctt agaactattt      3366 ccaaatatt tatatttcag ttttttatg gtactcgaaa aatcaaacct tctgaaaatt        3426
atgatatttg tacttcattt gtgtattagt tcattttctg tttctattac atagtttta       3486 aagtcaatga aagagattga gaatgttaac atttgttgat caatgtggag ctgtccacat      3546
tcggtatctt ttcattttta tatatatttt acagtttcaa gaaaacttag tactactagt      3606
atctgcctta ttttcttaag tctgatgtta atttttgttt caggagtgag atataaacat     3666
tttgcttttt ttcagttttg aaatatagtt tgtcatcctg tgaaaaccac ctcgtttgct     3726
ttttgtttgt ttgttttgct tttttagtgt agacctaaaa ttatttttgc ctataaacag    3786
tgaacttaat atgtttctgt gagagtgaca gagctgtgcc cgtttatctt cattgtatta    3846
attattacat aaagattaac aaatacattg caaatgcaaa ttaaaaaaaa aaaaaaaaa     3906 aaaaaaaaaa aaaaaaaaa aaaaa                                              3931
```

<210> SEQ ID NO 6
<211> LENGTH: 382
<212> TYPE: PRT
<213> ORGANISM: Homo Sapiens

<400> SEQUENCE: 6

```
Met Ser Val Leu Arg Arg Met Met Arg Val Ser Asn Arg Ser Leu Leu
  1               5                  10                  15

Ala Phe Ile Phe Phe Phe Ser Leu Ser Ser Ser Cys Leu Tyr Phe Ile
             20                  25                  30

Tyr Val Ala Pro Gly Ile Ala Asn Thr Tyr Leu Phe Met Val Gln Ala
         35                  40                  45

Arg Gly Ile Met Leu Arg Glu Asn Val Lys Thr Ile Gly His Met Ile
     50                  55                  60

Arg Leu Tyr Thr Asn Lys Asn Ser Thr Leu Asn Gly Thr Asp Tyr Pro
 65                  70                  75                  80

Glu Gly Asn Asn Ser Ser Asp Tyr Leu Val Gln Thr Thr Thr Tyr Leu
                 85                  90                  95
```

```
Pro Glu Asn Phe Thr Tyr Ser Pro Tyr Leu Pro Cys Pro Glu Lys Leu
            100                 105                 110

Pro Tyr Met Arg Gly Phe Leu Asn Val Asn Val Ser Glu Val Ser Phe
            115                 120                 125

Asp Glu Ile His Gln Leu Phe Ser Lys Asp Leu Asp Ile Glu Pro Gly
        130                 135                 140

Gly His Trp Arg Pro Lys Asp Cys Lys Pro Arg Trp Lys Val Ala Val
145                 150                 155                 160

Leu Ile Pro Phe Arg Asn Arg His Glu His Leu Pro Ile Phe Phe Leu
                165                 170                 175

His Leu Ile Pro Met Leu Gln Lys Gln Arg Leu Glu Phe Ala Phe Tyr
            180                 185                 190

Val Ile Glu Gln Thr Gly Thr Gln Pro Phe Asn Arg Ala Met Leu Phe
            195                 200                 205

Asn Val Gly Phe Lys Glu Ala Met Lys Asp Ser Val Trp Asp Cys Val
        210                 215                 220

Ile Phe His Asp Val Asp His Leu Pro Glu Asn Asp Arg Asn Tyr Tyr
225                 230                 235                 240

Gly Cys Gly Glu Met Pro Arg His Phe Ala Ala Lys Leu Asp Lys Tyr
                245                 250                 255

Met Tyr Ile Leu Pro Tyr Lys Glu Phe Phe Gly Gly Val Ser Gly Leu
            260                 265                 270

Thr Val Glu Gln Phe Arg Lys Ile Asn Gly Phe Pro Asn Ala Phe Trp
            275                 280                 285

Gly Trp Gly Gly Glu Asp Asp Asp Leu Trp Asn Arg Val His Tyr Ala
290                 295                 300

Gly Tyr Asn Val Thr Arg Pro Glu Gly Asp Leu Gly Lys Tyr Lys Ser
305                 310                 315                 320

Ile Pro His His Arg Gly Glu Val Gln Phe Leu Gly Arg Tyr Lys
                325                 330                 335

Leu Leu Arg Tyr Ser Lys Glu Arg Gln Tyr Ile Asp Gly Leu Asn Asn
            340                 345                 350

Leu Ile Tyr Arg Pro Lys Ile Leu Val Asp Arg Leu Tyr Thr Asn Ile
            355                 360                 365

Ser Val Asn Leu Met Pro Glu Leu Ala Pro Ile Glu Asp Tyr
370                 375                 380

<210> SEQ ID NO 7
<211> LENGTH: 3924
<212> TYPE: DNA
<213> ORGANISM: Homo Sapiens
<220> FEATURE:
<221> NAME/KEY: CDS
<222> LOCATION: (1)...(3168)

<400> SEQUENCE: 7 atg gct ctg cgg agg ctg ggg gcc gcg ctg ctg ctg ccg ctg ctc      48
Met Ala Leu Arg Arg Leu Gly Ala Ala Leu Leu Leu Pro Leu Leu
 1               5                  10                  15 gcc gcc gtg gaa gaa acg cta atg gac tcc act aca gcg act gct gag  96
Ala Ala Val Glu Glu Thr Leu Met Asp Ser Thr Thr Ala Thr Ala Glu
                20                  25                  30 ctg ggc tgg atg gtg cat cct cca tca ggg tgg gaa gag gtg agt ggc 144
Leu Gly Trp Met Val His Pro Pro Ser Gly Trp Glu Glu Val Ser Gly
            35                  40                  45
```

-continued

| | |
|---|---|
| tac gat gag aac atg aac acg atc cgc acg tac cag gtg tgc aac gtg<br>Tyr Asp Glu Asn Met Asn Thr Ile Arg Thr Tyr Gln Val Cys Asn Val<br>    50                        55                     60 | 192 |
| ttt gag tca agc cag aac aac tgg cta cgg acc aag ttt atc cgg cgc<br>Phe Glu Ser Ser Gln Asn Asn Trp Leu Arg Thr Lys Phe Ile Arg Arg<br>65                  70                    75                80 | 240 |
| cgt ggc gcc cac cgc atc cac gtg gag atg aag ttt tcg gtg cgt gac<br>Arg Gly Ala His Arg Ile His Val Glu Met Lys Phe Ser Val Arg Asp<br>                    85                    90                95 | 288 |
| tgc agc agc atc ccc agc gtg cct ggc tcc tgc aag gag acc ttc aac<br>Cys Ser Ser Ile Pro Ser Val Pro Gly Ser Cys Lys Glu Thr Phe Asn<br>           100                   105              110 | 336 |
| ctc tat tac tat gag gct gac ttt gac tcg gcc acc aag acc ttc ccc<br>Leu Tyr Tyr Tyr Glu Ala Asp Phe Asp Ser Ala Thr Lys Thr Phe Pro<br>      115                   120                 125 | 384 |
| aac tgg atg gag aat cca tgg gtg aag gtg gat acc att gca gcc gac<br>Asn Trp Met Glu Asn Pro Trp Val Lys Val Asp Thr Ile Ala Ala Asp<br>130                 135                 140 | 432 |
| gag agc ttc tcc cag gtg gac ctg ggt ggc cgc gtc atg aaa atc aac<br>Glu Ser Phe Ser Gln Val Asp Leu Gly Gly Arg Val Met Lys Ile Asn<br>145                 150                155              160 | 480 |
| acc gag gtg cgg agc ttc gga cct gtg tcc cgc agc ggc ttc tac ctg<br>Thr Glu Val Arg Ser Phe Gly Pro Val Ser Arg Ser Gly Phe Tyr Leu<br>                 165                170               175 | 528 |
| gcc ttc cag gac tat ggc ggc tgc atg tcc ctc atc gcc gtg cgt gtc<br>Ala Phe Gln Asp Tyr Gly Gly Cys Met Ser Leu Ile Ala Val Arg Val<br>           180                   185              190 | 576 |
| ttc tac cgc aag tgc ccc cgc atc atc cag aat ggc gcc atc ttc cag<br>Phe Tyr Arg Lys Cys Pro Arg Ile Ile Gln Asn Gly Ala Ile Phe Gln<br>      195                   200                 205 | 624 |
| gaa acc ctg tcg ggg gct gag agc aca tcg ctg gtg gct gcc cgg ggc<br>Glu Thr Leu Ser Gly Ala Glu Ser Thr Ser Leu Val Ala Ala Arg Gly<br>210                 215                220 | 672 |
| agc tgc atc gcc aat gcg gaa gag gtg gat gta ccc atc aag ctc tac<br>Ser Cys Ile Ala Asn Ala Glu Glu Val Asp Val Pro Ile Lys Leu Tyr<br>225                 230                235              240 | 720 |
| tgt aac ggg gac ggc gag tgg ctg gtg ccc atc ggg cgc tgc atg tgc<br>Cys Asn Gly Asp Gly Glu Trp Leu Val Pro Ile Gly Arg Cys Met Cys<br>                 245                250               255 | 768 |
| aaa gca ggc ttc gag gcc gtt gag aat ggc acc gtc tgc cga ggt tgt<br>Lys Ala Gly Phe Glu Ala Val Glu Asn Gly Thr Val Cys Arg Gly Cys<br>           260                   265              270 | 816 |
| cca tct ggg act ttc aag gcc aac caa ggg gat gag gcc tgt acc cac<br>Pro Ser Gly Thr Phe Lys Ala Asn Gln Gly Asp Glu Ala Cys Thr His<br>      275                   280                 285 | 864 |
| tgt ccc atc aac agc cgg acc act tct gaa ggg gcc acc aac tgt gtc<br>Cys Pro Ile Asn Ser Arg Thr Thr Ser Glu Gly Ala Thr Asn Cys Val<br>290                 295                300 | 912 |
| tgc cgc aat ggc tac tac aga gca gac ctg gac ccc ctg gac atg ccc<br>Cys Arg Asn Gly Tyr Tyr Arg Ala Asp Leu Asp Pro Leu Asp Met Pro<br>305                 310                315              320 | 960 |
| tgc aca acc atc ccc tcc gcg ccc cag gct gtg att tcc agt gtc aat<br>Cys Thr Thr Ile Pro Ser Ala Pro Gln Ala Val Ile Ser Ser Val Asn<br>                 325                330               335 | 1008 |
| gag acc tcc ctc atg ctg gag tgg acc cct ccc cgc gac tcc gga ggc<br>Glu Thr Ser Leu Met Leu Glu Trp Thr Pro Pro Arg Asp Ser Gly Gly<br>           340                   345              350 | 1056 |
| cga gag gac ctc gtc tac aac atc atc tgc aag agc tgt ggc tcg ggc<br>Arg Glu Asp Leu Val Tyr Asn Ile Ile Cys Lys Ser Cys Gly Ser Gly<br>      355                   360                 365 | 1104 |

```
cgg ggt gcc tgc acc cgc tgc ggg gac aat gta cag tac gca cca cgc      1152
Arg Gly Ala Cys Thr Arg Cys Gly Asp Asn Val Gln Tyr Ala Pro Arg
    370                 375                 380 cag cta ggc ctg acc gag cca cgc att tac atc agt gac ctg ctg gcc      1200
Gln Leu Gly Leu Thr Glu Pro Arg Ile Tyr Ile Ser Asp Leu Leu Ala
385                 390                 395                 400 cac acc cag tac acc ttc gag atc cag gct gtg aac ggc gtt act gac      1248
His Thr Gln Tyr Thr Phe Glu Ile Gln Ala Val Asn Gly Val Thr Asp
                405                 410                 415 cag agc ccc ttc tcg cct cag ttc gcc tct gtg aac atc acc acc aac      1296
Gln Ser Pro Phe Ser Pro Gln Phe Ala Ser Val Asn Ile Thr Thr Asn
            420                 425                 430 cag gca gct cca tcg gca gtg tcc atc atg cat cag gtg agc cgc acc      1344
Gln Ala Ala Pro Ser Ala Val Ser Ile Met His Gln Val Ser Arg Thr
        435                 440                 445 gtg gac agc att acc ctg tcg tgg tcc cag cca gac cag ccc aat ggc      1392
Val Asp Ser Ile Thr Leu Ser Trp Ser Gln Pro Asp Gln Pro Asn Gly
450                 455                 460 gtg atc ctg gac tat gag ctg cag tac tat gag aag gag ctc agt gag      1440
Val Ile Leu Asp Tyr Glu Leu Gln Tyr Tyr Glu Lys Glu Leu Ser Glu
465                 470                 475                 480 tac aac gcc aca gcc ata aaa agc ccc acc aac acg gtc acc gtg cag      1488
Tyr Asn Ala Thr Ala Ile Lys Ser Pro Thr Asn Thr Val Thr Val Gln
                485                 490                 495 ggc ctc aaa gcc ggc gcc atc tat gtc ttc cag gtg cgg gca cgc acc      1536
Gly Leu Lys Ala Gly Ala Ile Tyr Val Phe Gln Val Arg Ala Arg Thr
            500                 505                 510 gtg gca ggc tac ggg cgc tac agc ggc aag atg tac ttc cag acc atg      1584
Val Ala Gly Tyr Gly Arg Tyr Ser Gly Lys Met Tyr Phe Gln Thr Met
        515                 520                 525 aca gaa gcc gag tac cag aca agc atc cag gag aag ttg cca ctc atc      1632
Thr Glu Ala Glu Tyr Gln Thr Ser Ile Gln Glu Lys Leu Pro Leu Ile
530                 535                 540 atc ggc tcc tcg gcc gct ggc ctg gtc ttc ctc att gct gtg gtt gtc      1680
Ile Gly Ser Ser Ala Ala Gly Leu Val Phe Leu Ile Ala Val Val Val
545                 550                 555                 560 atc gcc atc gtg tgt aac aga cgg ggg ttt gag cgt gct gac tcg gag      1728
Ile Ala Ile Val Cys Asn Arg Arg Gly Phe Glu Arg Ala Asp Ser Glu
                565                 570                 575 tac acg gac aag ctg caa cac tac acc agt ggc cac atg acc cca ggc      1776
Tyr Thr Asp Lys Leu Gln His Tyr Thr Ser Gly His Met Thr Pro Gly
            580                 585                 590 atg aag atc tac atc gat cct ttc acc tac gag gac ccc aac gag gca      1824
Met Lys Ile Tyr Ile Asp Pro Phe Thr Tyr Glu Asp Pro Asn Glu Ala
        595                 600                 605 gtg cgg gag ttt gcc aag gaa att gac atc tcc tgt gtc aaa att gag      1872
Val Arg Glu Phe Ala Lys Glu Ile Asp Ile Ser Cys Val Lys Ile Glu
610                 615                 620 cag gtg atc gga gca ggg gag ttt ggc gag gtc tgc agt ggc cac ctg      1920
Gln Val Ile Gly Ala Gly Glu Phe Gly Glu Val Cys Ser Gly His Leu
625                 630                 635                 640 aag ctg cca ggc aag aga gag atc ttt gtg gcc atc aag acg ctc aag      1968
Lys Leu Pro Gly Lys Arg Glu Ile Phe Val Ala Ile Lys Thr Leu Lys
                645                 650                 655 tcg ggc tac acg gag aag cag cgc cgg gac ttc ctg agc gaa gcc tcc      2016
Ser Gly Tyr Thr Glu Lys Gln Arg Arg Asp Phe Leu Ser Glu Ala Ser
            660                 665                 670 atc atg ggc cag ttc gac cat ccc aac gtc atc cac ctg gag ggt gtc      2064
Ile Met Gly Gln Phe Asp His Pro Asn Val Ile His Leu Glu Gly Val
        675                 680                 685
```

-continued

| | |
|---|---|
| gtg acc aag agc aca cct gtg atg atc atc acc gag ttc atg gag aat<br>Val Thr Lys Ser Thr Pro Val Met Ile Ile Thr Glu Phe Met Glu Asn<br>690                         695                   700 | 2112 |
| ggc tcc ctg gac tcc ttt ctc cgg caa aac gat ggg cag ttc aca gtc<br>Gly Ser Leu Asp Ser Phe Leu Arg Gln Asn Asp Gly Gln Phe Thr Val<br>705                     710                     715                720 | 2160 |
| atc cag ctg gtg ggc atg ctt cgg ggc atc gca gct ggc atg aag tac<br>Ile Gln Leu Val Gly Met Leu Arg Gly Ile Ala Ala Gly Met Lys Tyr<br>               725                     730                     735 | 2208 |
| ctg gca gac atg aac tat gtt cac cgt gac ctg gct gcc cgc aac atc<br>Leu Ala Asp Met Asn Tyr Val His Arg Asp Leu Ala Ala Arg Asn Ile<br>           740                     745                     750 | 2256 |
| ctc gtc aac agc aac ctg gtc tgc aag gtg tcg gac ttt ggg ctc tca<br>Leu Val Asn Ser Asn Leu Val Cys Lys Val Ser Asp Phe Gly Leu Ser<br>755                         760                     765 | 2304 |
| cgc ttt cta gag gac gat acc tca gac ccc acc tac acc agt gcc ctg<br>Arg Phe Leu Glu Asp Asp Thr Ser Asp Pro Thr Tyr Thr Ser Ala Leu<br>770                         775                     780 | 2352 |
| ggc gga aag atc ccc atc cgc tgg aca gcc ccg gaa gcc atc cag tac<br>Gly Gly Lys Ile Pro Ile Arg Trp Thr Ala Pro Glu Ala Ile Gln Tyr<br>785                         790                     795                800 | 2400 |
| cgg aag ttc acc tcg gcc agt gat gtg tgg agc tac ggc att gtc atg<br>Arg Lys Phe Thr Ser Ala Ser Asp Val Trp Ser Tyr Gly Ile Val Met<br>                     805                     810                     815 | 2448 |
| tgg gag gtg atg tcc tat ggg gag cgg ccc tac tgg gac atg acc aac<br>Trp Glu Val Met Ser Tyr Gly Glu Arg Pro Tyr Trp Asp Met Thr Asn<br>           820                     825                     830 | 2496 |
| cag gat gta atc aat gcc att gag cag gac tat cgg ctg cca ccg ccc<br>Gln Asp Val Ile Asn Ala Ile Glu Gln Asp Tyr Arg Leu Pro Pro Pro<br>           835                     840                     845 | 2544 |
| atg gac tgc ccg agc gcc ctg cac caa ctc atg ctg gac tgt tgg cag<br>Met Asp Cys Pro Ser Ala Leu His Gln Leu Met Leu Asp Cys Trp Gln<br>850                         855                     860 | 2592 |
| aag gac cgc aac cac cgg ccc aag ttc ggc caa att gtc aac acg cta<br>Lys Asp Arg Asn His Arg Pro Lys Phe Gly Gln Ile Val Asn Thr Leu<br>865                         870                     875                880 | 2640 |
| gac aag atg atc cgc aat ccc aac agc ctc aaa gcc atg gcg ccc ctc<br>Asp Lys Met Ile Arg Asn Pro Asn Ser Leu Lys Ala Met Ala Pro Leu<br>               885                     890                     895 | 2688 |
| tcc tct ggc atc aac ctg ccg ctg ctg gac cgc acg atc ccc gac tac<br>Ser Ser Gly Ile Asn Leu Pro Leu Leu Asp Arg Thr Ile Pro Asp Tyr<br>           900                     905                     910 | 2736 |
| acc agc ttt aac acg gtg gac gag tgg ctg gag gcc atc aag atg ggg<br>Thr Ser Phe Asn Thr Val Asp Glu Trp Leu Glu Ala Ile Lys Met Gly<br>               915                     920                     925 | 2784 |
| cag tac aag gag agc ttc gcc aat gcc ggc ttc acc tcc ttt gac gtc<br>Gln Tyr Lys Glu Ser Phe Ala Asn Ala Gly Phe Thr Ser Phe Asp Val<br>930                         935                     940 | 2832 |
| gtg tct cag atg atg atg gag gac att ctc cgg gtt ggg gtc act ttg<br>Val Ser Gln Met Met Met Glu Asp Ile Leu Arg Val Gly Val Thr Leu<br>945                         950                     955                960 | 2880 |
| gct ggc cac cag aaa aaa atc ctg aac agt atc cag gtg atg cgg gcg<br>Ala Gly His Gln Lys Lys Ile Leu Asn Ser Ile Gln Val Met Arg Ala<br>               965                     970                     975 | 2928 |
| cag atg aac cag att cag tct gtg gag ggc cag cca ctc gcc agg agg<br>Gln Met Asn Gln Ile Gln Ser Val Glu Gly Gln Pro Leu Ala Arg Arg<br>           980                     985                     990 | 2976 |
| cca cgg gcc acg gga aga acc aag cgg tgc cag cca cga gac gtc acc<br>Pro Arg Ala Thr Gly Arg Thr Lys Arg Cys Gln Pro Arg Asp Val Thr<br>995                         1000                   1005 | 3024 |

```
aag aaa aca tgc aac tca aac gac gga aaa aaa aag gga atg gga aaa      3072
Lys Lys Thr Cys Asn Ser Asn Asp Gly Lys Lys Lys Gly Met Gly Lys
    1010                1015                1020 aag aaa aca gat cct ggg agg ggg cgg gaa ata caa gga ata ttt ttt      3120
Lys Lys Thr Asp Pro Gly Arg Gly Arg Glu Ile Gln Gly Ile Phe Phe
1025                1030                1035                1040 aaa gag gat tct cat aag gaa agc aat gac tgt tct tgc ggg gga taa      3168
Lys Glu Asp Ser His Lys Glu Ser Asn Asp Cys Ser Cys Gly Gly  *
                1045                1050                1055 aaaagggctt ggagattca tgcgatgtgt ccaatcggag acaaaagcag tttctctcca     3228
actccctctg ggaaggtgac ctggccagag ccaagaaaca ctttcagaaa acaaatgtg     3288 aaggggagag acaggggcca cccttggctc ctgtccctgc tgctcctcta ggcctcactc    3348
aacaaccaag cgcctggagg acgggacaga tggacagaca gccaccctga gaacccctct    3408
gggaaaatct attcctgcca ccactgggca acagaagaa ttttctgtc tttggagagt     3468 attttagaaa ctccaatgaa agacactgtt tctcctgttg gctcacaggg ctgaaagggg    3528
cttttgtcct cctgggtcag ggagaacgcg gggaccccag aaaggtcagc cttcctgagg    3588
atgggcaacc cccaggtctg cagctccagg tacatatcac gcgcacagcc tggcagcctg    3648
gccctcctgg tgcccactcc cgccagcccc tgcctcgagg actgatactg cagtgactgc    3708
cgtcagctcc gactgccgct gagaagggtt gatcctgcat ctgggtttgt ttacagcaat    3768
tcctggactc gggggtattt tggtcacagg gtggttttgg tttagggggt ttgtttgttg    3828
ggttgttttt tgtttttttgg ttttttttaa tgacaatgaa gtgacacttt gacatttcca   3888
aaaaaaaaaa aaaaaaaaa aaaaaaaaa aaaaa                                  3924

<210> SEQ ID NO 8
<211> LENGTH: 1055
<212> TYPE: PRT
<213> ORGANISM: Homo Sapiens

<400> SEQUENCE: 8

Met Ala Leu Arg Arg Leu Gly Ala Ala Leu Leu Leu Pro Leu Leu
1               5                   10                  15

Ala Ala Val Glu Glu Thr Leu Met Asp Ser Thr Thr Ala Thr Ala Glu
                20                  25                  30

Leu Gly Trp Met Val His Pro Pro Ser Gly Trp Glu Val Ser Gly
            35                  40                  45

Tyr Asp Glu Asn Met Asn Thr Ile Arg Thr Tyr Gln Val Cys Asn Val
    50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
                100                 105                 110

Leu Tyr Tyr Tyr Glu Ala Asp Phe Asp Ser Ala Thr Lys Thr Phe Pro
            115                 120                 125

Asn Trp Met Glu Asn Pro Trp Val Lys Val Asp Thr Ile Ala Ala Asp
    130                 135                 140

Glu Ser Phe Ser Gln Val Asp Leu Gly Gly Arg Val Met Lys Ile Asn
145                 150                 155                 160

Thr Glu Val Arg Ser Phe Gly Pro Val Ser Arg Ser Gly Phe Tyr Leu
                165                 170                 175
```

-continued

```
Ala Phe Gln Asp Tyr Gly Gly Cys Met Ser Leu Ile Ala Val Arg Val
            180                 185                 190

Phe Tyr Arg Lys Cys Pro Arg Ile Ile Gln Asn Gly Ala Ile Phe Gln
        195                 200                 205

Glu Thr Leu Ser Gly Ala Glu Ser Thr Ser Leu Val Ala Ala Arg Gly
    210                 215                 220

Ser Cys Ile Ala Asn Ala Glu Glu Val Asp Val Pro Ile Lys Leu Tyr
225                 230                 235                 240

Cys Asn Gly Asp Gly Glu Trp Leu Val Pro Ile Gly Arg Cys Met Cys
                245                 250                 255

Lys Ala Gly Phe Glu Ala Val Glu Asn Gly Thr Val Cys Arg Gly Cys
            260                 265                 270

Pro Ser Gly Thr Phe Lys Ala Asn Gln Gly Asp Glu Ala Cys Thr His
        275                 280                 285

Cys Pro Ile Asn Ser Arg Thr Thr Ser Glu Gly Ala Thr Asn Cys Val
    290                 295                 300

Cys Arg Asn Gly Tyr Tyr Arg Ala Asp Leu Asp Pro Leu Asp Met Pro
305                 310                 315                 320

Cys Thr Thr Ile Pro Ser Ala Pro Gln Ala Val Ile Ser Ser Val Asn
                325                 330                 335

Glu Thr Ser Leu Met Leu Glu Trp Thr Pro Pro Arg Asp Ser Gly Gly
            340                 345                 350

Arg Glu Asp Leu Val Tyr Asn Ile Ile Cys Lys Ser Cys Gly Ser Gly
        355                 360                 365

Arg Gly Ala Cys Thr Arg Cys Gly Asp Asn Val Gln Tyr Ala Pro Arg
    370                 375                 380

Gln Leu Gly Leu Thr Glu Pro Arg Ile Tyr Ile Ser Asp Leu Leu Ala
385                 390                 395                 400

His Thr Gln Tyr Thr Phe Glu Ile Gln Ala Val Asn Gly Val Thr Asp
                405                 410                 415

Gln Ser Pro Phe Ser Pro Gln Phe Ala Ser Val Asn Ile Thr Thr Asn
            420                 425                 430

Gln Ala Ala Pro Ser Ala Val Ser Ile Met His Gln Val Ser Arg Thr
        435                 440                 445

Val Asp Ser Ile Thr Leu Ser Trp Ser Gln Pro Asp Gln Pro Asn Gly
    450                 455                 460

Val Ile Leu Asp Tyr Glu Leu Gln Tyr Tyr Glu Lys Glu Leu Ser Glu
465                 470                 475                 480

Tyr Asn Ala Thr Ala Ile Lys Ser Pro Thr Asn Thr Val Thr Val Gln
                485                 490                 495

Gly Leu Lys Ala Gly Ala Ile Tyr Val Phe Gln Val Arg Ala Arg Thr
            500                 505                 510

Val Ala Gly Tyr Gly Arg Tyr Ser Gly Lys Met Tyr Phe Gln Thr Met
        515                 520                 525

Thr Glu Ala Glu Tyr Gln Thr Ser Ile Gln Glu Lys Leu Pro Leu Ile
    530                 535                 540

Ile Gly Ser Ser Ala Ala Gly Leu Val Phe Leu Ile Ala Val Val Val
545                 550                 555                 560

Ile Ala Ile Val Cys Asn Arg Arg Gly Phe Glu Arg Ala Asp Ser Glu
                565                 570                 575

Tyr Thr Asp Lys Leu Gln His Tyr Thr Ser Gly His Met Thr Pro Gly
            580                 585                 590
```

```
Met Lys Ile Tyr Ile Asp Pro Phe Thr Tyr Glu Asp Pro Asn Glu Ala
        595                 600                 605

Val Arg Glu Phe Ala Lys Glu Ile Asp Ile Ser Cys Val Lys Ile Glu
        610                 615                 620

Gln Val Ile Gly Ala Gly Glu Phe Gly Glu Val Cys Ser Gly His Leu
625                 630                 635                 640

Lys Leu Pro Gly Lys Arg Glu Ile Phe Val Ala Ile Lys Thr Leu Lys
                645                 650                 655

Ser Gly Tyr Thr Glu Lys Gln Arg Arg Asp Phe Leu Ser Glu Ala Ser
                660                 665                 670

Ile Met Gly Gln Phe Asp His Pro Asn Val Ile His Leu Glu Gly Val
        675                 680                 685

Val Thr Lys Ser Thr Pro Val Met Ile Ile Thr Glu Phe Met Glu Asn
690                 695                 700

Gly Ser Leu Asp Ser Phe Leu Arg Gln Asn Asp Gly Gln Phe Thr Val
705                 710                 715                 720

Ile Gln Leu Val Gly Met Leu Arg Gly Ile Ala Ala Gly Met Lys Tyr
                725                 730                 735

Leu Ala Asp Met Asn Tyr Val His Arg Asp Leu Ala Ala Arg Asn Ile
                740                 745                 750

Leu Val Asn Ser Asn Leu Val Cys Lys Val Ser Asp Phe Gly Leu Ser
                755                 760                 765

Arg Phe Leu Glu Asp Asp Thr Ser Asp Pro Thr Tyr Thr Ser Ala Leu
770                 775                 780

Gly Gly Lys Ile Pro Ile Arg Trp Thr Ala Pro Glu Ala Ile Gln Tyr
785                 790                 795                 800

Arg Lys Phe Thr Ser Ala Ser Asp Val Trp Ser Tyr Gly Ile Val Met
                805                 810                 815

Trp Glu Val Met Ser Tyr Gly Glu Arg Pro Tyr Trp Asp Met Thr Asn
                820                 825                 830

Gln Asp Val Ile Asn Ala Ile Glu Gln Asp Tyr Arg Leu Pro Pro Pro
        835                 840                 845

Met Asp Cys Pro Ser Ala Leu His Gln Leu Met Leu Asp Cys Trp Gln
850                 855                 860

Lys Asp Arg Asn His Arg Pro Lys Phe Gly Gln Ile Val Asn Thr Leu
865                 870                 875                 880

Asp Lys Met Ile Arg Asn Pro Asn Ser Leu Lys Ala Met Ala Pro Leu
                885                 890                 895

Ser Ser Gly Ile Asn Leu Pro Leu Leu Asp Arg Thr Ile Pro Asp Tyr
                900                 905                 910

Thr Ser Phe Asn Thr Val Asp Glu Trp Leu Glu Ala Ile Lys Met Gly
        915                 920                 925

Gln Tyr Lys Glu Ser Phe Ala Asn Ala Gly Phe Thr Ser Phe Asp Val
        930                 935                 940

Val Ser Gln Met Met Met Glu Asp Ile Leu Arg Val Gly Val Thr Leu
945                 950                 955                 960

Ala Gly His Gln Lys Lys Ile Leu Asn Ser Ile Gln Val Met Arg Ala
                965                 970                 975

Gln Met Asn Gln Ile Gln Ser Val Glu Gly Gln Pro Leu Ala Arg Arg
                980                 985                 990

Pro Arg Ala Thr Gly Arg Thr Lys Arg Cys Gln Pro Arg Asp Val Thr
                995                 1000                1005
```

```
                Lys Lys Thr Cys Asn Ser Asn Asp Gly Lys Lys Lys Gly Met Gly Lys
                    1010                1015                1020

Lys Lys Thr Asp Pro Gly Arg Gly Arg Glu Ile Gln Gly Ile Phe Phe
                1025                1030                1035                1040

Lys Glu Asp Ser His Lys Glu Ser Asn Asp Cys Ser Cys Gly Gly
                                1045                1050                1055

<210> SEQ ID NO 9
<211> LENGTH: 4234
<212> TYPE: DNA
<213> ORGANISM: Homo Sapiens
<220> FEATURE:
<221> NAME/KEY: CDS
<222> LOCATION: (863)...(2452)

<400> SEQUENCE: 9
aagcttactg gtgaggcaag tgtgcgtcta tttccatggc gccctggctc gcggcagccc      60
ctggctgggc gagggtgtg atgtgggagt gggtgggag gggcagcag gcggggcctg        120 ccacgtcact tggagagtgt gtgttgggaa ggaagggcag agcggagagc cgagccgctg     180
cagctgcggc ggcggcagcg aagccttgag ccgtggggag gtgggtcccc ggctcgggcg     240
ccggggcagc cccgggcctc tgcgaggcct gcggcgcggc tcctagggag gaggtggcgg     300
ctgtggcggc cggaaccgcg accttggccg gacccagccc cgcggtggac gcagggcgga     360
ggccgagccc cgcaggagtc tttgccgagc cggaggaggc gcatctggcg cttcggtacc     420
agcggcagcc ggggtccgg agcggctgga ggagcgcagt ggagaactgg gaagagctag      480
cccggctgga gggcggacct ctgcgtccgg gagccgggt ctcaaggcac cgctggggc       540 gaagcacggc gtcttttcgg gcagccagtt tcacacgcgc ctgtgtgccg gttccgggca    600
tcccagtaag ctctagcacc cgggcgcggg taacgggaag cgcagaacca aatccccagc    660
gcccaggtca cctccccaga cccagccttg cagggaccag ggctttaggg ctcacggacc    720
caacggccag gtcagaccgc gaaccgggag agcgcggccc cacccctaaag agggcgcacg   780 ggagctgggg agcgggtgcc gcgctccaga gattgtgtcg tgggcgccgt cctagtggcg    840
gggagcgcac ctccgagggg gc atg aga tcg gag aaa tcc ctt acg ctg gcg      892
                         Met Arg Ser Glu Lys Ser Leu Thr Leu Ala
                          1               5                   10 gcg ccg ggg gag gtc cgt ggg ccg gag ggg gag caa cag gat gcg gga       940
Ala Pro Gly Glu Val Arg Gly Pro Glu Gly Glu Gln Gln Asp Ala Gly
                15                  20                  25 gac ttc ccg gag gcc ggc ggg ggc ggg ggc tgc tgt agt agc gag cgg       988
Asp Phe Pro Glu Ala Gly Gly Gly Gly Gly Cys Cys Ser Ser Glu Arg
            30                  35                  40 ctg gtg atc aat atc tcc ggg ctg cgc ttt gag aca caa ttg cgc acc      1036
Leu Val Ile Asn Ile Ser Gly Leu Arg Phe Glu Thr Gln Leu Arg Thr
        45                  50                  55 ctg tcg ctg ttt ccg gac acg ctg ctc gga gac cct ggc cgg cga gtc      1084
Leu Ser Leu Phe Pro Asp Thr Leu Leu Gly Asp Pro Gly Arg Arg Val
    60                  65                  70 cgc ttc ttc gac ccc ctg agg aac gag tac ttc ttc gac cgc aac cgg      1132
Arg Phe Phe Asp Pro Leu Arg Asn Glu Tyr Phe Phe Asp Arg Asn Arg
75                  80                  85                  90 ccc agc ttc gac gcc atc ctc tac tac cag tct ggg ggc cgc ctg          1180
Pro Ser Phe Asp Ala Ile Leu Tyr Tyr Gln Ser Gly Gly Arg Leu
                95                  100                 105 cgg agg ccg gtc aac gtg ccc ctg gac att ttc ctg gag gag atc cgc      1228
Arg Arg Pro Val Asn Val Pro Leu Asp Ile Phe Leu Glu Glu Ile Arg
            110                 115                 120
```

-continued

| | | |
|---|---|---|
| ttc tac cag ctg ggg gac gag gcc ctg gcg gcc ttc cgg gag gac gag<br>Phe Tyr Gln Leu Gly Asp Glu Ala Leu Ala Ala Phe Arg Glu Asp Glu<br>125                                    130                            135 | 1276 |
| ggc tgc ctg ccc gaa ggt ggc gag gac gag aag ccg ctg ccc tcc cag<br>Gly Cys Leu Pro Glu Gly Gly Glu Asp Glu Lys Pro Leu Pro Ser Gln<br>140                         145                       150 | 1324 |
| ccc ttc cag cgc cag gtg tgg ctg ctc ttt gag tac cca gag agc tct<br>Pro Phe Gln Arg Gln Val Trp Leu Leu Phe Glu Tyr Pro Glu Ser Ser<br>155                     160                   165                 170 | 1372 |
| ggg ccg gcc agg ggc atc gcc atc gtc tcc gtg ttg gtc att ctc atc<br>Gly Pro Ala Arg Gly Ile Ala Ile Val Ser Val Leu Val Ile Leu Ile<br>                   175                   180                 185 | 1420 |
| tcc ata gtc atc ttt tgc ctg gag acc tta ccc cag ttc cgt gta gat<br>Ser Ile Val Ile Phe Cys Leu Glu Thr Leu Pro Gln Phe Arg Val Asp<br>190                         195                   200 | 1468 |
| ggt cga ggt gga aac aat ggt ggt gtg agt cga gtc tcc cca gtt tcc<br>Gly Arg Gly Gly Asn Asn Gly Gly Val Ser Arg Val Ser Pro Val Ser<br>                   205                   210                 215 | 1516 |
| agg ggg agt cag gag gaa gag gag gat gaa gac gat tcc tac aca ttt<br>Arg Gly Ser Gln Glu Glu Glu Glu Asp Glu Asp Asp Ser Tyr Thr Phe<br>220                         225                   230 | 1564 |
| cat cat ggc atc acc cct ggg gaa atg ggc acc ggg ggc tcc tcc tca<br>His His Gly Ile Thr Pro Gly Glu Met Gly Thr Gly Gly Ser Ser Ser<br>235                       240                   245                 250 | 1612 |
| ctc agt act ctt ggg ggc tcc ttc ttt aca gac ccc ttc ttt ctg gtg<br>Leu Ser Thr Leu Gly Gly Ser Phe Phe Thr Asp Pro Phe Phe Leu Val<br>                   255                   260                 265 | 1660 |
| gag acg ctg tgc att gtc tgg ttc act ttt gag ctc ctg gtg cgc ttc<br>Glu Thr Leu Cys Ile Val Trp Phe Thr Phe Glu Leu Leu Val Arg Phe<br>270                       275                   280 | 1708 |
| tcc gcc tgc cct agc aag ccg gcc ttc ttc cgg aac atc atg aac atc<br>Ser Ala Cys Pro Ser Lys Pro Ala Phe Phe Arg Asn Ile Met Asn Ile<br>                   285                   290                 295 | 1756 |
| att gac ttg gtg gct atc ttc ccc tac ttc atc acc ctg ggc act gag<br>Ile Asp Leu Val Ala Ile Phe Pro Tyr Phe Ile Thr Leu Gly Thr Glu<br>300                         305                   310 | 1804 |
| ctg gtg cag cag cag gag cag caa cca gcc agt gga gga ggc ggc cag<br>Leu Val Gln Gln Gln Glu Gln Gln Pro Ala Ser Gly Gly Gly Gly Gln<br>315                         320                   325                 330 | 1852 |
| aat ggg cag cag gcc atg tcc ctg gcc atc ctc cga gtc atc cgc ctg<br>Asn Gly Gln Gln Ala Met Ser Leu Ala Ile Leu Arg Val Ile Arg Leu<br>                   335                   340                 345 | 1900 |
| gtc cgg gtg ttc cgc atc ttc aag ctc tcc cgc cac tcc aag ggg ctg<br>Val Arg Val Phe Arg Ile Phe Lys Leu Ser Arg His Ser Lys Gly Leu<br>350                         355                   360 | 1948 |
| cag atc ctg ggc aag acc ttg cag gcc tcc atg agg gag ctg ggg ctg<br>Gln Ile Leu Gly Lys Thr Leu Gln Ala Ser Met Arg Glu Leu Gly Leu<br>                   365                   370                 375 | 1996 |
| ctc atc ttc ttc ctc ttc atc ggg gtc atc ctc ttc tcc agt gcc gtc<br>Leu Ile Phe Phe Leu Phe Ile Gly Val Ile Leu Phe Ser Ser Ala Val<br>380                         385                   390 | 2044 |
| tac ttc gca gag gct gac gat gac gat tcg ctt ttt ccc agc atc ccg<br>Tyr Phe Ala Glu Ala Asp Asp Asp Asp Ser Leu Phe Pro Ser Ile Pro<br>395                         400                   405                 410 | 2092 |
| gat gcc ttc tgg tgg gca gtg gtt aca atg acc acg gta ggt tac ggg<br>Asp Ala Phe Trp Trp Ala Val Val Thr Met Thr Thr Val Gly Tyr Gly<br>                   415                   420                 425 | 2140 |
| gac atg tac ccc atg act gtg ggg gga aag atc gtg ggc tcg ctg tgt<br>Asp Met Tyr Pro Met Thr Val Gly Gly Lys Ile Val Gly Ser Leu Cys<br>430                         435                   440 | 2188 |

```
gcc atc gct ggg gtc ctc acc att gcc ctg cct gtg ccc gtc atc gtc     2236
Ala Ile Ala Gly Val Leu Thr Ile Ala Leu Pro Val Pro Val Ile Val
            445                 450                 455 tcc aac ttc aac tac ttc tac cac cgg gag acg gag cag gag gag caa     2284
Ser Asn Phe Asn Tyr Phe Tyr His Arg Glu Thr Glu Gln Glu Glu Gln
    460                 465                 470 ggc cag tat acc cac gtc act tgt ggg cag cct gcg ccg gac ctg agg     2332
Gly Gln Tyr Thr His Val Thr Cys Gly Gln Pro Ala Pro Asp Leu Arg
475                 480                 485                 490 gca act gac aac gga ctt ggc aag cct gac ttc ccc gag gct aac cgg     2380
Ala Thr Asp Asn Gly Leu Gly Lys Pro Asp Phe Pro Glu Ala Asn Arg
                495                 500                 505 gaa cgg aga ccc agc tac ctt cct aca cca cat cgg gcc tat gca gag     2428
Glu Arg Arg Pro Ser Tyr Leu Pro Thr Pro His Arg Ala Tyr Ala Glu
            510                 515                 520 aaa aga atg ctc acg gag gtc tga cccatgcagg cagggcctgc aggaggggag    2482
Lys Arg Met Leu Thr Glu Val  *
            525 cactgagcta acagtctctt aggcttcctt ctcatttcca ctactcactc tagcttcagt   2542 tgacttcttg actctctccc ctacacccac tacctggcat ccaggaccaa atacctggac   2602 tatcaacctt gttgcttaat ccctgcagca ttcaaggtta atccatctaa gtgacatttt   2662 tgaaattcca gcggtgccac ccaatcatgc ccagcttctg tcatatgaat gagatataca   2722 tttatatgac agaagctggg catgattggg tggcaccgct ggaatttcaa aaatgtcaag   2782 gaacagcaaa tgtcaacagg atggaaacca gccctatctg agtcttcgct ccctcccttag 2842 tgttctttgc tttgggtcat gtgcgtttcc tagcttcagg ccacttggta actggaagaa   2902 gctggaggac agaagcagta ctcaacttgc tgttattcca gtgccctgta caaccactg    2962 gtcctcctgc agatgaccct tggtagagtc tttatttgca tagcctcaaa ataggttatt   3022 cgttctaaac ttggatggaa ttagagaata caatcaaact ttaccacttg gaggacacgg   3082 ggttagtcca ggaccaaaga ggccaatgga ttttcaaag tgtgccccag cacacagagg    3142 cactggtgtt cggtctacat ttagttctcc ccactctgat cccctgactc tccagcttcc   3202 aggaaggttc cttctcagag ccaaatactc tttgtgcaag tgccttcctg agcagaagaa   3262 ctggagaaag gaaccacag agccaggagg aatgtctgag cagagtcaag caactggctt    3322 gaccacagtc tgaagcaagg tgccacttaa acagatactg ttttctcaaa ggggcagagg   3382 aatcgtgttg cagatggcag cctttctcc ttcatttcc ccacatttc tctggccctc      3442 taccttgctt cctgggagtt tgatttagga ttgctgttga aggcttcctc aggcaaactc   3502 cagcttaaag ccctagacag gtaaaagcac acattggatg gcagcatggg tttcttccca   3562 ttttatgggc atgaaatatg tggtttagaa taaggaacaa gcattattcc tttgccaaca   3622 gcctcactct aagaggcttt tttgctgagt caagcaaaca cttgcctgct ctgcccttg    3682 gaggtgcatt tgacctgctc tcactggtaa ggtgacttgg tggcgttccc acttgattta   3742 gccattttct tccattgtga gaccactgcc atctatccac ctgcccacct cccctttgt    3802 ttctcagtaa cattgccatt tgttttttgc ctttgataaa ctgtgatgta ctgttctgag   3862 atctttttggg tgcagttctg aaactgaaag gactgttaac atgttttta ttttatatct   3922 atgctttcag actctttgat gataattttt tttttaaaa attatctctc gaagagcaac    3982 ttacgagagg acagccttat gagggtttgc ttgagaggca gtgtggcttc tgtgactgcc   4042 agctctaaat ctcgatcttg ccataacttt acagggtaac ttgggtccac agtcactctt   4102 tgtgcctcag tttacccacc cattaaatgg gaacattact gtcttcccct ccctacctca   4162
```

-continued

```
tggggaatgt ctgggaagct ggggacattg ctatgcaaat gtgtgaatct tagtcatgga      4222
tttgattttt ag                                                          4234
```

<210> SEQ ID NO 10
<211> LENGTH: 529
<212> TYPE: PRT
<213> ORGANISM: Homo Sapiens

<400> SEQUENCE: 10

```
Met Arg Ser Glu Lys Ser Leu Thr Leu Ala Ala Pro Gly Glu Val Arg
 1               5                  10                  15

Gly Pro Glu Gly Glu Gln Gln Asp Ala Gly Asp Phe Pro Glu Ala Gly
                20                  25                  30

Gly Gly Gly Gly Cys Cys Ser Ser Glu Arg Leu Val Ile Asn Ile Ser
            35                  40                  45

Gly Leu Arg Phe Glu Thr Gln Leu Arg Thr Leu Ser Leu Phe Pro Asp
    50                  55                  60

Thr Leu Leu Gly Asp Pro Gly Arg Arg Val Arg Phe Phe Asp Pro Leu
65                  70                  75                  80

Arg Asn Glu Tyr Phe Phe Asp Arg Asn Arg Pro Ser Phe Asp Ala Ile
                85                  90                  95

Leu Tyr Tyr Tyr Gln Ser Gly Gly Arg Leu Arg Arg Pro Val Asn Val
            100                 105                 110

Pro Leu Asp Ile Phe Leu Glu Glu Ile Arg Phe Tyr Gln Leu Gly Asp
        115                 120                 125

Glu Ala Leu Ala Ala Phe Arg Glu Asp Glu Gly Cys Leu Pro Glu Gly
    130                 135                 140

Gly Glu Asp Glu Lys Pro Leu Pro Ser Gln Pro Phe Gln Arg Gln Val
145                 150                 155                 160

Trp Leu Leu Phe Glu Tyr Pro Glu Ser Ser Gly Pro Ala Arg Gly Ile
                165                 170                 175

Ala Ile Val Ser Val Leu Val Ile Leu Ile Ser Ile Val Ile Phe Cys
            180                 185                 190

Leu Glu Thr Leu Pro Gln Phe Arg Val Asp Gly Arg Gly Gly Asn Asn
        195                 200                 205

Gly Gly Val Ser Arg Val Ser Pro Val Ser Arg Gly Ser Gln Glu Glu
    210                 215                 220

Glu Glu Asp Glu Asp Asp Ser Tyr Thr Phe His His Gly Ile Thr Pro
225                 230                 235                 240

Gly Glu Met Gly Thr Gly Gly Ser Ser Ser Leu Ser Thr Leu Gly Gly
                245                 250                 255

Ser Phe Phe Thr Asp Pro Phe Phe Leu Val Glu Thr Leu Cys Ile Val
            260                 265                 270

Trp Phe Thr Phe Glu Leu Leu Val Arg Phe Ser Ala Cys Pro Ser Lys
        275                 280                 285

Pro Ala Phe Phe Arg Asn Ile Met Asn Ile Ile Asp Leu Val Ala Ile
    290                 295                 300

Phe Pro Tyr Phe Ile Thr Leu Gly Thr Glu Leu Val Gln Gln Gln Glu
305                 310                 315                 320

Gln Gln Pro Ala Ser Gly Gly Gly Gln Asn Gly Gln Gln Ala Met
                325                 330                 335

Ser Leu Ala Ile Leu Arg Val Ile Arg Leu Val Arg Val Phe Arg Ile
            340                 345                 350
```

```
Phe Lys Leu Ser Arg His Ser Lys Gly Leu Gln Ile Leu Gly Lys Thr
            355                 360                 365

Leu Gln Ala Ser Met Arg Glu Leu Gly Leu Leu Ile Phe Phe Leu Phe
    370                 375                 380

Ile Gly Val Ile Leu Phe Ser Ser Ala Val Tyr Phe Ala Glu Ala Asp
385                 390                 395                 400

Asp Asp Asp Ser Leu Phe Pro Ser Ile Pro Asp Ala Phe Trp Trp Ala
                405                 410                 415

Val Val Thr Met Thr Thr Val Gly Tyr Gly Asp Met Tyr Pro Met Thr
            420                 425                 430

Val Gly Gly Lys Ile Val Gly Ser Leu Cys Ala Ile Ala Gly Val Leu
        435                 440                 445

Thr Ile Ala Leu Pro Val Pro Val Ile Val Ser Asn Phe Asn Tyr Phe
    450                 455                 460

Tyr His Arg Glu Thr Glu Gln Glu Gln Gly Gln Tyr Thr His Val
465                 470                 475                 480

Thr Cys Gly Gln Pro Ala Pro Asp Leu Arg Ala Thr Asp Asn Gly Leu
                485                 490                 495

Gly Lys Pro Asp Phe Pro Glu Ala Asn Arg Glu Arg Arg Pro Ser Tyr
                500                 505                 510

Leu Pro Thr Pro His Arg Ala Tyr Ala Glu Lys Arg Met Leu Thr Glu
            515                 520                 525

Val

<210> SEQ ID NO 11
<211> LENGTH: 2747
<212> TYPE: DNA
<213> ORGANISM: Homo Sapiens
<220> FEATURE:
<221> NAME/KEY: CDS
<222> LOCATION: (51)...(1310)
<220> FEATURE:
<221> NAME/KEY: misc_feature
<222> LOCATION: (1)...(2747)
<223> OTHER INFORMATION: n = A,T,C or G

<400> SEQUENCE: 11
cgaggccgtg ctggaacccg ggcctcagcc gcagccgcag cggggccgac atg acg           56
                                                        Met Thr
                                                        1 aca gct ccc cag gag ccc ccc gcc cgg ccc ctc cag gcg ggc agt gga        104
Thr Ala Pro Gln Glu Pro Pro Ala Arg Pro Leu Gln Ala Gly Ser Gly
        5                   10                  15 gct ggc ccg gcg cct ggg cgc gcc atg cgc agc acc acg ctc ctg gcc        152
Ala Gly Pro Ala Pro Gly Arg Ala Met Arg Ser Thr Thr Leu Leu Ala
    20                  25                  30 ctg ctg gcg ctg gtc ttg ctt tac ttg gtg tct ggt gcc ctg gtg ttc        200
Leu Leu Ala Leu Val Leu Leu Tyr Leu Val Ser Gly Ala Leu Val Phe
35                  40                  45                  50 cgg gcc ctg gag cag ccc cac gag cag cag gcc cag agg gag ctg ggg        248
Arg Ala Leu Glu Gln Pro His Glu Gln Gln Ala Gln Arg Glu Leu Gly
                55                  60                  65 gag gtc cga gag aag ttc ctg agg gcc cat ccg tgt gtg agc gac cag        296
Glu Val Arg Glu Lys Phe Leu Arg Ala His Pro Cys Val Ser Asp Gln
            70                  75                  80 gag ctg ggc ctc ctc atc aag gag gtg gct gat gcc ctg gga ggg ggt        344
Glu Leu Gly Leu Leu Ile Lys Glu Val Ala Asp Ala Leu Gly Gly Gly
        85                  90                  95
```

-continued

| | | |
|---|---|---|
| gcg gac cca gaa acc aac tcg acc agc aac agc agc cac tca gcc tgg<br>Ala Asp Pro Glu Thr Asn Ser Thr Ser Asn Ser Ser His Ser Ala Trp<br>100                            105                       110 | 392 |
| gac ctg ggc agc gcc ttc ttt ttc tca ggg acc atc atc acc acc atc<br>Asp Leu Gly Ser Ala Phe Phe Phe Ser Gly Thr Ile Ile Thr Thr Ile<br>115                  120                      125                   130 | 440 |
| ggc tat ggc aat gtg gcc ctg cgc aca gat gcc ggg cgc ctc ttc tgc<br>Gly Tyr Gly Asn Val Ala Leu Arg Thr Asp Ala Gly Arg Leu Phe Cys<br>                     135                      140                     145 | 488 |
| atc ttt tat gcg ctg gtg ggg att ccg ctg ttt ggg atc cta ctg gca<br>Ile Phe Tyr Ala Leu Val Gly Ile Pro Leu Phe Gly Ile Leu Leu Ala<br>         150                      155                      160 | 536 |
| ggg gtc ggg gac cgg ctg ggc tcc tcc ctg cgc cat ggc atc ggt cac<br>Gly Val Gly Asp Arg Leu Gly Ser Ser Leu Arg His Gly Ile Gly His<br>165                            170                       175 | 584 |
| att gaa gcc atc ttc ttg aag tgg cac gtg cca ccg gag cta gta aga<br>Ile Glu Ala Ile Phe Leu Lys Trp His Val Pro Pro Glu Leu Val Arg<br>180                            185                      190 | 632 |
| gtg ctg tcg gcg atg ctt ttc ctg ctg atc ggc tgc ctc ctc ttt gtc<br>Val Leu Ser Ala Met Leu Phe Leu Leu Ile Gly Cys Leu Leu Phe Val<br>195                          200                      205               210 | 680 |
| ctc acg ccc acg ttc gtg ttc tgc tat atg gag gac tgg agc aag ctg<br>Leu Thr Pro Thr Phe Val Phe Cys Tyr Met Glu Asp Trp Ser Lys Leu<br>                     215                      220                     225 | 728 |
| gag gcc atc tac ttt gtc ata gtg acg ctt acc acc gtg ggc ttt ggc<br>Glu Ala Ile Tyr Phe Val Ile Val Thr Leu Thr Thr Val Gly Phe Gly<br>                     230                      235                     240 | 776 |
| gac tat gtg gcc ggc gcg gac ccc agg cag gac tcc ccg gcc tat cag<br>Asp Tyr Val Ala Gly Ala Asp Pro Arg Gln Asp Ser Pro Ala Tyr Gln<br>         245                      250                      255 | 824 |
| ccg ctg gtg tgg ttc tgg atc ctg ctc ggc ctg gct tac ttc gcc tca<br>Pro Leu Val Trp Phe Trp Ile Leu Leu Gly Leu Ala Tyr Phe Ala Ser<br>260                            265                      270 | 872 |
| gtg ctc acc acc atc ggg aac tgg ctg cga gta gtg tcc cgc cgc act<br>Val Leu Thr Thr Ile Gly Asn Trp Leu Arg Val Val Ser Arg Arg Thr<br>275                          280                      285               290 | 920 |
| cgg gca gag atg ggc ggc ctc acg gct cag gct gcc agc tgg act ggc<br>Arg Ala Glu Met Gly Gly Leu Thr Ala Gln Ala Ala Ser Trp Thr Gly<br>                   295                      300                    305 | 968 |
| aca gtg aca gcg cgc gtg acc cag cga gcc ggg ccc gcc gcc ccg ccg<br>Thr Val Thr Ala Arg Val Thr Gln Arg Ala Gly Pro Ala Ala Pro Pro<br>                     310                      315                    320 | 1016 |
| ccg gag aag gag cag cca ctg ctg cct cca ccg ccc tgt cca gcg cag<br>Pro Glu Lys Glu Gln Pro Leu Leu Pro Pro Pro Cys Pro Ala Gln<br>325                            330                      335 | 1064 |
| ccg ctg ggc agg ccc cga tcc cct tcg ccc ccc gag aag gct cag ccg<br>Pro Leu Gly Arg Pro Arg Ser Pro Ser Pro Pro Glu Lys Ala Gln Pro<br>340                            345                      350 | 1112 |
| cct tcc ccg ccc acg gcc tcg gcc ctg gat tat ccc agc gag aac ctg<br>Pro Ser Pro Pro Thr Ala Ser Ala Leu Asp Tyr Pro Ser Glu Asn Leu<br>355                            360                      365               370 | 1160 |
| gcc ttc atc gac gag tcc tcg gat acg cag agc gag cgc ggc tgc ccg<br>Ala Phe Ile Asp Glu Ser Ser Asp Thr Gln Ser Glu Arg Gly Cys Pro<br>                     375                      380                     385 | 1208 |
| ctg ccc cgc gcg ccg aga ggt cgc cgc cgc cca aat ccc ccc agg aag<br>Leu Pro Arg Ala Pro Arg Gly Arg Arg Arg Pro Asn Pro Pro Arg Lys<br>         390                      395                      400 | 1256 |
| ccc gtg cgg ccc cgc ggc ccc ggg cgt ccc cga gac aaa ggc gtg ccg<br>Pro Val Arg Pro Arg Gly Pro Gly Arg Pro Arg Asp Lys Gly Val Pro<br>405                            410                      415 | 1304 |

```
gtg tag ggatccctgg ccgggcctct caagggcttc gtttctgctc tccccggcat    1360
Val * gcctggcttg tttgaccaaa gagccctctt tccacgagac tgaagtctgg ggaggaggct   1420
acagttgcct ctccgcctcc tccctggccc cggcccttcc ctcacttcca tccatctcta   1480
gaccccccca aggctttctg tgtcgctgcc ccgggcgggt gtatccctca cagcacctca   1540
cgactgtgcc tcaaagcctg catcaataaa tgaaaacggt ctgcaccgct gcgggcgtga   1600
cgctcccgga cgcgagtggg tgtggaattg ctttcctcgg ccaccgtgg gggcacctct   1660 ggcctcccgt gaccccagg ccgagggtcc ccccgggcac ccaggtcggt caagtctcgg   1720
ccctctcagg cccgcgtctc tgcctggagg agactgtgta gggtccggcg tggggatcag   1780
ccgggatggg ctgcgcgtct ccagcctctg cacacacatt ggcgggtggg gtgcagggag   1840
ggagaggcag gggagagaga atggcatctc gcgtggaggg ctgtcgtttg aactctccca   1900
gcgcgagaga ccctgccccg cccccttcct ggagcgttga ctcccttctc gtctcgaggc   1960
ctgtggcgtc tgggtccgtt ggggcagaac catggaggaa aagccttcga aagtgtcgct   2020
caagtcttcc gaccgccaag gctcggacga ggagagcgtg catagcgaca ctcgggacct   2080
gtggaccacg accacgctgt cccaggcaca gctgaacatg ccgctgtccg aggtctgcga   2140
gggcttcgac gatgagggcc gcaacattag caagacccgc gggtggcaca gcccggggcg   2200
gggctcgttg gacgaggggt acaaggccag ccacaagccg gaggaactgg acgagcacgc   2260
gctggtggag ctggagttgc accgcggcag ctccatggaa atcaatctgg gggagaagga   2320
cactgcatcc cagatcgagg ccgaaaagtc ttcctcaatg tcatcactca atattgcgaa   2380
gcacatgccc catcgagcct actgggcaga gcagcagagc aggctgccac tgcccctgat   2440
ggaactcatg gagaatgaag ctctggaaat cctcaccaaa gccctccggn gctaccagtt   2500
agggatcggc agggaccact tcctgactaa ggagctgcag cgatacatcg aagggctcaa   2560
gaagcgccgg agcaagaggc tgtacgtgaa ttaaaaacgc caccttgggc tcgagcagcg   2620
acccgaacca gccccgtgcc agcccggtcc cagacccaa gcctgacccc atccgagtgg   2680
aatttgagtc ctaaagaaat aaaagagtgg tgcttaaaaa aaaaaaaaaa aaaaaaaaa   2740 aaaaaaa                                                           2747
```

<210> SEQ ID NO 12
<211> LENGTH: 419
<212> TYPE: PRT
<213> ORGANISM: Homo Sapiens

<400> SEQUENCE: 12

```
Met Thr Thr Ala Pro Gln Glu Pro Pro Ala Arg Pro Leu Gln Ala Gly
  1               5                  10                  15

Ser Gly Ala Gly Pro Ala Pro Gly Arg Ala Met Arg Ser Thr Thr Leu
             20                  25                  30

Leu Ala Leu Leu Ala Leu Val Leu Leu Tyr Leu Val Ser Gly Ala Leu
         35                  40                  45

Val Phe Arg Ala Leu Glu Gln Pro His Glu Gln Gln Ala Gln Arg Glu
     50                  55                  60

Leu Gly Glu Val Arg Glu Lys Phe Leu Arg Ala His Pro Cys Val Ser
 65                  70                  75                  80

Asp Gln Glu Leu Gly Leu Leu Ile Lys Glu Val Ala Asp Ala Leu Gly
                 85                  90                  95

Gly Gly Ala Asp Pro Glu Thr Asn Ser Thr Ser Asn Ser Ser His Ser
            100                 105                 110
```

```
Ala Trp Asp Leu Gly Ser Ala Phe Phe Ser Gly Thr Ile Ile Thr
    115                 120                 125

Thr Ile Gly Tyr Gly Asn Val Ala Leu Arg Thr Asp Ala Gly Arg Leu
130                 135                 140

Phe Cys Ile Phe Tyr Ala Leu Val Gly Ile Pro Leu Phe Gly Ile Leu
145                 150                 155                 160

Leu Ala Gly Val Gly Asp Arg Leu Gly Ser Ser Leu Arg His Gly Ile
                165                 170                 175

Gly His Ile Glu Ala Ile Phe Leu Lys Trp His Val Pro Pro Glu Leu
                180                 185                 190

Val Arg Val Leu Ser Ala Met Leu Phe Leu Leu Ile Gly Cys Leu Leu
        195                 200                 205

Phe Val Leu Thr Pro Thr Phe Val Phe Cys Tyr Met Glu Asp Trp Ser
    210                 215                 220

Lys Leu Glu Ala Ile Tyr Phe Val Ile Val Thr Leu Thr Thr Val Gly
225                 230                 235                 240

Phe Gly Asp Tyr Val Ala Gly Ala Asp Pro Arg Gln Asp Ser Pro Ala
                245                 250                 255

Tyr Gln Pro Leu Val Trp Phe Trp Ile Leu Leu Gly Leu Ala Tyr Phe
                260                 265                 270

Ala Ser Val Leu Thr Thr Ile Gly Asn Trp Leu Arg Val Val Ser Arg
        275                 280                 285

Arg Thr Arg Ala Glu Met Gly Gly Leu Thr Ala Gln Ala Ala Ser Trp
    290                 295                 300

Thr Gly Thr Val Thr Ala Arg Val Thr Gln Arg Ala Gly Pro Ala Ala
305                 310                 315                 320

Pro Pro Pro Glu Lys Glu Gln Pro Leu Leu Pro Pro Pro Cys Pro
                325                 330                 335

Ala Gln Pro Leu Gly Arg Pro Arg Ser Pro Ser Pro Glu Lys Ala
                340                 345                 350

Gln Pro Pro Ser Pro Thr Ala Ser Ala Leu Asp Tyr Pro Ser Glu
            355                 360                 365

Asn Leu Ala Phe Ile Asp Glu Ser Ser Asp Thr Gln Ser Glu Arg Gly
370                 375                 380

Cys Pro Leu Pro Arg Ala Pro Arg Gly Arg Arg Pro Asn Pro Pro
385                 390                 395                 400

Arg Lys Pro Val Arg Pro Arg Gly Pro Gly Arg Pro Arg Asp Lys Gly
                405                 410                 415

Val Pro Val

<210> SEQ ID NO 13
<211> LENGTH: 3985
<212> TYPE: DNA
<213> ORGANISM: Homo Sapiens
<220> FEATURE:
<221> NAME/KEY: CDS
<222> LOCATION: (359)...(3610)

<400> SEQUENCE: 13
gcgtccgcgg acgcgtgggc cgagcgaagc ccgagcggaa gcccacccgc agccgacacg      60
cgagccgctg tcgcggaggg aggtgctgag agcgccgcgg ctgcggggcc tggagcccgg     120
gatttgtggg cggcgagggt gcgagggggtc gcgcgccatg ctccgggtcc cgacggcgcg     180 gacgcccccct cgcgcgcccg cggccggcgc gacccgagat cccggtctgg gcattgcccc    240
```

-continued

| | |
|---|---:|
| ccgacggctg cgctagggag cgcggggccc ggcgggggc ggccgagctg ggcgccctcc | 300 |
| cccggcgcg agtccccgca ccccggaggg atggggccgg cagccgcggg cgcctaag | 358 |

| | | | | | | | | | | | | | | | | |
|---|---|---|---|---|---|---|---|---|---|---|---|---|---|---|---|---:|
| atg | ccg | gcc | atg | cgg | ggc | ctc | ctg | gcg | ccg | cag | aac | acc | ttc | ctg | gac | 406 |
| Met | Pro | Ala | Met | Arg | Gly | Leu | Leu | Ala | Pro | Gln | Asn | Thr | Phe | Leu | Asp | |
| 1 | | | | 5 | | | | | 10 | | | | | 15 | | |

| | | | | | | | | | | | | | | | | |
|---|---|---|---|---|---|---|---|---|---|---|---|---|---|---|---|---:|
| acc | atc | gct | acg | cgc | ttc | gac | ggc | acg | cac | agt | aac | ttc | gtg | ctg | ggc | 454 |
| Thr | Ile | Ala | Thr | Arg | Phe | Asp | Gly | Thr | His | Ser | Asn | Phe | Val | Leu | Gly | |
| | | | 20 | | | | | 25 | | | | | 30 | | | |

| | | | | | | | | | | | | | | | | |
|---|---|---|---|---|---|---|---|---|---|---|---|---|---|---|---|---:|
| aac | gcc | cag | gtg | gcg | ggg | ctc | ttc | ccc | gtg | gtc | tac | tgc | tct | gat | ggc | 502 |
| Asn | Ala | Gln | Val | Ala | Gly | Leu | Phe | Pro | Val | Val | Tyr | Cys | Ser | Asp | Gly | |
| | | 35 | | | | | 40 | | | | | 45 | | | | |

| | | | | | | | | | | | | | | | | |
|---|---|---|---|---|---|---|---|---|---|---|---|---|---|---|---|---:|
| ttc | tgt | gac | ctc | acg | ggc | ttc | tcc | cgg | gct | gag | gtc | atg | cag | cgg | ggc | 550 |
| Phe | Cys | Asp | Leu | Thr | Gly | Phe | Ser | Arg | Ala | Glu | Val | Met | Gln | Arg | Gly | |
| | 50 | | | | | 55 | | | | | 60 | | | | | |

| | | | | | | | | | | | | | | | | |
|---|---|---|---|---|---|---|---|---|---|---|---|---|---|---|---|---:|
| tgt | gcc | tgc | tcc | ttc | ctt | tat | ggg | cca | gac | acc | agt | gag | ctc | gtc | cgc | 598 |
| Cys | Ala | Cys | Ser | Phe | Leu | Tyr | Gly | Pro | Asp | Thr | Ser | Glu | Leu | Val | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---:|
| caa | cag | atc | cgc | aag | gcc | ctg | gac | gag | cac | aag | gag | ttc | aag | gct | gag | 646 |
| Gln | Gln | Ile | Arg | Lys | Ala | Leu | Asp | Glu | His | Lys | Glu | Phe | Lys | Ala | Glu | |
| | | | | 85 | | | | | 90 | | | | | 95 | | |

| | | | | | | | | | | | | | | | | |
|---|---|---|---|---|---|---|---|---|---|---|---|---|---|---|---|---:|
| ctg | atc | ctg | tac | cgg | aag | agc | ggg | ctc | ccg | ttc | tgg | tgt | ctc | ctg | gat | 694 |
| Leu | Ile | Leu | Tyr | Arg | Lys | Ser | Gly | Leu | Pro | Phe | Trp | Cys | Leu | Leu | Asp | |
| | | | 100 | | | | | 105 | | | | | 110 | | | |

| | | | | | | | | | | | | | | | | |
|---|---|---|---|---|---|---|---|---|---|---|---|---|---|---|---|---:|
| gtg | ata | ccc | ata | aag | aat | gag | aaa | ggg | gag | gtg | gct | ctc | ttc | cta | gtc | 742 |
| Val | Ile | Pro | Ile | Lys | Asn | Glu | Lys | Gly | Glu | Val | Ala | Leu | Phe | Leu | Val | |
| | | 115 | | | | | 120 | | | | | 125 | | | | |

| | | | | | | | | | | | | | | | | |
|---|---|---|---|---|---|---|---|---|---|---|---|---|---|---|---|---:|
| tct | cac | aag | gac | atc | agc | gaa | acc | aag | aac | cga | ggg | ggc | ccy | gac | aga | 790 |
| Ser | His | Lys | Asp | Ile | Ser | Glu | Thr | Lys | Asn | Arg | Gly | Gly | Xaa | Asp | Arg | |
| | 130 | | | | | 135 | | | | | 140 | | | | | |

| | | | | | | | | | | | | | | | | |
|---|---|---|---|---|---|---|---|---|---|---|---|---|---|---|---|---:|
| tgg | aag | gag | aca | ggt | ggt | ggc | cgg | cgc | cga | tat | ggc | cgg | gca | cga | tcc | 838 |
| Trp | Lys | Glu | Thr | Gly | Gly | Gly | Arg | Arg | Arg | Tyr | Gly | Arg | Ala | Arg | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---:|
| aaa | ggc | ttc | aat | gcc | aac | cgg | cgg | cgg | agc | cgg | gcc | gtg | ctc | tac | cac | 886 |
| Lys | Gly | Phe | Asn | Ala | Asn | Arg | Arg | Arg | Ser | Arg | Ala | Val | Leu | Tyr | His | |
| | | | | 165 | | | | | 170 | | | | | 175 | | |

| | | | | | | | | | | | | | | | | |
|---|---|---|---|---|---|---|---|---|---|---|---|---|---|---|---|---:|
| ctg | tcc | ggg | cac | ctg | cag | aag | cag | ccc | aag | ggc | aag | cac | aag | ctc | aat | 934 |
| Leu | Ser | Gly | His | Leu | Gln | Lys | Gln | Pro | Lys | Gly | Lys | His | Lys | Leu | Asn | |
| | | | 180 | | | | | 185 | | | | | 190 | | | |

| | | | | | | | | | | | | | | | | |
|---|---|---|---|---|---|---|---|---|---|---|---|---|---|---|---|---:|
| aag | ggg | gtg | ttt | ggg | gag | aaa | cca | aac | ttg | cct | gag | tac | aaa | gta | gcc | 982 |
| Lys | Gly | Val | Phe | Gly | Glu | Lys | Pro | Asn | Leu | Pro | Glu | Tyr | Lys | Val | Ala | |
| | | 195 | | | | | 200 | | | | | 205 | | | | |

| | | | | | | | | | | | | | | | | |
|---|---|---|---|---|---|---|---|---|---|---|---|---|---|---|---|---:|
| gcc | atc | cgg | aag | tcg | ccc | ttc | atc | ctg | ttg | cac | tgt | ggg | gca | ctg | aga | 1030 |
| Ala | Ile | Arg | Lys | Ser | Pro | Phe | Ile | Leu | Leu | His | Cys | Gly | Ala | Leu | Arg | |
| 210 | | | | | 215 | | | | | 220 | | | | | | |

| | | | | | | | | | | | | | | | | |
|---|---|---|---|---|---|---|---|---|---|---|---|---|---|---|---|---:|
| gcc | acc | tgg | gat | ggc | ttc | atc | ctg | ctc | gcc | aca | ctc | tat | gtg | gct | gtc | 1078 |
| Ala | Thr | Trp | Asp | Gly | Phe | Ile | Leu | Leu | Ala | Thr | Leu | Tyr | Val | Ala | Val | |
| 225 | | | | 230 | | | | | 235 | | | | | 240 | | |

| | | | | | | | | | | | | | | | | |
|---|---|---|---|---|---|---|---|---|---|---|---|---|---|---|---|---:|
| act | gtg | ccc | tac | agc | gtg | tgt | gtg | agc | aca | gca | cgg | gag | ccc | agt | gcc | 1126 |
| Thr | Val | Pro | Tyr | Ser | Val | Cys | Val | Ser | Thr | Ala | Arg | Glu | Pro | Ser | Ala | |
| | | | | 245 | | | | | 250 | | | | | 255 | | |

| | | | | | | | | | | | | | | | | |
|---|---|---|---|---|---|---|---|---|---|---|---|---|---|---|---|---:|
| gcc | cgc | ggc | ccg | ccc | agc | gtc | tgt | gac | ctg | gcc | gtg | gag | gtc | ctc | ttc | 1174 |
| Ala | Arg | Gly | Pro | Pro | Ser | Val | Cys | Asp | Leu | Ala | Val | Glu | Val | Leu | Phe | |
| | | | 260 | | | | | 265 | | | | | 270 | | | |

| | | | | | | | | | | | | | | | | |
|---|---|---|---|---|---|---|---|---|---|---|---|---|---|---|---|---:|
| atc | ctt | gac | att | gtg | ctg | aat | ttc | cgt | acc | aca | ttc | gtg | tcc | aag | tcg | 1222 |
| Ile | Leu | Asp | Ile | Val | Leu | Asn | Phe | Arg | Thr | Thr | Phe | Val | Ser | Lys | Ser | |
| | | 275 | | | | | 280 | | | | | 285 | | | | |

| | | | | | | | | | | | | | | | | |
|---|---|---|---|---|---|---|---|---|---|---|---|---|---|---|---|---:|
| ggc | cag | gtg | gtg | ttt | gcc | cca | aag | tcc | att | tgc | ctc | cac | tac | gtc | acc | 1270 |
| Gly | Gln | Val | Val | Phe | Ala | Pro | Lys | Ser | Ile | Cys | Leu | His | Tyr | Val | Thr | |
| | 290 | | | | | 295 | | | | | 300 | | | | | |

```
acc tgg ttc ctg ctg gat gtc atc gca gcg ctg ccc ttt gac ctg ctg     1318
Thr Trp Phe Leu Leu Asp Val Ile Ala Ala Leu Pro Phe Asp Leu Leu
305                 310                 315                 320 cat gcc ttc aag gtc aac gtg tac ttc ggg gcc cac ctg ctg aag acg     1366
His Ala Phe Lys Val Asn Val Tyr Phe Gly Ala His Leu Leu Lys Thr
                325                 330                 335 gtg cgc ctg ctg cgc ctg ctg cgc ctg ctt ccg cgg ctg gac cgg tac     1414
Val Arg Leu Leu Arg Leu Leu Arg Leu Leu Pro Arg Leu Asp Arg Tyr
            340                 345                 350 tcg cag tac agc gcc gtg gtg ctg aca ctg ctc atg gcc gtg ttt gcc     1462
Ser Gln Tyr Ser Ala Val Val Leu Thr Leu Leu Met Ala Val Phe Ala
        355                 360                 365 ctg ctt gcg cac tgg gtt gcc tgc gtc tgg ttt tac att ggt cag cgg     1510
Leu Leu Ala His Trp Val Ala Cys Val Trp Phe Tyr Ile Gly Gln Arg
370                 375                 380 gag atc gag agc agc gaa tcc gag ctg cct gag att ggc tgg ctg cag     1558
Glu Ile Glu Ser Ser Glu Ser Glu Leu Pro Glu Ile Gly Trp Leu Gln
385                 390                 395                 400 gag ctg gcc cgc cga ctg gag acc ccc tac tac ttg gtg ggc cgg aga     1606
Glu Leu Ala Arg Arg Leu Glu Thr Pro Tyr Tyr Leu Val Gly Arg Arg
                405                 410                 415 cca gcc gga ggg aac agc tct ggc cag agt gac aac tgc agc agc agc     1654
Pro Ala Gly Gly Asn Ser Ser Gly Gln Ser Asp Asn Cys Ser Ser Ser
            420                 425                 430 agc gag gcc aac ggg acg ggg ctg gag ctg cta ggc ggc ccg tcg ctg     1702
Ser Glu Ala Asn Gly Thr Gly Leu Glu Leu Leu Gly Gly Pro Ser Leu
        435                 440                 445 cgc agc gcc tac atc acc tcc ctc tac ttc gca ctc agc agc ctc acc     1750
Arg Ser Ala Tyr Ile Thr Ser Leu Tyr Phe Ala Leu Ser Ser Leu Thr
450                 455                 460 agc gtg ggc ttc ggc aac gtg tcc gcc aac acg gac act gag aag atc     1798
Ser Val Gly Phe Gly Asn Val Ser Ala Asn Thr Asp Thr Glu Lys Ile
465                 470                 475                 480 ttc tcc atc tgc acc atg ctc atc ggc gcc ctg atg cac gcg gtg gtg     1846
Phe Ser Ile Cys Thr Met Leu Ile Gly Ala Leu Met His Ala Val Val
                485                 490                 495 ttc ggg aac gtg acg gcc atc atc cag cgc atg tac gcc cgc cgc ttt     1894
Phe Gly Asn Val Thr Ala Ile Ile Gln Arg Met Tyr Ala Arg Arg Phe
            500                 505                 510 ttg tac cac agc cgc acg cgc gac ctg cgc gac tac atc cgc atc cac     1942
Leu Tyr His Ser Arg Thr Arg Asp Leu Arg Asp Tyr Ile Arg Ile His
        515                 520                 525 cgt atc ccc aag ccc ctc aag cag cgc atg ctg gag tac ttc cag gcc     1990
Arg Ile Pro Lys Pro Leu Lys Gln Arg Met Leu Glu Tyr Phe Gln Ala
530                 535                 540 acc tgg gcg gtg aac aat ggc atc gac acc acc gag ctg ctg cag agc     2038
Thr Trp Ala Val Asn Asn Gly Ile Asp Thr Thr Glu Leu Leu Gln Ser
545                 550                 555                 560 ctc cct gac gag ctg cgc gca gac atc gcc atg cac ctg cac aag gag     2086
Leu Pro Asp Glu Leu Arg Ala Asp Ile Ala Met His Leu His Lys Glu
                565                 570                 575 gtc ctg cag ctg ccg ctg ttt gag gca gcc agc cgc ggc tgc ctg cgg     2134
Val Leu Gln Leu Pro Leu Phe Glu Ala Ala Ser Arg Gly Cys Leu Arg
            580                 585                 590 gca ctg tct ctg gcc ctg cgg ccc gcc ttc tgc acg ccg ggc gag tac     2182
Ala Leu Ser Leu Ala Leu Arg Pro Ala Phe Cys Thr Pro Gly Glu Tyr
        595                 600                 605 ctc atc cac caa ggc gat gcc ctg cag gcc ctc tac ttt gtc tgc tct     2230
Leu Ile His Gln Gly Asp Ala Leu Gln Ala Leu Tyr Phe Val Cys Ser
610                 615                 620
```

-continued

| | |
|---|---|
| ggc tcc atg gag gtg ctc aag ggt ggc acc gtg ctc gcc atc cta ggg<br>Gly Ser Met Glu Val Leu Lys Gly Gly Thr Val Leu Ala Ile Leu Gly<br>625                            630                          635                          640 | 2278 |
| aag ggt gac ctg atc ggc tgt gag ctg ccc cgg agg gag cag gtg gta<br>Lys Gly Asp Leu Ile Gly Cys Glu Leu Pro Arg Arg Glu Gln Val Val<br>                        645                          650                          655 | 2326 |
| aag gcc aac gcc gat gtg aag ggg ctg acg tac tgc gtc ctg cag tgt<br>Lys Ala Asn Ala Asp Val Lys Gly Leu Thr Tyr Cys Val Leu Gln Cys<br>                   660                          665                          670 | 2374 |
| ctg cag ctg gct ggc ctg cac gac agc ctt gcg ctc tac ccc gag ttt<br>Leu Gln Leu Ala Gly Leu His Asp Ser Leu Ala Leu Tyr Pro Glu Phe<br>675                            680                          685 | 2422 |
| gcc ccg cgc ttc agc cgt ggc ctc cga ggg gag ctc agc tac aac ctg<br>Ala Pro Arg Phe Ser Arg Gly Leu Arg Gly Glu Leu Ser Tyr Asn Leu<br>                   690                          695                          700 | 2470 |
| ggt gct ggg gga ggc tct gca gag gtg gac acc agc tcc ctg agc ggc<br>Gly Ala Gly Gly Gly Ser Ala Glu Val Asp Thr Ser Ser Leu Ser Gly<br>705                            710                          715                          720 | 2518 |
| gac aat acc ctt atg tcc acg ctg gag gag aag gag aca gat ggg gag<br>Asp Asn Thr Leu Met Ser Thr Leu Glu Glu Lys Glu Thr Asp Gly Glu<br>                        725                          730                          735 | 2566 |
| cag ggc ccc aca gtc tcc cca gcc cca gct gat gag ccc tcc agc ccc<br>Gln Gly Pro Thr Val Ser Pro Ala Pro Ala Asp Glu Pro Ser Ser Pro<br>                   740                          745                          750 | 2614 |
| cta ctg tcc cct ggt tgc acc tcc tca tcc tcg gct gcc aag ctg cta<br>Leu Leu Ser Pro Gly Cys Thr Ser Ser Ser Ser Ala Ala Lys Leu Leu<br>                755                          760                          765 | 2662 |
| tcc cca cgt cga aca gca ccc cgg cct cgt cta ggt ggc aga ggg aga<br>Ser Pro Arg Arg Thr Ala Pro Arg Pro Arg Leu Gly Gly Arg Gly Arg<br>770                            775                          780 | 2710 |
| cca ggc agg gca ggg gct ttg aag gct gag gct ggc ccc tct gct ccc<br>Pro Gly Arg Ala Gly Ala Leu Lys Ala Glu Ala Gly Pro Ser Ala Pro<br>785                            790                          795                          800 | 2758 |
| cca cgg gcc cta gag ggg cta cgg ctg ccc ccc atg cca tgg aat gtg<br>Pro Arg Ala Leu Glu Gly Leu Arg Leu Pro Pro Met Pro Trp Asn Val<br>                   805                          810                          815 | 2806 |
| ccc cca gat ctg agc ccc agg gta gta gat ggc att gaa gac ggc tgt<br>Pro Pro Asp Leu Ser Pro Arg Val Val Asp Gly Ile Glu Asp Gly Cys<br>                   820                          825                          830 | 2854 |
| ggc tcg gac cag ccc aag ttc tct ttc cgc atg ggc cag tct ggc ccg<br>Gly Ser Asp Gln Pro Lys Phe Ser Phe Arg Met Gly Gln Ser Gly Pro<br>                   835                          840                          845 | 2902 |
| gaa tgt agc agc agc ccc tcc cct gga cca gag agt ggc ctg ctc act<br>Glu Cys Ser Ser Ser Pro Ser Pro Gly Pro Glu Ser Gly Leu Leu Thr<br>850                            855                          860 | 2950 |
| gtc ccc cat ggg ccc agc gag gca agg aac aca gac aca ctg gac aag<br>Val Pro His Gly Pro Ser Glu Ala Arg Asn Thr Asp Thr Leu Asp Lys<br>865                            870                          875                          880 | 2998 |
| ctt cgg cag gcg gtg atg gag ctg tca gaa cag gtg ctg cag atg cgg<br>Leu Arg Gln Ala Val Met Glu Leu Ser Glu Gln Val Leu Gln Met Arg<br>                   885                          890                          895 | 3046 |
| gaa gga cta cag tca ctt cgc cag gtt gtg cag ctt gtc ctg gca ccc<br>Glu Gly Leu Gln Ser Leu Arg Gln Val Val Gln Leu Val Leu Ala Pro<br>                   900                          905                          910 | 3094 |
| cat agg gag ggt cca tgc cct cgg gcc tca gga gag ggg cca tgc cca<br>His Arg Glu Gly Pro Cys Pro Arg Ala Ser Gly Glu Gly Pro Cys Pro<br>                 915                          920                          925 | 3142 |
| gcc agc acc tcc ggg ctt ctg cag cct ctg tgt gtg gac act ggg gca<br>Ala Ser Thr Ser Gly Leu Leu Gln Pro Leu Cys Val Asp Thr Gly Ala<br>930                            935                          940 | 3190 |

-continued

| | |
|---|---|
| tcc tcc tac tgc ctg cag ccc cca gct ggc tct gtc ttg agt ggg act<br>Ser Ser Tyr Cys Leu Gln Pro Pro Ala Gly Ser Val Leu Ser Gly Thr<br>945                 950                     955                 960 | 3238 |
| tgg ccc cac cct cgt ccg ggg cct cct ccc ctc atg gca ccc tgg ccc<br>Trp Pro His Pro Arg Pro Gly Pro Pro Leu Met Ala Pro Trp Pro<br>                965                   970                   975 | 3286 |
| tgg ggt ccc cca gca tct cag agc tcc ccc tgg cct cga gcc aca gct<br>Trp Gly Pro Pro Ala Ser Gln Ser Ser Pro Trp Pro Arg Ala Thr Ala<br>           980                   985                   990 | 3334 |
| ttc tgg acc tcc acc tca gac tca gag ccc cct gcc tca gga gac ctc<br>Phe Trp Thr Ser Thr Ser Asp Ser Glu Pro Pro Ala Ser Gly Asp Leu<br>       995                   1000                 1005 | 3382 |
| tgc tct gag ccc agc acc cct gcc tca cct cct cct tct gag gaa ggg<br>Cys Ser Glu Pro Ser Thr Pro Ala Ser Pro Pro Pro Ser Glu Glu Gly<br>1010                1015                   1020 | 3430 |
| gct agg act ggg ccc cca gag cct gtg agc cag gct gag gct acc agc<br>Ala Arg Thr Gly Pro Pro Glu Pro Val Ser Gln Ala Glu Ala Thr Ser<br>1025                1030                   1035                 1040 | 3478 |
| act gga gag ccc ccg cca gtg tca ggg ggc ctg gcc ttg ccc tgg gac<br>Thr Gly Glu Pro Pro Pro Val Ser Gly Gly Leu Ala Leu Pro Trp Asp<br>                      1045                 1050                 1055 | 3526 |
| ccc cac agc ctg gag atg gtg ctt att ggc tgc cac ggc tct ggc aca<br>Pro His Ser Leu Glu Met Val Leu Ile Gly Cys His Gly Ser Gly Thr<br>                1060                   1065                 1070 | 3574 |
| gtc cag tgg acc cag gaa gaa ggc aca ggg gtc tga gtaccagccc<br>Val Gln Trp Thr Gln Glu Glu Gly Thr Gly Val *<br>1075                1080 | 3620 |
| tagaactcag tgttgccagg cgtgctgcca tctgctgttc agcccaacct cagagtgaag | 3680 |
| acagggtggc ggccacccca tggactccat gtggcccgct ggctcagggc agggagcctg | 3740 |
| gaagcaaagg agggcctggc tcctgactct cagagagggt gggctggagc cctggggcag | 3800 |
| gcccctcctc agcctgctcc tccgacctcc cggtctccct ctgcaggctg ggggcagaga | 3860 |
| cctgaggaca aggaagggct tgccatccc ctgcatgtgc ccctgcctct acctgtccca | 3920 |
| aatttttata ttaaaaaaaa taataataaa agaaactact ttggaaaaaa aaaaaaaaa | 3980 |
| aaaaa | 3985 |

<210> SEQ ID NO 14
<211> LENGTH: 1083
<212> TYPE: PRT
<213> ORGANISM: Homo Sapiens
<220> FEATURE:
<221> NAME/KEY: VARIANT
<222> LOCATION: (1)...(1083)
<223> OTHER INFORMATION: Xaa = Any Amino Acid
<400> SEQUENCE: 14

Met Pro Ala Met Arg Gly Leu Leu Ala Pro Gln Asn Thr Phe Leu Asp
 1               5                  10                  15

Thr Ile Ala Thr Arg Phe Asp Gly Thr His Ser Asn Phe Val Leu Gly
                20                  25                  30

Asn Ala Gln Val Ala Gly Leu Phe Pro Val Val Tyr Cys Ser Asp Gly
            35                  40                  45

Phe Cys Asp Leu Thr Gly Phe Ser Arg Ala Glu Val Met Gln Arg Gly
        50                  55                  60

Cys Ala Cys Ser Phe Leu Tyr Gly Pro Asp Thr Ser Glu Leu Val Arg
65                  70                  75                  80

Gln Gln Ile Arg Lys Ala Leu Asp Glu His Lys Glu Phe Lys Ala Glu
                85                  90                  95

-continued

```
Leu Ile Leu Tyr Arg Lys Ser Gly Leu Pro Phe Trp Cys Leu Leu Asp
            100                 105                 110

Val Ile Pro Ile Lys Asn Glu Lys Gly Glu Val Ala Leu Phe Leu Val
            115                 120                 125

Ser His Lys Asp Ile Ser Glu Thr Lys Asn Arg Gly Gly Xaa Asp Arg
        130                 135                 140

Trp Lys Glu Thr Gly Gly Arg Arg Tyr Gly Arg Ala Arg Ser
145                 150                 155                 160

Lys Gly Phe Asn Ala Asn Arg Arg Ser Arg Ala Val Leu Tyr His
                165                 170                 175

Leu Ser Gly His Leu Gln Lys Gln Pro Lys Gly Lys His Lys Leu Asn
            180                 185                 190

Lys Gly Val Phe Gly Glu Lys Pro Asn Leu Pro Glu Tyr Lys Val Ala
            195                 200                 205

Ala Ile Arg Lys Ser Pro Phe Ile Leu Leu His Cys Gly Ala Leu Arg
210                 215                 220

Ala Thr Trp Asp Gly Phe Ile Leu Ala Thr Leu Tyr Val Ala Val
225                 230                 235                 240

Thr Val Pro Tyr Ser Val Cys Val Ser Thr Ala Arg Glu Pro Ser Ala
                245                 250                 255

Ala Arg Gly Pro Pro Ser Val Cys Asp Leu Ala Val Glu Val Leu Phe
            260                 265                 270

Ile Leu Asp Ile Val Leu Asn Phe Arg Thr Thr Phe Val Ser Lys Ser
            275                 280                 285

Gly Gln Val Val Phe Ala Pro Lys Ser Ile Cys Leu His Tyr Val Thr
            290                 295                 300

Thr Trp Phe Leu Leu Asp Val Ile Ala Ala Leu Pro Phe Asp Leu Leu
305                 310                 315                 320

His Ala Phe Lys Val Asn Val Tyr Phe Gly Ala His Leu Leu Lys Thr
                325                 330                 335

Val Arg Leu Leu Arg Leu Leu Arg Leu Leu Pro Arg Leu Asp Arg Tyr
            340                 345                 350

Ser Gln Tyr Ser Ala Val Val Leu Thr Leu Leu Met Ala Val Phe Ala
            355                 360                 365

Leu Leu Ala His Trp Val Ala Cys Val Trp Phe Tyr Ile Gly Gln Arg
            370                 375                 380

Glu Ile Glu Ser Ser Glu Ser Glu Leu Pro Glu Ile Gly Trp Leu Gln
385                 390                 395                 400

Glu Leu Ala Arg Arg Leu Glu Thr Pro Tyr Tyr Leu Val Gly Arg Arg
                405                 410                 415

Pro Ala Gly Gly Asn Ser Ser Gly Gln Ser Asp Asn Cys Ser Ser Ser
            420                 425                 430

Ser Glu Ala Asn Gly Thr Gly Leu Glu Leu Leu Gly Gly Pro Ser Leu
            435                 440                 445

Arg Ser Ala Tyr Ile Thr Ser Leu Tyr Phe Ala Leu Ser Ser Leu Thr
        450                 455                 460

Ser Val Gly Phe Gly Asn Val Ser Ala Asn Thr Asp Thr Glu Lys Ile
465                 470                 475                 480

Phe Ser Ile Cys Thr Met Leu Ile Gly Ala Leu Met His Ala Val Val
                485                 490                 495

Phe Gly Asn Val Thr Ala Ile Ile Gln Arg Met Tyr Ala Arg Arg Phe
            500                 505                 510
```

-continued

```
Leu Tyr His Ser Arg Thr Arg Asp Leu Arg Asp Tyr Ile Arg Ile His
            515                 520                 525

Arg Ile Pro Lys Pro Leu Lys Gln Arg Met Leu Glu Tyr Phe Gln Ala
        530                 535                 540

Thr Trp Ala Val Asn Asn Gly Ile Asp Thr Thr Glu Leu Leu Gln Ser
545                 550                 555                 560

Leu Pro Asp Glu Leu Arg Ala Asp Ile Ala Met His Leu His Lys Glu
                565                 570                 575

Val Leu Gln Leu Pro Leu Phe Glu Ala Ala Ser Arg Gly Cys Leu Arg
            580                 585                 590

Ala Leu Ser Leu Ala Leu Arg Pro Ala Phe Cys Thr Pro Gly Glu Tyr
        595                 600                 605

Leu Ile His Gln Gly Asp Ala Leu Gln Ala Leu Tyr Phe Val Cys Ser
    610                 615                 620

Gly Ser Met Glu Val Leu Lys Gly Gly Thr Val Leu Ala Ile Leu Gly
625                 630                 635                 640

Lys Gly Asp Leu Ile Gly Cys Glu Leu Pro Arg Arg Glu Gln Val Val
                645                 650                 655

Lys Ala Asn Ala Asp Val Lys Gly Leu Thr Tyr Cys Val Leu Gln Cys
            660                 665                 670

Leu Gln Leu Ala Gly Leu His Asp Ser Leu Ala Leu Tyr Pro Glu Phe
        675                 680                 685

Ala Pro Arg Phe Ser Arg Gly Leu Arg Gly Glu Leu Ser Tyr Asn Leu
    690                 695                 700

Gly Ala Gly Gly Gly Ser Ala Glu Val Asp Thr Ser Ser Leu Ser Gly
705                 710                 715                 720

Asp Asn Thr Leu Met Ser Thr Leu Glu Glu Lys Glu Thr Asp Gly Glu
                725                 730                 735

Gln Gly Pro Thr Val Ser Pro Ala Pro Ala Asp Glu Pro Ser Ser Pro
            740                 745                 750

Leu Leu Ser Pro Gly Cys Thr Ser Ser Ser Ala Ala Lys Leu Leu
        755                 760                 765

Ser Pro Arg Arg Thr Ala Pro Arg Pro Leu Gly Gly Arg Gly Arg
    770                 775                 780

Pro Gly Arg Ala Gly Ala Leu Lys Ala Glu Ala Gly Pro Ser Ala Pro
785                 790                 795                 800

Pro Arg Ala Leu Glu Gly Leu Arg Leu Pro Pro Met Pro Trp Asn Val
                805                 810                 815

Pro Pro Asp Leu Ser Pro Arg Val Val Asp Gly Ile Glu Asp Gly Cys
            820                 825                 830

Gly Ser Asp Gln Pro Lys Phe Ser Phe Arg Met Gly Gln Ser Gly Pro
        835                 840                 845

Glu Cys Ser Ser Ser Pro Ser Pro Gly Pro Glu Ser Gly Leu Leu Thr
    850                 855                 860

Val Pro His Gly Pro Ser Glu Ala Arg Asn Thr Asp Thr Leu Asp Lys
865                 870                 875                 880

Leu Arg Gln Ala Val Met Glu Leu Ser Glu Gln Val Leu Gln Met Arg
                885                 890                 895

Glu Gly Leu Gln Ser Leu Arg Gln Val Val Gln Leu Val Leu Ala Pro
            900                 905                 910

His Arg Glu Gly Pro Cys Pro Arg Ala Ser Gly Glu Gly Pro Cys Pro
        915                 920                 925
```

```
Ala Ser Thr Ser Gly Leu Leu Gln Pro Leu Cys Val Asp Thr Gly Ala
    930                 935                 940

Ser Ser Tyr Cys Leu Gln Pro Pro Ala Gly Ser Val Leu Ser Gly Thr
945                 950                 955                 960

Trp Pro His Pro Arg Pro Gly Pro Pro Leu Met Ala Pro Trp Pro
                965                 970                 975

Trp Gly Pro Pro Ala Ser Gln Ser Ser Pro Trp Pro Arg Ala Thr Ala
                980                 985                 990

Phe Trp Thr Ser Thr Ser Asp Ser Glu Pro Pro Ala Ser Gly Asp Leu
            995                1000                1005

Cys Ser Glu Pro Ser Thr Pro Ala Ser Pro Pro Ser Glu Glu Gly
    1010                1015                1020

Ala Arg Thr Gly Pro Pro Glu Pro Val Ser Gln Ala Glu Ala Thr Ser
1025                1030                1035                1040

Thr Gly Glu Pro Pro Pro Val Ser Gly Gly Leu Ala Leu Pro Trp Asp
                1045                1050                1055

Pro His Ser Leu Glu Met Val Leu Ile Gly Cys His Gly Ser Gly Thr
                1060                1065                1070

Val Gln Trp Thr Gln Glu Glu Gly Thr Gly Val
            1075                1080

<210> SEQ ID NO 15
<211> LENGTH: 1764
<212> TYPE: DNA
<213> ORGANISM: Homo Sapiens
<220> FEATURE:
<221> NAME/KEY: CDS
<222> LOCATION: (268)...(1266)

<400> SEQUENCE: 15
cacgcgtccg ggcctagcag gtgggcaccc ccgcacacat ttgaggcggg gccagatgcc      60
cacagttcag agcctctttt tgtccctggg attggatccc agggctgggt ggggccaggc     120
tgtcccattc cccaacactc ctcctccccg gcgaaaccgg gcaccagcag gcgtttgcga     180
gaggagatac gagctggacg cctggccctt ccctcccacc gggtcctagt ccaccgctcc     240
cggcgccggc tccccgcctc tcccgct atg tac cga ccg cga gcc cgg gcg gct    294
                              Met Tyr Arg Pro Arg Ala Arg Ala Ala
                                1               5 ccc gag ggc agg gtc cgg ggc tgc gcg gtg ccc ggc acc gtg ctc ctg       342
Pro Glu Gly Arg Val Arg Gly Cys Ala Val Pro Gly Thr Val Leu Leu
 10                  15                  20                  25 ctg ctc gcc tac ctg gct tac ctg gcg ctg ggc acc ggc gtg ttc tgg       390
Leu Leu Ala Tyr Leu Ala Tyr Leu Ala Leu Gly Thr Gly Val Phe Trp
                 30                  35                  40 acg ctg gag ggc cgc gcg gcg cag gac tcc agc cgc agc ttc cag cgc       438
Thr Leu Glu Gly Arg Ala Ala Gln Asp Ser Ser Arg Ser Phe Gln Arg
             45                  50                  55 gac aag tgg gag ctg ttg cag aac ttc acg tgt ctg gac cgc ccg gcg       486
Asp Lys Trp Glu Leu Leu Gln Asn Phe Thr Cys Leu Asp Arg Pro Ala
         60                  65                  70 ctg gac tcg ctg atc cgg gat gtc gtc caa gca tac aaa aac gga gcc       534
Leu Asp Ser Leu Ile Arg Asp Val Val Gln Ala Tyr Lys Asn Gly Ala
     75                  80                  85 agc ctc ctc agc aac acc acc agc atg ggg cgc tgg gag ctc gtg ggc       582
Ser Leu Leu Ser Asn Thr Thr Ser Met Gly Arg Trp Glu Leu Val Gly
 90                  95                 100                 105
```

| | |
|---|---|
| tcc ttc ttc ttt tct gtg tcc acc atc acc acc att ggc tat ggc aac<br>Ser Phe Phe Phe Ser Val Ser Thr Ile Thr Thr Ile Gly Tyr Gly Asn<br>110                 115              120 | 630 |
| ctg agc ccc aac acg atg gct gcc cgc ctc ttc tgc atc ttc ttt gcc<br>Leu Ser Pro Asn Thr Met Ala Ala Arg Leu Phe Cys Ile Phe Phe Ala<br>      125                130               135 | 678 |
| ctt gtg ggg atc cca ctc aac ctc gtg gtg ctc aac cga ctg ggg cat<br>Leu Val Gly Ile Pro Leu Asn Leu Val Val Leu Asn Arg Leu Gly His<br>140                 145              150 | 726 |
| ctc atg cag cag gga gta aac cac tgg gcc agc agg ctg ggg ggc acc<br>Leu Met Gln Gln Gly Val Asn His Trp Ala Ser Arg Leu Gly Gly Thr<br>    155                160              165 | 774 |
| tgg cag gat cct gac aag gcg cgg tgg ctg gcg ggc tct ggc gcc ctc<br>Trp Gln Asp Pro Asp Lys Ala Arg Trp Leu Ala Gly Ser Gly Ala Leu<br>170                175              180          185 | 822 |
| ctc tcg ggc ctc ctg ctc ttc ctg ctg ctg cca ccg ctg ctc ttc tcc<br>Leu Ser Gly Leu Leu Leu Phe Leu Leu Leu Pro Pro Leu Leu Phe Ser<br>          190                195              200 | 870 |
| cac atg gag ggc tgg agc tac aca gag ggc ttc tac ttc gcc ttc atc<br>His Met Glu Gly Trp Ser Tyr Thr Glu Gly Phe Tyr Phe Ala Phe Ile<br>    205                210              215 | 918 |
| acc ctc agc acc gtg ggc ttc ggc gac tac gtg att gga atg aac ccc<br>Thr Leu Ser Thr Val Gly Phe Gly Asp Tyr Val Ile Gly Met Asn Pro<br>220                225              230 | 966 |
| tcc cag agg tac cca ctg tgg tac aag aac atg gtg tcc ctg tgg atc<br>Ser Gln Arg Tyr Pro Leu Trp Tyr Lys Asn Met Val Ser Leu Trp Ile<br>      235              240              245 | 1014 |
| ctc ttt ggg atg gca tgg ctg gcc ttg atc atc aaa ctc atc ctc tcc<br>Leu Phe Gly Met Ala Trp Leu Ala Leu Ile Ile Lys Leu Ile Leu Ser<br>250                255              260          265 | 1062 |
| cag ctg gag acg cca ggg agg gta tgt tcc tgc tgc cac cac agc tct<br>Gln Leu Glu Thr Pro Gly Arg Val Cys Ser Cys Cys His His Ser Ser<br>          270                275              280 | 1110 |
| aag gaa gac ttc aag tcc caa agc tgg aga cag gga cct gac cgg gag<br>Lys Glu Asp Phe Lys Ser Gln Ser Trp Arg Gln Gly Pro Asp Arg Glu<br>    285                290              295 | 1158 |
| cca gag tcc cac tcc cca cag caa gga tgc tat cca gag gga ccc atg<br>Pro Glu Ser His Ser Pro Gln Gln Gly Cys Tyr Pro Glu Gly Pro Met<br>300                305              310 | 1206 |
| gga atc ata cag cat ctg gaa cct tct gct cac gct gca ggc tgt ggc<br>Gly Ile Ile Gln His Leu Glu Pro Ser Ala His Ala Ala Gly Cys Gly<br>      315                320              325 | 1254 |
| aag gac agc tag ttatactcca ttctttggtc gtcgtcctcg gtagcaagac<br>Lys Asp Ser   *<br>330 | 1306 |
| ccctgatttt aagctttgca catgtccacc caaactaaag actacatttt ccatccaccc | 1366 |
| tagaggctgg gtgcagctat atgattaatt ctgcccaata gggtatacag agacatgtcc | 1426 |
| tgggtgacat gggatgtgac tttcgggtgt cggggcagca tgcccttctc ccccacttcc | 1486 |
| ttactttagc gggctgcaat gccgccgata tgatggctgg gagctctggc agccatacgg | 1546 |
| caccatgaag tagcggcaat gtttgagcgg cacaataaga taggaagagt ctggatctct | 1606 |
| gatgatcaca gagccatcct aacaaacgga atatcacccg acctccttta tgtgagagag | 1666 |
| aaataaacat cttatgtaaa atccccaaaa aaaaaaaaaa aaaaaaaaaa aaaaaaaaaa | 1726 |
| aaaaaaaaaa aaaaaaaaaa aaaaaaaaaa aaaaaaaa | 1764 |

```
<210> SEQ ID NO 16
<211> LENGTH: 332
<212> TYPE: PRT
<213> ORGANISM: Homo Sapiens

<400> SEQUENCE: 16

Met Tyr Arg Pro Arg Ala Arg Ala Ala Pro Glu Gly Arg Val Arg Gly
 1               5                  10                  15

Cys Ala Val Pro Gly Thr Val Leu Leu Leu Ala Tyr Leu Ala Tyr
            20                  25                  30

Leu Ala Leu Gly Thr Gly Val Phe Trp Thr Leu Glu Gly Arg Ala Ala
            35                  40                  45

Gln Asp Ser Ser Arg Ser Phe Gln Arg Asp Lys Trp Glu Leu Leu Gln
 50                      55                  60

Asn Phe Thr Cys Leu Asp Arg Pro Ala Leu Asp Ser Leu Ile Arg Asp
 65                  70                  75                  80

Val Val Gln Ala Tyr Lys Asn Gly Ala Ser Leu Leu Ser Asn Thr Thr
                 85                  90                  95

Ser Met Gly Arg Trp Glu Leu Val Gly Ser Phe Phe Phe Ser Val Ser
                100                 105                 110

Thr Ile Thr Thr Ile Gly Tyr Gly Asn Leu Ser Pro Asn Thr Met Ala
            115                 120                 125

Ala Arg Leu Phe Cys Ile Phe Phe Ala Leu Val Gly Ile Pro Leu Asn
130                 135                 140

Leu Val Val Leu Asn Arg Leu Gly His Leu Met Gln Gln Gly Val Asn
145                 150                 155                 160

His Trp Ala Ser Arg Leu Gly Gly Thr Trp Gln Asp Pro Asp Lys Ala
                165                 170                 175

Arg Trp Leu Ala Gly Ser Gly Ala Leu Leu Ser Gly Leu Leu Leu Phe
            180                 185                 190

Leu Leu Leu Pro Pro Leu Leu Phe Ser His Met Glu Gly Trp Ser Tyr
            195                 200                 205

Thr Glu Gly Phe Tyr Phe Ala Phe Ile Thr Leu Ser Thr Val Gly Phe
210                 215                 220

Gly Asp Tyr Val Ile Gly Met Asn Pro Ser Gln Arg Tyr Pro Leu Trp
225                 230                 235                 240

Tyr Lys Asn Met Val Ser Leu Trp Ile Leu Phe Gly Met Ala Trp Leu
                245                 250                 255

Ala Leu Ile Ile Lys Leu Ile Leu Ser Gln Leu Glu Thr Pro Gly Arg
            260                 265                 270

Val Cys Ser Cys Cys His His Ser Lys Glu Asp Phe Lys Ser Gln
            275                 280                 285

Ser Trp Arg Gln Gly Pro Asp Arg Glu Pro Glu Ser His Ser Pro Gln
290                 295                 300

Gln Gly Cys Tyr Pro Glu Gly Pro Met Gly Ile Ile Gln His Leu Glu
305                 310                 315                 320

Pro Ser Ala His Ala Ala Gly Cys Gly Lys Asp Ser
                325                 330

<210> SEQ ID NO 17
<211> LENGTH: 3227
<212> TYPE: DNA
<213> ORGANISM: Homo Sapiens
<220> FEATURE:
<221> NAME/KEY: CDS
<222> LOCATION: (345)...(2483)
```

-continued

```
<400> SEQUENCE: 17 cccttctcg ggaagcgcgc cattgtgttg gtacccggga attcgcggcc gcgtcgaccc      60
ccctgcggag ttgtgttttc tgggaatcag caacaaaytg caaagaaatg gctcaaaagc    120
ttcagctctt tctgtgccct gggagctgag atgcacgtca gtggccttgc cagcgtggcc    180
aattctctgc tgactgccag aaaaagagg ccaggaagaa agaggaaaga gaagagatcg     240
ctcagggtct gtggtgtgtg gtccatcctc ttgctgagca cattgaaagg aactggctat    300
ctttgatctc ttcctccaga tcagagtcaa ggaatgtgtt tata atg gac act tca     356
                                              Met Asp Thr Ser
                                                1
```

| | | | | | | | | | | | | | | | | |
|---|---|---|---|---|---|---|---|---|---|---|---|---|---|---|---|---|
| tcc | aaa | gaa | aat | atc | cag | ttg | ttc | tgc | aaa | act | tca | gtg | caa | cct | gtt | 404 |
| Ser | Lys | Glu | Asn | Ile | Gln | Leu | Phe | Cys | Lys | Thr | Ser | Val | Gln | Pro | Val | |
| 5 | | | | 10 | | | | | 15 | | | | | 20 | | |
| gga | agg | cct | tct | ttt | aaa | aca | gaa | tat | ccc | tcc | tca | gaa | gaa | aag | caa | 452 |
| Gly | Arg | Pro | Ser | Phe | Lys | Thr | Glu | Tyr | Pro | Ser | Ser | Glu | Glu | Lys | Gln | |
| | | | 25 | | | | | 30 | | | | | 35 | | | |
| cca | tgc | tgt | ggt | gaa | cta | aag | gtg | ttc | ttg | tgt | gcc | ttg | tct | ttt | gtt | 500 |
| Pro | Cys | Cys | Gly | Glu | Leu | Lys | Val | Phe | Leu | Cys | Ala | Leu | Ser | Phe | Val | |
| | | 40 | | | | | 45 | | | | | 50 | | | | |
| tac | ttt | gcc | aaa | gca | ttg | gca | gaa | ggc | tat | ctg | aag | agc | acc | atc | act | 548 |
| Tyr | Phe | Ala | Lys | Ala | Leu | Ala | Glu | Gly | Tyr | Leu | Lys | Ser | Thr | Ile | Thr | |
| | 55 | | | | | 60 | | | | | 65 | | | | | |
| cag | ata | gag | aga | agg | ttt | gat | atc | cct | tct | tca | ctg | gtg | gga | gtt | att | 596 |
| Gln | Ile | Glu | Arg | Arg | Phe | Asp | Ile | Pro | Ser | Ser | Leu | Val | Gly | Val | Ile | |
| 70 | | | | | 75 | | | | | 80 | | | | | | |
| gat | ggt | agt | ttt | gaa | att | ggg | aat | ctc | tta | gtt | ata | aca | ttt | gtt | agc | 644 |
| Asp | Gly | Ser | Phe | Glu | Ile | Gly | Asn | Leu | Leu | Val | Ile | Thr | Phe | Val | Ser | |
| 85 | | | | | 90 | | | | | 95 | | | | | 100 | |
| tac | ttt | gga | gcc | aaa | ctt | cac | agg | cca | aaa | ata | att | gga | gca | ggg | tgt | 692 |
| Tyr | Phe | Gly | Ala | Lys | Leu | His | Arg | Pro | Lys | Ile | Ile | Gly | Ala | Gly | Cys | |
| | | | | 105 | | | | | 110 | | | | | 115 | | |
| gta | atc | atg | gga | gtt | gga | aca | ctg | ctc | att | gca | atg | cct | cag | ttc | ttc | 740 |
| Val | Ile | Met | Gly | Val | Gly | Thr | Leu | Leu | Ile | Ala | Met | Pro | Gln | Phe | Phe | |
| | | | 120 | | | | | 125 | | | | | 130 | | | |
| atg | gag | cag | tac | aaa | tat | gag | aga | tat | tct | cct | tcc | tcc | aat | tct | act | 788 |
| Met | Glu | Gln | Tyr | Lys | Tyr | Glu | Arg | Tyr | Ser | Pro | Ser | Ser | Asn | Ser | Thr | |
| | | 135 | | | | | 140 | | | | | 145 | | | | |
| ctc | agc | atc | tct | ccg | tgt | ctc | cta | gag | tca | agc | agt | caa | tta | cca | gtt | 836 |
| Leu | Ser | Ile | Ser | Pro | Cys | Leu | Leu | Glu | Ser | Ser | Ser | Gln | Leu | Pro | Val | |
| | 150 | | | | | 155 | | | | | 160 | | | | | |
| tca | gtt | atg | gaa | aaa | tca | aaa | tcc | aaa | ata | agt | aac | gaa | tgt | gaa | gtg | 884 |
| Ser | Val | Met | Glu | Lys | Ser | Lys | Ser | Lys | Ile | Ser | Asn | Glu | Cys | Glu | Val | |
| 165 | | | | | 170 | | | | | 175 | | | | | 180 | |
| gac | act | agc | tct | tcc | atg | tgg | att | tat | gtt | ttc | ctg | ggc | aat | ctt | ctt | 932 |
| Asp | Thr | Ser | Ser | Ser | Met | Trp | Ile | Tyr | Val | Phe | Leu | Gly | Asn | Leu | Leu | |
| | | | | 185 | | | | | 190 | | | | | 195 | | |
| cgt | gga | ata | gga | gaa | act | ccc | att | cag | cct | ttg | ggc | att | gcc | tac | ctg | 980 |
| Arg | Gly | Ile | Gly | Glu | Thr | Pro | Ile | Gln | Pro | Leu | Gly | Ile | Ala | Tyr | Leu | |
| | | | 200 | | | | | 205 | | | | | 210 | | | |
| gat | gat | ttt | gcc | agt | gaa | gac | aat | gca | gct | ttc | tat | att | ggg | tgt | gtg | 1028 |
| Asp | Asp | Phe | Ala | Ser | Glu | Asp | Asn | Ala | Ala | Phe | Tyr | Ile | Gly | Cys | Val | |
| | | 215 | | | | | 220 | | | | | 225 | | | | |
| cag | acg | gtt | gca | att | ata | gga | cca | atc | ttt | ggt | ttc | ctg | tta | ggc | tca | 1076 |
| Gln | Thr | Val | Ala | Ile | Ile | Gly | Pro | Ile | Phe | Gly | Phe | Leu | Leu | Gly | Ser | |
| | 230 | | | | | 235 | | | | | 240 | | | | | |
| tta | tgt | gcc | aaa | cta | tat | gtt | gac | att | ggc | ttt | gta | aac | cta | gat | cac | 1124 |
| Leu | Cys | Ala | Lys | Leu | Tyr | Val | Asp | Ile | Gly | Phe | Val | Asn | Leu | Asp | His | |
| 245 | | | | | 250 | | | | | 255 | | | | | 260 | |

-continued

| | |
|---|---|
| ata acc att acc cca aaa gat ccc cag tgg gta gga gcc tgg tgg ctt<br>Ile Thr Ile Thr Pro Lys Asp Pro Gln Trp Val Gly Ala Trp Trp Leu<br>265 270 275 | 1172 |
| ggc tat cta ata gca gga atc ata agt ctt ctt gca gct gtg cct ttc<br>Gly Tyr Leu Ile Ala Gly Ile Ile Ser Leu Leu Ala Ala Val Pro Phe<br>280 285 290 | 1220 |
| tgg tat tta cca aag agt tta cca aga tcc caa agt aga gag gat tct<br>Trp Tyr Leu Pro Lys Ser Leu Pro Arg Ser Gln Ser Arg Glu Asp Ser<br>295 300 305 | 1268 |
| aat tct tcc tct gag aaa tcc aag ttt att ata gat gat cac aca gac<br>Asn Ser Ser Ser Glu Lys Ser Lys Phe Ile Ile Asp Asp His Thr Asp<br>310 315 320 | 1316 |
| tac caa aca ccc cag gga gaa aat gca aaa ata atg gaa atg gca aga<br>Tyr Gln Thr Pro Gln Gly Glu Asn Ala Lys Ile Met Glu Met Ala Arg<br>325 330 335 340 | 1364 |
| gat ttt ctt cca tca ctg aag aat ctt ttt gga aac cca gta tac ttc<br>Asp Phe Leu Pro Ser Leu Lys Asn Leu Phe Gly Asn Pro Val Tyr Phe<br>345 350 355 | 1412 |
| cta tat tta tgt aca agc act gtt cag ttc aat tct ctg ttc ggc atg<br>Leu Tyr Leu Cys Thr Ser Thr Val Gln Phe Asn Ser Leu Phe Gly Met<br>360 365 370 | 1460 |
| gtg acg tac aaa cca aag tac att gag cag cag tat gga cag tca tcc<br>Val Thr Tyr Lys Pro Lys Tyr Ile Glu Gln Gln Tyr Gly Gln Ser Ser<br>375 380 385 | 1508 |
| tcc agg gcc aac ttt gtg atc ggg ctc atc aac att cca gca gtg gcc<br>Ser Arg Ala Asn Phe Val Ile Gly Leu Ile Asn Ile Pro Ala Val Ala<br>390 395 400 | 1556 |
| ctt gga ata ttc tct ggg ggg ata gtt atg aaa aaa ttc aga atc agt<br>Leu Gly Ile Phe Ser Gly Gly Ile Val Met Lys Lys Phe Arg Ile Ser<br>405 410 415 420 | 1604 |
| gtg tgt gga gct gca aaa ctc tac ttg gga tca tct gtc ttt ggt tac<br>Val Cys Gly Ala Ala Lys Leu Tyr Leu Gly Ser Ser Val Phe Gly Tyr<br>425 430 435 | 1652 |
| ctc cta ttt ctt tcc ctg ttt gca ctg ggc tgt gaa aat tct gat gtg<br>Leu Leu Phe Leu Ser Leu Phe Ala Leu Gly Cys Glu Asn Ser Asp Val<br>440 445 450 | 1700 |
| gca gga cta act gtc tcc tac caa gga acc aaa cct gtc tct tat cat<br>Ala Gly Leu Thr Val Ser Tyr Gln Gly Thr Lys Pro Val Ser Tyr His<br>455 460 465 | 1748 |
| gaa cga gct ctc ttt tca gat tgc aac tca aga tgc aaa tgt tca gag<br>Glu Arg Ala Leu Phe Ser Asp Cys Asn Ser Arg Cys Lys Cys Ser Glu<br>470 475 480 | 1796 |
| aca aaa tgg gaa ccc atg tgc ggt gaa aat gga atc aca tat gta tca<br>Thr Lys Trp Glu Pro Met Cys Gly Glu Asn Gly Ile Thr Tyr Val Ser<br>485 490 495 500 | 1844 |
| gct tgt ctt gct ggt tgt caa acc tcc aac agg agt gga aaa aat att<br>Ala Cys Leu Ala Gly Cys Gln Thr Ser Asn Arg Ser Gly Lys Asn Ile<br>505 510 515 | 1892 |
| ata ttt tac aac tgc act tgt gtg gga att gca gct tct aaa tcc gga<br>Ile Phe Tyr Asn Cys Thr Cys Val Gly Ile Ala Ala Ser Lys Ser Gly<br>520 525 530 | 1940 |
| aat tcc tca ggc ata gtg gga aga tgt cag aaa gac aat gga tgt ccc<br>Asn Ser Ser Gly Ile Val Gly Arg Cys Gln Lys Asp Asn Gly Cys Pro<br>535 540 545 | 1988 |
| caa atg ttt ctg tat ttc ctt gta att tca gtc atc aca tcc tat act<br>Gln Met Phe Leu Tyr Phe Leu Val Ile Ser Val Ile Thr Ser Tyr Thr<br>550 555 560 | 2036 |
| tta tcc cta ggt ggc ata cct gga tac ata tta ctt ctg agg tgc att<br>Leu Ser Leu Gly Gly Ile Pro Gly Tyr Ile Leu Leu Leu Arg Cys Ile<br>565 570 575 580 | 2084 |

-continued

| | | |
|---|---|---|
| aag cca cag ctt aag tct ttt gcc ttg ggt atc tac aca tta gca ata<br>Lys Pro Gln Leu Lys Ser Phe Ala Leu Gly Ile Tyr Thr Leu Ala Ile<br>585 590 595 | 2132 | |
| aga gtt ctt gca gga atc cca gct cca gtg tat ttt gga gtt ttg att<br>Arg Val Leu Ala Gly Ile Pro Ala Pro Val Tyr Phe Gly Val Leu Ile<br>600 605 610 | 2180 | |
| gat act tca tgc ctc aaa tgg gga ttt aaa aga tgt gga agt aga gga<br>Asp Thr Ser Cys Leu Lys Trp Gly Phe Lys Arg Cys Gly Ser Arg Gly<br>615 620 625 | 2228 | |
| tca tgc aga tta tat gat tca aat gtc ttc aga cat ata tat ctg gga<br>Ser Cys Arg Leu Tyr Asp Ser Asn Val Phe Arg His Ile Tyr Leu Gly<br>630 635 640 | 2276 | |
| cta act gtg ata ctg ggc aca gtg tca att ctc cta agc att gca gta<br>Leu Thr Val Ile Leu Gly Thr Val Ser Ile Leu Leu Ser Ile Ala Val<br>645 650 655 660 | 2324 | |
| ctt ttc att tta aag aaa aat tat gtt tca aaa cac aga agt ttt ata<br>Leu Phe Ile Leu Lys Lys Asn Tyr Val Ser Lys His Arg Ser Phe Ile<br>665 670 675 | 2372 | |
| acc aag aga gaa aga aca atg gtg tct aca aga ttc caa aag gaa aat<br>Thr Lys Arg Glu Arg Thr Met Val Ser Thr Arg Phe Gln Lys Glu Asn<br>680 685 690 | 2420 | |
| tac act aca agt gat cat ctg cta caa ccc aac tac tgg cca ggc aag<br>Tyr Thr Thr Ser Asp His Leu Leu Gln Pro Asn Tyr Trp Pro Gly Lys<br>695 700 705 | 2468 | |
| gaa act caa ctt tag aaacatgatg actggaagtc atgtcttcta attggttgac<br>Glu Thr Gln Leu *<br>710 | 2523 | |
| attttgcaaa caaataaatt gtaatcaaaa gagctctaaa tttgtaattt ctttctcctt | 2583 | |
| tcaaaaaatg tctactttgt tttggtccta ggcattaggt aatataactg ataatatact | 2643 | |
| gaaacatata atggaagatg cagatgataa aactaatttt gaacttttta atttatataa | 2703 | |
| attatttat atcacttact tatttcactt tattttgctt tgtgctcatt gatatatatt | 2763 | |
| agctgtactc ctagaagaac aattgtctct attgtcacac atggttatat ttaaagtaat | 2823 | |
| ttctgaactg tgtaatgtgt ctagagtaag caaatactgc taacaattaa ctcatacctt | 2883 | |
| gggttccttc aagtattact cctatagtat tttctcccat agctgtcttc atctgtgtat | 2943 | |
| tttaataatg atcttaggat ggagcagaac atggagagga agatttcatt ttaagctcct | 3003 | |
| ccttttcttt gaaatacaat aatttatata gaaatgtgta gcagcaaatt atattgggga | 3063 | |
| ttagaatttt gaattaatag ctctcctact attaatttac atgtgctttt tgtgtggcgc | 3123 | |
| tataagtgac tatggttgta aagtaataaa attgatgtta acatgcccaa aaaaaaaaa | 3183 | |
| aaaaaaacc aaaaaaaaaa aaaaaaaagg gcgggccgct agac | 3227 | |

<210> SEQ ID NO 18
<211> LENGTH: 712
<212> TYPE: PRT
<213> ORGANISM: Homo Sapiens

<400> SEQUENCE: 18

Met Asp Thr Ser Ser Lys Glu Asn Ile Gln Leu Phe Cys Lys Thr Ser
1               5                   10                  15

Val Gln Pro Val Gly Arg Pro Ser Phe Lys Thr Glu Tyr Pro Ser Ser
            20                  25                  30

Glu Glu Lys Gln Pro Cys Cys Gly Glu Leu Lys Val Phe Leu Cys Ala
        35                  40                  45

Leu Ser Phe Val Tyr Phe Ala Lys Ala Leu Ala Glu Gly Tyr Leu Lys
    50                  55                  60

-continued

```
Ser Thr Ile Thr Gln Ile Glu Arg Arg Phe Asp Ile Pro Ser Ser Leu
 65                  70                  75                  80

Val Gly Val Ile Asp Gly Ser Phe Glu Ile Gly Asn Leu Leu Val Ile
                 85                  90                  95

Thr Phe Val Ser Tyr Phe Gly Ala Lys Leu His Arg Pro Lys Ile Ile
            100                 105                 110

Gly Ala Gly Cys Val Ile Met Gly Val Gly Thr Leu Leu Ile Ala Met
        115                 120                 125

Pro Gln Phe Phe Met Glu Gln Tyr Lys Tyr Glu Arg Tyr Ser Pro Ser
    130                 135                 140

Ser Asn Ser Thr Leu Ser Ile Ser Pro Cys Leu Leu Glu Ser Ser Ser
145                 150                 155                 160

Gln Leu Pro Val Ser Val Met Glu Lys Ser Lys Ser Lys Ile Ser Asn
                165                 170                 175

Glu Cys Glu Val Asp Thr Ser Ser Met Trp Ile Tyr Val Phe Leu
            180                 185                 190

Gly Asn Leu Leu Arg Gly Ile Gly Glu Thr Pro Ile Gln Pro Leu Gly
        195                 200                 205

Ile Ala Tyr Leu Asp Asp Phe Ala Ser Glu Asp Asn Ala Ala Phe Tyr
    210                 215                 220

Ile Gly Cys Val Gln Thr Val Ala Ile Ile Gly Pro Ile Phe Gly Phe
225                 230                 235                 240

Leu Leu Gly Ser Leu Cys Ala Lys Leu Tyr Val Asp Ile Gly Phe Val
                245                 250                 255

Asn Leu Asp His Ile Thr Ile Thr Pro Lys Asp Pro Gln Trp Val Gly
            260                 265                 270

Ala Trp Trp Leu Gly Tyr Leu Ile Ala Gly Ile Ile Ser Leu Leu Ala
        275                 280                 285

Ala Val Pro Phe Trp Tyr Leu Pro Lys Ser Leu Pro Arg Ser Gln Ser
    290                 295                 300

Arg Glu Asp Ser Asn Ser Ser Ser Glu Lys Ser Lys Phe Ile Ile Asp
305                 310                 315                 320

Asp His Thr Asp Tyr Gln Thr Pro Gln Gly Glu Asn Ala Lys Ile Met
                325                 330                 335

Glu Met Ala Arg Asp Phe Leu Pro Ser Leu Lys Asn Leu Phe Gly Asn
            340                 345                 350

Pro Val Tyr Phe Leu Tyr Leu Cys Thr Ser Thr Val Gln Phe Asn Ser
        355                 360                 365

Leu Phe Gly Met Val Thr Tyr Lys Pro Lys Tyr Ile Glu Gln Gln Tyr
    370                 375                 380

Gly Gln Ser Ser Ser Arg Ala Asn Phe Val Ile Gly Leu Ile Asn Ile
385                 390                 395                 400

Pro Ala Val Ala Leu Gly Ile Phe Ser Gly Gly Ile Val Met Lys Lys
                405                 410                 415

Phe Arg Ile Ser Val Cys Gly Ala Ala Lys Leu Tyr Leu Gly Ser Ser
            420                 425                 430

Val Phe Gly Tyr Leu Leu Phe Leu Ser Leu Phe Ala Leu Gly Cys Glu
        435                 440                 445

Asn Ser Asp Val Ala Gly Leu Thr Val Ser Tyr Gln Gly Thr Lys Pro
    450                 455                 460

Val Ser Tyr His Glu Arg Ala Leu Phe Ser Asp Cys Asn Ser Arg Cys
465                 470                 475                 480
```

```
Lys Cys Ser Glu Thr Lys Trp Glu Pro Met Cys Gly Glu Asn Gly Ile
                485                 490                 495

Thr Tyr Val Ser Ala Cys Leu Ala Gly Cys Gln Thr Ser Asn Arg Ser
            500                 505                 510

Gly Lys Asn Ile Ile Phe Tyr Asn Cys Thr Cys Val Gly Ile Ala Ala
        515                 520                 525

Ser Lys Ser Gly Asn Ser Ser Gly Ile Val Gly Arg Cys Gln Lys Asp
    530                 535                 540

Asn Gly Cys Pro Gln Met Phe Leu Tyr Phe Leu Val Ile Ser Val Ile
545                 550                 555                 560

Thr Ser Tyr Thr Leu Ser Leu Gly Gly Ile Pro Gly Tyr Ile Leu Leu
                565                 570                 575

Leu Arg Cys Ile Lys Pro Gln Leu Lys Ser Phe Ala Leu Gly Ile Tyr
            580                 585                 590

Thr Leu Ala Ile Arg Val Leu Ala Gly Ile Pro Ala Pro Val Tyr Phe
        595                 600                 605

Gly Val Leu Ile Asp Thr Ser Cys Leu Lys Trp Gly Phe Lys Arg Cys
    610                 615                 620

Gly Ser Arg Gly Ser Cys Arg Leu Tyr Asp Ser Asn Val Phe Arg His
625                 630                 635                 640

Ile Tyr Leu Gly Leu Thr Val Ile Leu Gly Thr Val Ser Ile Leu Leu
                645                 650                 655

Ser Ile Ala Val Leu Phe Ile Leu Lys Lys Asn Tyr Val Ser Lys His
            660                 665                 670

Arg Ser Phe Ile Thr Lys Arg Glu Arg Thr Met Val Ser Thr Arg Phe
        675                 680                 685

Gln Lys Glu Asn Tyr Thr Thr Ser Asp His Leu Leu Gln Pro Asn Tyr
    690                 695                 700

Trp Pro Gly Lys Glu Thr Gln Leu
705                 710

<210> SEQ ID NO 19
<211> LENGTH: 2133
<212> TYPE: DNA
<213> ORGANISM: Homo Sapiens
<220> FEATURE:
<221> NAME/KEY: CDS
<222> LOCATION: (1)...(2133)

<400> SEQUENCE: 19 atg cag ggg aag aag ccg ggc ggt tcg tcg ggc ggc ggc cgg agc ggc      48
Met Gln Gly Lys Lys Pro Gly Gly Ser Ser Gly Gly Gly Arg Ser Gly
1               5                   10                  15 gag ctg cag ggg gac gag gcg cag agg aac aag aaa aag aaa aag aag      96
Glu Leu Gln Gly Asp Glu Ala Gln Arg Asn Lys Lys Lys Lys Lys Lys
            20                  25                  30 gtg tcc tgc ttt tcc aac atc aag atc ttc ctg gtg tcc gag tgc gcc     144
Val Ser Cys Phe Ser Asn Ile Lys Ile Phe Leu Val Ser Glu Cys Ala
        35                  40                  45 ctg atg ctg gcg cag ggc acg gtg ggc gcc tac ctg gtg agc gtc ctg     192
Leu Met Leu Ala Gln Gly Thr Val Gly Ala Tyr Leu Val Ser Val Leu
    50                  55                  60 acc acc ctg gag cgt agg ttc aac ctg cag agc gct gac gtg ggt gtg     240
Thr Thr Leu Glu Arg Arg Phe Asn Leu Gln Ser Ala Asp Val Gly Val
65                  70                  75                  80 atc gct agc agc ttc gag atc ggg aac ctg gcg ctc atc ctc ttc gtg     288
Ile Ala Ser Ser Phe Glu Ile Gly Asn Leu Ala Leu Ile Leu Phe Val
                85                  90                  95
```

-continued

| | |
|---|---|
| agc tac ttc ggg gca cgc ggg cac cgg ccg cgc ctg atc ggc tgc ggc<br>Ser Tyr Phe Gly Ala Arg Gly His Arg Pro Arg Leu Ile Gly Cys Gly<br>            100                    105                  110 | 336 |
| ggc atc gtc atg gcg ctg ggc gcg ctg ctg tcg gcg ctg ccc gag ttc<br>Gly Ile Val Met Ala Leu Gly Ala Leu Leu Ser Ala Leu Pro Glu Phe<br>        115                    120                  125 | 384 |
| ctg acc cac cag tac aag tac gag gcg ggc gag atc cgc tgg ggc gcc<br>Leu Thr His Gln Tyr Lys Tyr Glu Ala Gly Glu Ile Arg Trp Gly Ala<br>130                    135                  140 | 432 |
| gag ggc cgc gac gtc tgc gca gcc aac ggc tcg ggc gac gag ggg<br>Glu Gly Arg Asp Val Cys Ala Ala Asn Gly Ser Gly Gly Asp Glu Gly<br>145                    150                  155                  160 | 480 |
| ccc gac ccc gac ctc atc tgc cgc aac cgg acg gct acc aac atg atg<br>Pro Asp Pro Asp Leu Ile Cys Arg Asn Arg Thr Ala Thr Asn Met Met<br>                  165                  170                  175 | 528 |
| tac ttg ctg ctc att ggg gcc cag gtg ctc ctg ggc atc ggt gct acc<br>Tyr Leu Leu Leu Ile Gly Ala Gln Val Leu Leu Gly Ile Gly Ala Thr<br>                  180                  185                  190 | 576 |
| cct gtg cag ccc ctg ggc gtc tcc tac atc gac gac cac gtg cgg agg<br>Pro Val Gln Pro Leu Gly Val Ser Tyr Ile Asp Asp His Val Arg Arg<br>        195                    200                  205 | 624 |
| aag gac tcc tcg ctc tat ata gga atc ctg ttc acg atg ctg gta ttt<br>Lys Asp Ser Ser Leu Tyr Ile Gly Ile Leu Phe Thr Met Leu Val Phe<br>210                    215                  220 | 672 |
| gga cca gcc tgc ggg ttt atc ctg ggc tct ttc tgt acc aaa atc tac<br>Gly Pro Ala Cys Gly Phe Ile Leu Gly Ser Phe Cys Thr Lys Ile Tyr<br>225                    230                  235                  240 | 720 |
| gtg gat gcg gtc ttc att gac aca agt aac ctg gac atc act ccg gac<br>Val Asp Ala Val Phe Ile Asp Thr Ser Asn Leu Asp Ile Thr Pro Asp<br>                  245                  250                  255 | 768 |
| gac ccc cgc tgg atc gga gcc tgg tgg ggt ggc ttt ctg ctc tgc ggt<br>Asp Pro Arg Trp Ile Gly Ala Trp Trp Gly Gly Phe Leu Leu Cys Gly<br>                  260                  265                  270 | 816 |
| gcc tta ctc ttc ttc tct tcc ctc ttg atg ttt ggg ttt cca cag tcc<br>Ala Leu Leu Phe Phe Ser Ser Leu Leu Met Phe Gly Phe Pro Gln Ser<br>                275                  280                  285 | 864 |
| ctg ccc ccg cac tca gac ccc gcc atg gaa agc gag cag gcc atg ctc<br>Leu Pro Pro His Ser Asp Pro Ala Met Glu Ser Glu Gln Ala Met Leu<br>290                    295                  300 | 912 |
| tcc gaa aga gaa tac gag aga ccc aag ccc agc aac ggg gtc ctg agg<br>Ser Glu Arg Glu Tyr Glu Arg Pro Lys Pro Ser Asn Gly Val Leu Arg<br>305                    310                  315                  320 | 960 |
| cac ccc ctg gag cca gac agc agt gcc tcc tgt ttc cag cag ctg aga<br>His Pro Leu Glu Pro Asp Ser Ser Ala Ser Cys Phe Gln Gln Leu Arg<br>                  325                  330                  335 | 1008 |
| gtg atc ccg aag gtc acc aag cac ctg ctc tca aac cct gtg ttc acc<br>Val Ile Pro Lys Val Thr Lys His Leu Leu Ser Asn Pro Val Phe Thr<br>                340                  345                  350 | 1056 |
| tgc atc atc ctg gcc gcc tgc atg gag att gca gtg gtg gct ggc ttc<br>Cys Ile Ile Leu Ala Ala Cys Met Glu Ile Ala Val Val Ala Gly Phe<br>        355                    360                  365 | 1104 |
| gct gcc ttt ttg ggg aag tac ctg gag cag cag ttt aac ctc acc acc<br>Ala Ala Phe Leu Gly Lys Tyr Leu Glu Gln Gln Phe Asn Leu Thr Thr<br>370                    375                  380 | 1152 |
| tct tct gcc aac cag ctg ctt ggg atg act gcg atc ccg tgt gct tgt<br>Ser Ser Ala Asn Gln Leu Leu Gly Met Thr Ala Ile Pro Cys Ala Cys<br>385                    390                  395                  400 | 1200 |
| ctg ggt atc ttc ctg gga ggt ctt ttg gtg aag aag ctc agc ctg tct<br>Leu Gly Ile Phe Leu Gly Gly Leu Leu Val Lys Lys Leu Ser Leu Ser<br>                  405                  410                  415 | 1248 |

```
gcc ctg ggg gcc att cgg atg gcc atg ctc gtc aac ctg gtg tcc act    1296
Ala Leu Gly Ala Ile Arg Met Ala Met Leu Val Asn Leu Val Ser Thr
            420                 425                 430 gct tgc tac gtc tcc ttc ctc ttc ctg ggc tgc gac act ggc cct gtg    1344
Ala Cys Tyr Val Ser Phe Leu Phe Leu Gly Cys Asp Thr Gly Pro Val
            435                 440                 445 gct ggg gtt act gtt ccc tat gga aac agc aca gca cct ggc tca gcc    1392
Ala Gly Val Thr Val Pro Tyr Gly Asn Ser Thr Ala Pro Gly Ser Ala
        450                 455                 460 ctg gac ccc tac tcg ccc tgc aat aat aac tgt gaa tgc caa acc gat    1440
Leu Asp Pro Tyr Ser Pro Cys Asn Asn Asn Cys Glu Cys Gln Thr Asp
465                 470                 475                 480 tcc ttc act cca gtg tgt ggg gca gat ggc atc acc tac ctg tct gcc    1488
Ser Phe Thr Pro Val Cys Gly Ala Asp Gly Ile Thr Tyr Leu Ser Ala
                485                 490                 495 tgc ttt gct ggc tgc aac agc acg aat ctc acg ggc tgt gcg tgc ctc    1536
Cys Phe Ala Gly Cys Asn Ser Thr Asn Leu Thr Gly Cys Ala Cys Leu
            500                 505                 510 acc acc gtc cct gct gag aac gca acc gtg gtt cct gga aaa tgc ccc    1584
Thr Thr Val Pro Ala Glu Asn Ala Thr Val Val Pro Gly Lys Cys Pro
            515                 520                 525 agt cct ggg tgc caa gag gcc ttc ctc act ttc ctc tgt gtg atg tgt    1632
Ser Pro Gly Cys Gln Glu Ala Phe Leu Thr Phe Leu Cys Val Met Cys
530                 535                 540 atc tgc agc ctg atc ggt gcc atg gca cag aca ccc tca gtc atc atc    1680
Ile Cys Ser Leu Ile Gly Ala Met Ala Gln Thr Pro Ser Val Ile Ile
545                 550                 555                 560 ctc atc agg aca gtc agc cct gaa ctc aag tct tac gct ttg gga gtt    1728
Leu Ile Arg Thr Val Ser Pro Glu Leu Lys Ser Tyr Ala Leu Gly Val
                565                 570                 575 ctt ttt ctc ctc ctt cgt ttg ttg ggc ttc atc cct cca ccc ctc atc    1776
Leu Phe Leu Leu Leu Arg Leu Leu Gly Phe Ile Pro Pro Pro Leu Ile
            580                 585                 590 ttc ggg gct ggc atc gac tcc acc tgc ctg ttc tgg agc acg ttc tgt    1824
Phe Gly Ala Gly Ile Asp Ser Thr Cys Leu Phe Trp Ser Thr Phe Cys
            595                 600                 605 ggg gag caa ggc gcc tgc gtc ctc tac gac aat gtg gtc tac cga tac    1872
Gly Glu Gln Gly Ala Cys Val Leu Tyr Asp Asn Val Val Tyr Arg Tyr
        610                 615                 620 ctg tat gtc agc atc gcc atc gcg ctc aaa tcc ttc gcc ttc atc ctg    1920
Leu Tyr Val Ser Ile Ala Ile Ala Leu Lys Ser Phe Ala Phe Ile Leu
625                 630                 635                 640 tac acc acc acg tgg cag tgc ctg agg aaa aac tat aaa cgc tac atc    1968
Tyr Thr Thr Thr Trp Gln Cys Leu Arg Lys Asn Tyr Lys Arg Tyr Ile
                645                 650                 655 aaa aac cac gag ggc ggg ctg agc acc agt gag ttc ttt gcc tct act    2016
Lys Asn His Glu Gly Gly Leu Ser Thr Ser Glu Phe Phe Ala Ser Thr
            660                 665                 670 ctg acc cta gac aac ctg ggg agg gac cct gtg ccc gca aac cag aca    2064
Leu Thr Leu Asp Asn Leu Gly Arg Asp Pro Val Pro Ala Asn Gln Thr
            675                 680                 685 cat agg aca aag ttt atc tat aac ctg gaa gac cat gag tgg tgt gaa    2112
His Arg Thr Lys Phe Ile Tyr Asn Leu Glu Asp His Glu Trp Cys Glu
        690                 695                 700 aac atg gag tcc gtt tta tag                                        2133
Asn Met Glu Ser Val Leu  *
705                 710
```

-continued

```
<210> SEQ ID NO 20
<211> LENGTH: 710
<212> TYPE: PRT
<213> ORGANISM: Homo Sapiens

<400> SEQUENCE: 20
```

| | | | | | | | | | | | | | | | |
|---|---|---|---|---|---|---|---|---|---|---|---|---|---|---|---|
| Met | Gln | Gly | Lys | Lys | Pro | Gly | Gly | Ser | Gly | Gly | Gly | Arg | Ser | Gly |
| 1 | | | | 5 | | | | | 10 | | | | | 15 |
| Glu | Leu | Gln | Gly | Asp | Glu | Ala | Gln | Arg | Asn | Lys | Lys | Lys | Lys | Lys | Lys |
| | | | 20 | | | | | 25 | | | | | 30 | | |
| Val | Ser | Cys | Phe | Ser | Asn | Ile | Lys | Ile | Phe | Leu | Val | Ser | Glu | Cys | Ala |
| | | 35 | | | | | 40 | | | | | 45 | | | |
| Leu | Met | Leu | Ala | Gln | Gly | Thr | Val | Gly | Ala | Tyr | Leu | Val | Ser | Val | Leu |
| | 50 | | | | | 55 | | | | | 60 | | | | |
| Thr | Thr | Leu | Glu | Arg | Arg | Phe | Asn | Leu | Gln | Ser | Ala | Asp | Val | Gly | Val |
| 65 | | | | | 70 | | | | | 75 | | | | | 80 |
| Ile | Ala | Ser | Ser | Phe | Glu | Ile | Gly | Asn | Leu | Ala | Leu | Ile | Leu | Phe | Val |
| | | | | 85 | | | | | 90 | | | | | 95 | |
| Ser | Tyr | Phe | Gly | Ala | Arg | Gly | His | Arg | Pro | Arg | Leu | Ile | Gly | Cys | Gly |
| | | | 100 | | | | | 105 | | | | | 110 | | |
| Gly | Ile | Val | Met | Ala | Leu | Gly | Ala | Leu | Leu | Ser | Ala | Leu | Pro | Glu | Phe |
| | | | 115 | | | | | 120 | | | | | 125 | | |
| Leu | Thr | His | Gln | Tyr | Lys | Tyr | Glu | Ala | Gly | Glu | Ile | Arg | Trp | Gly | Ala |
| | 130 | | | | | 135 | | | | | 140 | | | | |
| Glu | Gly | Arg | Asp | Val | Cys | Ala | Ala | Asn | Gly | Ser | Gly | Gly | Asp | Glu | Gly |
| 145 | | | | | 150 | | | | | 155 | | | | | 160 |
| Pro | Asp | Pro | Asp | Leu | Ile | Cys | Arg | Asn | Arg | Thr | Ala | Thr | Asn | Met | Met |
| | | | | 165 | | | | | 170 | | | | | 175 | |
| Tyr | Leu | Leu | Leu | Ile | Gly | Ala | Gln | Val | Leu | Leu | Gly | Ile | Gly | Ala | Thr |
| | | | 180 | | | | | 185 | | | | | 190 | | |
| Pro | Val | Gln | Pro | Leu | Gly | Val | Ser | Tyr | Ile | Asp | Asp | His | Val | Arg | Arg |
| | | 195 | | | | | 200 | | | | | 205 | | | |
| Lys | Asp | Ser | Ser | Leu | Tyr | Ile | Gly | Ile | Leu | Phe | Thr | Met | Leu | Val | Phe |
| | 210 | | | | | 215 | | | | | 220 | | | | |
| Gly | Pro | Ala | Cys | Gly | Phe | Ile | Leu | Gly | Ser | Phe | Cys | Thr | Lys | Ile | Tyr |
| 225 | | | | | 230 | | | | | 235 | | | | | 240 |
| Val | Asp | Ala | Val | Phe | Ile | Asp | Thr | Ser | Asn | Leu | Asp | Ile | Thr | Pro | Asp |
| | | | | 245 | | | | | 250 | | | | | 255 | |
| Asp | Pro | Arg | Trp | Ile | Gly | Ala | Trp | Trp | Gly | Gly | Phe | Leu | Leu | Cys | Gly |
| | | | 260 | | | | | 265 | | | | | 270 | | |
| Ala | Leu | Leu | Phe | Phe | Ser | Ser | Leu | Leu | Met | Phe | Gly | Phe | Pro | Gln | Ser |
| | | 275 | | | | | 280 | | | | | 285 | | | |
| Leu | Pro | Pro | His | Ser | Asp | Pro | Ala | Met | Glu | Ser | Glu | Gln | Ala | Met | Leu |
| | 290 | | | | | 295 | | | | | 300 | | | | |
| Ser | Glu | Arg | Glu | Tyr | Glu | Arg | Pro | Lys | Pro | Ser | Asn | Gly | Val | Leu | Arg |
| 305 | | | | | 310 | | | | | 315 | | | | | 320 |
| His | Pro | Leu | Glu | Pro | Asp | Ser | Ser | Ala | Ser | Cys | Phe | Gln | Gln | Leu | Arg |
| | | | | 325 | | | | | 330 | | | | | 335 | |
| Val | Ile | Pro | Lys | Val | Thr | Lys | His | Leu | Leu | Ser | Asn | Pro | Val | Phe | Thr |
| | | | 340 | | | | | 345 | | | | | 350 | | |
| Cys | Ile | Ile | Leu | Ala | Ala | Cys | Met | Glu | Ile | Ala | Val | Val | Ala | Gly | Phe |
| | | 355 | | | | | 360 | | | | | 365 | | | |
| Ala | Ala | Phe | Leu | Gly | Lys | Tyr | Leu | Glu | Gln | Gln | Phe | Asn | Leu | Thr | Thr |
| | 370 | | | | | 375 | | | | | 380 | | | | |

```
Ser Ser Ala Asn Gln Leu Leu Gly Met Thr Ala Ile Pro Cys Ala Cys
385                 390                 395                 400

Leu Gly Ile Phe Leu Gly Gly Leu Leu Val Lys Lys Leu Ser Leu Ser
            405                 410                 415

Ala Leu Gly Ala Ile Arg Met Ala Met Leu Val Asn Leu Val Ser Thr
        420                 425                 430

Ala Cys Tyr Val Ser Phe Leu Phe Leu Gly Cys Asp Thr Gly Pro Val
    435                 440                 445

Ala Gly Val Thr Val Pro Tyr Gly Asn Ser Thr Ala Pro Gly Ser Ala
450                 455                 460

Leu Asp Pro Tyr Ser Pro Cys Asn Asn Cys Glu Cys Gln Thr Asp
465                 470                 475                 480

Ser Phe Thr Pro Val Cys Gly Ala Asp Gly Ile Thr Tyr Leu Ser Ala
                485                 490                 495

Cys Phe Ala Gly Cys Asn Ser Thr Asn Leu Thr Gly Cys Ala Cys Leu
            500                 505                 510

Thr Thr Val Pro Ala Glu Asn Ala Thr Val Val Pro Gly Lys Cys Pro
        515                 520                 525

Ser Pro Gly Cys Gln Glu Ala Phe Leu Thr Phe Leu Cys Val Met Cys
    530                 535                 540

Ile Cys Ser Leu Ile Gly Ala Met Ala Gln Thr Pro Ser Val Ile Ile
545                 550                 555                 560

Leu Ile Arg Thr Val Ser Pro Glu Leu Lys Ser Tyr Ala Leu Gly Val
                565                 570                 575

Leu Phe Leu Leu Leu Arg Leu Leu Gly Phe Ile Pro Pro Leu Ile
            580                 585                 590

Phe Gly Ala Gly Ile Asp Ser Thr Cys Leu Phe Trp Ser Thr Phe Cys
        595                 600                 605

Gly Glu Gln Gly Ala Cys Val Leu Tyr Asp Asn Val Val Tyr Arg Tyr
    610                 615                 620

Leu Tyr Val Ser Ile Ala Ile Ala Leu Lys Ser Phe Ala Phe Ile Leu
625                 630                 635                 640

Tyr Thr Thr Thr Trp Gln Cys Leu Arg Lys Asn Tyr Lys Arg Tyr Ile
                645                 650                 655

Lys Asn His Glu Gly Gly Leu Ser Thr Ser Glu Phe Ala Ser Thr
            660                 665                 670

Leu Thr Leu Asp Asn Leu Gly Arg Asp Pro Val Pro Ala Asn Gln Thr
        675                 680                 685

His Arg Thr Lys Phe Ile Tyr Asn Leu Glu Asp His Glu Trp Cys Glu
690                 695                 700

Asn Met Glu Ser Val Leu
705                 710

<210> SEQ ID NO 21
<211> LENGTH: 4197
<212> TYPE: DNA
<213> ORGANISM: Homo Sapiens
<220> FEATURE:
<221> NAME/KEY: CDS
<222> LOCATION: (1)...(3348)

<400> SEQUENCE: 21 atg agg aga ctg agt ttg tgg tgg ctg ctg agc agg gtc tgt ctg ctg      48
Met Arg Arg Leu Ser Leu Trp Trp Leu Leu Ser Arg Val Cys Leu Leu
1               5                   10                  15
```

```
                                    -continued
ttg ccg ccg ccc tgc gca ctg gtg ctg gcc ggg gtg ccc agc tcc tcc      96
Leu Pro Pro Pro Cys Ala Leu Val Leu Ala Gly Val Pro Ser Ser Ser
         20                  25                  30 tcg cac ccg cag ccc tgc cag atc ctc aag cgc atc ggg cac gcg gtg     144
Ser His Pro Gln Pro Cys Gln Ile Leu Lys Arg Ile Gly His Ala Val
     35                  40                  45 agg gtg ggc gcg gtg cac ttg cag ccc tgg acc acc gcc ccc cgc gcg     192
Arg Val Gly Ala Val His Leu Gln Pro Trp Thr Thr Ala Pro Arg Ala
 50                  55                  60 gcc agc cgc gct ccg gac gac agc cga gca gga gcc cag agg gat gag     240
Ala Ser Arg Ala Pro Asp Asp Ser Arg Ala Gly Ala Gln Arg Asp Glu
 65                  70                  75                  80 ccg gag cca ggg act agg cgg tcc ccg gcg ccc tcg ccg ggc gca cgc     288
Pro Glu Pro Gly Thr Arg Arg Ser Pro Ala Pro Ser Pro Gly Ala Arg
                 85                  90                  95 tgg ttg ggg agc acc ctg cat ggc cgg ggg ccg ccg ggc tcc cgt aag     336
Trp Leu Gly Ser Thr Leu His Gly Arg Gly Pro Pro Gly Ser Arg Lys
             100                 105                 110 ccc ggg gag ggc gcc agg gcg gag gcc ctg tgg cca cgg gac gcc ctc     384
Pro Gly Glu Gly Ala Arg Ala Glu Ala Leu Trp Pro Arg Asp Ala Leu
         115                 120                 125 cta ttt gcc gtg gac aac ctg aac cgc gtg gaa ggg ctg cta ccc tac     432
Leu Phe Ala Val Asp Asn Leu Asn Arg Val Glu Gly Leu Leu Pro Tyr
130                 135                 140 aac ctg tct ttg gaa gta gtg atg gcc atc gag gca ggc ctg ggc gat     480
Asn Leu Ser Leu Glu Val Val Met Ala Ile Glu Ala Gly Leu Gly Asp
145                 150                 155                 160 ctg cca ctt ttg ccc ttc tcc tcc cct agt tcg cca tgg agc agt gac     528
Leu Pro Leu Leu Pro Phe Ser Ser Pro Ser Ser Pro Trp Ser Ser Asp
                 165                 170                 175 cct ttc tcc ttc ctg caa agt gtg tgc cat acc gtg gtg gtg caa ggg     576
Pro Phe Ser Phe Leu Gln Ser Val Cys His Thr Val Val Val Gln Gly
             180                 185                 190 gtg tcg gcg ctg ctc gcc ttc ccc cag agc cag ggc gaa atg atg gag     624
Val Ser Ala Leu Leu Ala Phe Pro Gln Ser Gln Gly Glu Met Met Glu
         195                 200                 205 ctc gac ttg gtc agc tta gtc ctg cac att cca gtg atc agc atc gtg     672
Leu Asp Leu Val Ser Leu Val Leu His Ile Pro Val Ile Ser Ile Val
     210                 215                 220 cgc cac gag ttt ccg cgg gag agt cag aat ccc ctt cac cta caa ctg     720
Arg His Glu Phe Pro Arg Glu Ser Gln Asn Pro Leu His Leu Gln Leu
225                 230                 235                 240 agt tta gaa aat tca tta agt tct gat gct gat gtc act gtc tca atc     768
Ser Leu Glu Asn Ser Leu Ser Ser Asp Ala Asp Val Thr Val Ser Ile
                 245                 250                 255 ctg acc atg aac aac tgg tac aat ttt agc ttg ttg ctg tgc cag gaa     816
Leu Thr Met Asn Asn Trp Tyr Asn Phe Ser Leu Leu Leu Cys Gln Glu
             260                 265                 270 gac tgg aac atc acc gac ttc ctc ctc ctt acc cag aat aat tcc aag     864
Asp Trp Asn Ile Thr Asp Phe Leu Leu Leu Thr Gln Asn Asn Ser Lys
         275                 280                 285 ttc cac ctt ggt tct atc atc aac atc acc gct aac ctc ccc tcc acc     912
Phe His Leu Gly Ser Ile Ile Asn Ile Thr Ala Asn Leu Pro Ser Thr
     290                 295                 300 cag gac ctc ttg agc ttc cta cag atc cag ctt gag agt att aag aac     960
Gln Asp Leu Leu Ser Phe Leu Gln Ile Gln Leu Glu Ser Ile Lys Asn
305                 310                 315                 320 agc aca ccc aca gtg gtg atg ttt ggc tgc gac atg gaa agt atc cgg    1008
Ser Thr Pro Thr Val Val Met Phe Gly Cys Asp Met Glu Ser Ile Arg
                 325                 330                 335
```

-continued

| | | |
|---|---|---|
| cgg att ttc gaa att aca acc cag ttt ggg gtc atg ccc cct gaa ctt<br>Arg Ile Phe Glu Ile Thr Thr Gln Phe Gly Val Met Pro Pro Glu Leu<br>340 345 350 | 1056 |
| cgt tgg gtg ctg gga gat tcc cag aat atg gag gaa ctg agg aca gag<br>Arg Trp Val Leu Gly Asp Ser Gln Asn Met Glu Glu Leu Arg Thr Glu<br>355 360 365 | 1104 |
| ggt ctg ccc tta gga ctc att gct cat gga aaa aca aca cag tct gtc<br>Gly Leu Pro Leu Gly Leu Ile Ala His Gly Lys Thr Thr Gln Ser Val<br>370 375 380 | 1152 |
| ttt gag cac tac gta caa gat gct atg gag ctg gtc gca aga gct gta<br>Phe Glu His Tyr Val Gln Asp Ala Met Glu Leu Val Ala Arg Ala Val<br>385 390 395 400 | 1200 |
| gcc aca gcc acc atg atc caa cca gaa ctt gct ctc att ccc agc acg<br>Ala Thr Ala Thr Met Ile Gln Pro Glu Leu Ala Leu Ile Pro Ser Thr<br>405 410 415 | 1248 |
| atg aac tgc atg gag gtg gaa act aca aat ctc act tca gga caa tat<br>Met Asn Cys Met Glu Val Glu Thr Thr Asn Leu Thr Ser Gly Gln Tyr<br>420 425 430 | 1296 |
| tta tca agg ttt cta gcc aat acc act ttc aga ggc ctc agt ggt tcc<br>Leu Ser Arg Phe Leu Ala Asn Thr Thr Phe Arg Gly Leu Ser Gly Ser<br>435 440 445 | 1344 |
| att aga gta aaa ggt tcc acc atc gtc agc tca gaa aac aac ttt ttc<br>Ile Arg Val Lys Gly Ser Thr Ile Val Ser Ser Glu Asn Asn Phe Phe<br>450 455 460 | 1392 |
| atc tgg aat ctt caa cat gac ccc atg gga aag cca atg tgg acc cgc<br>Ile Trp Asn Leu Gln His Asp Pro Met Gly Lys Pro Met Trp Thr Arg<br>465 470 475 480 | 1440 |
| ttg ggc agc tgg cag ggg aga aag att gtc atg gac tat gga ata tgg<br>Leu Gly Ser Trp Gln Gly Arg Lys Ile Val Met Asp Tyr Gly Ile Trp<br>485 490 495 | 1488 |
| cca gag cag gcc cag aga cac aaa acc cac ttc caa cat cca agt aag<br>Pro Glu Gln Ala Gln Arg His Lys Thr His Phe Gln His Pro Ser Lys<br>500 505 510 | 1536 |
| cta cac ttg aga gtg gtt acc ctg att gag cat cct ttt gtc ttc aca<br>Leu His Leu Arg Val Val Thr Leu Ile Glu His Pro Phe Val Phe Thr<br>515 520 525 | 1584 |
| agg gag gta gat gat gaa ggc ttg tgc cct gct ggc caa ctc tgt cta<br>Arg Glu Val Asp Asp Glu Gly Leu Cys Pro Ala Gly Gln Leu Cys Leu<br>530 535 540 | 1632 |
| gac ccc atg act aat gac tct tcc aca ctg gac agc ctt ttt agc agc<br>Asp Pro Met Thr Asn Asp Ser Ser Thr Leu Asp Ser Leu Phe Ser Ser<br>545 550 555 560 | 1680 |
| ctc cat agc agt aat gat aca gtg ccc att aaa ttc aag aag tgc tgc<br>Leu His Ser Ser Asn Asp Thr Val Pro Ile Lys Phe Lys Lys Cys Cys<br>565 570 575 | 1728 |
| tat gga tat tgc att gat ctg ctg gaa aag ata gca gaa gac atg aac<br>Tyr Gly Tyr Cys Ile Asp Leu Leu Glu Lys Ile Ala Glu Asp Met Asn<br>580 585 590 | 1776 |
| ttt gac ttc gac ctc tat att gta ggg gat gga aag tat gga gca tgg<br>Phe Asp Phe Asp Leu Tyr Ile Val Gly Asp Gly Lys Tyr Gly Ala Trp<br>595 600 605 | 1824 |
| aaa aat ggg cac tgg act ggg cta gtg ggt gat ctc ctg aga ggg act<br>Lys Asn Gly His Trp Thr Gly Leu Val Gly Asp Leu Leu Arg Gly Thr<br>610 615 620 | 1872 |
| gcc cac atg gca gtc act tcc ttt agc atc aat act gca cgg agc cag<br>Ala His Met Ala Val Thr Ser Phe Ser Ile Asn Thr Ala Arg Ser Gln<br>625 630 635 640 | 1920 |
| gtg ata gac ttc acc agc cct ttc ttc tcc acc agc ttg ggc atc tta<br>Val Ile Asp Phe Thr Ser Pro Phe Phe Ser Thr Ser Leu Gly Ile Leu<br>645 650 655 | 1968 |

-continued

```
gtg agg acc cga gat aca gca gct ccc att gga gcc ttc atg tgg cca       2016
Val Arg Thr Arg Asp Thr Ala Ala Pro Ile Gly Ala Phe Met Trp Pro
         660                 665                 670 ctc cac tgg aca atg tgg ctg ggg att ttt gtg gct ctg cac atc act       2064
Leu His Trp Thr Met Trp Leu Gly Ile Phe Val Ala Leu His Ile Thr
675                 680                 685 gcc gtc ttc ctc act ctg tat gaa tgg aag agt cca ttt ggt ttg act       2112
Ala Val Phe Leu Thr Leu Tyr Glu Trp Lys Ser Pro Phe Gly Leu Thr
         690                 695                 700 ccc aag ggg cga aat aga agt aaa gtc ttc tcc ttt tct tca gcc ttg       2160
Pro Lys Gly Arg Asn Arg Ser Lys Val Phe Ser Phe Ser Ser Ala Leu
705                 710                 715                 720 aac atc tgt tat gcc ctc ttg ttt ggc aga aca gtg gcc atc aaa cct       2208
Asn Ile Cys Tyr Ala Leu Leu Phe Gly Arg Thr Val Ala Ile Lys Pro
             725                 730                 735 cca aaa tgt tgg act gga agg ttt cta atg aac ttt ggc att ttc          2256
Pro Lys Cys Trp Thr Gly Arg Phe Leu Met Asn Leu Trp Ala Ile Phe
         740                 745                 750 tgt atg ttt tgc ctt tcc aca tac acg gca aac ttg gct gct gtc atg       2304
Cys Met Phe Cys Leu Ser Thr Tyr Thr Ala Asn Leu Ala Ala Val Met
             755                 760                 765 gta ggt gag aag atc tat gaa gag ctt tct gga ata cat gac ccc aag       2352
Val Gly Glu Lys Ile Tyr Glu Glu Leu Ser Gly Ile His Asp Pro Lys
770                 775                 780 tta cat cat cct tcc caa gga ttc cgc ttt gga act gtc cga gaa agc       2400
Leu His His Pro Ser Gln Gly Phe Arg Phe Gly Thr Val Arg Glu Ser
785                 790                 795                 800 agt gct gaa gat tat gtg aga caa agt ttc cca gag atg cat gaa tat       2448
Ser Ala Glu Asp Tyr Val Arg Gln Ser Phe Pro Glu Met His Glu Tyr
                 805                 810                 815 atg aga agg tac aat gtt cca gcc acc cct gat gga gtg gag tat ctg       2496
Met Arg Arg Tyr Asn Val Pro Ala Thr Pro Asp Gly Val Glu Tyr Leu
             820                 825                 830 aag aat gat cca gag aaa cta gac gcc ttc atc atg gac aaa gcc ctt       2544
Lys Asn Asp Pro Glu Lys Leu Asp Ala Phe Ile Met Asp Lys Ala Leu
         835                 840                 845 ctg gat tat gaa gtg tca ata gat gct gac tgc aaa ctt ctc act gtg       2592
Leu Asp Tyr Glu Val Ser Ile Asp Ala Asp Cys Lys Leu Leu Thr Val
850                 855                 860 ggg aag cca ttt gcc ata gaa gga tac ggc att ggc ctc cca ccc aac       2640
Gly Lys Pro Phe Ala Ile Glu Gly Tyr Gly Ile Gly Leu Pro Pro Asn
865                 870                 875                 880 tct cca ttg acc gcc aac ata tcc gag cta atc agt caa tac aag tca       2688
Ser Pro Leu Thr Ala Asn Ile Ser Glu Leu Ile Ser Gln Tyr Lys Ser
                 885                 890                 895 cat ggg ttt atg gat atg ctc cat gac aag tgg tac agg gtg gtt ccc       2736
His Gly Phe Met Asp Met Leu His Asp Lys Trp Tyr Arg Val Val Pro
             900                 905                 910 tgt ggc aag aga agt ttt gct gtc acg gag act ttg caa atg ggc atc       2784
Cys Gly Lys Arg Ser Phe Ala Val Thr Glu Thr Leu Gln Met Gly Ile
         915                 920                 925 aaa cac ttc tct ggg ctc ttt gtg ctg ctg tgc att gga ttt ggt ctg       2832
Lys His Phe Ser Gly Leu Phe Val Leu Leu Cys Ile Gly Phe Gly Leu
930                 935                 940 tcc att ttg acc acc att ggt gag cac ata gta tac agg ctg ctg cta       2880
Ser Ile Leu Thr Thr Ile Gly Glu His Ile Val Tyr Arg Leu Leu Leu
945                 950                 955                 960 cca cga atc aaa aac aaa tcc aag ctg caa tac tgg ctc cac acc agc       2928
Pro Arg Ile Lys Asn Lys Ser Lys Leu Gln Tyr Trp Leu His Thr Ser
             965                 970                 975
```

| | | |
|---|---|---|
| cag aga tta cac aga gca ata aat aca tca ttt ata gag gaa aag cag<br>Gln Arg Leu His Arg Ala Ile Asn Thr Ser Phe Ile Glu Glu Lys Gln<br>       980                      985                 990 | | 2976 |
| cag cat ttc aag acc aaa cgt gtg gaa aag agg tct aat gtg gga ccc<br>Gln His Phe Lys Thr Lys Arg Val Glu Lys Arg Ser Asn Val Gly Pro<br>        995                   1000              1005 | | 3024 |
| cgt cag ctt acc gta tgg aat act tcc aat ctg agt cat gac aac cga<br>Arg Gln Leu Thr Val Trp Asn Thr Ser Asn Leu Ser His Asp Asn Arg<br>1010                   1015               1020 | | 3072 |
| cgg aaa tac atc ttt agt gat gag gaa gga caa aac cag ctg ggc atc<br>Arg Lys Tyr Ile Phe Ser Asp Glu Glu Gly Gln Asn Gln Leu Gly Ile<br>1025                 1030               1035               1040 | | 3120 |
| cag atc cac cag gac atc ccc ctc cct cca agg aga aga gag ctc cct<br>Gln Ile His Gln Asp Ile Pro Leu Pro Pro Arg Arg Arg Glu Leu Pro<br>                1045               1050               1055 | | 3168 |
| gcc ttg cgg acc acc aat ggg aaa gca gac tcc cta aat gta tct cgg<br>Ala Leu Arg Thr Thr Asn Gly Lys Ala Asp Ser Leu Asn Val Ser Arg<br>              1060               1065               1070 | | 3216 |
| aac tca gtg atg cag gaa ctc tca gag ctc gag aag cag att cag gtg<br>Asn Ser Val Met Gln Glu Leu Ser Glu Leu Glu Lys Gln Ile Gln Val<br>1075                   1080               1085 | | 3264 |
| atc cgt cag gag ctg cag ctg gct gtg agc agg aaa acg gag ctg gag<br>Ile Arg Gln Glu Leu Gln Leu Ala Val Ser Arg Lys Thr Glu Leu Glu<br>         1090               1095               1100 | | 3312 |
| gag tat caa agg aca agt cgg act tgt gag tcc tag gtgaccacac<br>Glu Tyr Gln Arg Thr Ser Arg Thr Cys Glu Ser  *<br>1105                   1110               1115 | | 3358 |
| tgcttccctt tctcagttcc tgaccttcct ctgagcccctt gagacacttt gtaatgctct | | 3418 |
| tttgtaacta tcgacaaagg tgtggggaag ctgaggtcta ggtcttctta aaggtcaagt | | 3478 |
| ctgctctccc tcgcctaaag tgcagcagca gctcctctca agctcactct ctaggtctcc | | 3538 |
| agggtaggag tgttttttcta gcaagaatct tagtcaggag taagctctgt gcgagagatc | | 3598 |
| tgtgaataac cagataaccc cagctgccgt taacctttttc accaggtgcc acagtaatat | | 3658 |
| ttctggtttt tagcccctttc tctgcactac caacaagaga taaaattgtt actcacactt | | 3718 |
| atgtcttact gggttgctgg ttttcatcgt aacacagaac gaggttatct agggttgtag | | 3778 |
| cttttgatac aactccccga tctagattta ttcctacatt ctgaatgggg agcaggtaag | | 3838 |
| agcagagcac ctcccactgg gggtggggta tttaaaaatt aactcattag tatcataaac | | 3898 |
| gtcaaggatt gattggacca ggcaagagcc atgtttttga aaggttctg gatctctgac | | 3958 |
| tccatcctga ctgtttagta agagcatgct tacaccctac tgtgaaaagg ggaggggatg | | 4018 |
| tggtaagcag aaacagaaga caggcagcag aggcattaaa aatgcatacc atgctttcag | | 4078 |
| aacaaaagct ctgggccaga aaggcaattt ggctaaaaaa tgaataagac tacttctaat | | 4138 |
| gtaactaagc atctccacta tggtgtgtgc cttttataaa ggaaaaaaaa aaaaaaagg | | 4197 |

<210> SEQ ID NO 22
<211> LENGTH: 1115
<212> TYPE: PRT
<213> ORGANISM: Homo Sapiens

<400> SEQUENCE: 22

Met Arg Arg Leu Ser Leu Trp Trp Leu Leu Ser Arg Val Cys Leu Leu
1               5                   10                15

Leu Pro Pro Pro Cys Ala Leu Val Leu Ala Gly Val Pro Ser Ser Ser
              20                 25                30

```
Ser His Pro Gln Pro Cys Gln Ile Leu Lys Arg Ile Gly His Ala Val
        35                  40                  45

Arg Val Gly Ala Val His Leu Gln Pro Trp Thr Thr Ala Pro Arg Ala
50                  55                  60

Ala Ser Arg Ala Pro Asp Asp Ser Arg Ala Gly Ala Gln Arg Asp Glu
65                  70                  75                  80

Pro Glu Pro Gly Thr Arg Arg Ser Pro Ala Pro Ser Pro Gly Ala Arg
                85                  90                  95

Trp Leu Gly Ser Thr Leu His Gly Arg Gly Pro Pro Gly Ser Arg Lys
                100                 105                 110

Pro Gly Glu Gly Ala Arg Ala Glu Ala Leu Trp Pro Arg Asp Ala Leu
        115                 120                 125

Leu Phe Ala Val Asp Asn Leu Asn Arg Val Glu Gly Leu Leu Pro Tyr
130                 135                 140

Asn Leu Ser Leu Glu Val Val Met Ala Ile Glu Ala Gly Leu Gly Asp
145                 150                 155                 160

Leu Pro Leu Leu Pro Phe Ser Ser Pro Ser Ser Pro Trp Ser Ser Asp
                165                 170                 175

Pro Phe Ser Phe Leu Gln Ser Val Cys His Thr Val Val Val Gln Gly
                180                 185                 190

Val Ser Ala Leu Leu Ala Phe Pro Gln Ser Gln Gly Glu Met Met Glu
        195                 200                 205

Leu Asp Leu Val Ser Leu Val Leu His Ile Pro Val Ile Ser Ile Val
        210                 215                 220

Arg His Glu Phe Pro Arg Glu Ser Gln Asn Pro Leu His Leu Gln Leu
225                 230                 235                 240

Ser Leu Glu Asn Ser Leu Ser Ser Asp Ala Asp Val Thr Val Ser Ile
                245                 250                 255

Leu Thr Met Asn Asn Trp Tyr Asn Phe Ser Leu Leu Leu Cys Gln Glu
                260                 265                 270

Asp Trp Asn Ile Thr Asp Phe Leu Leu Leu Thr Gln Asn Asn Ser Lys
                275                 280                 285

Phe His Leu Gly Ser Ile Ile Asn Ile Thr Ala Asn Leu Pro Ser Thr
        290                 295                 300

Gln Asp Leu Leu Ser Phe Leu Gln Ile Gln Leu Glu Ser Ile Lys Asn
305                 310                 315                 320

Ser Thr Pro Thr Val Val Met Phe Gly Cys Asp Met Glu Ser Ile Arg
                325                 330                 335

Arg Ile Phe Glu Ile Thr Thr Gln Phe Gly Val Met Pro Pro Glu Leu
                340                 345                 350

Arg Trp Val Leu Gly Asp Ser Gln Asn Met Glu Glu Leu Arg Thr Glu
                355                 360                 365

Gly Leu Pro Leu Gly Leu Ile Ala His Gly Lys Thr Thr Gln Ser Val
        370                 375                 380

Phe Glu His Tyr Val Gln Asp Ala Met Glu Leu Val Ala Arg Ala Val
385                 390                 395                 400

Ala Thr Ala Thr Met Ile Gln Pro Glu Leu Ala Leu Ile Pro Ser Thr
                405                 410                 415

Met Asn Cys Met Glu Val Glu Thr Thr Asn Leu Thr Ser Gly Gln Tyr
                420                 425                 430

Leu Ser Arg Phe Leu Ala Asn Thr Thr Phe Arg Gly Leu Ser Gly Ser
        435                 440                 445
```

```
Ile Arg Val Lys Gly Ser Thr Ile Val Ser Ser Glu Asn Asn Phe Phe
    450                 455                 460

Ile Trp Asn Leu Gln His Asp Pro Met Gly Lys Pro Met Trp Thr Arg
465                 470                 475                 480

Leu Gly Ser Trp Gln Gly Arg Lys Ile Val Met Asp Tyr Gly Ile Trp
                    485                 490                 495

Pro Glu Gln Ala Gln Arg His Lys Thr His Phe Gln His Pro Ser Lys
                500                 505                 510

Leu His Leu Arg Val Val Thr Leu Ile Glu His Pro Phe Val Phe Thr
            515                 520                 525

Arg Glu Val Asp Asp Glu Gly Leu Cys Pro Ala Gly Gln Leu Cys Leu
        530                 535                 540

Asp Pro Met Thr Asn Asp Ser Ser Thr Leu Asp Ser Leu Phe Ser Ser
545                 550                 555                 560

Leu His Ser Ser Asn Asp Thr Val Pro Ile Lys Phe Lys Lys Cys Cys
                565                 570                 575

Tyr Gly Tyr Cys Ile Asp Leu Leu Glu Lys Ile Ala Glu Asp Met Asn
                580                 585                 590

Phe Asp Phe Asp Leu Tyr Ile Val Gly Asp Gly Lys Tyr Gly Ala Trp
        595                 600                 605

Lys Asn Gly His Trp Thr Gly Leu Val Gly Asp Leu Leu Arg Gly Thr
610                 615                 620

Ala His Met Ala Val Thr Ser Phe Ser Ile Asn Thr Ala Arg Ser Gln
625                 630                 635                 640

Val Ile Asp Phe Thr Ser Pro Phe Phe Ser Thr Ser Leu Gly Ile Leu
                645                 650                 655

Val Arg Thr Arg Asp Thr Ala Ala Pro Ile Gly Ala Phe Met Trp Pro
                660                 665                 670

Leu His Trp Thr Met Trp Leu Gly Ile Phe Val Ala Leu His Ile Thr
        675                 680                 685

Ala Val Phe Leu Thr Leu Tyr Glu Trp Lys Ser Pro Phe Gly Leu Thr
690                 695                 700

Pro Lys Gly Arg Asn Arg Ser Lys Val Phe Ser Phe Ser Ser Ala Leu
705                 710                 715                 720

Asn Ile Cys Tyr Ala Leu Leu Phe Gly Arg Thr Val Ala Ile Lys Pro
                725                 730                 735

Pro Lys Cys Trp Thr Gly Arg Phe Leu Met Asn Leu Trp Ala Ile Phe
                740                 745                 750

Cys Met Phe Cys Leu Ser Thr Tyr Thr Ala Asn Leu Ala Ala Val Met
        755                 760                 765

Val Gly Glu Lys Ile Tyr Glu Glu Leu Ser Gly Ile His Asp Pro Lys
770                 775                 780

Leu His His Pro Ser Gln Gly Phe Arg Phe Gly Thr Val Arg Glu Ser
785                 790                 795                 800

Ser Ala Glu Asp Tyr Val Arg Gln Ser Phe Pro Glu Met His Glu Tyr
                805                 810                 815

Met Arg Arg Tyr Asn Val Pro Ala Thr Pro Asp Gly Val Glu Tyr Leu
                820                 825                 830

Lys Asn Asp Pro Glu Lys Leu Asp Ala Phe Ile Met Asp Lys Ala Leu
            835                 840                 845

Leu Asp Tyr Glu Val Ser Ile Asp Ala Asp Cys Lys Leu Leu Thr Val
850                 855                 860
```

```
Gly Lys Pro Phe Ala Ile Glu Gly Tyr Gly Ile Gly Leu Pro Pro Asn
865                 870                 875                 880

Ser Pro Leu Thr Ala Asn Ile Ser Glu Leu Ile Ser Gln Tyr Lys Ser
            885                 890                 895

His Gly Phe Met Asp Met Leu His Asp Lys Trp Tyr Arg Val Val Pro
                900                 905                 910

Cys Gly Lys Arg Ser Phe Ala Val Thr Glu Thr Leu Gln Met Gly Ile
            915                 920                 925

Lys His Phe Ser Gly Leu Phe Val Leu Leu Cys Ile Gly Phe Gly Leu
        930                 935                 940

Ser Ile Leu Thr Thr Ile Gly Glu His Ile Val Tyr Arg Leu Leu Leu
945                 950                 955                 960

Pro Arg Ile Lys Asn Lys Ser Lys Leu Gln Tyr Trp Leu His Thr Ser
                965                 970                 975

Gln Arg Leu His Arg Ala Ile Asn Thr Ser Phe Ile Glu Glu Lys Gln
            980                 985                 990

Gln His Phe Lys Thr Lys Arg Val Glu Lys Arg Ser Asn Val Gly Pro
        995                 1000                1005

Arg Gln Leu Thr Val Trp Asn Thr Ser Asn Leu Ser His Asp Asn Arg
    1010                1015                1020

Arg Lys Tyr Ile Phe Ser Asp Glu Glu Gly Gln Asn Gln Leu Gly Ile
1025                1030                1035                1040

Gln Ile His Gln Asp Ile Pro Leu Pro Pro Arg Arg Glu Leu Pro
                1045                1050                1055

Ala Leu Arg Thr Thr Asn Gly Lys Ala Asp Ser Leu Asn Val Ser Arg
            1060                1065                1070

Asn Ser Val Met Gln Glu Leu Ser Glu Leu Gly Lys Gln Ile Gln Val
        1075                1080                1085

Ile Arg Gln Glu Leu Gln Leu Ala Val Ser Arg Lys Thr Glu Leu Glu
    1090                1095                1100

Glu Tyr Gln Arg Thr Ser Arg Thr Cys Glu Ser
1105                1110                1115

<210> SEQ ID NO 23
<211> LENGTH: 2561
<212> TYPE: DNA
<213> ORGANISM: Homo Sapiens
<220> FEATURE:
<221> NAME/KEY: CDS
<222> LOCATION: (184)...(1830)
<220> FEATURE:
<221> NAME/KEY: misc_feature
<222> LOCATION: (1)...(2561)
<223> OTHER INFORMATION: n = A,T,C or G

<400> SEQUENCE: 23
ccacgcgtcc gggctttgtc tcgtgggctg gtcccagcg  gctccctccc cgaacagctg      60
ctgctccagg gaggaagcgg cgcgggtgct gtccagcttc ccggtgctga aaaccggagg     120
gctcgtcatc caccactacc atgtaagggc catgagaagg gctcatcctg gcgcagcgcg     180 gac atg gag gag gac tta ttc cag cta agg cag ctg ccg gtt gtg aaa      228
    Met Glu Glu Asp Leu Phe Gln Leu Arg Gln Leu Pro Val Val Lys
    1               5                   10                  15 ttc cgt cgc aca ggc gag agt gca agg tca gag gac gac acg gct tca     276
Phe Arg Arg Thr Gly Glu Ser Ala Arg Ser Glu Asp Asp Thr Ala Ser
            20                  25                  30
```

-continued

| | | |
|---|---|---|
| gga gag cat gaa gtc cag att gaa ggg gtc cac gtg ggc cta gag gct<br>Gly Glu His Glu Val Gln Ile Glu Gly Val His Val Gly Leu Glu Ala<br>35                  40                  45 | 324 |
| gtg gag ctg gat gat ggg gca gct gtg ccc aag gag ttt gcc aat ccc<br>Val Glu Leu Asp Asp Gly Ala Ala Val Pro Lys Glu Phe Ala Asn Pro<br>50                    55                  60 | 372 |
| acc gat gat act ttc atg gtg gaa gat gca gtg gaa gcc att ggc ttt<br>Thr Asp Asp Thr Phe Met Val Glu Asp Ala Val Glu Ala Ile Gly Phe<br>65                    70                  75 | 420 |
| gga aaa ttt cag tgg aag ctg tct gtt ctc act ggc ttg gct tgg atg<br>Gly Lys Phe Gln Trp Lys Leu Ser Val Leu Thr Gly Leu Ala Trp Met<br>80                    85                  90                  95 | 468 |
| gct gat gcc atg gag atg atg atc ctc agc atc ctg gca cca cag ctg<br>Ala Asp Ala Met Glu Met Met Ile Leu Ser Ile Leu Ala Pro Gln Leu<br>100                 105               110 | 516 |
| cat tgc gag tgg agg ctc cca agc tgg cag gtg gca ttg ctg acc tcg<br>His Cys Glu Trp Arg Leu Pro Ser Trp Gln Val Ala Leu Leu Thr Ser<br>115                 120               125 | 564 |
| gtg gtc ttt gta ggc atg atg tcc agc tcc acg ctc tgg gga aat atc<br>Val Val Phe Val Gly Met Met Ser Ser Ser Thr Leu Trp Gly Asn Ile<br>130                 135               140 | 612 |
| tca gac cag tac ggc agg aaa aca ggg ctg aag atc agc gtg ctg tgg<br>Ser Asp Gln Tyr Gly Arg Lys Thr Gly Leu Lys Ile Ser Val Leu Trp<br>145                 150               155 | 660 |
| act ctg tac tat ggc atc ctt agt gca ttt gcg ccc gtg tat agc tgg<br>Thr Leu Tyr Tyr Gly Ile Leu Ser Ala Phe Ala Pro Val Tyr Ser Trp<br>160                 165               170               175 | 708 |
| atc ctg gtg ctc cgg ggc ctg gtg ggc ttc ggg atc gga gga gtt ccc<br>Ile Leu Val Leu Arg Gly Leu Val Gly Phe Gly Ile Gly Gly Val Pro<br>180                 185               190 | 756 |
| cag tcg gtg acg ctg tat gcc gag ttc ctt ccc atg aaa gcc aga gct<br>Gln Ser Val Thr Leu Tyr Ala Glu Phe Leu Pro Met Lys Ala Arg Ala<br>195                 200               205 | 804 |
| aaa tgt att ttg ctg att gag gta ttc tgg gcc atc ggg aca gtg ttc<br>Lys Cys Ile Leu Leu Ile Glu Val Phe Trp Ala Ile Gly Thr Val Phe<br>210                 215               220 | 852 |
| gag gtc gtc ctg gct gtg ttc gtg atg ccc agc ctg ggc tgg cgt tgg<br>Glu Val Val Leu Ala Val Phe Val Met Pro Ser Leu Gly Trp Arg Trp<br>225                 230               235 | 900 |
| ctc ctc atc ctc tca gct gtc ccg ctc ctc ctc ttt gcc gtg ctg tgt<br>Leu Leu Ile Leu Ser Ala Val Pro Leu Leu Leu Phe Ala Val Leu Cys<br>240                 245               250               255 | 948 |
| ttc tgg ctg cct gaa agt gca agg tat gat gtg ctg tca ggg aac cag<br>Phe Trp Leu Pro Glu Ser Ala Arg Tyr Asp Val Leu Ser Gly Asn Gln<br>260                 265               270 | 996 |
| gaa aag gca atc gcc acc tta aag agg ata gca act gaa aac gga gct<br>Glu Lys Ala Ile Ala Thr Leu Lys Arg Ile Ala Thr Glu Asn Gly Ala<br>275                 280               285 | 1044 |
| ccc atg ccg ctg ggg aaa ctc atc atc tcc aga cag gaa gac cga ggc<br>Pro Met Pro Leu Gly Lys Leu Ile Ile Ser Arg Gln Glu Asp Arg Gly<br>290                 295               300 | 1092 |
| aaa atg agg gac ctt ttc aca ccc cat ttt aga tgg aca act ttg ctg<br>Lys Met Arg Asp Leu Phe Thr Pro His Phe Arg Trp Thr Thr Leu Leu<br>305                 310               315 | 1140 |
| ctg tgg ttt ata tgg ttt tcc aat gca ttc tct tac tac ggg tta gtt<br>Leu Trp Phe Ile Trp Phe Ser Asn Ala Phe Ser Tyr Tyr Gly Leu Val<br>320                 325               330               335 | 1188 |
| cta ctc acc aca gaa ctc ttc cag gca gga gat gtc tgc ggc atc tcc<br>Leu Leu Thr Thr Glu Leu Phe Gln Ala Gly Asp Val Cys Gly Ile Ser<br>340                 345               350 | 1236 |

```
                                                -continued agt cgg aag aag gct gta gag gca aaa tgc agc ctg gcc tgc gag tac      1284
Ser Arg Lys Lys Ala Val Glu Ala Lys Cys Ser Leu Ala Cys Glu Tyr
        355                 360                 365 ctg agt gag gag gat tac atg gac ttg ctg tgg acc acc ctc tct gag      1332
Leu Ser Glu Glu Asp Tyr Met Asp Leu Leu Trp Thr Thr Leu Ser Glu
    370                 375                 380 ttt cca ggt gtc ctt gtg act ctg tgg att att gac cgc ctg ggg cgc      1380
Phe Pro Gly Val Leu Val Thr Leu Trp Ile Ile Asp Arg Leu Gly Arg
385                 390                 395 aag aag acc atg gcc ctg tgc ttt gtc atc ttc tcc ttc tgc agc ctc      1428
Lys Lys Thr Met Ala Leu Cys Phe Val Ile Phe Ser Phe Cys Ser Leu
400                 405                 410                 415 ctg ctg ttt atc tgt gtt gga aga aat gtg ctc act ctg tta ctc ttc      1476
Leu Leu Phe Ile Cys Val Gly Arg Asn Val Leu Thr Leu Leu Leu Phe
            420                 425                 430 att gca aga gcg ttt att tct gga ggc ttt caa gcg gca tat gtt tac      1524
Ile Ala Arg Ala Phe Ile Ser Gly Gly Phe Gln Ala Ala Tyr Val Tyr
        435                 440                 445 aca cct gag gtc tac ccc acg gca acg cgg gcc ctc ggc ctg ggc acc      1572
Thr Pro Glu Val Tyr Pro Thr Ala Thr Arg Ala Leu Gly Leu Gly Thr
    450                 455                 460 tgc agc ggc atg gca aga gtg ggt gct ctc atc act ccg ttc atc gcc      1620
Cys Ser Gly Met Ala Arg Val Gly Ala Leu Ile Thr Pro Phe Ile Ala
465                 470                 475 cag gtg atg ctg gaa tcc tct gtg tac ctg act ctg gca gtt tac agt      1668
Gln Val Met Leu Glu Ser Ser Val Tyr Leu Thr Leu Ala Val Tyr Ser
480                 485                 490                 495 ggc tgc tgc ctc ctg gct gcc ctg gcc tcc tgc ttt ttg ccc att gag      1716
Gly Cys Cys Leu Leu Ala Ala Leu Ala Ser Cys Phe Leu Pro Ile Glu
            500                 505                 510 acc aaa ggc gga gga ctg cag gag tcc agc cac cgg gag tgg ggc cag      1764
Thr Lys Gly Gly Gly Leu Gln Glu Ser Ser His Arg Glu Trp Gly Gln
        515                 520                 525 gag atg gtc ggc cga gga atg cac ggt gca ggt gtt acc agg tcg aac      1812
Glu Met Val Gly Arg Gly Met His Gly Ala Gly Val Thr Arg Ser Asn
    530                 535                 540 tct ggc tct cag gaa tag tgaccgatgg gggactgagc tggtctttga             1860
Ser Gly Ser Gln Glu *
545 ggctgcagag cttgggggc tggcaggccc caactggggc actgattgtc actgccgaca     1920 tcaagaactc acccaagagt atgacctgga ccaacagggt tttgtgtctt gactcagttt    1980 gctcatcttc attgaggtcc acccagggat ggggagatgt tgctctagg ggttctctg      2040 tatatgtggt gaaagctttg ttcataacct gtggatctac atgggaagac tacccatatt    2100 aggagggtct ggtaatgcca gcaaccaatc agacaccacc cagagtcacc cggccaaacc    2160 ctcagtgaac aaccaaaata tctctctgta gataccgtcc aggctcaggc ccatgtgaca    2220 cctgctgtcc acccaccgga cctgttcagt aggtttctcc cacacccaca gccccaggct    2280 ttcttctttg aaattgcagg cgatctaggt gtggtctgag cagctatttc ctggcagggg    2340 ccccccggtt tgcctcccta gagcctgacc agtggattct ctggcagatg gacatggtgc    2400 attcaaactg gagccacatg cccccaccca gccctnttg gagttgcccg ttgttggcac     2460 caagagatcc agatgtgtcc tggggacagc tgggtcttgc accaggtgac aacctcaaaa    2520 cgccgttacc ccctggggaa ctgaggactg agngccaagt g                       2561
```

<210> SEQ ID NO 24
<211> LENGTH: 548
<212> TYPE: PRT
<213> ORGANISM: Homo Sapiens

<400> SEQUENCE: 24

```
Met Glu Glu Asp Leu Phe Gln Leu Arg Gln Leu Pro Val Val Lys Phe
 1               5                  10                  15

Arg Arg Thr Gly Glu Ser Ala Arg Ser Glu Asp Asp Thr Ala Ser Gly
             20                  25                  30

Glu His Glu Val Gln Ile Glu Gly Val His Val Gly Leu Glu Ala Val
         35                  40                  45

Glu Leu Asp Asp Gly Ala Ala Val Pro Lys Glu Phe Ala Asn Pro Thr
     50                  55                  60

Asp Asp Thr Phe Met Val Glu Asp Ala Val Glu Ala Ile Gly Phe Gly
 65                  70                  75                  80

Lys Phe Gln Trp Lys Leu Ser Val Leu Thr Gly Leu Ala Trp Met Ala
                 85                  90                  95

Asp Ala Met Glu Met Met Ile Leu Ser Ile Leu Ala Pro Gln Leu His
            100                 105                 110

Cys Glu Trp Arg Leu Pro Ser Trp Gln Val Ala Leu Leu Thr Ser Val
        115                 120                 125

Val Phe Val Gly Met Met Ser Ser Ser Thr Leu Trp Gly Asn Ile Ser
    130                 135                 140

Asp Gln Tyr Gly Arg Lys Thr Gly Leu Lys Ile Ser Val Leu Trp Thr
145                 150                 155                 160

Leu Tyr Tyr Gly Ile Leu Ser Ala Phe Ala Pro Val Tyr Ser Trp Ile
                165                 170                 175

Leu Val Leu Arg Gly Leu Val Gly Phe Gly Ile Gly Gly Val Pro Gln
            180                 185                 190

Ser Val Thr Leu Tyr Ala Glu Phe Leu Pro Met Lys Ala Arg Ala Lys
        195                 200                 205

Cys Ile Leu Leu Ile Glu Val Phe Trp Ala Ile Gly Thr Val Phe Glu
    210                 215                 220

Val Val Leu Ala Val Phe Val Met Pro Ser Leu Gly Trp Arg Trp Leu
225                 230                 235                 240

Leu Ile Leu Ser Ala Val Pro Leu Leu Phe Ala Val Leu Cys Phe
                245                 250                 255

Trp Leu Pro Glu Ser Ala Arg Tyr Asp Val Leu Ser Gly Asn Gln Glu
            260                 265                 270

Lys Ala Ile Ala Thr Leu Lys Arg Ile Ala Thr Glu Asn Gly Ala Pro
        275                 280                 285

Met Pro Leu Gly Lys Leu Ile Ile Ser Arg Gln Glu Asp Arg Gly Lys
    290                 295                 300

Met Arg Asp Leu Phe Thr Pro His Phe Arg Trp Thr Thr Leu Leu Leu
305                 310                 315                 320

Trp Phe Ile Trp Phe Ser Asn Ala Phe Ser Tyr Tyr Gly Leu Val Leu
                325                 330                 335

Leu Thr Thr Glu Leu Phe Gln Ala Gly Asp Val Cys Gly Ile Ser Ser
            340                 345                 350

Arg Lys Lys Ala Val Glu Ala Lys Cys Ser Leu Ala Cys Glu Tyr Leu
        355                 360                 365

Ser Glu Glu Asp Tyr Met Asp Leu Leu Trp Thr Thr Leu Ser Glu Phe
    370                 375                 380
```

-continued

```
Pro Gly Val Leu Val Thr Leu Trp Ile Ile Asp Arg Leu Gly Arg Lys
385                 390                 395                 400

Lys Thr Met Ala Leu Cys Phe Val Ile Phe Ser Phe Cys Ser Leu Leu
            405                 410                 415

Leu Phe Ile Cys Val Gly Arg Asn Val Leu Thr Leu Leu Leu Phe Ile
        420                 425                 430

Ala Arg Ala Phe Ile Ser Gly Gly Phe Gln Ala Ala Tyr Val Tyr Thr
    435                 440                 445

Pro Glu Val Tyr Pro Thr Ala Thr Arg Ala Leu Gly Leu Gly Thr Cys
450                 455                 460

Ser Gly Met Ala Arg Val Gly Ala Leu Ile Thr Pro Phe Ile Ala Gln
465                 470                 475                 480

Val Met Leu Glu Ser Ser Val Tyr Leu Thr Leu Ala Val Tyr Ser Gly
                485                 490                 495

Cys Cys Leu Leu Ala Ala Leu Ala Ser Cys Phe Leu Pro Ile Glu Thr
            500                 505                 510

Lys Gly Gly Gly Leu Gln Glu Ser Ser His Arg Glu Trp Gly Gln Glu
        515                 520                 525

Met Val Gly Arg Gly Met His Gly Ala Gly Val Thr Arg Ser Asn Ser
    530                 535                 540

Gly Ser Gln Glu
545
```

<210> SEQ ID NO 25
<211> LENGTH: 2500
<212> TYPE: DNA
<213> ORGANISM: Homo Sapiens
<220> FEATURE:
<221> NAME/KEY: CDS
<222> LOCATION: (105)...(2258)

<400> SEQUENCE: 25

```
gtcgacccac gcgtccggaa atgatggagt aagagactct tttctaagca actcaagttt      60
gcagtgattc aggcctactt ctgaagagac agcctttat ctca atg aat gac aca       116
                                              Met Asn Asp Thr
                                                1 gaa aaa cca gca gat act ccc tct gag gaa gag gac ttt ggt gat cca       164
Glu Lys Pro Ala Asp Thr Pro Ser Glu Glu Glu Asp Phe Gly Asp Pro
 5              10                  15                  20 agg aca tat gac cca gat ttc aag ggg cct gtt gcc aac agg agt tgt       212
Arg Thr Tyr Asp Pro Asp Phe Lys Gly Pro Val Ala Asn Arg Ser Cys
             25                  30                  35 aca gat gtt ctg tgc tgt atg atc ttc cta ctg tgt att att ggc tac       260
Thr Asp Val Leu Cys Cys Met Ile Phe Leu Leu Cys Ile Ile Gly Tyr
         40                  45                  50 att gtt tta gga ctt gtg gcc tgg gta cat ggg gac ccc aga aga gca       308
Ile Val Leu Gly Leu Val Ala Trp Val His Gly Asp Pro Arg Arg Ala
     55                  60                  65 gcc tat cct aca gac agc cag ggc cac ttt tgt ggc cag aag ggc act       356
Ala Tyr Pro Thr Asp Ser Gln Gly His Phe Cys Gly Gln Lys Gly Thr
 70                  75                  80 ccc aat gag aac aag acc att ttg ttt tac ttt aac ctg tta cgc tgt       404
Pro Asn Glu Asn Lys Thr Ile Leu Phe Tyr Phe Asn Leu Leu Arg Cys
 85              90                  95                 100 acc agt ccc tcc gtg ttg cta aac cta cag tgc cct acc aca cag atc       452
Thr Ser Pro Ser Val Leu Leu Asn Leu Gln Cys Pro Thr Thr Gln Ile
             105                 110                 115
```

-continued

```
tgt gtc tcc aag tgc cca gaa aaa ttt tta acc tat gtg gaa atg caa        500
Cys Val Ser Lys Cys Pro Glu Lys Phe Leu Thr Tyr Val Glu Met Gln
        120                 125                 130 ctt ttg tac aca aaa gac aaa agc tac tgg gaa gac tac cgt cag ttc        548
Leu Leu Tyr Thr Lys Asp Lys Ser Tyr Trp Glu Asp Tyr Arg Gln Phe
                135                 140                 145 tgt aag acc act gct aag cct gtg aag tct ctc aca cag ctt tta ctg        596
Cys Lys Thr Thr Ala Lys Pro Val Lys Ser Leu Thr Gln Leu Leu Leu
150                 155                 160 gat gat gat tgt cca aca gcg att ttt ccc agc aaa cct ttt ctc cag        644
Asp Asp Asp Cys Pro Thr Ala Ile Phe Pro Ser Lys Pro Phe Leu Gln
165                 170                 175                 180 aga tgt ttc cct gac ttc tct acc aaa aat ggc act tta aca ata gga        692
Arg Cys Phe Pro Asp Phe Ser Thr Lys Asn Gly Thr Leu Thr Ile Gly
                185                 190                 195 agt aag atg atg ttt caa gat gga aat gga ggg aca aga agt gtt gta        740
Ser Lys Met Met Phe Gln Asp Gly Asn Gly Gly Thr Arg Ser Val Val
                    200                 205                 210 gaa ctc ggg att gct gca aat ggt atc aat aaa ctt ctt gat gca aag        788
Glu Leu Gly Ile Ala Ala Asn Gly Ile Asn Lys Leu Leu Asp Ala Lys
                215                 220                 225 tca ctt gga ttg aaa gtg ttt gaa gac tat gca aga act tgg tat tgg        836
Ser Leu Gly Leu Lys Val Phe Glu Asp Tyr Ala Arg Thr Trp Tyr Trp
230                 235                 240 att ctt att ggc ctg acg atc gcc atg gtc ctt agt tgg ata ttt ttg        884
Ile Leu Ile Gly Leu Thr Ile Ala Met Val Leu Ser Trp Ile Phe Leu
245                 250                 255                 260 ata ctt ctg agg ttc ata gct gga tgc ctc ttc tgg gtc ttc atg att        932
Ile Leu Leu Arg Phe Ile Ala Gly Cys Leu Phe Trp Val Phe Met Ile
                265                 270                 275 ggt gtg att gga att ata ggt tat gga ata tgg cac tgt tac cag cag        980
Gly Val Ile Gly Ile Ile Gly Tyr Gly Ile Trp His Cys Tyr Gln Gln
                280                 285                 290 tac acc aat ctt cag gaa cgc cca agt tct gta tta act atc tat gac       1028
Tyr Thr Asn Leu Gln Glu Arg Pro Ser Ser Val Leu Thr Ile Tyr Asp
                295                 300                 305 atc ggg att cag act aac ata agc atg tac ttt gaa ctg caa caa aca       1076
Ile Gly Ile Gln Thr Asn Ile Ser Met Tyr Phe Glu Leu Gln Gln Thr
    310                 315                 320 tgg ttc aca ttt atg ata ata ctc tgc atc att gaa gtg att gtc atc       1124
Trp Phe Thr Phe Met Ile Ile Leu Cys Ile Ile Glu Val Ile Val Ile
325                 330                 335                 340 ctc atg ctg atc ttc ctc agg aat cga atc cga gtc gcc att atc ctg       1172
Leu Met Leu Ile Phe Leu Arg Asn Arg Ile Arg Val Ala Ile Ile Leu
                345                 350                 355 ctg aag gaa gga agc aaa gcc att gga tat gtt cct agt aca tta gtc       1220
Leu Lys Glu Gly Ser Lys Ala Ile Gly Tyr Val Pro Ser Thr Leu Val
                360                 365                 370 tat cca gct tta act ttc att ttg ctc tca atc tgc att tgc tac tgg       1268
Tyr Pro Ala Leu Thr Phe Ile Leu Leu Ser Ile Cys Ile Cys Tyr Trp
                375                 380                 385 gtc gtg aca gca gtt ttc ttg gcg aca tcg ggg gta cct gta tac aaa       1316
Val Val Thr Ala Val Phe Leu Ala Thr Ser Gly Val Pro Val Tyr Lys
        390                 395                 400 gtc ata gct cca ggg ggg cat tgt ata cat gaa aat caa acc tgt gac       1364
Val Ile Ala Pro Gly Gly His Cys Ile His Glu Asn Gln Thr Cys Asp
405                 410                 415                 420 cca gag att ttt aat aca act gaa att gcc aaa gct tgc cct ggg gct       1412
Pro Glu Ile Phe Asn Thr Thr Glu Ile Ala Lys Ala Cys Pro Gly Ala
                425                 430                 435
```

```
                                                           -continued ctg tgt aac ttt gct ttc tat ggt gga aag agc ttg tac cat cag tac   1460
Leu Cys Asn Phe Ala Phe Tyr Gly Gly Lys Ser Leu Tyr His Gln Tyr
        440                 445                 450 atc cct acc ttc cat gta tac aac tta ttt gtc ttt ctc tgg ctt ata   1508
Ile Pro Thr Phe His Val Tyr Asn Leu Phe Val Phe Leu Trp Leu Ile
455                 460                 465 aac ttc gtc att gca tta ggt cag tgc gcc ctt gct ggt gca ttc gct   1556
Asn Phe Val Ile Ala Leu Gly Gln Cys Ala Leu Ala Gly Ala Phe Ala
        470                 475                 480 act tat tac tgg gcc atg aaa aaa cct gat gac atc cca cga tat cca   1604
Thr Tyr Tyr Trp Ala Met Lys Lys Pro Asp Asp Ile Pro Arg Tyr Pro
485                 490                 495                 500 ctt ttt act gca ttt gga cga gcc ata cga tat cac aca gga tcc cta   1652
Leu Phe Thr Ala Phe Gly Arg Ala Ile Arg Tyr His Thr Gly Ser Leu
        505                 510                 515 gca ttt gga tct tta att att gca tta att caa atg ttt aaa att gta   1700
Ala Phe Gly Ser Leu Ile Ile Ala Leu Ile Gln Met Phe Lys Ile Val
        520                 525                 530 cta gaa tac ttg gac cac cgt ctt aaa cgt acc cag aac aca ttg tct   1748
Leu Glu Tyr Leu Asp His Arg Leu Lys Arg Thr Gln Asn Thr Leu Ser
        535                 540                 545 aaa ttc cta cag tgc tgc ctg aga tgc tgc ttc tgg tgt ttg gaa aat   1796
Lys Phe Leu Gln Cys Cys Leu Arg Cys Cys Phe Trp Cys Leu Glu Asn
550                 555                 560 gca ata aag ttt tta aac aga aat gcc tat att atg att gca ata tat   1844
Ala Ile Lys Phe Leu Asn Arg Asn Ala Tyr Ile Met Ile Ala Ile Tyr
565                 570                 575                 580 ggc aga aac ttc tgc agg tca gca aaa gat gct ttc aat ctg ctg atg   1892
Gly Arg Asn Phe Cys Arg Ser Ala Lys Asp Ala Phe Asn Leu Leu Met
                585                 590                 595 aga aat gtt ttg aaa gtt gca gtt aca gat gaa gtt aca tac ttt gta   1940
Arg Asn Val Leu Lys Val Ala Val Thr Asp Glu Val Thr Tyr Phe Val
        600                 605                 610 tta ttc ctg ggg aaa ctt cta gtt gct gga agt ata ggt gtt ctg gcc   1988
Leu Phe Leu Gly Lys Leu Leu Val Ala Gly Ser Ile Gly Val Leu Ala
        615                 620                 625 ttc cta ttc ttc aca caa aga ctg cca gtg att gca caa gga cca gca   2036
Phe Leu Phe Phe Thr Gln Arg Leu Pro Val Ile Ala Gln Gly Pro Ala
        630                 635                 640 tct tta aat tac tac tgg gta cct ttg ctg aca gtc att ttt ggg tct   2084
Ser Leu Asn Tyr Tyr Trp Val Pro Leu Leu Thr Val Ile Phe Gly Ser
645                 650                 655                 660 tac ctg att gca cat ggg ttc ttc agc gtc tat gca atg tgt gtt gaa   2132
Tyr Leu Ile Ala His Gly Phe Phe Ser Val Tyr Ala Met Cys Val Glu
                665                 670                 675 aca att ttc atc tgc ttc ttg gaa gat tta gaa aga aat gat ggt tct   2180
Thr Ile Phe Ile Cys Phe Leu Glu Asp Leu Glu Arg Asn Asp Gly Ser
        680                 685                 690 act gca aga cct tat tat gtg agt caa cct ttg ctg aag att ttc cag   2228
Thr Ala Arg Pro Tyr Tyr Val Ser Gln Pro Leu Leu Lys Ile Phe Gln
        695                 700                 705 gag gaa aat cca caa act agg aag cag tag aagagcaaac tggtcgtcct    2278
Glu Glu Asn Pro Gln Thr Arg Lys Gln *
        710                 715 acagctgtgt gttacctttt ctccatctgc tgtgtctgtg caacatttgt ttcataagtg   2338
ctttgtgttt agcaacactg tattcacgac cttgttggct tgcatttgca tgttttatac   2398
caaagcttat actgtactat gtgaagccat cagaagtcgc aagggaattg ttaataacat   2458
aaaacatttt tatactaaaa aaaaaaaaaa aagggcggcc gc                      2500
```

<210> SEQ ID NO 26
<211> LENGTH: 717
<212> TYPE: PRT
<213> ORGANISM: Homo Sapiens

<400> SEQUENCE: 26

```
Met Asn Asp Thr Glu Lys Pro Ala Asp Thr Pro Ser Glu Glu Glu Asp
1               5                   10                  15

Phe Gly Asp Pro Arg Thr Tyr Asp Pro Asp Phe Lys Gly Pro Val Ala
            20                  25                  30

Asn Arg Ser Cys Thr Asp Val Leu Cys Cys Met Ile Phe Leu Leu Cys
        35                  40                  45

Ile Ile Gly Tyr Ile Val Leu Gly Leu Val Ala Trp Val His Gly Asp
    50                  55                  60

Pro Arg Arg Ala Ala Tyr Pro Thr Asp Ser Gln Gly His Phe Cys Gly
65                  70                  75                  80

Gln Lys Gly Thr Pro Asn Glu Asn Lys Thr Ile Leu Phe Tyr Phe Asn
                85                  90                  95

Leu Leu Arg Cys Thr Ser Pro Ser Val Leu Asn Leu Gln Cys Pro
            100                 105                 110

Thr Thr Gln Ile Cys Val Ser Lys Cys Pro Glu Lys Phe Leu Thr Tyr
            115                 120                 125

Val Glu Met Gln Leu Leu Tyr Thr Lys Asp Lys Ser Tyr Trp Glu Asp
130                 135                 140

Tyr Arg Gln Phe Cys Lys Thr Thr Ala Lys Pro Val Lys Ser Leu Thr
145                 150                 155                 160

Gln Leu Leu Leu Asp Asp Cys Pro Thr Ala Ile Phe Pro Ser Lys
                165                 170                 175

Pro Phe Leu Gln Arg Cys Phe Pro Asp Phe Ser Thr Lys Asn Gly Thr
            180                 185                 190

Leu Thr Ile Gly Ser Lys Met Met Phe Gln Asp Gly Asn Gly Gly Thr
        195                 200                 205

Arg Ser Val Val Glu Leu Gly Ile Ala Ala Asn Gly Ile Asn Lys Leu
    210                 215                 220

Leu Asp Ala Lys Ser Leu Gly Leu Lys Val Phe Glu Asp Tyr Ala Arg
225                 230                 235                 240

Thr Trp Tyr Trp Ile Leu Ile Gly Leu Thr Ile Ala Met Val Leu Ser
                245                 250                 255

Trp Ile Phe Leu Ile Leu Leu Arg Phe Ile Ala Gly Cys Leu Phe Trp
            260                 265                 270

Val Phe Met Ile Gly Val Ile Gly Ile Ile Gly Tyr Gly Ile Trp His
        275                 280                 285

Cys Tyr Gln Gln Tyr Thr Asn Leu Gln Glu Arg Pro Ser Ser Val Leu
    290                 295                 300

Thr Ile Tyr Asp Ile Gly Ile Gln Thr Asn Ile Ser Met Tyr Phe Glu
305                 310                 315                 320

Leu Gln Gln Thr Trp Phe Thr Phe Met Ile Ile Leu Cys Ile Ile Glu
                325                 330                 335

Val Ile Val Ile Leu Met Leu Ile Phe Leu Arg Asn Arg Ile Arg Val
            340                 345                 350

Ala Ile Ile Leu Leu Lys Glu Gly Ser Lys Ala Ile Gly Tyr Val Pro
        355                 360                 365

Ser Thr Leu Val Tyr Pro Ala Leu Thr Phe Ile Leu Leu Ser Ile Cys
    370                 375                 380
```

```
Ile Cys Tyr Trp Val Val Thr Ala Val Phe Leu Ala Thr Ser Gly Val
385                 390                 395                 400

Pro Val Tyr Lys Val Ile Ala Pro Gly Gly His Cys Ile His Glu Asn
            405                 410                 415

Gln Thr Cys Asp Pro Glu Ile Phe Asn Thr Thr Glu Ile Ala Lys Ala
        420                 425                 430

Cys Pro Gly Ala Leu Cys Asn Phe Ala Phe Tyr Gly Gly Lys Ser Leu
            435                 440                 445

Tyr His Gln Tyr Ile Pro Thr Phe His Val Tyr Asn Leu Phe Val Phe
    450                 455                 460

Leu Trp Leu Ile Asn Phe Val Ile Ala Leu Gly Gln Cys Ala Leu Ala
465                 470                 475                 480

Gly Ala Phe Ala Thr Tyr Tyr Trp Ala Met Lys Lys Pro Asp Asp Ile
                485                 490                 495

Pro Arg Tyr Pro Leu Phe Thr Ala Phe Gly Arg Ala Ile Arg Tyr His
            500                 505                 510

Thr Gly Ser Leu Ala Phe Gly Ser Leu Ile Ile Ala Leu Ile Gln Met
        515                 520                 525

Phe Lys Ile Val Leu Glu Tyr Leu Asp His Arg Leu Lys Arg Thr Gln
530                 535                 540

Asn Thr Leu Ser Lys Phe Leu Gln Cys Cys Leu Arg Cys Cys Phe Trp
545                 550                 555                 560

Cys Leu Glu Asn Ala Ile Lys Phe Leu Asn Arg Asn Ala Tyr Ile Met
                565                 570                 575

Ile Ala Ile Tyr Gly Arg Asn Phe Cys Arg Ser Ala Lys Asp Ala Phe
                580                 585                 590

Asn Leu Leu Met Arg Asn Val Leu Lys Val Ala Val Thr Asp Glu Val
            595                 600                 605

Thr Tyr Phe Val Leu Phe Leu Gly Lys Leu Leu Val Ala Gly Ser Ile
    610                 615                 620

Gly Val Leu Ala Phe Leu Phe Thr Gln Arg Leu Pro Val Ile Ala
625                 630                 635                 640

Gln Gly Pro Ala Ser Leu Asn Tyr Tyr Trp Val Pro Leu Leu Thr Val
            645                 650                 655

Ile Phe Gly Ser Tyr Leu Ile Ala His Gly Phe Phe Ser Val Tyr Ala
            660                 665                 670

Met Cys Val Glu Thr Ile Phe Ile Cys Phe Leu Glu Asp Leu Glu Arg
            675                 680                 685

Asn Asp Gly Ser Thr Ala Arg Pro Tyr Tyr Val Ser Gln Pro Leu Leu
690                 695                 700

Lys Ile Phe Gln Glu Glu Asn Pro Gln Thr Arg Lys Gln
705                 710                 715

<210> SEQ ID NO 27
<211> LENGTH: 2763
<212> TYPE: DNA
<213> ORGANISM: Homo Sapiens
<220> FEATURE:
<221> NAME/KEY: CDS
<222> LOCATION: (34)...(1626)

<400> SEQUENCE: 27
ggaccccagg ccgggccggg ccgagaggct gcc atg ggc tcc gtg ggg agc cag    54
                                    Met Gly Ser Val Gly Ser Gln
                                     1               5
```

-continued

```
cgc ctt gag gag ccc agc gtg gca ggc aca cca gac ccg ggc gta gtg      102
Arg Leu Glu Glu Pro Ser Val Ala Gly Thr Pro Asp Pro Gly Val Val
         10                  15                  20 atg agc ttc acc ttc gac agt cac cag ctg gag gag gcg gcg gag gcg      150
Met Ser Phe Thr Phe Asp Ser His Gln Leu Glu Glu Ala Ala Glu Ala
     25                  30                  35 gct cag ggc cag ggc ctt agg gcc agg ggc gtc cca gct ttc acg gat      198
Ala Gln Gly Gln Gly Leu Arg Ala Arg Gly Val Pro Ala Phe Thr Asp
 40                  45                  50                  55 act aca ttg gac gag cca gtg ccc gat gac cgt tat cac gcc atc tac      246
Thr Thr Leu Asp Glu Pro Val Pro Asp Asp Arg Tyr His Ala Ile Tyr
                 60                  65                  70 ttt gcg atg ctg ctg gct ggc gtg ggc ttc ctg ctg cca tac aac agc      294
Phe Ala Met Leu Leu Ala Gly Val Gly Phe Leu Leu Pro Tyr Asn Ser
             75                  80                  85 ttc atc acg gac gtg gac tac ctg cat cac aag tac cca ggg acc tcc      342
Phe Ile Thr Asp Val Asp Tyr Leu His His Lys Tyr Pro Gly Thr Ser
         90                  95                 100 atc gtg ttt gac atg agc ctc acc tac atc ttg gtg gca ctg gca gct      390
Ile Val Phe Asp Met Ser Leu Thr Tyr Ile Leu Val Ala Leu Ala Ala
     105                 110                 115 gtc ctc ctg aac aac gtc ctg gtg gag aga ctg acc ctg cac acc agg      438
Val Leu Leu Asn Asn Val Leu Val Glu Arg Leu Thr Leu His Thr Arg
120                 125                 130                 135 atc acc gca ggc tac ctc tta gcc ttg ggc cct ctc ctt ttt atc agc      486
Ile Thr Ala Gly Tyr Leu Leu Ala Leu Gly Pro Leu Leu Phe Ile Ser
                 140                 145                 150 atc tgc gac gtg tgg ctg cag ctc ttc tct cgg gac cag gcc tac gcc      534
Ile Cys Asp Val Trp Leu Gln Leu Phe Ser Arg Asp Gln Ala Tyr Ala
             155                 160                 165 atc aac ctg gcc gct gtg ggc acc gtg gcc ttc ggc tgc aca gtg cag      582
Ile Asn Leu Ala Ala Val Gly Thr Val Ala Phe Gly Cys Thr Val Gln
         170                 175                 180 caa tcc agc ttc tac ggg tac acg ggg atg ctg ccc aag cgg tac acg      630
Gln Ser Ser Phe Tyr Gly Tyr Thr Gly Met Leu Pro Lys Arg Tyr Thr
     185                 190                 195 cag ggg gtg atg acc ggg gag agc acg gcg ggc gtg atg atc tct ctg      678
Gln Gly Val Met Thr Gly Glu Ser Thr Ala Gly Val Met Ile Ser Leu
200                 205                 210                 215 agc cgc atc ctc acg aag ctg ctg ctg ccc gac gag cgc gcc agc acg      726
Ser Arg Ile Leu Thr Lys Leu Leu Leu Pro Asp Glu Arg Ala Ser Thr
                 220                 225                 230 ctc atc ttc ttc ctg gtg tcg gtg gcg ctg gag ctg ctg tgt ttc ctg      774
Leu Ile Phe Phe Leu Val Ser Val Ala Leu Glu Leu Leu Cys Phe Leu
             235                 240                 245 ctg cac ctg tta gtg cgg cgc agc cgc ttc gtg ctc ttc tat acc aca      822
Leu His Leu Leu Val Arg Arg Ser Arg Phe Val Leu Phe Tyr Thr Thr
         250                 255                 260 cgg ccg cgt gac agc cac cgg ggc agg cca ggc ctg ggc agg ggc tat      870
Arg Pro Arg Asp Ser His Arg Gly Arg Pro Gly Leu Gly Arg Gly Tyr
     265                 270                 275 ggc tac cgc gtg cac cac gac gtt gtc gcc ggg gac gtc cac ttc gag      918
Gly Tyr Arg Val His His Asp Val Val Ala Gly Asp Val His Phe Glu
280                 285                 290                 295 cac cca gcc ccg gcc ctg gcc ccc aac gag tcc cca aag gac agc cca      966
His Pro Ala Pro Ala Leu Ala Pro Asn Glu Ser Pro Lys Asp Ser Pro
                 300                 305                 310 gcc cac gag gtg acc ggc agc ggc ggg gcc tac atg cgc ttt gac gtg     1014
Ala His Glu Val Thr Gly Ser Gly Gly Ala Tyr Met Arg Phe Asp Val
             315                 320                 325
```

-continued

```
ccg cgg cca agg gtc cag cgc agc tgg ccc acc ttc aga gcc ctg tta    1062
Pro Arg Pro Arg Val Gln Arg Ser Trp Pro Thr Phe Arg Ala Leu Leu
        330                 335                 340 ctg cac cgc tac gtg gtg gcg cgg gtg atc tgg gcc gac atg ctc tcc    1110
Leu His Arg Tyr Val Val Ala Arg Val Ile Trp Ala Asp Met Leu Ser
345                 350                 355 atc gcc gtg acc tac ttc atc acg ctg tgc ctg ttc ccc ggc ctc gag    1158
Ile Ala Val Thr Tyr Phe Ile Thr Leu Cys Leu Phe Pro Gly Leu Glu
360                 365                 370                 375 tct gag atc cgc cac tgc atc ctg ggc gag tgg ctg ccc atc ctc atc    1206
Ser Glu Ile Arg His Cys Ile Leu Gly Glu Trp Leu Pro Ile Leu Ile
            380                 385                 390 atg gct gtg ttc aac ctg tca gac ttc gtg ggc aag atc ctg gca gcc    1254
Met Ala Val Phe Asn Leu Ser Asp Phe Val Gly Lys Ile Leu Ala Ala
                395                 400                 405 ctg ccc gtg gac tgg cgg ggc acc cac ctg ctg gcc tgc tcc tgc ctg    1302
Leu Pro Val Asp Trp Arg Gly Thr His Leu Leu Ala Cys Ser Cys Leu
                    410                 415                 420 cgt gtg gtc ttc atc ccc ctc ttc atc ctg tgc gtc tac ccc agc ggc    1350
Arg Val Val Phe Ile Pro Leu Phe Ile Leu Cys Val Tyr Pro Ser Gly
                        425                 430                 435 atg ccc gcc ctc cgt cac ccc gcc tgg ccc tgc atc ttc tca ctg ctc    1398
Met Pro Ala Leu Arg His Pro Ala Trp Pro Cys Ile Phe Ser Leu Leu
440                 445                 450                 455 atg ggc atc agc aac ggc tac ttc ggc agc gtg ccc atg atc ctg gcg    1446
Met Gly Ile Ser Asn Gly Tyr Phe Gly Ser Val Pro Met Ile Leu Ala
                460                 465                 470 gca ggc aaa gtg agc ccc aag cag cgg gag ctg gca ggg aac acc atg    1494
Ala Gly Lys Val Ser Pro Lys Gln Arg Glu Leu Ala Gly Asn Thr Met
                    475                 480                 485 acc gtg tcc tac atg tca ggg ctg acg ctg ggg tcc gcc gtg gcc tac    1542
Thr Val Ser Tyr Met Ser Gly Leu Thr Leu Gly Ser Ala Val Ala Tyr
                        490                 495                 500 tgc acc tac agc ctc acc cgc gac gct cac ggc agc tgc ctg cac gcc    1590
Cys Thr Tyr Ser Leu Thr Arg Asp Ala His Gly Ser Cys Leu His Ala
505                 510                 515 tcc acc gcc aat ggt tcc atc ctc gca ggc ctc tga gccagcccg          1636
Ser Thr Ala Asn Gly Ser Ile Leu Ala Gly Leu  *
520                 525                 530 cccactgcca gggacgccga gggcctgacc aggggccccg aggcctgagg gcccctcccc   1696
tgtccccacc tcagtgcctg cggggccctg agcctccccc tgtgccagca gccccactcc   1756
ctcagggtcc agccatgccc cacccctgac tgaagttctg caaagtcctc cgaggaccgg   1816
aacacgtttc tgcgacccgg ggctctggcc agcactgtgt tctgcgtttg gtctcatacc   1876
tgcgtctacc ttccatctgt gtccagcggc cccggctcca gcccagccag cactctgcag   1936
ggtcacacgc accgtgtccc cacccaggac agcagacacc cgccagagtg tgcgcgccca   1996
gtgactgcac cccggccctc atcacccacc ggcactgatc ggggcaccgc ctggcccagc   2056
ctccaccagg gacccctcct catgaactct ggagccctga gggagaggg gcagcccccc    2116 accttgtcac cctcagggct tcccttctg tcctcattct tagagactgc ttctcccaaa    2176
cataacgcgt tagccatgaa ggagtcggag ccctgggtcc gaatggaccc gcctgcggtc   2236
tgcatcagcc tctgggaaac cacagcagtg atgccagctg gcacgtcag gacctcccca    2296 cacacccaca cgatgccaca ggtcagggg ctgtgcctga ctagggagcc ctcccattgc    2356
cttcctggcc cggatagaa gaggggaggt aagtctgggg gctacgaagc cgggccccca    2416
caccctggct gaagtcagct tgacctaggt cttgacccct atccagcaag ggactcgaca   2476
```

-continued

```
gacccaaggg tccctggaac gtagggaggg gctgggggtc actccagccc gggcctccca      2536
gaacaccagg cccgtgtggg tggcaccctg aggtcagggg atcctaaggg tgtccttcca      2596
gagacggtgt ttccagggggg aggaccgccc ccgcttccag atccccggcc ccggctgtga     2656
ctgccctgtt tcaccctgc tgtgtccat cccccgtctg tccactaact gtaccgcacc        2716
ggccatttaa agatgaaggc agaccgctgc caaaaaaaaa aaaaaaa                    2763
```

<210> SEQ ID NO 28
<211> LENGTH: 530
<212> TYPE: PRT
<213> ORGANISM: Homo Sapiens

<400> SEQUENCE: 28

```
Met Gly Ser Val Gly Ser Gln Arg Leu Glu Glu Pro Ser Val Ala Gly
 1               5                  10                  15

Thr Pro Asp Pro Gly Val Val Met Ser Phe Thr Phe Asp Ser His Gln
            20                  25                  30

Leu Glu Glu Ala Ala Glu Ala Ala Gln Gly Gln Gly Leu Arg Ala Arg
        35                  40                  45

Gly Val Pro Ala Phe Thr Asp Thr Thr Leu Asp Glu Pro Val Pro Asp
    50                  55                  60

Asp Arg Tyr His Ala Ile Tyr Phe Ala Met Leu Leu Ala Gly Val Gly
65                  70                  75                  80

Phe Leu Leu Pro Tyr Asn Ser Phe Ile Thr Asp Val Asp Tyr Leu His
                85                  90                  95

His Lys Tyr Pro Gly Thr Ser Ile Val Phe Asp Met Ser Leu Thr Tyr
            100                 105                 110

Ile Leu Val Ala Leu Ala Ala Val Leu Leu Asn Asn Val Leu Val Glu
        115                 120                 125

Arg Leu Thr Leu His Thr Arg Ile Thr Ala Gly Tyr Leu Leu Ala Leu
    130                 135                 140

Gly Pro Leu Leu Phe Ile Ser Ile Cys Asp Val Trp Leu Gln Leu Phe
145                 150                 155                 160

Ser Arg Asp Gln Ala Tyr Ala Ile Asn Leu Ala Ala Val Gly Thr Val
                165                 170                 175

Ala Phe Gly Cys Thr Val Gln Gln Ser Ser Phe Tyr Gly Tyr Thr Gly
            180                 185                 190

Met Leu Pro Lys Arg Tyr Thr Gln Gly Val Met Thr Gly Glu Ser Thr
        195                 200                 205

Ala Gly Val Met Ile Ser Leu Ser Arg Ile Leu Thr Lys Leu Leu Leu
    210                 215                 220

Pro Asp Glu Arg Ala Ser Thr Leu Ile Phe Phe Leu Val Ser Val Ala
225                 230                 235                 240

Leu Glu Leu Leu Cys Phe Leu Leu His Leu Leu Val Arg Arg Ser Arg
                245                 250                 255

Phe Val Leu Phe Tyr Thr Thr Arg Pro Arg Asp Ser His Arg Gly Arg
            260                 265                 270

Pro Gly Leu Gly Arg Gly Tyr Gly Tyr Arg Val His His Asp Val Val
        275                 280                 285

Ala Gly Asp Val His Phe Glu His Pro Ala Pro Ala Leu Ala Pro Asn
    290                 295                 300

Glu Ser Pro Lys Asp Ser Pro Ala His Glu Val Thr Gly Ser Gly Gly
305                 310                 315                 320
```

```
Ala Tyr Met Arg Phe Asp Val Pro Arg Pro Arg Val Gln Arg Ser Trp
            325                 330                 335

Pro Thr Phe Arg Ala Leu Leu Leu His Arg Tyr Val Ala Arg Val
            340                 345                 350

Ile Trp Ala Asp Met Leu Ser Ile Ala Val Thr Tyr Phe Ile Thr Leu
            355                 360                 365

Cys Leu Phe Pro Gly Leu Glu Ser Glu Ile Arg His Cys Ile Leu Gly
            370                 375                 380

Glu Trp Leu Pro Ile Leu Ile Met Ala Val Phe Asn Leu Ser Asp Phe
385                 390                 395                 400

Val Gly Lys Ile Leu Ala Ala Leu Pro Val Asp Trp Arg Gly Thr His
                405                 410                 415

Leu Leu Ala Cys Ser Cys Leu Arg Val Val Phe Ile Pro Leu Phe Ile
            420                 425                 430

Leu Cys Val Tyr Pro Ser Gly Met Pro Ala Leu Arg His Pro Ala Trp
            435                 440                 445

Pro Cys Ile Phe Ser Leu Leu Met Gly Ile Ser Asn Gly Tyr Phe Gly
            450                 455                 460

Ser Val Pro Met Ile Leu Ala Ala Gly Lys Val Ser Pro Lys Gln Arg
465                 470                 475                 480

Glu Leu Ala Gly Asn Thr Met Thr Val Ser Tyr Met Ser Gly Leu Thr
                485                 490                 495

Leu Gly Ser Ala Val Ala Tyr Cys Thr Tyr Ser Leu Thr Arg Asp Ala
            500                 505                 510

His Gly Ser Cys Leu His Ala Ser Thr Ala Asn Gly Ser Ile Leu Ala
            515                 520                 525

Gly Leu
    530

<210> SEQ ID NO 29
<211> LENGTH: 1107
<212> TYPE: DNA
<213> ORGANISM: Homo Sapiens
<220> FEATURE:
<221> NAME/KEY: CDS
<222> LOCATION: (56)...(688)

<400> SEQUENCE: 29 cgccggggc gggaggggc ggggggagca cgccagccgc cgagagtggg gggcg atg      58
                                                            Met
                                                             1 gcg aag ctc cgg gtg gct tac gag tac acg gaa gcc gag gac aag agc    106
Ala Lys Leu Arg Val Ala Tyr Glu Tyr Thr Glu Ala Glu Asp Lys Ser
        5                   10                  15 atc cgg ctc ggc ttg ttt ctc atc atc tcc ggc gtc gtg tcg ctc ttc    154
Ile Arg Leu Gly Leu Phe Leu Ile Ile Ser Gly Val Val Ser Leu Phe
            20                  25                  30 atc ttc ggc ttc tgc tgg ctg agt ccc gcg ctg cag gat ctg caa gcc    202
Ile Phe Gly Phe Cys Trp Leu Ser Pro Ala Leu Gln Asp Leu Gln Ala
    35                  40                  45 acg gag gcc aat tgc acg gtg ctg tcg gtg cag cag atc ggc gag gtg    250
Thr Glu Ala Asn Cys Thr Val Leu Ser Val Gln Gln Ile Gly Glu Val
50                  55                  60                  65 ttc gag tgc acc ttc acc tgt ggc gcc gac tgc agg ggc acc tcg cag    298
Phe Glu Cys Thr Phe Thr Cys Gly Ala Asp Cys Arg Gly Thr Ser Gln
                70                  75                  80
```

```
tac ccc tgc gtc cag gtc tac gtg aac aac tct gag tcc aac tct agg      346
Tyr Pro Cys Val Gln Val Tyr Val Asn Asn Ser Glu Ser Asn Ser Arg
            85                  90                  95 gcg ctg ctg cac agc gac gag cac cag ctc ctg acc aac ccc aag tgc      394
Ala Leu Leu His Ser Asp Glu His Gln Leu Leu Thr Asn Pro Lys Cys
        100                 105                 110 tcc tat atc cct ccc tgt aag aga gaa aat cag aag aat ttg gaa agt      442
Ser Tyr Ile Pro Pro Cys Lys Arg Glu Asn Gln Lys Asn Leu Glu Ser
    115                 120                 125 gtc atg aat tgg caa cag tac tgg aaa gat gag att ggt tcc cag cca      490
Val Met Asn Trp Gln Gln Tyr Trp Lys Asp Glu Ile Gly Ser Gln Pro
130                 135                 140                 145 ttt act tgc tat ttt aat caa cat caa aga cca gat gat gtg ctt ctg      538
Phe Thr Cys Tyr Phe Asn Gln His Gln Arg Pro Asp Asp Val Leu Leu
                150                 155                 160 cat cgc act cat gat gag att gtc ctc ctg cat tgc ttc ctc tgg ccc      586
His Arg Thr His Asp Glu Ile Val Leu Leu His Cys Phe Leu Trp Pro
            165                 170                 175 ctg gtg aca ttt gtg gtg ggc gtt ctc att gtg gtc ctg acc atc tgt      634
Leu Val Thr Phe Val Val Gly Val Leu Ile Val Val Leu Thr Ile Cys
        180                 185                 190 gcc aag agc ttg gcg gtc aag gcg gaa gcc atg aag aag cgc aag ttc      682
Ala Lys Ser Leu Ala Val Lys Ala Glu Ala Met Lys Lys Arg Lys Phe
    195                 200                 205 tct taa aggggaagga ggcttgtaga aagcaaagta cagaagctgt actcatcggc      738
Ser *
210 acgcgtccac ctgcggaacc tgtgtttcct ggcgcaggag atggacaggg ccacgacagg     798 gctctgagag gctcatccct cagtggcaac agaaacaggc acaactgaaa gacttggaac     858 ctcaaagctt gtattccatc tgctgtagca atggctaaag ggtcaagatc ttagctgtat     918 ggagtaacta tttcagaaaa ccctataaga agttcatttt ctttcaaaag taacagtata     978 ttatttgtac agtgtagtat acaaaccatt atgatttatg ctacttaaaa atattaaaat    1038 agagtggtct gtgttatttt ctatttcctt ttttatgctt agaacaccag ggttaaaaaa    1098 aaaaaaaaa                                                             1107

<210> SEQ ID NO 30
<211> LENGTH: 210
<212> TYPE: PRT
<213> ORGANISM: Homo Sapiens

<400> SEQUENCE: 30

Met Ala Lys Leu Arg Val Ala Tyr Glu Tyr Thr Glu Ala Glu Asp Lys
 1               5                  10                  15

Ser Ile Arg Leu Gly Leu Phe Leu Ile Ile Ser Gly Val Val Ser Leu
            20                  25                  30

Phe Ile Phe Gly Phe Cys Trp Leu Ser Pro Ala Leu Gln Asp Leu Gln
        35                  40                  45

Ala Thr Glu Ala Asn Cys Thr Val Leu Ser Val Gln Gln Ile Gly Glu
    50                  55                  60

Val Phe Glu Cys Thr Phe Thr Cys Gly Ala Asp Cys Arg Gly Thr Ser
65                  70                  75                  80

Gln Tyr Pro Cys Val Gln Val Tyr Val Asn Asn Ser Glu Ser Asn Ser
                85                  90                  95

Arg Ala Leu Leu His Ser Asp Glu His Gln Leu Leu Thr Asn Pro Lys
            100                 105                 110
```

-continued

```
Cys Ser Tyr Ile Pro Pro Cys Lys Arg Glu Asn Gln Lys Asn Leu Glu
    115                 120                 125

Ser Val Met Asn Trp Gln Gln Tyr Trp Lys Asp Glu Ile Gly Ser Gln
130                 135                 140

Pro Phe Thr Cys Tyr Phe Asn Gln His Gln Arg Pro Asp Asp Val Leu
145                 150                 155                 160

Leu His Arg Thr His Asp Glu Ile Val Leu Leu His Cys Phe Leu Trp
                165                 170                 175

Pro Leu Val Thr Phe Val Val Gly Val Leu Ile Val Val Leu Thr Ile
                180                 185                 190

Cys Ala Lys Ser Leu Ala Val Lys Ala Glu Ala Met Lys Lys Arg Lys
                195                 200                 205

Phe Ser
    210
```

<210> SEQ ID NO 31
<211> LENGTH: 3083
<212> TYPE: DNA
<213> ORGANISM: Homo Sapiens
<220> FEATURE:
<221> NAME/KEY: CDS
<222> LOCATION: (37)...(3006)

<400> SEQUENCE: 31

```
aattccgggc ccgccggacc ccgagctgct gggagg atg acc atg gct ggg ggc          54
                                        Met Thr Met Ala Gly Gly
                                        1               5 agg agg gga cta gtg gcc cct caa aac acg ttt ctg gag aat att gtt         102
Arg Arg Gly Leu Val Ala Pro Gln Asn Thr Phe Leu Glu Asn Ile Val
            10                  15                  20 cgg cgg tcc aat gat act aat ttt gtg ttg ggg aat gct cag ata gtg         150
Arg Arg Ser Asn Asp Thr Asn Phe Val Leu Gly Asn Ala Gln Ile Val
        25                  30                  35 gac tgg cct att gtg tac agc aat gat gga ttt tgc aag ctg tct ggc         198
Asp Trp Pro Ile Val Tyr Ser Asn Asp Gly Phe Cys Lys Leu Ser Gly
    40                  45                  50 tat cac agg gca gaa gtg atg caa aaa agc agc acc tgc agt ttt atg         246
Tyr His Arg Ala Glu Val Met Gln Lys Ser Ser Thr Cys Ser Phe Met
55                  60                  65                  70 tat ggg gag ctg act gat aaa gac acg att gaa aaa gtg cgg caa aca         294
Tyr Gly Glu Leu Thr Asp Lys Asp Thr Ile Glu Lys Val Arg Gln Thr
                75                  80                  85 ttt gag aac tat gag atg aat tcc ttt gaa att ctg atg tac aag aag         342
Phe Glu Asn Tyr Glu Met Asn Ser Phe Glu Ile Leu Met Tyr Lys Lys
            90                  95                  100 aac agg aca cct gtg tgg ttc ttt gtg aaa att gct cca att cga aac         390
Asn Arg Thr Pro Val Trp Phe Phe Val Lys Ile Ala Pro Ile Arg Asn
        105                 110                 115 gaa cag gat aaa gtg gtt tta ttt ctt tgc act ttc agt gac ata aca         438
Glu Gln Asp Lys Val Val Leu Phe Leu Cys Thr Phe Ser Asp Ile Thr
    120                 125                 130 gct ttc aaa cag cca att gag gat gat tca tgt aaa ggc tgg ggg aag         486
Ala Phe Lys Gln Pro Ile Glu Asp Asp Ser Cys Lys Gly Trp Gly Lys
135                 140                 145                 150 ttt gct cgg cta aca aga gca ctg aca agc agc agg ggt gtc ctg cag         534
Phe Ala Arg Leu Thr Arg Ala Leu Thr Ser Ser Arg Gly Val Leu Gln
                155                 160                 165 cag ctg gct cca agc gtg caa aaa ggc gag aat gtc cac aag cac tcc         582
Gln Leu Ala Pro Ser Val Gln Lys Gly Glu Asn Val His Lys His Ser
            170                 175                 180
```

```
cgc ctg gca gag gtc cta cag ctg ggc tca gac atc ctt ccc cag tac        630
Arg Leu Ala Glu Val Leu Gln Leu Gly Ser Asp Ile Leu Pro Gln Tyr
        185                 190                 195 aag caa gag gca cca aag act ccc cct cac atc atc tta cat tat tgt        678
Lys Gln Glu Ala Pro Lys Thr Pro Pro His Ile Ile Leu His Tyr Cys
200                 205                 210 gtt ttt aag acc acg tgg gat tgg atc atc ttg atc ttg acc ttc tat        726
Val Phe Lys Thr Thr Trp Asp Trp Ile Ile Leu Ile Leu Thr Phe Tyr
215                 220                 225                 230 aca gcc atc ttg gtc cct tat aat gtc tcc ttc aaa acc agg cag aat        774
Thr Ala Ile Leu Val Pro Tyr Asn Val Ser Phe Lys Thr Arg Gln Asn
            235                 240                 245 aat gtg gcc tgg ctg gtt gtt gat agc atc gtg gat gtt atc ttt ttg        822
Asn Val Ala Trp Leu Val Val Asp Ser Ile Val Asp Val Ile Phe Leu
            250                 255                 260 gtg gac att gtg ctc aat ttt cat acc acc ttt gtt gga cca gca ggg        870
Val Asp Ile Val Leu Asn Phe His Thr Thr Phe Val Gly Pro Ala Gly
            265                 270                 275 gag gtg att tct gac ccc aaa ctt atc cgc atg aac tac ctg aag acg        918
Glu Val Ile Ser Asp Pro Lys Leu Ile Arg Met Asn Tyr Leu Lys Thr
        280                 285                 290 tgg ttt gtg att gac ctt ctg tcc tgt ttg cca tat gat gtc atc aac        966
Trp Phe Val Ile Asp Leu Leu Ser Cys Leu Pro Tyr Asp Val Ile Asn
295                 300                 305                 310 gct ttt gag aac gtg gat gag gtt agt gcc ttt atg ggt gat cca ggg       1014
Ala Phe Glu Asn Val Asp Glu Val Ser Ala Phe Met Gly Asp Pro Gly
                315                 320                 325 aag att ggt ttt gct gat cag att cca cca cca ctg gag ggg aga gag       1062
Lys Ile Gly Phe Ala Asp Gln Ile Pro Pro Pro Leu Glu Gly Arg Glu
        330                 335                 340 agt cag ggc atc agc agc ctg ttc agc tct cta aaa gtt gtc cgg ctg       1110
Ser Gln Gly Ile Ser Ser Leu Phe Ser Ser Leu Lys Val Val Arg Leu
            345                 350                 355 ctc cgt ctt ggg cga gtg gcc cgt aag ctg gac cac tac att gaa tat       1158
Leu Arg Leu Gly Arg Val Ala Arg Lys Leu Asp His Tyr Ile Glu Tyr
        360                 365                 370 gga gct gct gtg ctg gtc ctg ctg gtg tgt gtg ttt ggg ctg gct gca       1206
Gly Ala Ala Val Leu Val Leu Leu Val Cys Val Phe Gly Leu Ala Ala
375                 380                 385                 390 cac tgg atg gcc tgc atc tgg tac agc att ggg gac tat gag atc ttt       1254
His Trp Met Ala Cys Ile Trp Tyr Ser Ile Gly Asp Tyr Glu Ile Phe
                395                 400                 405 gac gag gac acc aag aca atc cgc aac aac agc tgg ctg tac caa cta       1302
Asp Glu Asp Thr Lys Thr Ile Arg Asn Asn Ser Trp Leu Tyr Gln Leu
        410                 415                 420 gcg atg gac att ggc acc cct tac cag ttt aat ggg tct ggc tca ggg       1350
Ala Met Asp Ile Gly Thr Pro Tyr Gln Phe Asn Gly Ser Gly Ser Gly
            425                 430                 435 aag tgg gaa ggt ggt ccc agc aag aat tct gtc tac atc tcc tcg ttg       1398
Lys Trp Glu Gly Gly Pro Ser Lys Asn Ser Val Tyr Ile Ser Ser Leu
440                 445                 450 tat ttc aca atg acc agc ctc acc agt gtg ggc ttt ggg aac atc gcc       1446
Tyr Phe Thr Met Thr Ser Leu Thr Ser Val Gly Phe Gly Asn Ile Ala
455                 460                 465                 470 cca tcc aca gac att gag aag atc ttt gca gtg gcc atc atg atg att       1494
Pro Ser Thr Asp Ile Glu Lys Ile Phe Ala Val Ala Ile Met Met Ile
                475                 480                 485 ggc tca ctt ctc tat gcc acc atc ttc ggg aat gtg acg act att ttc       1542
Gly Ser Leu Leu Tyr Ala Thr Ile Phe Gly Asn Val Thr Thr Ile Phe
            490                 495                 500
```

-continued

| | | |
|---|---|---|
| caa cag atg tat gcc aac acc aac aga tac cat gag atg ctc aac agt<br>Gln Gln Met Tyr Ala Asn Thr Asn Arg Tyr His Glu Met Leu Asn Ser<br>505 510 515 | | 1590 |
| gtt cgg gac ttc ctg aag ctc tac cag gtg cca aaa gga ttg agt gag<br>Val Arg Asp Phe Leu Lys Leu Tyr Gln Val Pro Lys Gly Leu Ser Glu<br>520 525 530 | | 1638 |
| cga gta atg gat tat att gtg tcc act tgg tcc atg tcc aga ggc att<br>Arg Val Met Asp Tyr Ile Val Ser Thr Trp Ser Met Ser Arg Gly Ile<br>535 540 545 550 | | 1686 |
| gac aca gag aag gtc ctg cag atc tgc ccc aag gac atg aga gcc gac<br>Asp Thr Glu Lys Val Leu Gln Ile Cys Pro Lys Asp Met Arg Ala Asp<br>555 560 565 | | 1734 |
| atc tgc gtg cac ctg aac cgc aag gtg ttc aag gag cac ccg gcc ttc<br>Ile Cys Val His Leu Asn Arg Lys Val Phe Lys Glu His Pro Ala Phe<br>570 575 580 | | 1782 |
| cgg ctg gcc agt gat ggc tgc ctc cgg gca ctg gcc atg gag ttc cag<br>Arg Leu Ala Ser Asp Gly Cys Leu Arg Ala Leu Ala Met Glu Phe Gln<br>585 590 595 | | 1830 |
| acg gtg cac tgt gcc cca ggg gac ctc atc tac cat gca gga gag agc<br>Thr Val His Cys Ala Pro Gly Asp Leu Ile Tyr His Ala Gly Glu Ser<br>600 605 610 | | 1878 |
| gtt gac agc ctc tgc ttt gtg gtt tct ggc tcc ctg gag gtg atc caa<br>Val Asp Ser Leu Cys Phe Val Val Ser Gly Ser Leu Glu Val Ile Gln<br>615 620 625 630 | | 1926 |
| gat gat gag gtg gtg gcc att cta gga aaa gga gac gtg ttt gga gat<br>Asp Asp Glu Val Val Ala Ile Leu Gly Lys Gly Asp Val Phe Gly Asp<br>635 640 645 | | 1974 |
| gtg ttc tgg aag gaa gcc acc ctt gcc cag tcc tgt gcc aat gtt agg<br>Val Phe Trp Lys Glu Ala Thr Leu Ala Gln Ser Cys Ala Asn Val Arg<br>650 655 660 | | 2022 |
| gcc ttg acc tac tgt gat ctg cat gtg atc aag cgg gat gcc ctg cag<br>Ala Leu Thr Tyr Cys Asp Leu His Val Ile Lys Arg Asp Ala Leu Gln<br>665 670 675 | | 2070 |
| aaa gtg ctg gaa ttc tac acg gcc ttc tcc cat tcc ttc tcc cgg aac<br>Lys Val Leu Glu Phe Tyr Thr Ala Phe Ser His Ser Phe Ser Arg Asn<br>680 685 690 | | 2118 |
| ctg att ctg acg tac aac ttg agg aag agg att gtg ttc cgg aag atc<br>Leu Ile Leu Thr Tyr Asn Leu Arg Lys Arg Ile Val Phe Arg Lys Ile<br>695 700 705 710 | | 2166 |
| agc gat gtg aaa cgt gaa gag gaa gaa cgc atg aaa cga aag aat gag<br>Ser Asp Val Lys Arg Glu Glu Glu Glu Arg Met Lys Arg Lys Asn Glu<br>715 720 725 | | 2214 |
| gcc ccc ctg atc ttg ccc ccg gac cac cct gtc cgg cgc ctc ttc cag<br>Ala Pro Leu Ile Leu Pro Pro Asp His Pro Val Arg Arg Leu Phe Gln<br>730 735 740 | | 2262 |
| aga ttc cga cag cag aaa gag gcc agg ctg gca gct gag aga ggg ggc<br>Arg Phe Arg Gln Gln Lys Glu Ala Arg Leu Ala Ala Glu Arg Gly Gly<br>745 750 755 | | 2310 |
| cgg gac ctg gat gac cta gat gtg gag aag ggc aat gtc ctt aca gag<br>Arg Asp Leu Asp Asp Leu Asp Val Glu Lys Gly Asn Val Leu Thr Glu<br>760 765 770 | | 2358 |
| cat gcc tcc gcc aac cac agc ctc gtg aag gcc agc gtg gtc acc gtg<br>His Ala Ser Ala Asn His Ser Leu Val Lys Ala Ser Val Val Thr Val<br>775 780 785 790 | | 2406 |
| cgt gag agt cct gcc acg ccc gta tcc ttc cag gca gcc tcc acc tcc<br>Arg Glu Ser Pro Ala Thr Pro Val Ser Phe Gln Ala Ala Ser Thr Ser<br>795 800 805 | | 2454 |
| ggg gtg cca gac cac gca aag cta cag gcg cca ggg tcc gag tgc ctg<br>Gly Val Pro Asp His Ala Lys Leu Gln Ala Pro Gly Ser Glu Cys Leu<br>810 815 820 | | 2502 |

```
ggc ccc aag ggg ggc ggg ggc gat tgt gcc aag cgc aaa agc tgg gcc    2550
Gly Pro Lys Gly Gly Gly Gly Asp Cys Ala Lys Arg Lys Ser Trp Ala
        825                 830                 835 cgc ttc aaa gat gct tgc ggg aag agt gag gac tgg aac aag gtg tcc    2598
Arg Phe Lys Asp Ala Cys Gly Lys Ser Glu Asp Trp Asn Lys Val Ser
840                 845                 850 aag gct gag tcg atg gag aca ctt ccc gag agg aca aaa gcg tca ggc    2646
Lys Ala Glu Ser Met Glu Thr Leu Pro Glu Arg Thr Lys Ala Ser Gly
855                 860                 865                 870 gag gcc aca ctg aag aag aca gac tcg tgt gac agt ggc atc acc aag    2694
Glu Ala Thr Leu Lys Lys Thr Asp Ser Cys Asp Ser Gly Ile Thr Lys
            875                 880                 885 agc gac ttg cgc ctg gac aac gtg ggt gag gcc agg agt ccc cag gat    2742
Ser Asp Leu Arg Leu Asp Asn Val Gly Glu Ala Arg Ser Pro Gln Asp
        890                 895                 900 cgg agt ccc atc ctg gca gag gtc aag cat tcg ttc tac ccc atc cct    2790
Arg Ser Pro Ile Leu Ala Glu Val Lys His Ser Phe Tyr Pro Ile Pro
    905                 910                 915 gag cag acg ctg cag gcc aca gtc ctg gag gtg agg cac gag ctg aag    2838
Glu Gln Thr Leu Gln Ala Thr Val Leu Glu Val Arg His Glu Leu Lys
920                 925                 930 gag gac atc aag gcc tta aac gcc aaa atg acc aat att gag aaa cag    2886
Glu Asp Ile Lys Ala Leu Asn Ala Lys Met Thr Asn Ile Glu Lys Gln
935                 940                 945                 950 ctc tct gag ata ctc agg ata tta act tcc aga aga tcc tct cag tct    2934
Leu Ser Glu Ile Leu Arg Ile Leu Thr Ser Arg Arg Ser Ser Gln Ser
            955                 960                 965 cct cag gag ttg ttt gaa ata tcg agg cca cag tcc cca gaa tca gag    2982
Pro Gln Glu Leu Phe Glu Ile Ser Arg Pro Gln Ser Pro Glu Ser Glu
        970                 975                 980 aga gac att ttt gga gcc agc tga gaggtctatt taaaaaaaaa gtcagagaca   3036
Arg Asp Ile Phe Gly Ala Ser  *
    985 gatacctcca accctgccgt caccaccacc cctaccaccc ggaattc                3083
```

<210> SEQ ID NO 32
<211> LENGTH: 989
<212> TYPE: PRT
<213> ORGANISM: Homo Sapiens

<400> SEQUENCE: 32

```
Met Thr Met Ala Gly Gly Arg Arg Gly Leu Val Ala Pro Gln Asn Thr
 1               5                  10                  15

Phe Leu Glu Asn Ile Val Arg Arg Ser Asn Asp Thr Asn Phe Val Leu
             20                  25                  30

Gly Asn Ala Gln Ile Val Asp Trp Pro Ile Val Tyr Ser Asn Asp Gly
         35                  40                  45

Phe Cys Lys Leu Ser Gly Tyr His Arg Ala Glu Val Met Gln Lys Ser
     50                  55                  60

Ser Thr Cys Ser Phe Met Tyr Gly Glu Leu Thr Asp Lys Asp Thr Ile
 65                  70                  75                  80

Glu Lys Val Arg Gln Thr Phe Glu Asn Tyr Glu Met Asn Ser Phe Glu
                 85                  90                  95

Ile Leu Met Tyr Lys Lys Asn Arg Thr Pro Val Trp Phe Phe Val Lys
            100                 105                 110

Ile Ala Pro Ile Arg Asn Glu Gln Asp Lys Val Val Leu Phe Leu Cys
        115                 120                 125
```

```
Thr Phe Ser Asp Ile Thr Ala Phe Lys Gln Pro Ile Glu Asp Asp Ser
    130                 135                 140

Cys Lys Gly Trp Gly Lys Phe Ala Arg Leu Thr Arg Ala Leu Thr Ser
145                 150                 155                 160

Ser Arg Gly Val Leu Gln Gln Leu Ala Pro Ser Val Gln Lys Gly Glu
                165                 170                 175

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
        195                 200                 205

Ile Ile Leu His Tyr Cys Val Phe Lys Thr Thr Trp Asp Trp Ile Ile
    210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
                245                 250                 255

Val Asp Val Ile Phe Leu Val Asp Ile Val Leu Asn Phe His Thr Thr
                260                 265                 270

Phe Val Gly Pro Ala Gly Glu Val Ile Ser Asp Pro Lys Leu Ile Arg
            275                 280                 285

Met Asn Tyr Leu Lys Thr Trp Phe Val Ile Asp Leu Leu Ser Cys Leu
    290                 295                 300

Pro Tyr Asp Val Ile Asn Ala Phe Glu Asn Val Asp Glu Val Ser Ala
305                 310                 315                 320

Phe Met Gly Asp Pro Gly Lys Ile Gly Phe Ala Asp Gln Ile Pro Pro
                325                 330                 335

Pro Leu Glu Gly Arg Glu Ser Gln Gly Ile Ser Ser Leu Phe Ser Ser
            340                 345                 350

Leu Lys Val Val Arg Leu Leu Arg Leu Gly Arg Val Ala Arg Lys Leu
    355                 360                 365

Asp His Tyr Ile Glu Tyr Gly Ala Ala Val Leu Val Leu Leu Val Cys
    370                 375                 380

Val Phe Gly Leu Ala Ala His Trp Met Ala Cys Ile Trp Tyr Ser Ile
385                 390                 395                 400

Gly Asp Tyr Glu Ile Phe Asp Glu Asp Thr Lys Thr Ile Arg Asn Asn
                405                 410                 415

Ser Trp Leu Tyr Gln Leu Ala Met Asp Ile Gly Thr Pro Tyr Gln Phe
                420                 425                 430

Asn Gly Ser Gly Ser Gly Lys Trp Glu Gly Gly Pro Ser Lys Asn Ser
            435                 440                 445

Val Tyr Ile Ser Ser Leu Tyr Phe Thr Met Thr Ser Leu Thr Ser Val
    450                 455                 460

Gly Phe Gly Asn Ile Ala Pro Ser Thr Asp Ile Glu Lys Ile Phe Ala
465                 470                 475                 480

Val Ala Ile Met Met Ile Gly Ser Leu Leu Tyr Ala Thr Ile Phe Gly
                485                 490                 495

Asn Val Thr Thr Ile Phe Gln Gln Met Tyr Ala Asn Thr Asn Arg Tyr
            500                 505                 510

His Glu Met Leu Asn Ser Val Arg Asp Phe Leu Lys Leu Tyr Gln Val
        515                 520                 525

Pro Lys Gly Leu Ser Glu Arg Val Met Asp Tyr Ile Val Ser Thr Trp
        530                 535                 540
```

-continued

```
Ser Met Ser Arg Gly Ile Asp Thr Glu Lys Val Leu Gln Ile Cys Pro
545                 550                 555                 560

Lys Asp Met Arg Ala Asp Ile Cys Val His Leu Asn Arg Lys Val Phe
                565                 570                 575

Lys Glu His Pro Ala Phe Arg Leu Ala Ser Asp Gly Cys Leu Arg Ala
                580                 585                 590

Leu Ala Met Glu Phe Gln Thr Val His Cys Ala Pro Gly Asp Leu Ile
                595                 600                 605

Tyr His Ala Gly Glu Ser Val Asp Ser Leu Cys Phe Val Ser Gly
        610                 615                 620

Ser Leu Glu Val Ile Gln Asp Asp Glu Val Val Ala Ile Leu Gly Lys
625                 630                 635                 640

Gly Asp Val Phe Gly Asp Val Phe Trp Lys Glu Ala Thr Leu Ala Gln
                645                 650                 655

Ser Cys Ala Asn Val Arg Ala Leu Thr Tyr Cys Asp Leu His Val Ile
                660                 665                 670

Lys Arg Asp Ala Leu Gln Lys Val Leu Glu Phe Tyr Thr Ala Phe Ser
                675                 680                 685

His Ser Phe Ser Arg Asn Leu Ile Leu Thr Tyr Asn Leu Arg Lys Arg
690                 695                 700

Ile Val Phe Arg Lys Ile Ser Asp Val Lys Arg Glu Glu Glu Arg
705                 710                 715                 720

Met Lys Arg Lys Asn Glu Ala Pro Leu Ile Leu Pro Pro Asp His Pro
                725                 730                 735

Val Arg Arg Leu Phe Gln Arg Phe Arg Gln Lys Glu Ala Arg Leu
                740                 745                 750

Ala Ala Glu Arg Gly Gly Arg Asp Leu Asp Asp Leu Asp Val Glu Lys
                755                 760                 765

Gly Asn Val Leu Thr Glu His Ala Ser Ala Asn His Ser Leu Val Lys
770                 775                 780

Ala Ser Val Val Thr Val Arg Glu Ser Pro Ala Thr Pro Val Ser Phe
785                 790                 795                 800

Gln Ala Ala Ser Thr Ser Gly Val Pro Asp His Ala Lys Leu Gln Ala
                805                 810                 815

Pro Gly Ser Glu Cys Leu Gly Pro Lys Gly Gly Gly Asp Cys Ala
                820                 825                 830

Lys Arg Lys Ser Trp Ala Arg Phe Lys Asp Ala Cys Gly Lys Ser Glu
                835                 840                 845

Asp Trp Asn Lys Val Ser Lys Ala Glu Ser Met Glu Thr Leu Pro Glu
850                 855                 860

Arg Thr Lys Ala Ser Gly Glu Ala Thr Leu Lys Lys Thr Asp Ser Cys
865                 870                 875                 880

Asp Ser Gly Ile Thr Lys Ser Asp Leu Arg Leu Asp Asn Val Gly Glu
                885                 890                 895

Ala Arg Ser Pro Gln Asp Arg Ser Pro Ile Leu Ala Glu Val Lys His
                900                 905                 910

Ser Phe Tyr Pro Ile Pro Glu Gln Thr Leu Gln Ala Thr Val Leu Glu
                915                 920                 925

Val Arg His Glu Leu Lys Glu Asp Ile Lys Ala Leu Asn Ala Lys Met
                930                 935                 940

Thr Asn Ile Glu Lys Gln Leu Ser Glu Ile Leu Arg Ile Leu Thr Ser
945                 950                 955                 960
```

```
                          Arg Arg Ser Ser Gln Ser Pro Gln Glu Leu Phe Glu Ile Ser Arg Pro
                                          965                 970                 975

Gln Ser Pro Glu Ser Glu Arg Asp Ile Phe Gly Ala Ser
                                      980                 985

<210> SEQ ID NO 33
<211> LENGTH: 6313
<212> TYPE: DNA
<213> ORGANISM: Homo Sapiens
<220> FEATURE:
<221> NAME/KEY: CDS
<222> LOCATION: (348)...(3713)

<400> SEQUENCE: 33
ggcatcccag gatttggaat tcagctgtga gctcatgagc tgatggatgt ttccaggagt    60
accctgaaga ccacccaggt gggagtgtaa gataaccttc cagataaaga gttgctgcta   120
ccaaaagagt gctgacacca tcacagtatg ttcccttctc aaccctggac atggttcaga   180
aacagctaaa gcagacaaga atctggggca gccaatattg taccacctgc caaagcttgg   240
cacaaacaat ctggaagcca aaaattgcac atactgtgga acagagcaag tggttctggc   300
ctccctggga tttggatcct ggtttccaga gctaagaaca caaagtc atg aag gtg     356
                                                    Met Lys Val
                                                    1 aag gag gag aag gct ggg gta gga aag ctg gac cac act aac cac agg     404
Lys Glu Glu Lys Ala Gly Val Gly Lys Leu Asp His Thr Asn His Arg
  5                  10                  15 agg aga ttt ccg gat cag aaa gaa tgc cct cct atc cac att ggg ctt     452
Arg Arg Phe Pro Asp Gln Lys Glu Cys Pro Pro Ile His Ile Gly Leu
 20                  25                  30                  35 cca gta ccc act tac cct caa aga aaa act gac cag aag gga cat ctt     500
Pro Val Pro Thr Tyr Pro Gln Arg Lys Thr Asp Gln Lys Gly His Leu
                 40                  45                  50 tca ggc ctg caa aaa gtc cac tgg ggc ctg cgg cca gac cag cca cag     548
Ser Gly Leu Gln Lys Val His Trp Gly Leu Arg Pro Asp Gln Pro Gln
             55                  60                  65 cag gaa ctg act ggc cca ggg agt ggg gca agc agc cag gac agc agc     596
Gln Glu Leu Thr Gly Pro Gly Ser Gly Ala Ser Ser Gln Asp Ser Ser
         70                  75                  80 atg gat ctt atc agc agg act cgg tcc cca gct gct gag cag ctc cag     644
Met Asp Leu Ile Ser Arg Thr Arg Ser Pro Ala Ala Glu Gln Leu Gln
     85                  90                  95 gac atc ctg ggg gag gaa gat gag gct ccc aac ccc acc ctc ttt aca     692
Asp Ile Leu Gly Glu Glu Asp Glu Ala Pro Asn Pro Thr Leu Phe Thr
100                 105                 110                 115 gag atg gat act ctg cag cat gac gga gac cag atg gag tgg aag gag     740
Glu Met Asp Thr Leu Gln His Asp Gly Asp Gln Met Glu Trp Lys Glu
                120                 125                 130 tca gcc agg tgg ata aag ttt gaa gaa aag gta gag gaa ggc ggc gaa     788
Ser Ala Arg Trp Ile Lys Phe Glu Glu Lys Val Glu Glu Gly Gly Glu
            135                 140                 145 cgc tgg agc aag ccc cac gtg tcc aca cta tcc ctg cac agc ctc ttc     836
Arg Trp Ser Lys Pro His Val Ser Thr Leu Ser Leu His Ser Leu Phe
        150                 155                 160 gag ctc cgt acc tgc ctg cag acg ggg acg gtg ctg ctg gat ttg gac     884
Glu Leu Arg Thr Cys Leu Gln Thr Gly Thr Val Leu Leu Asp Leu Asp
    165                 170                 175 agt ggc tcc tta cca cag atc ata gat gat gtc att gag aag cag att     932
Ser Gly Ser Leu Pro Gln Ile Ile Asp Asp Val Ile Glu Lys Gln Ile
180                 185                 190                 195
```

```
                                                                -continued gag gat ggt ctc ctg cgg cca gag ctc cgg gag agg gtc agt tac gtc          980
Glu Asp Gly Leu Leu Arg Pro Glu Leu Arg Glu Arg Val Ser Tyr Val
            200                 205                 210 ctc ctg agg agg cac cgc cac caa acc aag aag ccc atc cac cgc tcc         1028
Leu Leu Arg Arg His Arg His Gln Thr Lys Lys Pro Ile His Arg Ser
        215                 220                 225 tta gct gac att ggg aag tca gtc tcc acc aca aat cgc agt cct gcc         1076
Leu Ala Asp Ile Gly Lys Ser Val Ser Thr Thr Asn Arg Ser Pro Ala
    230                 235                 240 cgg agc cct ggt gct ggc ccg agt cta cac cac tcc acg gaa gac ctg         1124
Arg Ser Pro Gly Ala Gly Pro Ser Leu His His Ser Thr Glu Asp Leu
245                 250                 255 cgg atg cgg cag agt gca aat tac gga cgt ctg tgt cat gcc cag agc         1172
Arg Met Arg Gln Ser Ala Asn Tyr Gly Arg Leu Cys His Ala Gln Ser
260                 265                 270                 275 aga agc atg aat gac att tct ctc acc cca aac aca gac cag cgg aaa         1220
Arg Ser Met Asn Asp Ile Ser Leu Thr Pro Asn Thr Asp Gln Arg Lys
            280                 285                 290 aac aaa ttc atg aag aag atc ccc aag gac tca gaa gcg tcc aac gtg         1268
Asn Lys Phe Met Lys Lys Ile Pro Lys Asp Ser Glu Ala Ser Asn Val
        295                 300                 305 ctc gtg ggc gag gtg gac ttc cta gac cag cca ttc atc gcg ttc gtg         1316
Leu Val Gly Glu Val Asp Phe Leu Asp Gln Pro Phe Ile Ala Phe Val
    310                 315                 320 cgc ctc atc cag tcg gcc atg ctg gga gga gtg acc gag gtg cct gtc         1364
Arg Leu Ile Gln Ser Ala Met Leu Gly Gly Val Thr Glu Val Pro Val
325                 330                 335 ccc acc aga ttt ctg ttt ata cta ctg gga cct tct ggg aga gca aaa         1412
Pro Thr Arg Phe Leu Phe Ile Leu Leu Gly Pro Ser Gly Arg Ala Lys
340                 345                 350                 355 tcc tac aat gaa att ggc cgt gcc att gca acc ctc atg gta gat gat         1460
Ser Tyr Asn Glu Ile Gly Arg Ala Ile Ala Thr Leu Met Val Asp Asp
            360                 365                 370 ctc ttc agt gac gtg gcc tac aaa gcc cgc aat cgg gaa gat ctg atc         1508
Leu Phe Ser Asp Val Ala Tyr Lys Ala Arg Asn Arg Glu Asp Leu Ile
        375                 380                 385 gca gga att gat gaa ttt ctg gat gag gtc atc gtc ctt cct cct gga         1556
Ala Gly Ile Asp Glu Phe Leu Asp Glu Val Ile Val Leu Pro Pro Gly
    390                 395                 400 gaa tgg gac cca aat atc cgg att gag ccc ccc aag aag gtg ccc tct         1604
Glu Trp Asp Pro Asn Ile Arg Ile Glu Pro Pro Lys Lys Val Pro Ser
405                 410                 415 gct gac aag agg aaa tct gtg ttc tcc cta gca gag ctg ggc cag atg         1652
Ala Asp Lys Arg Lys Ser Val Phe Ser Leu Ala Glu Leu Gly Gln Met
420                 425                 430                 435 aat ggc tct gtg gga gga ggc ggc gga gct cct gga gga ggc aat gga         1700
Asn Gly Ser Val Gly Gly Gly Gly Ala Pro Gly Gly Gly Asn Gly
            440                 445                 450 ggt ggt ggt ggt ggt ggc agt ggc ggc ggg gct ggc agt ggc ggg gcc         1748
Gly Gly Gly Gly Gly Gly Ser Gly Gly Gly Ala Gly Ser Gly Gly Ala
        455                 460                 465 ggc gga aca agc agc ggg gat gat gga gag atg cca gcc atg cat gaa         1796
Gly Gly Thr Ser Ser Gly Asp Asp Gly Glu Met Pro Ala Met His Glu
    470                 475                 480 atc ggg gag gaa ctt atc tgg aca gga agg ttc ttc ggt ggc ctg tgt         1844
Ile Gly Glu Glu Leu Ile Trp Thr Gly Arg Phe Phe Gly Gly Leu Cys
485                 490                 495 ctg gat atc aag agg aag ttg ccc tgg ttc cca agt gac ttc tat gat         1892
Leu Asp Ile Lys Arg Lys Leu Pro Trp Phe Pro Ser Asp Phe Tyr Asp
500                 505                 510                 515
```

```
ggc ttc cac att cag tcc atc tct gcc atc cta ttc atc tac ctc ggc      1940
Gly Phe His Ile Gln Ser Ile Ser Ala Ile Leu Phe Ile Tyr Leu Gly
                520                 525                 530 tgt atc acc aac gcg atc acc ttt ggt ggg ctt ctg ggg gat gcc acc      1988
Cys Ile Thr Asn Ala Ile Thr Phe Gly Gly Leu Leu Gly Asp Ala Thr
            535                 540                 545 gac aat tat cag gga gtg atg gag agc ttc ctg ggc act gcc atg gct      2036
Asp Asn Tyr Gln Gly Val Met Glu Ser Phe Leu Gly Thr Ala Met Ala
        550                 555                 560 ggc tcc ttg ttc tgc ctc ttc tcg gga cag cct ctc atc att ctc agc      2084
Gly Ser Leu Phe Cys Leu Phe Ser Gly Gln Pro Leu Ile Ile Leu Ser
    565                 570                 575 agc acg ggg ccc atc ctc atc ttt gag aag ctc ctc ttc gac ttc agc      2132
Ser Thr Gly Pro Ile Leu Ile Phe Glu Lys Leu Leu Phe Asp Phe Ser
580                 585                 590                 595 aaa ggc aat ggc ctg gac tac atg gag ttc cgc ctc tgg att ggc cta      2180
Lys Gly Asn Gly Leu Asp Tyr Met Glu Phe Arg Leu Trp Ile Gly Leu
                600                 605                 610 cac tca gct gtc cag tgc ctt atc cta gtg gcc aca gat gcc agc ttt      2228
His Ser Ala Val Gln Cys Leu Ile Leu Val Ala Thr Asp Ala Ser Phe
            615                 620                 625 atc atc aaa tat atc acc cgc ttc acc gag gag ggc ttc tcc acc ctt      2276
Ile Ile Lys Tyr Ile Thr Arg Phe Thr Glu Glu Gly Phe Ser Thr Leu
        630                 635                 640 atc agc ttc atc ttc atc tac gat gcc atc aag aag atg atc ggt gcc      2324
Ile Ser Phe Ile Phe Ile Tyr Asp Ala Ile Lys Lys Met Ile Gly Ala
    645                 650                 655 ttc aag tac tac cct atc aat atg gac ttc aag cca aac ttc atc act      2372
Phe Lys Tyr Tyr Pro Ile Asn Met Asp Phe Lys Pro Asn Phe Ile Thr
660                 665                 670                 675 acc tac aag tgc gag tgt gtc gcc cct gac aca gtg aat aca acc gtg      2420
Thr Tyr Lys Cys Glu Cys Val Ala Pro Asp Thr Val Asn Thr Thr Val
                680                 685                 690 ttc aat gct tca gcc cca ttg gca cca gac acc aac gct tct ctg tac      2468
Phe Asn Ala Ser Ala Pro Leu Ala Pro Asp Thr Asn Ala Ser Leu Tyr
            695                 700                 705 aac ctc ctt aac ctc aca gcg ttg gac tgg tcc ctg ctg agc aag aag      2516
Asn Leu Leu Asn Leu Thr Ala Leu Asp Trp Ser Leu Leu Ser Lys Lys
        710                 715                 720 gag tgt ctg agc tac ggc ggg cgc ctg ctt ggg aat tcc tgc aag ttt      2564
Glu Cys Leu Ser Tyr Gly Gly Arg Leu Leu Gly Asn Ser Cys Lys Phe
    725                 730                 735 atc cca gac ctg gcg ctc atg tcc ttc atc ctt ttc ttt ggg aca tac      2612
Ile Pro Asp Leu Ala Leu Met Ser Phe Ile Leu Phe Phe Gly Thr Tyr
740                 745                 750                 755 tcc atg acc ctg acc ctg aag aag ttc aaa ttc agc cgc tat ttt cct      2660
Ser Met Thr Leu Thr Leu Lys Lys Phe Lys Phe Ser Arg Tyr Phe Pro
                760                 765                 770 acc aag gtc cgg gcc ctg gtg gct gac ttt tcc att gtt ttc tcc atc      2708
Thr Lys Val Arg Ala Leu Val Ala Asp Phe Ser Ile Val Phe Ser Ile
            775                 780                 785 ctg atg ttc tgt gga atc gat gcc tgt ttt ggc cta gaa act ccc aag      2756
Leu Met Phe Cys Gly Ile Asp Ala Cys Phe Gly Leu Glu Thr Pro Lys
        790                 795                 800 ctg cat gtg ccc agt gtc atc aag cca acg cgg cct gac cga ggc tgg      2804
Leu His Val Pro Ser Val Ile Lys Pro Thr Arg Pro Asp Arg Gly Trp
    805                 810                 815 ttc gtg gcc ccc ttt ggg aag aac ccg tgg tgg gta tac cca gca agc      2852
Phe Val Ala Pro Phe Gly Lys Asn Pro Trp Trp Val Tyr Pro Ala Ser
820                 825                 830                 835
```

-continued

| | | |
|---|---|---|
| atc ctg ccc gcc ctg ctg gtg acc atc ctg atc ttc atg gac cag cag<br>Ile Leu Pro Ala Leu Leu Val Thr Ile Leu Ile Phe Met Asp Gln Gln<br>840                    845                  850 | | 2900 |
| atc act gcc gtc att gtc aac cgg aag gag aac aaa ctg aag aag gct<br>Ile Thr Ala Val Ile Val Asn Arg Lys Glu Asn Lys Leu Lys Lys Ala<br>855                    860                  865 | | 2948 |
| gcc ggc tac cat ctg gac ctg ttc tgg gtg ggc atc ctc atg gct ttg<br>Ala Gly Tyr His Leu Asp Leu Phe Trp Val Gly Ile Leu Met Ala Leu<br>870                      875                  880 | | 2996 |
| tgc tcc ttt atg ggg ctc ccc tgg tac gtg gct gcc acg gtc atc tcc<br>Cys Ser Phe Met Gly Leu Pro Trp Tyr Val Ala Ala Thr Val Ile Ser<br>885                    890                  895 | | 3044 |
| atc gcc cac atc gac agc ctc aag atg gag aca gag acc agt gcc cct<br>Ile Ala His Ile Asp Ser Leu Lys Met Glu Thr Glu Thr Ser Ala Pro<br>900                    905                  910                  915 | | 3092 |
| ggg gag cag ccc cag ttt ctg gga gtc agg gaa cag aga gta acc ggc<br>Gly Glu Gln Pro Gln Phe Leu Gly Val Arg Glu Gln Arg Val Thr Gly<br>920                    925                  930 | | 3140 |
| atc atc gtc ttc atc ctg acg gga atc tct gtc ttc ctg gct ccc atc<br>Ile Ile Val Phe Ile Leu Thr Gly Ile Ser Val Phe Leu Ala Pro Ile<br>935                    940                  945 | | 3188 |
| cta aag tgt atc ccc ctg ccg gtg ctg tac gga gtc ttc ctc tac atg<br>Leu Lys Cys Ile Pro Leu Pro Val Leu Tyr Gly Val Phe Leu Tyr Met<br>950                    955                  960 | | 3236 |
| ggc gtg gcc tcc ctg aat ggc atc cag ttc tgg gaa cgc tgc aag ctc<br>Gly Val Ala Ser Leu Asn Gly Ile Gln Phe Trp Glu Arg Cys Lys Leu<br>965                    970                  975 | | 3284 |
| ttc ctg atg cca gcc aag cac cag ccg gac cat gcc ttc ctg cgg cac<br>Phe Leu Met Pro Ala Lys His Gln Pro Asp His Ala Phe Leu Arg His<br>980                    985                  990                  995 | | 3332 |
| gtg ccg ctg cgc cgg atc cac ctc ttc acc ctg gtg cag atc ctc tgc<br>Val Pro Leu Arg Arg Ile His Leu Phe Thr Leu Val Gln Ile Leu Cys<br>1000                  1005                1010 | | 3380 |
| ctg gcg gtg ctc tgg atc ctc aaa tcc acg gtg gct gcc atc atc ttc<br>Leu Ala Val Leu Trp Ile Leu Lys Ser Thr Val Ala Ala Ile Ile Phe<br>1015                  1020                1025 | | 3428 |
| ccg gtc atg atc ctg ggc ctc atc atc gtt cga agg ctt ctg gat ttc<br>Pro Val Met Ile Leu Gly Leu Ile Ile Val Arg Arg Leu Leu Asp Phe<br>1030                  1035                1040 | | 3476 |
| atc ttt tcc cag cac gac ctg gcc tgg att gac aac atc ctc cca gag<br>Ile Phe Ser Gln His Asp Leu Ala Trp Ile Asp Asn Ile Leu Pro Glu<br>1045                  1050                1055 | | 3524 |
| aag gaa aaa aag gag aca gac aag aag agg aag aga aaa aaa ggg gcc<br>Lys Glu Lys Lys Glu Thr Asp Lys Lys Arg Lys Arg Lys Lys Gly Ala<br>1060                  1065                1070                1075 | | 3572 |
| cac gag gac tgt gat gag gag ccc cag ttc cct cct ccc tcg gtt ata<br>His Glu Asp Cys Asp Glu Glu Pro Gln Phe Pro Pro Pro Ser Val Ile<br>1080                  1085                1090 | | 3620 |
| aag att ccc atg gaa agt gtc caa tca gat ccc caa aac ggt atc cac<br>Lys Ile Pro Met Glu Ser Val Gln Ser Asp Pro Gln Asn Gly Ile His<br>1095                  1100                1105 | | 3668 |
| tgc att gcc aga aaa aga tct tcc agt tgg agt tac tca ctc tga<br>Cys Ile Ala Arg Lys Arg Ser Ser Ser Trp Ser Tyr Ser Leu *<br>1110                  1115                1120 | | 3713 |
| ttcttccttc agtgacacag aacttgaccg aagcatcacc ttgcacttca aaatatcctg | | 3773 |
| tccagcttca cctgctttca gctactcacg gaacccagtg ttcatggtgc cacaggtgaa | | 3833 |
| gatagagatg gagtcagact atgacttcac agacatggat aaataccgaa gagaaactga | | 3893 |

```
cagtgagacc accctctagg atgaagcagc ttctcccaga tgggagatgg agagcctggc    3953
ttagtcttca ctgggagggt cttaacttct ctgtgcctgt ttccttcttt atcaaacaga    4013
gggagtccgt ctgcctatag aaaactggag atctattgat gaaaagtatt gcttagatgc    4073
aaagctctcc cctttgtagt aattaaaata cctaaagcta atattatat tttattttaa     4133 aatgcagttc agcatagaaa ttctaacatt tctttggaaa taaaaaaatg cttgtttccc    4193
caaaccatag ctaagataaa ggggcaatag tcaattcata tttaaaacaa atatcaattt    4253
aaaattgttt aaaggttaga tttaaatata gatgttctca aacaaacttg taatatactt    4313
ttatgtcact agaccatctt tggaatattt ggcaattctg catattaaga aatgctgaaa    4373
aggtcctatc ttttctccct gtcacatcca atttcctaag ggttatatga aaagtttgaa    4433 ccagccggc acagtggcac acgcctgtaa tcctagcact tgggaggcc gaggcaggtg      4493 aattgcctga gctcaggagt tcgagaccag cctaggcaac acggtgaaac cccgtctcta    4553
ctaaactaca aaaaattagc cgggtgtggt ggcatgcacc tgtagtccca gctattcggg    4613
aggctgaggc aggagaatcg cttgaaccca ggaggcagaa gttgcagtga gctgagatgg    4673
caccactgca ctccagccta ggcaacagag tgagactccg tatccaaaca aaaaaaaagt    4733
ttgaaccatc tgcattatgg gccttgctcc agaagtgtga ctgggctttt cccagattga    4793
aaagccagtt ccaaaactct gttaatgaaa gaaccaatgc atctgagtgg ataaatgttt    4853
ctaaaataaa atagttcttg ttaaagtgaa atttgaaacc acatgttaaa tcaaaatgat    4913
cctttaaatt agtatcactg ttttttcata cctggaatca catttcatga tacatttggg    4973
tgggtcctcc ctgcaaattt tcaatgttta ttcccaaagt caaactccca ttcatgtgaa    5033
caatacaggt tagacagagg taaggtcaca ttttacatta caactttgca atattaatca    5093
acctagtact ttaaaggaat gattgaaaac tatttgggaa gataaaaacc agtttcaatg    5153
aagcaaacct attcctcatg aaacttaaga tcagtcattt tatcttcaat ccacatttaa    5213
tgaacaccaa ccatgttgat ttaatgccta ctatgaccct gacagccaca gtgcatctga    5273
cacttacttt ctccaaaaca actatgattt aaaccttgag taaatcactt gaaccttgag    5333
gttagagtta ctatatttgc tcaagatgac aaatgcaggt gctttctttt ttaaagaaaa    5393
atgacactag atcattaaca ccttgagtat aggacaggta attgcctctg taattcccag    5453
cgtctagtgt agtgcctggt ccatagaaag ctctcaataa gtgtttgatt acatttaatc    5513
tcagagctcc cttccaaggg atactgccaa gaggtaaagc tccaaacctc tactcttact    5573
gagagcagaa tttcttagaa tttccagaac catctcctat gcttaagtat aaattcttgt    5633
cagacacagt ggctcacacc tgtaatcccg ctacttggga ggcagaggtg gggggaatca    5693
gcagaggtca ggaggtcaag accagcctgg gcaacatagt gagacccatc tctaaacaaa    5753
tgtttaaaaa ttagctaggc atgctggcac acacctgtag tcccagccat ttcgagggct    5813
gatgcaggag gatcgtttaa gtccaggagt tcaaggctgc agtgagctat aatcatgcca    5873
ctgcactcca gccagggaga cagctggaat ccatgtctta taaacaataa taattaattt    5933
ttaaaaaaag tatttatcat ccacaccaat cctggggaag ctaacaatcc acccttaaca    5993
catttcagtt ttaaaacctg gctgatctgg aatagaactt tgtccaaatt aaattgtaga    6053
aatgctatgg attcaagagt aaacctgctt gattaatcaa acaagctgga aaactactgt    6113
taatttcttt gttgtaaatt gatcactgta attttacctt acatgtcatt tatattttgt    6173
atatacatga acatttttaat ttccatagct tttaacaggt tgacataata cttctccatg   6233
```

-continued

```
cagtaagtca gtcattttt ccacttgtaa ctgtaattca ataaattta atcctgtctg     6293 gtcaaaaaaa aaaaaaaaaa                                                6313
```

<210> SEQ ID NO 34
<211> LENGTH: 1121
<212> TYPE: PRT
<213> ORGANISM: Homo Sapiens

<400> SEQUENCE: 34

```
Met Lys Val Lys Glu Lys Ala Gly Val Gly Lys Leu Asp His Thr
 1               5                  10                  15

Asn His Arg Arg Phe Pro Asp Gln Lys Glu Cys Pro Pro Ile His
             20                  25                  30

Ile Gly Leu Pro Val Pro Thr Tyr Pro Gln Arg Lys Thr Asp Gln Lys
         35                  40                  45

Gly His Leu Ser Gly Leu Gln Lys Val His Trp Gly Leu Arg Pro Asp
     50                  55                  60

Gln Pro Gln Gln Glu Leu Thr Gly Pro Gly Ser Gly Ala Ser Ser Gln
 65                  70                  75                  80

Asp Ser Ser Met Asp Leu Ile Ser Arg Thr Arg Ser Pro Ala Ala Glu
                 85                  90                  95

Gln Leu Gln Asp Ile Leu Gly Glu Glu Asp Glu Ala Pro Asn Pro Thr
            100                 105                 110

Leu Phe Thr Glu Met Asp Thr Leu Gln His Asp Gly Asp Gln Met Glu
        115                 120                 125

Trp Lys Glu Ser Ala Arg Trp Ile Lys Phe Glu Glu Lys Val Glu Glu
    130                 135                 140

Gly Gly Glu Arg Trp Ser Lys Pro His Val Ser Thr Leu Ser Leu His
145                 150                 155                 160

Ser Leu Phe Glu Leu Arg Thr Cys Leu Gln Thr Gly Thr Val Leu Leu
                165                 170                 175

Asp Leu Asp Ser Gly Ser Leu Pro Gln Ile Ile Asp Asp Val Ile Glu
            180                 185                 190

Lys Gln Ile Glu Asp Gly Leu Leu Arg Pro Glu Leu Arg Glu Arg Val
        195                 200                 205

Ser Tyr Val Leu Leu Arg Arg His Arg His Gln Thr Lys Lys Pro Ile
    210                 215                 220

His Arg Ser Leu Ala Asp Ile Gly Lys Ser Val Ser Thr Thr Asn Arg
225                 230                 235                 240

Ser Pro Ala Arg Ser Pro Gly Ala Gly Pro Ser Leu His His Ser Thr
                245                 250                 255

Glu Asp Leu Arg Met Arg Gln Ser Ala Asn Tyr Gly Arg Leu Cys His
            260                 265                 270

Ala Gln Ser Arg Ser Met Asn Asp Ile Ser Leu Thr Pro Asn Thr Asp
        275                 280                 285

Gln Arg Lys Asn Lys Phe Met Lys Lys Ile Pro Lys Asp Ser Glu Ala
    290                 295                 300

Ser Asn Val Leu Val Gly Glu Val Asp Phe Leu Asp Gln Pro Phe Ile
305                 310                 315                 320

Ala Phe Val Arg Leu Ile Gln Ser Ala Met Leu Gly Gly Val Thr Glu
                325                 330                 335

Val Pro Val Pro Thr Arg Phe Leu Phe Ile Leu Leu Gly Pro Ser Gly
            340                 345                 350
```

-continued

```
Arg Ala Lys Ser Tyr Asn Glu Ile Gly Arg Ala Ile Ala Thr Leu Met
        355                 360                 365
Val Asp Asp Leu Phe Ser Asp Val Ala Tyr Lys Ala Arg Asn Arg Glu
370                 375                 380
Asp Leu Ile Ala Gly Ile Asp Glu Phe Leu Asp Glu Val Ile Val Leu
385                 390                 395                 400
Pro Pro Gly Glu Trp Asp Pro Asn Ile Arg Ile Glu Pro Pro Lys Lys
                    405                 410                 415
Val Pro Ser Ala Asp Lys Arg Lys Ser Val Phe Ser Leu Ala Glu Leu
            420                 425                 430
Gly Gln Met Asn Gly Ser Val Gly Gly Gly Gly Ala Pro Gly Gly
        435                 440                 445
Gly Asn Gly Gly Gly Gly Gly Gly Ser Gly Gly Ala Gly Ser
        450                 455                 460
Gly Gly Ala Gly Gly Thr Ser Ser Gly Asp Asp Gly Glu Met Pro Ala
465                 470                 475                 480
Met His Glu Ile Gly Glu Leu Ile Trp Thr Gly Arg Phe Phe Gly
                    485                 490                 495
Gly Leu Cys Leu Asp Ile Lys Arg Lys Leu Pro Trp Phe Pro Ser Asp
                500                 505                 510
Phe Tyr Asp Gly Phe His Ile Gln Ser Ile Ser Ala Ile Leu Phe Ile
                    515                 520                 525
Tyr Leu Gly Cys Ile Thr Asn Ala Ile Thr Phe Gly Gly Leu Leu Gly
            530                 535                 540
Asp Ala Thr Asp Asn Tyr Gln Gly Val Met Glu Ser Phe Leu Gly Thr
545                 550                 555                 560
Ala Met Ala Gly Ser Leu Phe Cys Leu Phe Ser Gly Gln Pro Leu Ile
                565                 570                 575
Ile Leu Ser Ser Thr Gly Pro Ile Leu Ile Phe Glu Lys Leu Leu Phe
                580                 585                 590
Asp Phe Ser Lys Gly Asn Gly Leu Asp Tyr Met Glu Phe Arg Leu Trp
            595                 600                 605
Ile Gly Leu His Ser Ala Val Gln Cys Leu Ile Leu Val Ala Thr Asp
        610                 615                 620
Ala Ser Phe Ile Ile Lys Tyr Ile Thr Arg Phe Thr Glu Glu Gly Phe
625                 630                 635                 640
Ser Thr Leu Ile Ser Phe Ile Phe Ile Tyr Asp Ala Ile Lys Lys Met
                    645                 650                 655
Ile Gly Ala Phe Lys Tyr Tyr Pro Ile Asn Met Asp Phe Lys Pro Asn
                660                 665                 670
Phe Ile Thr Thr Tyr Lys Cys Glu Cys Val Ala Pro Asp Thr Val Asn
            675                 680                 685
Thr Thr Val Phe Asn Ala Ser Ala Pro Leu Ala Pro Asp Thr Asn Ala
        690                 695                 700
Ser Leu Tyr Asn Leu Leu Asn Leu Thr Ala Leu Asp Trp Ser Leu Leu
705                 710                 715                 720
Ser Lys Lys Glu Cys Leu Ser Tyr Gly Gly Arg Leu Leu Gly Asn Ser
                    725                 730                 735
Cys Lys Phe Ile Pro Asp Leu Ala Leu Met Ser Phe Ile Leu Phe Phe
                740                 745                 750
Gly Thr Tyr Ser Met Thr Leu Thr Leu Lys Lys Phe Lys Phe Ser Arg
            755                 760                 765
```

Tyr Phe Pro Thr Lys Val Arg Ala Leu Val Ala Asp Phe Ser Ile Val
770                 775                 780

Phe Ser Ile Leu Met Phe Cys Gly Ile Asp Ala Cys Phe Gly Leu Glu
785                 790                 795                 800

Thr Pro Lys Leu His Val Pro Ser Val Ile Lys Pro Thr Arg Pro Asp
                805                 810                 815

Arg Gly Trp Phe Val Ala Pro Phe Gly Lys Asn Pro Trp Trp Val Tyr
                820                 825                 830

Pro Ala Ser Ile Leu Pro Ala Leu Leu Val Thr Ile Leu Ile Phe Met
                835                 840                 845

Asp Gln Gln Ile Thr Ala Val Ile Val Asn Arg Lys Glu Asn Lys Leu
850                 855                 860

Lys Lys Ala Ala Gly Tyr His Leu Asp Leu Phe Trp Val Gly Ile Leu
865                 870                 875                 880

Met Ala Leu Cys Ser Phe Met Gly Leu Pro Trp Tyr Val Ala Ala Thr
                885                 890                 895

Val Ile Ser Ile Ala His Ile Asp Ser Leu Lys Met Glu Thr Glu Thr
                900                 905                 910

Ser Ala Pro Gly Glu Gln Pro Gln Phe Leu Gly Val Arg Glu Gln Arg
                915                 920                 925

Val Thr Gly Ile Ile Val Phe Ile Leu Thr Gly Ile Ser Val Phe Leu
930                 935                 940

Ala Pro Ile Leu Lys Cys Ile Pro Leu Pro Val Leu Tyr Gly Val Phe
945                 950                 955                 960

Leu Tyr Met Gly Val Ala Ser Leu Asn Gly Ile Gln Phe Trp Glu Arg
                965                 970                 975

Cys Lys Leu Phe Leu Met Pro Ala Lys His Gln Pro Asp His Ala Phe
                980                 985                 990

Leu Arg His Val Pro Leu Arg Arg Ile His Leu Phe Thr Leu Val Gln
                995                 1000                1005

Ile Leu Cys Leu Ala Val Leu Trp Ile Leu Lys Ser Thr Val Ala Ala
        1010                1015                1020

Ile Ile Phe Pro Val Met Ile Leu Gly Leu Ile Ile Val Arg Arg Leu
1025                1030                1035                1040

Leu Asp Phe Ile Phe Ser Gln His Asp Leu Ala Trp Ile Asp Asn Ile
                1045                1050                1055

Leu Pro Glu Lys Glu Lys Lys Glu Thr Asp Lys Lys Arg Lys Arg Lys
                1060                1065                1070

Lys Gly Ala His Glu Asp Cys Asp Glu Glu Pro Gln Phe Pro Pro Pro
                1075                1080                1085

Ser Val Ile Lys Ile Pro Met Glu Ser Val Gln Ser Asp Pro Gln Asn
                1090                1095                1100

Gly Ile His Cys Ile Ala Arg Lys Arg Ser Ser Trp Ser Tyr Ser
1105                1110                1115                1120

Leu

<210> SEQ ID NO 35
<211> LENGTH: 3761
<212> TYPE: DNA
<213> ORGANISM: Homo Sapiens
<220> FEATURE:
<221> NAME/KEY: CDS
<222> LOCATION: (70)...(2760)

<400> SEQUENCE: 35

```
gtggcggacg ggcggacgcg ggccggcggc cgctgcggtg ccgggagggc ggctgggcag      60
```

| | | | | | | | | | | | | | | | | |
|---|---|---|---|---|---|---|---|---|---|---|---|---|---|---|---|---|
| gcggcagga | atg | ctg | cgc | gcc | gcc | ctg | tcc | ctg | ctc | gcg | ctg | ccc | ctg | gcg | | 111 |
| | Met | Leu | Arg | Ala | Ala | Leu | Ser | Leu | Leu | Ala | Leu | Pro | Leu | Ala | | |
| | 1 | | | 5 | | | | | 10 | | | | | | | |

| ggg | gcg | gcc | gaa | gag | ccc | acc | cag | aag | cca | gag | tcc | ccg | ggc | gag | cct | 159 |
|---|---|---|---|---|---|---|---|---|---|---|---|---|---|---|---|---|
| Gly | Ala | Ala | Glu | Glu | Pro | Thr | Gln | Lys | Pro | Glu | Ser | Pro | Gly | Glu | Pro | |
| 15 | | | | | 20 | | | | | 25 | | | | | 30 | |

| ccc | cca | ggc | tta | gag | ctc | ttc | cgc | tgg | cag | tgg | cac | gag | gtg | gag | gcg | 207 |
|---|---|---|---|---|---|---|---|---|---|---|---|---|---|---|---|---|
| Pro | Pro | Gly | Leu | Glu | Leu | Phe | Arg | Trp | Gln | Trp | His | Glu | Val | Glu | Ala | |
| | | | | 35 | | | | | 40 | | | | | 45 | | |

| ccc | tac | ctg | gtg | gcc | ctg | tgg | atc | ctg | gtg | gcc | agt | ctg | gcc | aaa | atc | 255 |
|---|---|---|---|---|---|---|---|---|---|---|---|---|---|---|---|---|
| Pro | Tyr | Leu | Val | Ala | Leu | Trp | Ile | Leu | Val | Ala | Ser | Leu | Ala | Lys | Ile | |
| | | | 50 | | | | | 55 | | | | | 60 | | | |

| gtg | ttt | cac | ctg | tct | cgg | aaa | gta | aca | tct | ctg | gtc | cct | gag | agc | tgc | 303 |
|---|---|---|---|---|---|---|---|---|---|---|---|---|---|---|---|---|
| Val | Phe | His | Leu | Ser | Arg | Lys | Val | Thr | Ser | Leu | Val | Pro | Glu | Ser | Cys | |
| | | 65 | | | | | 70 | | | | | 75 | | | | |

| ctg | ctg | att | ttg | ctg | ggc | ctg | gtg | cta | ggg | gga | att | gtt | ttg | gct | gtg | 351 |
|---|---|---|---|---|---|---|---|---|---|---|---|---|---|---|---|---|
| Leu | Leu | Ile | Leu | Leu | Gly | Leu | Val | Leu | Gly | Gly | Ile | Val | Leu | Ala | Val | |
| 80 | | | | | 85 | | | | | 90 | | | | | | |

| gcc | aag | aaa | gct | gag | tac | cag | ctg | gag | cca | ggc | acc | ttc | ttc | ctc | ttc | 399 |
|---|---|---|---|---|---|---|---|---|---|---|---|---|---|---|---|---|
| Ala | Lys | Lys | Ala | Glu | Tyr | Gln | Leu | Glu | Pro | Gly | Thr | Phe | Phe | Leu | Phe | |
| 95 | | | | | 100 | | | | | 105 | | | | | 110 | |

| ctg | ctg | cct | cct | att | gtg | ttg | gac | tca | ggc | tat | ttc | atg | cct | agc | agg | 447 |
|---|---|---|---|---|---|---|---|---|---|---|---|---|---|---|---|---|
| Leu | Leu | Pro | Pro | Ile | Val | Leu | Asp | Ser | Gly | Tyr | Phe | Met | Pro | Ser | Arg | |
| | | | | 115 | | | | | 120 | | | | | 125 | | |

| ctg | ttc | ttt | gac | aac | ttg | ggt | gcc | atc | ctc | acc | tat | gcc | gtg | gta | ggc | 495 |
|---|---|---|---|---|---|---|---|---|---|---|---|---|---|---|---|---|
| Leu | Phe | Phe | Asp | Asn | Leu | Gly | Ala | Ile | Leu | Thr | Tyr | Ala | Val | Val | Gly | |
| | | | 130 | | | | | 135 | | | | | 140 | | | |

| aca | ctc | tgg | aat | gcc | ttc | aca | aca | ggc | gct | gcc | ctc | tgg | ggc | ttg | cag | 543 |
|---|---|---|---|---|---|---|---|---|---|---|---|---|---|---|---|---|
| Thr | Leu | Trp | Asn | Ala | Phe | Thr | Thr | Gly | Ala | Ala | Leu | Trp | Gly | Leu | Gln | |
| | | 145 | | | | | 150 | | | | | 155 | | | | |

| cag | gct | gga | ctt | gta | gcc | cct | agg | gtg | cag | gct | ggc | tta | ctg | gac | ttc | 591 |
|---|---|---|---|---|---|---|---|---|---|---|---|---|---|---|---|---|
| Gln | Ala | Gly | Leu | Val | Ala | Pro | Arg | Val | Gln | Ala | Gly | Leu | Leu | Asp | Phe | |
| | 160 | | | | | 165 | | | | | 170 | | | | | |

| ctg | ctg | ttt | ggg | agc | ctc | atc | tcg | gcg | gtg | gac | ccc | gtg | gcc | gtg | cta | 639 |
|---|---|---|---|---|---|---|---|---|---|---|---|---|---|---|---|---|
| Leu | Leu | Phe | Gly | Ser | Leu | Ile | Ser | Ala | Val | Asp | Pro | Val | Ala | Val | Leu | |
| 175 | | | | | 180 | | | | | 185 | | | | | 190 | |

| gct | gtc | ttt | gag | gag | gtg | cac | gtc | aat | gag | act | ctc | ttt | atc | atc | gtc | 687 |
|---|---|---|---|---|---|---|---|---|---|---|---|---|---|---|---|---|
| Ala | Val | Phe | Glu | Glu | Val | His | Val | Asn | Glu | Thr | Leu | Phe | Ile | Ile | Val | |
| | | | | 195 | | | | | 200 | | | | | 205 | | |

| ttt | ggc | gag | tcc | ctg | ctc | aac | gat | gct | gtc | acc | gtg | gtg | ctg | tac | aag | 735 |
|---|---|---|---|---|---|---|---|---|---|---|---|---|---|---|---|---|
| Phe | Gly | Glu | Ser | Leu | Leu | Asn | Asp | Ala | Val | Thr | Val | Val | Leu | Tyr | Lys | |
| | | | 210 | | | | | 215 | | | | | 220 | | | |

| gtc | tgc | aac | tcc | ttt | gtg | gag | atg | ggc | tct | gcc | aat | gtg | cag | gcc | act | 783 |
|---|---|---|---|---|---|---|---|---|---|---|---|---|---|---|---|---|
| Val | Cys | Asn | Ser | Phe | Val | Glu | Met | Gly | Ser | Ala | Asn | Val | Gln | Ala | Thr | |
| | | 225 | | | | | 230 | | | | | 235 | | | | |

| gac | tac | ctg | aag | gga | gtc | gcc | tcc | ctg | ttt | gtg | gtc | agt | ctg | ggc | ggg | 831 |
|---|---|---|---|---|---|---|---|---|---|---|---|---|---|---|---|---|
| Asp | Tyr | Leu | Lys | Gly | Val | Ala | Ser | Leu | Phe | Val | Val | Ser | Leu | Gly | Gly | |
| | 240 | | | | | 245 | | | | | 250 | | | | | |

| gca | gcc | gtg | ggc | tta | gtc | ttt | gcc | ttc | ctc | ctg | gcc | ctg | acc | aca | cgc | 879 |
|---|---|---|---|---|---|---|---|---|---|---|---|---|---|---|---|---|
| Ala | Ala | Val | Gly | Leu | Val | Phe | Ala | Phe | Leu | Leu | Ala | Leu | Thr | Thr | Arg | |
| 255 | | | | | 260 | | | | | 265 | | | | | 270 | |

| ttc | acc | aag | cgg | gtc | cgc | atc | atc | gag | ccg | ctg | ctg | gtc | ttc | ctc | ctc | 927 |
|---|---|---|---|---|---|---|---|---|---|---|---|---|---|---|---|---|
| Phe | Thr | Lys | Arg | Val | Arg | Ile | Ile | Glu | Pro | Leu | Leu | Val | Phe | Leu | Leu | |
| | | | | 275 | | | | | 280 | | | | | 285 | | |

| gcc | tac | gca | gcc | tac | ctc | act | gct | gaa | atg | gcc | tcg | ctc | tcc | gcc | att | 975 |
|---|---|---|---|---|---|---|---|---|---|---|---|---|---|---|---|---|
| Ala | Tyr | Ala | Ala | Tyr | Leu | Thr | Ala | Glu | Met | Ala | Ser | Leu | Ser | Ala | Ile | |
| | 290 | | | | | 295 | | | | | 300 | | | | | |

-continued

| | | |
|---|---|---|
| ctt gcg gtg acc atg tgt ggc ctg ggc tgt aag aag tac gtg gag gcc<br>Leu Ala Val Thr Met Cys Gly Leu Gly Cys Lys Lys Tyr Val Glu Ala<br>305 310 315 | 1023 |
| aac atc tcc cat aag tca cgc aca act gtc aaa tat aca atg aag act<br>Asn Ile Ser His Lys Ser Arg Thr Thr Val Lys Tyr Thr Met Lys Thr<br>320 325 330 | 1071 |
| cta gcc agc tgt gct gag acc gtg atc ttc atg ctg ctt ggc atc tca<br>Leu Ala Ser Cys Ala Glu Thr Val Ile Phe Met Leu Leu Gly Ile Ser<br>335 340 345 350 | 1119 |
| gcc gtg gac tct tct aag tgg gcc tgg gat tct ggg ctg gtg ctg ggc<br>Ala Val Asp Ser Ser Lys Trp Ala Trp Asp Ser Gly Leu Val Leu Gly<br>355 360 365 | 1167 |
| acc ctc atc ttc atc ctg ttc ttc cga gcc ctc ggc gta gtc ctg cag<br>Thr Leu Ile Phe Ile Leu Phe Phe Arg Ala Leu Gly Val Val Leu Gln<br>370 375 380 | 1215 |
| acc tgg gtg ctg aat cag ttc cgg cta gtc cct ctg gac aag att gac<br>Thr Trp Val Leu Asn Gln Phe Arg Leu Val Pro Leu Asp Lys Ile Asp<br>385 390 395 | 1263 |
| caa gtg gtg atg tcc tat ggg ggc ctg cgg ggg gct gtg gcc ttt gct<br>Gln Val Val Met Ser Tyr Gly Gly Leu Arg Gly Ala Val Ala Phe Ala<br>400 405 410 | 1311 |
| ctc gtc atc cta ctg gat agg acc aag gtc cct gcc aag gac tac ttt<br>Leu Val Ile Leu Leu Asp Arg Thr Lys Val Pro Ala Lys Asp Tyr Phe<br>415 420 425 430 | 1359 |
| gta gcc acc act att gta gtg gtc ttc ttc aca gtc atc gtg cag ggc<br>Val Ala Thr Thr Ile Val Val Val Phe Phe Thr Val Ile Val Gln Gly<br>435 440 445 | 1407 |
| ttg acc atc aag cca ctg gtc aaa tgg ctg aag gtg aag agg agt gag<br>Leu Thr Ile Lys Pro Leu Val Lys Trp Leu Lys Val Lys Arg Ser Glu<br>450 455 460 | 1455 |
| cat cac aaa ccc acc ctg aac cag gag ctg cat gaa cac act ttt gac<br>His His Lys Pro Thr Leu Asn Gln Glu Leu His Glu His Thr Phe Asp<br>465 470 475 | 1503 |
| cac att ctg gct gca gtg gag gac gtt gtg ggg cac cat ggc tac cac<br>His Ile Leu Ala Ala Val Glu Asp Val Val Gly His His Gly Tyr His<br>480 485 490 | 1551 |
| tac tgg agg gac agg tgg gag cag ttt gac aag aaa tac ctg agt cag<br>Tyr Trp Arg Asp Arg Trp Glu Gln Phe Asp Lys Lys Tyr Leu Ser Gln<br>495 500 505 510 | 1599 |
| ctg ctg atg cga cga tca gcc tac cgc atc cgg gac cag atc tgg gat<br>Leu Leu Met Arg Arg Ser Ala Tyr Arg Ile Arg Asp Gln Ile Trp Asp<br>515 520 525 | 1647 |
| gtg tac tac agg ctt aac atc cgg gat gcc atc agc ttt gtg gac cag<br>Val Tyr Tyr Arg Leu Asn Ile Arg Asp Ala Ile Ser Phe Val Asp Gln<br>530 535 540 | 1695 |
| gga ggc cac gtc ttg tct tcc aca ggt ctc act ctg cct tct atg ccc<br>Gly Gly His Val Leu Ser Ser Thr Gly Leu Thr Leu Pro Ser Met Pro<br>545 550 555 | 1743 |
| agc cgc aat tct gtg gca gaa act tct gtc acc aac ctg ctg agg gag<br>Ser Arg Asn Ser Val Ala Glu Thr Ser Val Thr Asn Leu Leu Arg Glu<br>560 565 570 | 1791 |
| agt ggc agt gga gcg tgt ctg gat ctg cag gtg att gac aca gta cgc<br>Ser Gly Ser Gly Ala Cys Leu Asp Leu Gln Val Ile Asp Thr Val Arg<br>575 580 585 590 | 1839 |
| agc ggc cgg gat cgt gag gat gct gtg atg cat cat ctg ctc tgc gga<br>Ser Gly Arg Asp Arg Glu Asp Ala Val Met His His Leu Leu Cys Gly<br>595 600 605 | 1887 |
| ggc ctc tac aag ccg cgc cgt agg tac aaa gcc agc tgc agt cgc cac<br>Gly Leu Tyr Lys Pro Arg Arg Arg Tyr Lys Ala Ser Cys Ser Arg His<br>610 615 620 | 1935 |

-continued

| | |
|---|---|
| ttc atc tca gag gat gcg cag gag cgg cag gac aag gag gtc ttc cag<br>Phe Ile Ser Glu Asp Ala Gln Glu Arg Gln Asp Lys Glu Val Phe Gln<br>625                        630                        635 | 1983 |
| cag aac atg aag cgg cgg ctg gag tcc ttt aag tcc acc aag cac aac<br>Gln Asn Met Lys Arg Arg Leu Glu Ser Phe Lys Ser Thr Lys His Asn<br>640                        645                        650 | 2031 |
| atc tgc ttc acc aag agc aag cca cga ccc cgc aag act ggc cgc agg<br>Ile Cys Phe Thr Lys Ser Lys Pro Arg Pro Arg Lys Thr Gly Arg Arg<br>655                        660                        665                        670 | 2079 |
| aag aag gat ggt gtg gcg aat gct gag gct aca aat ggg aaa cat cga<br>Lys Lys Asp Gly Val Ala Asn Ala Glu Ala Thr Asn Gly Lys His Arg<br>                        675                        680                        685 | 2127 |
| ggc ctg ggc ttt cag gac aca gct gct gtg ata tta acc gtg gag tct<br>Gly Leu Gly Phe Gln Asp Thr Ala Ala Val Ile Leu Thr Val Glu Ser<br>                        690                        695                        700 | 2175 |
| gag gag gag gag gag gag agc gac agt tca gag aca gag aag gag gac<br>Glu Glu Glu Glu Glu Glu Ser Asp Ser Ser Glu Thr Glu Lys Glu Asp<br>705                        710                        715 | 2223 |
| gat gag ggg atc atc ttt gtg gct cgt gcc acc agt gag gtt ctc caa<br>Asp Glu Gly Ile Ile Phe Val Ala Arg Ala Thr Ser Glu Val Leu Gln<br>720                        725                        730 | 2271 |
| gag ggc aag gtc tca gga agc ctt gag gtg tgc cca agc cca cga atc<br>Glu Gly Lys Val Ser Gly Ser Leu Glu Val Cys Pro Ser Pro Arg Ile<br>735                        740                        745                        750 | 2319 |
| att ccc ccc tcc cca acc tgt gca gaa aag gag ctc ccc tgg aag agt<br>Ile Pro Pro Ser Pro Thr Cys Ala Glu Lys Glu Leu Pro Trp Lys Ser<br>                        755                        760                        765 | 2367 |
| ggg cag ggg gac ctg gca gtg tac gtg tcc tcg gaa acc acc aag att<br>Gly Gln Gly Asp Leu Ala Val Tyr Val Ser Ser Glu Thr Thr Lys Ile<br>                        770                        775                        780 | 2415 |
| gtg cct gtg gac atg cag acg ggt tgg aac cag agc atc tca tcc ctg<br>Val Pro Val Asp Met Gln Thr Gly Trp Asn Gln Ser Ile Ser Ser Leu<br>785                        790                        795 | 2463 |
| gag agc cta gcg tcc cct ccc tgt aac cag gcc cca att ctg acc tgc<br>Glu Ser Leu Ala Ser Pro Pro Cys Asn Gln Ala Pro Ile Leu Thr Cys<br>800                        805                        810 | 2511 |
| ctg cct ccc cat cca cgg ggc act gaa gag ccc cag gtc cct ctc cac<br>Leu Pro Pro His Pro Arg Gly Thr Glu Glu Pro Gln Val Pro Leu His<br>815                        820                        825                        830 | 2559 |
| cta cct tct gat cca cgc tct agc ttc gcc ttc cca ccg agc ctg gcc<br>Leu Pro Ser Asp Pro Arg Ser Ser Phe Ala Phe Pro Pro Ser Leu Ala<br>                        835                        840                        845 | 2607 |
| aag gct ggc cgc tct cgc agt gag agc agc gct gac ctc ccc cag cag<br>Lys Ala Gly Arg Ser Arg Ser Glu Ser Ser Ala Asp Leu Pro Gln Gln<br>                        850                        855                        860 | 2655 |
| cag gag ctg cag ccc ctc atg ggc cac aag gac cac acc cat ctc agc<br>Gln Glu Leu Gln Pro Leu Met Gly His Lys Asp His Thr His Leu Ser<br>865                        870                        875 | 2703 |
| cca ggc acc gct acc tcc cac tgg tgc atc cag ttc aac aga ggc agc<br>Pro Gly Thr Ala Thr Ser His Trp Cys Ile Gln Phe Asn Arg Gly Ser<br>880                        885                        890 | 2751 |
| cgg ctg tag ctcaaggcct cggggaggag caggaggtgg aatccctgtg<br>Arg Leu *<br>895 | 2800 |
| ggaagtgctc cctgggtgat gggtagagcc ctcgaaactt gacatggggc cagaagggcc | 2860 |
| tgggttgaag tagtaattgg gcttccttgg agctagtcag aggggtcacc taagctggtc | 2920 |
| ctcacagggg cctttctcac cacctccctg tccctaaccc ctgccacttt ctgtttcatt | 2980 |
| aaggcctcta ctctggctca ggacccagtc caggccttct acgggctagg cccagagact | 3040 |

```
tgggttgctg gtcccccttc cctagtgggt tttcccgggg actctatagg cagctgctcc    3100
tgcccgcaaa gcaagagcat cattcctatt cttcagtgga tgccagcttc cctgcccaa    3160 tcctccccag catggtcatg ttcgtggtgt cctggcagtg aagctccgtg agggggctgg    3220
cccttagagg aactggggtg ggaagtgggg caggcctcac ccttgggctt tgctgccctg    3280
ttgggtcagc tacccatagt ccatttttt agggcagtgg gaacctctgc ctccacttcc    3340
tgctttagcc ccttcccttt gctgccaggt attggggtaa tatttcctcc ttttccaaga    3400
ccaaggccaa gaggctgggc caggcttcag ttcaggcctg ttgcttaact ggggtcaccc    3460
tgggatctgc tgctctgggt ctaagtctaa acctttctga tccttgggtc tgggttttt    3520 gaggaaggga catagtggcc tctgggctgc catgtcacca cctgcaacat tccccaaaca    3580
gataagaacc catcatctca gggccactgc tccattgctc tgggggctgg gattcctggc    3640
taagcagggg ctgacagggt ggcaggtgac tttctaggga tcagcacctg ccctgtgttt    3700
tgtaccttga acctaagata tattaaacat ctctcagatg gaaaaaaaaa aaaaaaaaa    3760 a                                                                    3761
```

<210> SEQ ID NO 36
<211> LENGTH: 896
<212> TYPE: PRT
<213> ORGANISM: Homo Sapiens

<400> SEQUENCE: 36

```
Met Leu Arg Ala Ala Leu Ser Leu Leu Ala Leu Pro Leu Ala Gly Ala
 1               5                  10                  15

Ala Glu Glu Pro Thr Gln Lys Pro Glu Ser Pro Gly Glu Pro Pro Pro
                20                  25                  30

Gly Leu Glu Leu Phe Arg Trp Gln Trp His Glu Val Glu Ala Pro Tyr
            35                  40                  45

Leu Val Ala Leu Trp Ile Leu Val Ala Ser Leu Ala Lys Ile Val Phe
        50                  55                  60

His Leu Ser Arg Lys Val Thr Ser Leu Val Pro Glu Ser Cys Leu Leu
65                  70                  75                  80

Ile Leu Leu Gly Leu Val Leu Gly Gly Ile Val Leu Ala Val Ala Lys
                85                  90                  95

Lys Ala Glu Tyr Gln Leu Glu Pro Gly Thr Phe Phe Leu Phe Leu Leu
               100                 105                 110

Pro Pro Ile Val Leu Asp Ser Gly Tyr Phe Met Pro Ser Arg Leu Phe
           115                 120                 125

Phe Asp Asn Leu Gly Ala Ile Leu Thr Tyr Ala Val Val Gly Thr Leu
       130                 135                 140

Trp Asn Ala Phe Thr Thr Gly Ala Ala Leu Trp Gly Leu Gln Gln Ala
145                 150                 155                 160

Gly Leu Val Ala Pro Arg Val Gln Ala Gly Leu Leu Asp Phe Leu Leu
               165                 170                 175

Phe Gly Ser Leu Ile Ser Ala Val Asp Pro Val Ala Val Leu Ala Val
           180                 185                 190

Phe Glu Glu Val His Val Asn Glu Thr Leu Phe Ile Ile Val Phe Gly
       195                 200                 205

Glu Ser Leu Leu Asn Asp Ala Val Thr Val Val Leu Tyr Lys Val Cys
   210                 215                 220

Asn Ser Phe Val Glu Met Gly Ser Ala Asn Val Gln Ala Thr Asp Tyr
225                 230                 235                 240
```

-continued

```
Leu Lys Gly Val Ala Ser Leu Phe Val Ser Leu Gly Gly Ala Ala
            245                 250                 255

Val Gly Leu Val Phe Ala Phe Leu Leu Ala Leu Thr Thr Arg Phe Thr
        260                 265                 270

Lys Arg Val Arg Ile Ile Glu Pro Leu Leu Val Phe Leu Leu Ala Tyr
        275                 280                 285

Ala Ala Tyr Leu Thr Ala Glu Met Ala Ser Leu Ser Ala Ile Leu Ala
        290                 295                 300

Val Thr Met Cys Gly Leu Gly Cys Lys Lys Tyr Val Glu Ala Asn Ile
305                 310                 315                 320

Ser His Lys Ser Arg Thr Thr Val Lys Tyr Thr Met Lys Thr Leu Ala
            325                 330                 335

Ser Cys Ala Glu Thr Val Ile Phe Met Leu Leu Gly Ile Ser Ala Val
            340                 345                 350

Asp Ser Ser Lys Trp Ala Trp Asp Ser Gly Leu Val Leu Gly Thr Leu
            355                 360                 365

Ile Phe Ile Leu Phe Phe Arg Ala Leu Gly Val Val Leu Gln Thr Trp
        370                 375                 380

Val Leu Asn Gln Phe Arg Leu Val Pro Leu Asp Lys Ile Asp Gln Val
385                 390                 395                 400

Val Met Ser Tyr Gly Gly Leu Arg Gly Ala Val Ala Phe Ala Leu Val
            405                 410                 415

Ile Leu Leu Asp Arg Thr Lys Val Pro Ala Lys Asp Tyr Phe Val Ala
            420                 425                 430

Thr Thr Ile Val Val Phe Phe Thr Val Ile Val Gln Gly Leu Thr
        435                 440                 445

Ile Lys Pro Leu Val Lys Trp Leu Lys Val Lys Arg Ser Glu His His
    450                 455                 460

Lys Pro Thr Leu Asn Gln Glu Leu His Glu His Thr Phe Asp His Ile
465                 470                 475                 480

Leu Ala Ala Val Glu Asp Val Val Gly His His Gly Tyr His Tyr Trp
            485                 490                 495

Arg Asp Arg Trp Glu Gln Phe Asp Lys Lys Tyr Leu Ser Gln Leu Leu
        500                 505                 510

Met Arg Arg Ser Ala Tyr Arg Ile Arg Asp Gln Ile Trp Asp Val Tyr
        515                 520                 525

Tyr Arg Leu Asn Ile Arg Asp Ala Ile Ser Phe Val Asp Gln Gly Gly
        530                 535                 540

His Val Leu Ser Ser Thr Gly Leu Thr Leu Pro Ser Met Pro Ser Arg
545                 550                 555                 560

Asn Ser Val Ala Glu Thr Ser Val Thr Asn Leu Leu Arg Glu Ser Gly
            565                 570                 575

Ser Gly Ala Cys Leu Asp Leu Gln Val Ile Asp Thr Val Arg Ser Gly
            580                 585                 590

Arg Asp Arg Glu Asp Ala Val Met His His Leu Leu Cys Gly Gly Leu
        595                 600                 605

Tyr Lys Pro Arg Arg Tyr Lys Ala Ser Cys Ser Arg His Phe Ile
        610                 615                 620

Ser Glu Asp Ala Gln Glu Arg Gln Asp Lys Glu Val Phe Gln Gln Asn
625                 630                 635                 640

Met Lys Arg Arg Leu Glu Ser Phe Lys Ser Thr Lys His Asn Ile Cys
            645                 650                 655
```

```
Phe Thr Lys Ser Lys Pro Arg Pro Arg Lys Thr Gly Arg Arg Lys Lys
            660                 665                 670

Asp Gly Val Ala Asn Ala Glu Ala Thr Asn Gly Lys His Arg Gly Leu
            675                 680                 685

Gly Phe Gln Asp Thr Ala Ala Val Ile Leu Thr Val Glu Ser Glu Glu
            690                 695                 700

Glu Glu Glu Glu Ser Asp Ser Ser Glu Thr Glu Lys Glu Asp Asp Glu
705                 710                 715                 720

Gly Ile Ile Phe Val Ala Arg Ala Thr Ser Glu Val Leu Gln Glu Gly
                725                 730                 735

Lys Val Ser Gly Ser Leu Glu Val Cys Pro Ser Pro Arg Ile Ile Pro
                740                 745                 750

Pro Ser Pro Thr Cys Ala Glu Lys Glu Leu Pro Trp Lys Ser Gly Gln
                755                 760                 765

Gly Asp Leu Ala Val Tyr Val Ser Ser Glu Thr Thr Lys Ile Val Pro
            770                 775                 780

Val Asp Met Gln Thr Gly Trp Asn Gln Ser Ile Ser Ser Leu Glu Ser
785                 790                 795                 800

Leu Ala Ser Pro Pro Cys Asn Gln Ala Pro Ile Leu Thr Cys Leu Pro
                805                 810                 815

Pro His Pro Arg Gly Thr Glu Glu Pro Gln Val Pro Leu His Leu Pro
            820                 825                 830

Ser Asp Pro Arg Ser Ser Phe Ala Phe Pro Pro Ser Leu Ala Lys Ala
            835                 840                 845

Gly Arg Ser Arg Ser Glu Ser Ser Ala Asp Leu Pro Gln Gln Gln Glu
            850                 855                 860

Leu Gln Pro Leu Met Gly His Lys Asp His Thr His Leu Ser Pro Gly
865                 870                 875                 880

Thr Ala Thr Ser His Trp Cys Ile Gln Phe Asn Arg Gly Ser Arg Leu
                885                 890                 895

<210> SEQ ID NO 37
<211> LENGTH: 4069
<212> TYPE: DNA
<213> ORGANISM: Homo Sapiens
<220> FEATURE:
<221> NAME/KEY: CDS
<222> LOCATION: (43)...(2691)

<400> SEQUENCE: 37
cgagtctgga gcccgcgccg tcgccggccg cgtcctccgg gc atg gaa gga ggc        54
                                                Met Glu Gly Gly
                                                  1 ggc aag ccc aac tct tcg tct aac agc cgg gac gat ggc aac agc gtc      102
Gly Lys Pro Asn Ser Ser Ser Asn Ser Arg Asp Asp Gly Asn Ser Val
  5                  10                  15                  20 ttc ccc gcc aag gcg tcc gcg ccg ggc gcg ggg ccg gcc gcg gcc gag      150
Phe Pro Ala Lys Ala Ser Ala Pro Gly Ala Gly Pro Ala Ala Ala Glu
                 25                  30                  35 aag cgc ctg ggc acc ccg ccg ggg ggc ggc ggg gcc ggc gcg aag gag      198
Lys Arg Leu Gly Thr Pro Pro Gly Gly Gly Gly Ala Gly Ala Lys Glu
             40                  45                  50 cac ggc aac tcc gtg tgc ttc aag gtg gac ggc ggt ggc ggc gag gag      246
His Gly Asn Ser Val Cys Phe Lys Val Asp Gly Gly Gly Gly Glu Glu
         55                  60                  65 ccg gcg ggg ggc ttc gaa gac gcc gag ggg ccc cgg cgg cag tac ggc      294
Pro Ala Gly Gly Phe Glu Asp Ala Glu Gly Pro Arg Arg Gln Tyr Gly
     70                  75                  80
```

-continued

```
ttc atg cag agg cag ttc acc tcc atg ctg cag ccc ggg gtc aac aaa      342
Phe Met Gln Arg Gln Phe Thr Ser Met Leu Gln Pro Gly Val Asn Lys
 85                  90                  95                 100 ttc tcc ctc cgc atg ttt ggg agc cag aag gcg gtg gaa aag gag cag      390
Phe Ser Leu Arg Met Phe Gly Ser Gln Lys Ala Val Glu Lys Glu Gln
            105                 110                 115 gaa agg gtt aaa act gca ggc ttc tgg att atc cac cct tac agt gat      438
Glu Arg Val Lys Thr Ala Gly Phe Trp Ile Ile His Pro Tyr Ser Asp
        120                 125                 130 ttc agg ttt tac tgg gat tta ata atg ctt ata atg atg gtt gga aat      486
Phe Arg Phe Tyr Trp Asp Leu Ile Met Leu Ile Met Met Val Gly Asn
    135                 140                 145 cta gtc atc ata cca gtt gga atc aca ttc ttt aca gag caa aca aca      534
Leu Val Ile Ile Pro Val Gly Ile Thr Phe Phe Thr Glu Gln Thr Thr
150                 155                 160 aca cca tgg att att ttc aat gtg gcg tca gat aca gtt ttc cta ttg      582
Thr Pro Trp Ile Ile Phe Asn Val Ala Ser Asp Thr Val Phe Leu Leu
165                 170                 175                 180 gac ctg atc atg aat ttt agg act ggg act gtc aat gaa gac agt tct      630
Asp Leu Ile Met Asn Phe Arg Thr Gly Thr Val Asn Glu Asp Ser Ser
                185                 190                 195 gaa atc atc ctg gac ccc aaa gtg atc aag atg aat tat tta aaa agc      678
Glu Ile Ile Leu Asp Pro Lys Val Ile Lys Met Asn Tyr Leu Lys Ser
            200                 205                 210 tgg ttt gtg gtt gac ttc atc tca tcc atc cca gtg gat tat atc ttt      726
Trp Phe Val Val Asp Phe Ile Ser Ser Ile Pro Val Asp Tyr Ile Phe
        215                 220                 225 ctt att gta gaa aaa gga atg gat tct gaa gtt tac aag aca gcc agg      774
Leu Ile Val Glu Lys Gly Met Asp Ser Glu Val Tyr Lys Thr Ala Arg
    230                 235                 240 gcm ctt cgc att gtg agg ttt aca aaa att ctc agt ctc ttg cgt tta      822
Xaa Leu Arg Ile Val Arg Phe Thr Lys Ile Leu Ser Leu Leu Arg Leu
245                 250                 255                 260 tta cga ctt tca agg tta att aga tac ata cat caa tgg gaa gag ata      870
Leu Arg Leu Ser Arg Leu Ile Arg Tyr Ile His Gln Trp Glu Glu Ile
                265                 270                 275 ttc cac atg aca tat gat ctc gcc agt gca gtg gtg aga att ttt aat      918
Phe His Met Thr Tyr Asp Leu Ala Ser Ala Val Val Arg Ile Phe Asn
            280                 285                 290 ctc atc ggc atg atg ctc ctc tgc cac tgg gat ggt tgt ctt cag          966
Leu Ile Gly Met Met Leu Leu Cys His Trp Asp Gly Cys Leu Gln
        295                 300                 305 ttc tta gta cca cta ctg cag gac ttc cca cca gat tgc tgg gtg tct     1014
Phe Leu Val Pro Leu Leu Gln Asp Phe Pro Pro Asp Cys Trp Val Ser
    310                 315                 320 tta aat gaa atg gtt aat gat tct tgg gga aag cag tat tca tac gca     1062
Leu Asn Glu Met Val Asn Asp Ser Trp Gly Lys Gln Tyr Ser Tyr Ala
325                 330                 335                 340 ctc ttc aaa gct atg agt cac atg ctg tgc att ggg tat gga gcc caa     1110
Leu Phe Lys Ala Met Ser His Met Leu Cys Ile Gly Tyr Gly Ala Gln
                345                 350                 355 gcc cca gtc agc atg tct gac ctc tgg att acc atg ctg agc atg atc     1158
Ala Pro Val Ser Met Ser Asp Leu Trp Ile Thr Met Leu Ser Met Ile
            360                 365                 370 gtc ggg gcc acc tgc tat gcc atg ttt gtc ggc cat gcc acc gct tta     1206
Val Gly Ala Thr Cys Tyr Ala Met Phe Val Gly His Ala Thr Ala Leu
        375                 380                 385 atc cag tct ctg gat tct tcg agg cgg cag tat caa gag aag tat aag     1254
Ile Gln Ser Leu Asp Ser Ser Arg Arg Gln Tyr Gln Glu Lys Tyr Lys
    390                 395                 400
```

| | | |
|---|---|---|
| caa gtg gaa caa tac atg tca ttc cat aag tta cca gct gat atg cgt<br>Gln Val Glu Gln Tyr Met Ser Phe His Lys Leu Pro Ala Asp Met Arg<br>405                          410                          415                          420 | | 1302 |
| cag aag ata cat gat tac tat gaa cac aga tac caa ggc aaa atc ttt<br>Gln Lys Ile His Asp Tyr Tyr Glu His Arg Tyr Gln Gly Lys Ile Phe<br>                        425                          430                          435 | | 1350 |
| gat gag gaa aat att ctc aat gaa ctc aat gat cct ctg aga gag gag<br>Asp Glu Glu Asn Ile Leu Asn Glu Leu Asn Asp Pro Leu Arg Glu Glu<br>                    440                          445                          450 | | 1398 |
| ata gtc aac ttc aac tgt cgg aaa ctg gtg gct aca atg cct tta ttt<br>Ile Val Asn Phe Asn Cys Arg Lys Leu Val Ala Thr Met Pro Leu Phe<br>455                          460                          465 | | 1446 |
| gct aat gcg gat cct aat ttt gtg act gcc atg ctg agc aag ttg aga<br>Ala Asn Ala Asp Pro Asn Phe Val Thr Ala Met Leu Ser Lys Leu Arg<br>      470                          475                          480 | | 1494 |
| ttt gag gtg ttt caa cct gga gat tat atc ata cga gaa gga gcc gtg<br>Phe Glu Val Phe Gln Pro Gly Asp Tyr Ile Ile Arg Glu Gly Ala Val<br>485                          490                          495                          500 | | 1542 |
| ggt aaa aaa atg tat ttc att caa cac ggt gtt gct ggt gtc att aca<br>Gly Lys Lys Met Tyr Phe Ile Gln His Gly Val Ala Gly Val Ile Thr<br>                          505                          510                          515 | | 1590 |
| aaa tcc agt aaa gaa atg aag ctg aca gat ggc tct tac ttt gga gag<br>Lys Ser Ser Lys Glu Met Lys Leu Thr Asp Gly Ser Tyr Phe Gly Glu<br>              520                          525                          530 | | 1638 |
| att tgc ctg ctg acc aaa gga cgt cgt act gcc agt gtt cga gct gat<br>Ile Cys Leu Leu Thr Lys Gly Arg Arg Thr Ala Ser Val Arg Ala Asp<br>            535                        540                          545 | | 1686 |
| aca tat tgt cgt ctt tac tca ctt tcc gtg gac aat ttc aac gag gtc<br>Thr Tyr Cys Arg Leu Tyr Ser Leu Ser Val Asp Asn Phe Asn Glu Val<br>550                          555                          560 | | 1734 |
| ctg gag gaa tat cca atg atg agg aga gcc ttt gag aca gtt gcc att<br>Leu Glu Glu Tyr Pro Met Met Arg Arg Ala Phe Glu Thr Val Ala Ile<br>565                          570                          575                          580 | | 1782 |
| gac cga cta gat cga ata gga aag aaa aat tca att ctt ctg caa aag<br>Asp Arg Leu Asp Arg Ile Gly Lys Lys Asn Ser Ile Leu Leu Gln Lys<br>                    585                          590                          595 | | 1830 |
| ttc cag aag gat ctg aac act ggt gtt ttc aac aat cag gag aac gaa<br>Phe Gln Lys Asp Leu Asn Thr Gly Val Phe Asn Asn Gln Glu Asn Glu<br>              600                          605                          610 | | 1878 |
| atc ctc aag cag att gtg aaa cat gac agg gag atg gtg cag gca atc<br>Ile Leu Lys Gln Ile Val Lys His Asp Arg Glu Met Val Gln Ala Ile<br>            615                        620                          625 | | 1926 |
| gct ccc atc aat tat cct caa atg aca acc ctg aat tcc aca tcg tct<br>Ala Pro Ile Asn Tyr Pro Gln Met Thr Thr Leu Asn Ser Thr Ser Ser<br>630                          635                          640 | | 1974 |
| act acg acc ccg acc tcc cgc atg agg aca caa tct cca ccg gtg tac<br>Thr Thr Thr Pro Thr Ser Arg Met Arg Thr Gln Ser Pro Pro Val Tyr<br>645                          650                          655                          660 | | 2022 |
| aca gcg acc agc ctg tct cac agc aac ctg cac tcc ccc agt ccc agc<br>Thr Ala Thr Ser Leu Ser His Ser Asn Leu His Ser Pro Ser Pro Ser<br>                        665                          670                          675 | | 2070 |
| aca cag acc ccc cag cca tca gcc atc ctg tca ccc tgc tcc tac acc<br>Thr Gln Thr Pro Gln Pro Ser Ala Ile Leu Ser Pro Cys Ser Tyr Thr<br>              680                          685                          690 | | 2118 |
| acc gcg gtc tgc agc cct cct gta cag agc cct ctg gcc gct cga act<br>Thr Ala Val Cys Ser Pro Pro Val Gln Ser Pro Leu Ala Ala Arg Thr<br>            695                        700                          705 | | 2166 |
| ttc cac tat gcc tcc ccc acc gcc tcc cag ctg tca ctc atg caa cag<br>Phe His Tyr Ala Ser Pro Thr Ala Ser Gln Leu Ser Leu Met Gln Gln<br>710                          715                          720 | | 2214 |

```
cag ccg cag cag cag gta cag cag tcc cag ccg ccg cag act cag cca        2262
Gln Pro Gln Gln Gln Val Gln Gln Ser Gln Pro Pro Gln Thr Gln Pro
725                 730                 735                 740 cag cag ccg tcc ccg cag cca cag aca cct ggc agc tcc acg ccg aaa        2310
Gln Gln Pro Ser Pro Gln Pro Gln Thr Pro Gly Ser Ser Thr Pro Lys
            745                 750                 755 aat gaa gtg cac aag agc acg cag gcg ctt cac aac acc aac ctg acc        2358
Asn Glu Val His Lys Ser Thr Gln Ala Leu His Asn Thr Asn Leu Thr
        760                 765                 770 cgg gaa gtc agg cca ctc tcc gcc tcg cag ccc tcg ctg ccc cat gag        2406
Arg Glu Val Arg Pro Leu Ser Ala Ser Gln Pro Ser Leu Pro His Glu
    775                 780                 785 gtg tcc act ctg att tcc aga cct cat ccc act gtg ggc gag tcc ctg        2454
Val Ser Thr Leu Ile Ser Arg Pro His Pro Thr Val Gly Glu Ser Leu
790                 795                 800 gcc tcc atc cct caa ccc gtg acg gcg gtc ccc gga acg ggc ctt cag        2502
Ala Ser Ile Pro Gln Pro Val Thr Ala Val Pro Gly Thr Gly Leu Gln
805                 810                 815                 820 gca ggg ggc agg agc act gtc ccg cag cgc gtc acc ctc ttc cga cag        2550
Ala Gly Gly Arg Ser Thr Val Pro Gln Arg Val Thr Leu Phe Arg Gln
            825                 830                 835 atg tcg tcg gga gcc atc ccc ccg aac cga gga gtc cct cca gca ccc        2598
Met Ser Ser Gly Ala Ile Pro Pro Asn Arg Gly Val Pro Pro Ala Pro
        840                 845                 850 cct cca cca gca gct gct ctt cca aga gaa tct tcc tca gtc tta aac        2646
Pro Pro Pro Ala Ala Ala Leu Pro Arg Glu Ser Ser Ser Val Leu Asn
    855                 860                 865 aca gac cca gac gca gaa aag cca cga ttt gct tca aat tta tga            2691
Thr Asp Pro Asp Ala Glu Lys Pro Arg Phe Ala Ser Asn Leu *
870                 875                 880 tccctgctga ttgtcaaagc agaaagaaat actctcataa actgagacta tactcagatc      2751
ttattttatt ctatctcctg atagatccct ctagcctact atgaagagat attttagaca      2811
gctgtggcct acacgtgaaa tgtaaaaata tatatacata tactataaaa tatatatcta      2871
aattcccaag agagggtcaa aagacctgtt tagcattcag tgtttatatgt cttcctttct     2931 ttaaatcatt aaaggattta aaatgtcgtt gtaagattat ttatttctaa cctactttta      2991
cttaagtcct tgatatgta tatttctcta tttttatgaag agttcttgga ttcaatggaa      3051
acaaaactga ttttaaaaag gcaactcaaa tgaactagta aatagcacca atcaaaactt      3111
tctttcatta gctgtgtctc tgcatctaaa ttgttaatca ttaatggtgg agaattaaat      3171
aacaaatccc attttataga tctaaattgt atttcggtgc tttcaatttc aaattaggtt      3231
aaagaatgca ctacttgctt ggccaccgta ggagactagc attgccactg tttgttaaga     3291
atatcactaa cctcaaacat gttcattgat cttttcagaaa gctgagggaa aattaatatt    3351
tgtcttcatg tgttatcgga cttttaccaa gactcgatca atgttagttg taaataactt     3411
tttcaaccca aataaaaata gctattctgt gttgtatgaa ggtaaaagtc attgtttaag    3471
aatttagttt tattgcttca cttcaaaact tagagtttta aattttacaa aacctgattg     3531
tgagaattat tcaattgtaa tgcaatggct tgaaacctac aatattattt taacctgcaa     3591
tgttttatgc aaaattgtat gctcgaatct acaaattgct tgtattacac caaaaatcgt    3651 tactttttctt tcttccttgcc ataatcaagc atctgaaaat agtccctgca tgcttstggg  3711
gaaaaaaaaa taggttcaaa tcagtcattg tagagaaagg cttacagtat ttctcgtttc    3771
tagaaaagca taacaattca ttaattgcct atcttataat tcctataagg ctgacttgga   3831
tctctgactt aagtctagaa gtgaggtttt cacttttatt taatattatt gctattatta   3891
```

```
tttaaataat tatttgtaaa ccacagcttg atttggagtt aagtgttgtc tgtgtcttca    3951
ctgtagctgg taatttacta tggtattaat twaaaraaaw aaawwmaawa marmawmaaa    4011
aaaaaaaaaa aaaaaaaaaa aaaaaaaaaa aaaaaaarrr mrrmmrmaaa aaaaaaaa     4069
```

<210> SEQ ID NO 38
<211> LENGTH: 882
<212> TYPE: PRT
<213> ORGANISM: Homo Sapiens
<220> FEATURE:
<221> NAME/KEY: VARIANT
<222> LOCATION: (1)...(882)
<223> OTHER INFORMATION: Xaa = Any Amino Acid

<400> SEQUENCE: 38

```
Met Glu Gly Gly Gly Lys Pro Asn Ser Ser Asn Ser Arg Asp Asp
 1               5                  10                  15

Gly Asn Ser Val Phe Pro Ala Lys Ala Ser Pro Gly Ala Gly Pro
                20                  25                  30

Ala Ala Ala Glu Lys Arg Leu Gly Thr Pro Pro Gly Gly Gly Ala
                35                  40                  45

Gly Ala Lys Glu His Gly Asn Ser Val Cys Phe Lys Val Asp Gly
 50                  55                  60

Gly Gly Glu Pro Ala Gly Gly Phe Glu Asp Ala Glu Gly Pro Arg
 65                  70                  75                  80

Arg Gln Tyr Gly Phe Met Gln Arg Gln Phe Thr Ser Met Leu Gln Pro
                85                  90                  95

Gly Val Asn Lys Phe Ser Leu Arg Met Phe Gly Ser Gln Lys Ala Val
                100                 105                 110

Glu Lys Glu Gln Glu Arg Val Lys Thr Ala Gly Phe Trp Ile Ile His
                115                 120                 125

Pro Tyr Ser Asp Phe Arg Phe Tyr Trp Asp Leu Ile Met Leu Ile Met
130                 135                 140

Met Val Gly Asn Leu Val Ile Ile Pro Val Gly Ile Thr Phe Phe Thr
145                 150                 155                 160

Glu Gln Thr Thr Thr Pro Trp Ile Ile Phe Asn Val Ala Ser Asp Thr
                165                 170                 175

Val Phe Leu Leu Asp Leu Ile Met Asn Phe Arg Thr Gly Thr Val Asn
                180                 185                 190

Glu Asp Ser Ser Glu Ile Ile Leu Asp Pro Lys Val Ile Lys Met Asn
                195                 200                 205

Tyr Leu Lys Ser Trp Phe Val Val Asp Phe Ile Ser Ser Ile Pro Val
210                 215                 220

Asp Tyr Ile Phe Leu Ile Val Glu Lys Gly Met Asp Ser Glu Val Tyr
225                 230                 235                 240

Lys Thr Ala Arg Xaa Leu Arg Ile Val Arg Phe Thr Lys Ile Leu Ser
                245                 250                 255

Leu Leu Arg Leu Leu Arg Leu Ser Arg Leu Ile Arg Tyr Ile His Gln
                260                 265                 270

Trp Glu Glu Ile Phe His Met Thr Tyr Asp Leu Ala Ser Ala Val Val
                275                 280                 285

Arg Ile Phe Asn Leu Ile Gly Met Met Leu Leu Cys His Trp Asp
290                 295                 300

Gly Cys Leu Gln Phe Leu Val Pro Leu Leu Gln Asp Phe Pro Pro Asp
305                 310                 315                 320
```

```
Cys Trp Val Ser Leu Asn Glu Met Val Asn Asp Ser Trp Gly Lys Gln
                325                 330                 335

Tyr Ser Tyr Ala Leu Phe Lys Ala Met Ser His Met Leu Cys Ile Gly
            340                 345                 350

Tyr Gly Ala Gln Ala Pro Val Ser Met Ser Asp Leu Trp Ile Thr Met
        355                 360                 365

Leu Ser Met Ile Val Gly Ala Thr Cys Tyr Ala Met Phe Val Gly His
370                 375                 380

Ala Thr Ala Leu Ile Gln Ser Leu Asp Ser Ser Arg Arg Gln Tyr Gln
385                 390                 395                 400

Glu Lys Tyr Lys Gln Val Glu Gln Tyr Met Ser Phe His Lys Leu Pro
                405                 410                 415

Ala Asp Met Arg Gln Lys Ile His Asp Tyr Tyr Glu His Arg Tyr Gln
            420                 425                 430

Gly Lys Ile Phe Asp Glu Glu Asn Ile Leu Asn Glu Leu Asn Asp Pro
        435                 440                 445

Leu Arg Glu Glu Ile Val Asn Phe Asn Cys Arg Lys Leu Val Ala Thr
    450                 455                 460

Met Pro Leu Phe Ala Asn Ala Asp Pro Asn Phe Val Thr Ala Met Leu
465                 470                 475                 480

Ser Lys Leu Arg Phe Glu Val Phe Gln Pro Gly Asp Tyr Ile Ile Arg
                485                 490                 495

Glu Gly Ala Val Gly Lys Lys Met Tyr Phe Ile Gln His Gly Val Ala
            500                 505                 510

Gly Val Ile Thr Lys Ser Ser Lys Glu Met Lys Leu Thr Asp Gly Ser
        515                 520                 525

Tyr Phe Gly Glu Ile Cys Leu Leu Thr Lys Gly Arg Arg Thr Ala Ser
530                 535                 540

Val Arg Ala Asp Thr Tyr Cys Arg Leu Tyr Ser Leu Ser Val Asp Asn
545                 550                 555                 560

Phe Asn Glu Val Leu Glu Glu Tyr Pro Met Met Arg Arg Ala Phe Glu
                565                 570                 575

Thr Val Ala Ile Asp Arg Leu Asp Arg Ile Gly Lys Lys Asn Ser Ile
            580                 585                 590

Leu Leu Gln Lys Phe Gln Lys Asp Leu Asn Thr Gly Val Phe Asn Asn
        595                 600                 605

Gln Glu Asn Glu Ile Leu Lys Gln Ile Val Lys His Asp Arg Glu Met
    610                 615                 620

Val Gln Ala Ile Ala Pro Ile Asn Tyr Pro Gln Met Thr Thr Leu Asn
625                 630                 635                 640

Ser Thr Ser Ser Thr Thr Pro Thr Ser Arg Met Arg Thr Gln Ser
                645                 650                 655

Pro Pro Val Tyr Thr Ala Thr Ser Leu Ser His Ser Asn Leu His Ser
            660                 665                 670

Pro Ser Pro Ser Thr Gln Thr Pro Gln Pro Ser Ala Ile Leu Ser Pro
        675                 680                 685

Cys Ser Tyr Thr Thr Ala Val Cys Ser Pro Val Gln Ser Pro Leu
    690                 695                 700

Ala Ala Arg Thr Phe His Tyr Ala Ser Pro Thr Ala Ser Gln Leu Ser
705                 710                 715                 720

Leu Met Gln Gln Gln Pro Gln Gln Gln Val Gln Ser Gln Pro Pro
                725                 730                 735
```

-continued

```
Gln Thr Gln Pro Gln Gln Pro Ser Pro Gln Pro Gln Thr Pro Gly Ser
                740                 745                 750
Ser Thr Pro Lys Asn Glu Val His Lys Ser Thr Gln Ala Leu His Asn
            755                 760                 765
Thr Asn Leu Thr Arg Glu Val Arg Pro Leu Ser Ala Ser Gln Pro Ser
        770                 775                 780
Leu Pro His Glu Val Ser Thr Leu Ile Ser Arg Pro His Pro Thr Val
785                 790                 795                 800
Gly Glu Ser Leu Ala Ser Ile Pro Gln Pro Val Thr Ala Val Pro Gly
                805                 810                 815
Thr Gly Leu Gln Ala Gly Gly Arg Ser Thr Val Pro Gln Arg Val Thr
            820                 825                 830
Leu Phe Arg Gln Met Ser Ser Gly Ala Ile Pro Pro Asn Arg Gly Val
        835                 840                 845
Pro Pro Ala Pro Pro Pro Ala Ala Leu Pro Arg Glu Ser Ser
850                 855                 860
Ser Val Leu Asn Thr Asp Pro Asp Ala Glu Lys Pro Arg Phe Ala Ser
865                 870                 875                 880
Asn Leu

<210> SEQ ID NO 39
<211> LENGTH: 4452
<212> TYPE: DNA
<213> ORGANISM: Homo Sapiens
<220> FEATURE:
<221> NAME/KEY: CDS
<222> LOCATION: (36)...(2045)

<400> SEQUENCE: 39
cgccggtgag gtagggggcgg gaggcggggg gagac atg gct cgg cgc ggc tgg        53
                                       Met Ala Arg Arg Gly Trp
                                       1               5 cgg cgg gca ccc ctc cgc cgt ggc gtc ggc agc agt ccc cga gcc cgc       101
Arg Arg Ala Pro Leu Arg Arg Gly Val Gly Ser Ser Pro Arg Ala Arg
            10                  15                  20 agg ctc atg cgg ccc ctt tgg ttg ctc ctc gca gtg ggc gtc ttt gac       149
Arg Leu Met Arg Pro Leu Trp Leu Leu Leu Ala Val Gly Val Phe Asp
        25                  30                  35 tgg gca ggg gct tcg gac ggc ggc ggc gga gag gct aga gcc atg gac       197
Trp Ala Gly Ala Ser Asp Gly Gly Gly Gly Glu Ala Arg Ala Met Asp
    40                  45                  50 gag gag atc gtg tcc gag aag caa gcc gag gag agc cac cgg cag gac       245
Glu Glu Ile Val Ser Glu Lys Gln Ala Glu Glu Ser His Arg Gln Asp
55                  60                  65                  70 agc gcc aac ctg ctc atc ttc atc ctg ctg ctc acc ctc acc att ctc       293
Ser Ala Asn Leu Leu Ile Phe Ile Leu Leu Leu Thr Leu Thr Ile Leu
                75                  80                  85 aca atc tgg ctc ttc aag cac cgc cgg gcc cgc ttc ctg cac gaa acc       341
Thr Ile Trp Leu Phe Lys His Arg Arg Ala Arg Phe Leu His Glu Thr
            90                  95                 100 ggc ctg gct atg att tat ggt ctt ttg gtg ggc ctt gtg ctt cgg tat       389
Gly Leu Ala Met Ile Tyr Gly Leu Leu Val Gly Leu Val Leu Arg Tyr
        105                 110                 115 ggc att cat gtt ccg agt gat gta aat aat gtg acc ctg agc tgt gaa       437
Gly Ile His Val Pro Ser Asp Val Asn Asn Val Thr Leu Ser Cys Glu
    120                 125                 130 gtg cag tca agt cca act acc tta ctg gtt act ttt gat cca gaa gta       485
Val Gln Ser Ser Pro Thr Thr Leu Leu Val Thr Phe Asp Pro Glu Val
135                 140                 145                 150
```

```
                                                           -continued ttt ttc aac ata tta ctt cct cct atc ata ttt tat gca ggt tat agc       533
Phe Phe Asn Ile Leu Leu Pro Pro Ile Ile Phe Tyr Ala Gly Tyr Ser
                155                 160                 165 ctg aaa agg aga cat ttt ttt cga aat ctt ggg tct atc cta gca tac       581
Leu Lys Arg Arg His Phe Phe Arg Asn Leu Gly Ser Ile Leu Ala Tyr
            170                 175                 180 gct ttt ctt gga aca gca att tct tgt ttc gtt att ggg tca ata atg       629
Ala Phe Leu Gly Thr Ala Ile Ser Cys Phe Val Ile Gly Ser Ile Met
        185                 190                 195 tat ggc tgt gta acg ctg atg aag gta acg gga caa ctt gca gga gat       677
Tyr Gly Cys Val Thr Leu Met Lys Val Thr Gly Gln Leu Ala Gly Asp
    200                 205                 210 ttt tac ttt aca gat tgc cta ctg ttt ggt gcc att gta tca gca act       725
Phe Tyr Phe Thr Asp Cys Leu Leu Phe Gly Ala Ile Val Ser Ala Thr
215                 220                 225                 230 gat cca gtg act gtt ctt gct ata ttc cac gag ctt caa gtt gat gtt       773
Asp Pro Val Thr Val Leu Ala Ile Phe His Glu Leu Gln Val Asp Val
                235                 240                 245 gaa ctc tat gca ctt ctt ttt ggt gaa agt gtc ctc aat gat gct gtt       821
Glu Leu Tyr Ala Leu Leu Phe Gly Glu Ser Val Leu Asn Asp Ala Val
            250                 255                 260 gcc ata gtg ctg tcc tcc tca ata gtg gca tac cag cca gct gga gac       869
Ala Ile Val Leu Ser Ser Ser Ile Val Ala Tyr Gln Pro Ala Gly Asp
        265                 270                 275 aac agt cac acc ttt gat gtc aca gcg atg ttc aag tct att ggg atc       917
Asn Ser His Thr Phe Asp Val Thr Ala Met Phe Lys Ser Ile Gly Ile
    280                 285                 290 ttc ctt gga atc ttc agt gga tct ttt gca atg ggt gct gct act gga       965
Phe Leu Gly Ile Phe Ser Gly Ser Phe Ala Met Gly Ala Ala Thr Gly
295                 300                 305                 310 gtg gtg aca gct tta gtg aca aag ttc acc aaa tta cgg gag ttc cag      1013
Val Val Thr Ala Leu Val Thr Lys Phe Thr Lys Leu Arg Glu Phe Gln
                315                 320                 325 ttg ttg gag aca ggc ctg ttc ttc ttg atg tcc tgg agt acc ttc ctc      1061
Leu Leu Glu Thr Gly Leu Phe Phe Leu Met Ser Trp Ser Thr Phe Leu
            330                 335                 340 ttg gct gaa gca tgg ggc ttc aca ggt gta gtt gca gta ttg ttt tgt      1109
Leu Ala Glu Ala Trp Gly Phe Thr Gly Val Val Ala Val Leu Phe Cys
        345                 350                 355 ggc atc aca caa gca cat tat acg tat aat aat ttg tcc acg gag tct      1157
Gly Ile Thr Gln Ala His Tyr Thr Tyr Asn Asn Leu Ser Thr Glu Ser
    360                 365                 370 cag cat aga act aaa cag ttg ttt gag ctt ctc aat ttc ttg gca gag      1205
Gln His Arg Thr Lys Gln Leu Phe Glu Leu Leu Asn Phe Leu Ala Glu
375                 380                 385                 390 aat ttc atc ttc tcc tac atg ggg ctg aca ctg ttc acc ttc cag aac      1253
Asn Phe Ile Phe Ser Tyr Met Gly Leu Thr Leu Phe Thr Phe Gln Asn
                395                 400                 405 cat gtc ttt aac cca aca ttt gta gta gga gca ttt gtt gct att ttc      1301
His Val Phe Asn Pro Thr Phe Val Val Gly Ala Phe Val Ala Ile Phe
            410                 415                 420 ttg gga aga gct gcc aat att tac ccc ttg tcc ctc tta ctt aat ttg      1349
Leu Gly Arg Ala Ala Asn Ile Tyr Pro Leu Ser Leu Leu Leu Asn Leu
        425                 430                 435 ggt aga aga agt aag att gga tca aat ttt caa cac atg atg atg ttt      1397
Gly Arg Arg Ser Lys Ile Gly Ser Asn Phe Gln His Met Met Met Phe
    440                 445                 450 gct ggc ctt cgt ggt gca atg gca ttt gcc ttg gcc att cga gat act      1445
Ala Gly Leu Arg Gly Ala Met Ala Phe Ala Leu Ala Ile Arg Asp Thr
455                 460                 465                 470
```

```
gcc act tat gca cgg caa atg atg ttc agc acc acg ctt ctg att gtg    1493
Ala Thr Tyr Ala Arg Gln Met Met Phe Ser Thr Thr Leu Leu Ile Val
            475                 480                 485 ttt ttt acc gtg tgg gta ttt ggt ggt ggc acc act gca atg ctg tca    1541
Phe Phe Thr Val Trp Val Phe Gly Gly Gly Thr Thr Ala Met Leu Ser
            490                 495                 500 tgc ttg cat atc agg gtt ggt gtt gat tca gac caa gaa cac ttg ggt    1589
Cys Leu His Ile Arg Val Gly Val Asp Ser Asp Gln Glu His Leu Gly
            505                 510                 515 gtt cct gaa aat gaa agg aga act acc aaa gca gag agt gct tgg ctt    1637
Val Pro Glu Asn Glu Arg Arg Thr Thr Lys Ala Glu Ser Ala Trp Leu
        520                 525                 530 ttc cgg atg tgg tac aac ttt gat cat aac tat ctg aag cct ctg ctg    1685
Phe Arg Met Trp Tyr Asn Phe Asp His Asn Tyr Leu Lys Pro Leu Leu
535                 540                 545                 550 acc cac agc ggg cct ccg ctg aca aca aca ctc cct gcc tgc tgt gga    1733
Thr His Ser Gly Pro Pro Leu Thr Thr Thr Leu Pro Ala Cys Cys Gly
                555                 560                 565 ccc atc gcc agg tgc ctc acc agc ccc cag gct tac gaa aac cag gaa    1781
Pro Ile Ala Arg Cys Leu Thr Ser Pro Gln Ala Tyr Glu Asn Gln Glu
            570                 575                 580 cag ttg aaa gat gat gat tct gat ctt att ctc aat gat ggt gac atc    1829
Gln Leu Lys Asp Asp Asp Ser Asp Leu Ile Leu Asn Asp Gly Asp Ile
            585                 590                 595 agt ttg aca tat gga gat tct act gtg aac act gaa ccg gcc aca tcc    1877
Ser Leu Thr Tyr Gly Asp Ser Thr Val Asn Thr Glu Pro Ala Thr Ser
        600                 605                 610 agc gcc cca agg aga ttt atg gga aac agt tct gaa gat gcc ttg gat    1925
Ser Ala Pro Arg Arg Phe Met Gly Asn Ser Ser Glu Asp Ala Leu Asp
615                 620                 625                 630 cgg gag ctt gca ttt ggg gac cat gaa ctg gtc att cga gga aca cgc    1973
Arg Glu Leu Ala Phe Gly Asp His Glu Leu Val Ile Arg Gly Thr Arg
                635                 640                 645 ctg gtt ctt cca atg gat gat tct gaa ccc ccg cta aat ttg tta gat    2021
Leu Val Leu Pro Met Asp Asp Ser Glu Pro Pro Leu Asn Leu Leu Asp
            650                 655                 660 aat acg aga cat ggt cca gcc taa gcttactaat actcacttag tgatttgtaa   2075
Asn Thr Arg His Gly Pro Ala *
            665 aatttgcaca tgtgattgtg aagaaatttg tactacctaa aagtcccagt gcatgtctct  2135 gaatgtgtaa gctatataaa tgctatttat atggcataga aagaatataa atatcctgta  2195 cacggcagat tgtgaacaaa ctatattcct ttaagttttc ctggttgcac tctgtagact  2255 ggatctgttt taggaagtta ctttcacagt gatgttgtgt gttctgttag ttttatgtct  2315 cagttaaagt gtaaaaagtg acggattttc tctttcttaa acttacctga cacttaacca  2375 gagtaccagt tctcgtgatg tgaattaatt ttttttgtgtg ctaggggagg gagagtgagg  2435 agggagtgtt atttccttgg gaacctaggg aggagaggtt cctttgttgg gaaacttttg  2495 ttgatagctg ctgcctttgt cctgatcgtt ttctttccct tttctctggt ggcctgttgt  2555 ggtgcaacga gctgatggca tttgatcttg ccccattcag gttggggagt gaagtgtggg  2615 gaccctttc ccccgcttgc tgtgaaagca cagattcatt gactacagta cactgttgtt   2675 cagaaaagaa ggctgcaaat gacttctgag actttatgtc ttttcttcca gaccaagacc  2735 gtagaaggag tcacatctag ccggcttagc caaagtacag gtgtatatag ttcagggcac  2795 ttgatttaga tttggagggg ctggggtggg cagagagcaa gaggcgagta aagagaatgg  2855 tggtttcaga gatctctctt cccaaatgtg taaatattct ataccagata agtttaaata  2915
```

-continued

```
agaaatttaa ttgctgctta attttttgatt atgtacttta tctgtatagc aggctttgtc   2975
gtcagaagtt tttatatcga tttaaattgc tgctctttag cagccaaaca ggagcaaaat   3035
gtaaaatttt tgaacttact gtgtctaatc atcatttgtt agtctgtagt taatgtcaac   3095
agttaattta tgaacccacg atcgttccac actgcaccaa agtcagtcat aagagaaatc   3155
gaatattctg gagcactgat tgcagcaggg tggctccttt gtgtgcagca ggtgtagtag   3215
tcttcatttt catggtacgt tttaatatta attacctaag ctgccatgca tttttttttt   3275
acagttctca aggaagagca cagaacaatt tctcatttca tatttggagt atgaaagtag   3335
attctatttt gtaatgctga taatacctaa agatgcattg aatgcttgga agaatgcttt   3395
ttgatgttga ttttgacctg ttcatgattc agaagaaaaa caacttttt tggattttt    3455 ttccctcagg tctgagtagc attgccttaa atcttatcca gttagaacat tgatttattt   3515
acatgatgtt cagatttcc agtgaaaaat acccttctga acaaacatg tacttactct    3575 ccgaaaggca tctatctgtg ctattgcaaa cactccttga gattttaggg gaattctaat   3635
gttgtaccct ttcgtggcag ctttgactgt tggcatagcc atttgttatg tagtggtagc   3695
gactttcctg ctatgcagga atccctccca tgacgtgtat gttttacatg atgtgtgcct   3755
cttcacgcag taaatagttt cttgttaatg tatgtttgag gagtttgaac gtcagtgtca   3815
cttacccaca aagttattca agttgtaaaa ggttataaat aatttaacaa ctaccttttt   3875
tattctgtcg ggttactgac ctcactttat gtaaatactt cgcatgacaa attcagtaac   3935
tcgtctattt cagcatgcat aagactttc actagggaaa ctgataaagc ttgagtcaac   3995
taaatctgcc ttcatacttt atcaagggga accaagcctg ctgtgcttac atcagcatct   4055
ggaagacttt cctctcctct aatctgtgta cacatctcca agcaaggaag aaaaaacaaa   4115
ctctgctcag acgccatga aacacctgaa tgaactttga tgaagtacag tctgagttac    4175
catcatgcac aagtagaact gctcttggac ttgttttcct gttgtttgtg aacctacgc   4235 gtttgaatgg cttgaacgtt gcatctttta aagttatttt ttaaggtttc ttggcattta   4295
tcctagttgt ccgtgtttgg caatgtgctg ttaaagtaat agactttaa tctttatgta    4355 ttttttgttt tctctggagt acttggacag atgttatagt ggtttctttt aggaaaatct   4415
gtcattaaaa aagttatagc cttgcaaata accactc                             4452
```

<210> SEQ ID NO 40
<211> LENGTH: 669
<212> TYPE: PRT
<213> ORGANISM: Homo Sapiens

<400> SEQUENCE: 40

```
Met Ala Arg Arg Gly Trp Arg Arg Ala Pro Leu Arg Arg Gly Val Gly
  1               5                  10                  15

Ser Ser Pro Arg Ala Arg Arg Leu Met Arg Pro Leu Trp Leu Leu Leu
             20                  25                  30

Ala Val Gly Val Phe Asp Trp Ala Gly Ala Ser Asp Gly Gly Gly
         35                  40                  45

Glu Ala Arg Ala Met Asp Glu Glu Ile Val Ser Glu Lys Gln Ala Glu
     50                  55                  60

Glu Ser His Arg Gln Asp Ser Ala Asn Leu Leu Ile Phe Ile Leu Leu
 65                  70                  75                  80

Leu Thr Leu Thr Ile Leu Thr Ile Trp Leu Phe Lys His Arg Arg Ala
                 85                  90                  95
```

```
Arg Phe Leu His Glu Thr Gly Leu Ala Met Ile Tyr Gly Leu Leu Val
            100                 105                 110

Gly Leu Val Leu Arg Tyr Gly Ile His Val Pro Ser Asp Val Asn Asn
            115                 120                 125

Val Thr Leu Ser Cys Glu Val Gln Ser Ser Pro Thr Thr Leu Leu Val
            130                 135                 140

Thr Phe Asp Pro Glu Val Phe Phe Asn Ile Leu Leu Pro Pro Ile Ile
145                 150                 155                 160

Phe Tyr Ala Gly Tyr Ser Leu Lys Arg Arg His Phe Arg Asn Leu
                165                 170                 175

Gly Ser Ile Leu Ala Tyr Ala Phe Leu Gly Thr Ala Ile Ser Cys Phe
            180                 185                 190

Val Ile Gly Ser Ile Met Tyr Gly Cys Val Thr Leu Met Lys Val Thr
            195                 200                 205

Gly Gln Leu Ala Gly Asp Phe Tyr Phe Thr Asp Cys Leu Leu Phe Gly
            210                 215                 220

Ala Ile Val Ser Ala Thr Asp Pro Val Thr Val Leu Ala Ile Phe His
225                 230                 235                 240

Glu Leu Gln Val Asp Val Glu Leu Tyr Ala Leu Leu Phe Gly Glu Ser
                245                 250                 255

Val Leu Asn Asp Ala Val Ala Ile Val Leu Ser Ser Ser Ile Val Ala
            260                 265                 270

Tyr Gln Pro Ala Gly Asp Asn Ser His Thr Phe Asp Val Thr Ala Met
            275                 280                 285

Phe Lys Ser Ile Gly Ile Phe Leu Gly Ile Phe Ser Gly Ser Phe Ala
            290                 295                 300

Met Gly Ala Ala Thr Gly Val Val Thr Ala Leu Val Thr Lys Phe Thr
305                 310                 315                 320

Lys Leu Arg Glu Phe Gln Leu Leu Glu Thr Gly Leu Phe Phe Leu Met
                325                 330                 335

Ser Trp Ser Thr Phe Leu Leu Ala Glu Ala Trp Gly Phe Thr Gly Val
            340                 345                 350

Val Ala Val Leu Phe Cys Gly Ile Thr Gln Ala His Tyr Thr Tyr Asn
            355                 360                 365

Asn Leu Ser Thr Glu Ser Gln His Arg Thr Lys Gln Leu Phe Glu Leu
            370                 375                 380

Leu Asn Phe Leu Ala Glu Asn Phe Ile Phe Ser Tyr Met Gly Leu Thr
385                 390                 395                 400

Leu Phe Thr Phe Gln Asn His Val Phe Asn Pro Thr Phe Val Val Gly
                405                 410                 415

Ala Phe Val Ala Ile Phe Leu Gly Arg Ala Ala Asn Ile Tyr Pro Leu
            420                 425                 430

Ser Leu Leu Leu Asn Leu Gly Arg Arg Ser Lys Ile Gly Ser Asn Phe
            435                 440                 445

Gln His Met Met Met Phe Ala Gly Leu Arg Gly Ala Met Ala Phe Ala
            450                 455                 460

Leu Ala Ile Arg Asp Thr Ala Thr Tyr Ala Arg Gln Met Met Phe Ser
465                 470                 475                 480

Thr Thr Leu Leu Ile Val Phe Phe Thr Val Trp Val Phe Gly Gly Gly
                485                 490                 495

Thr Thr Ala Met Leu Ser Cys Leu His Ile Arg Val Gly Val Asp Ser
            500                 505                 510
```

-continued

```
Asp Gln Glu His Leu Gly Val Pro Glu Asn Glu Arg Arg Thr Thr Lys
            515                 520                 525

Ala Glu Ser Ala Trp Leu Phe Arg Met Trp Tyr Asn Phe Asp His Asn
        530                 535                 540

Tyr Leu Lys Pro Leu Leu Thr His Ser Gly Pro Pro Leu Thr Thr Thr
545                 550                 555                 560

Leu Pro Ala Cys Cys Gly Pro Ile Ala Arg Cys Leu Thr Ser Pro Gln
                565                 570                 575

Ala Tyr Glu Asn Gln Glu Gln Leu Lys Asp Asp Ser Asp Leu Ile
            580                 585                 590

Leu Asn Asp Gly Asp Ile Ser Leu Thr Tyr Gly Asp Ser Thr Val Asn
        595                 600                 605

Thr Glu Pro Ala Thr Ser Ser Ala Pro Arg Arg Phe Met Gly Asn Ser
    610                 615                 620

Ser Glu Asp Ala Leu Asp Arg Glu Leu Ala Phe Gly Asp His Glu Leu
625                 630                 635                 640

Val Ile Arg Gly Thr Arg Leu Val Leu Pro Met Asp Asp Ser Glu Pro
                645                 650                 655

Pro Leu Asn Leu Leu Asp Asn Thr Arg His Gly Pro Ala
            660                 665

<210> SEQ ID NO 41
<211> LENGTH: 3116
<212> TYPE: DNA
<213> ORGANISM: Homo Sapiens
<220> FEATURE:
<221> NAME/KEY: CDS
<222> LOCATION: (205)...(2493)

<400> SEQUENCE: 41
ggcacgaggg ccagctgctg tagaagaggg gaggaaacaa gccagtgcaa ggggagcaaa      60
agagaaaagg agccaggctg gcttcctga tcccacagca tcgcagagct cgggaggcac     120
agctcacaga cacaggaaac acaggactgc tattctgctc tcctgcccac ggtgatctgg    180
tgccagctgg tggaacagtg ggtg atg gcg tcc ctg ctg caa gac cag ctg       231
                          Met Ala Ser Leu Leu Gln Asp Gln Leu
                            1               5 acc act gat cag gac ttg ctg ctg atg cag gaa ggc atg ccg atg cgc      279
Thr Thr Asp Gln Asp Leu Leu Leu Met Gln Glu Gly Met Pro Met Arg
 10                  15                  20                  25 aag gtg agg tcc aaa agc tgg aag aag cta aga tac ttc aga ctt cag      327
Lys Val Arg Ser Lys Ser Trp Lys Lys Leu Arg Tyr Phe Arg Leu Gln
                 30                  35                  40 aat gac ggc atg aca gtc tgg cat gca cgg cag gcc agg ggc agt gcc      375
Asn Asp Gly Met Thr Val Trp His Ala Arg Gln Ala Arg Gly Ser Ala
             45                  50                  55 aag ccc agc ttc tca atc tct gat gtg gag aca ata cgt aat ggc cat      423
Lys Pro Ser Phe Ser Ile Ser Asp Val Glu Thr Ile Arg Asn Gly His
         60                  65                  70 gat tcc gag ttg ctg cgt agc ctg gca gag gag ctc ccc ctg gag cag      471
Asp Ser Glu Leu Leu Arg Ser Leu Ala Glu Glu Leu Pro Leu Glu Gln
 75                  80                  85 ggc ttc acc att gtc ttc cat ggc cgc cgc tcc aac ctg gac ctg atg      519
Gly Phe Thr Ile Val Phe His Gly Arg Arg Ser Asn Leu Asp Leu Met
 90                  95                 100                 105 gcc aac agt gtt gag gag gcc cag ata tgg atg cga ggg ctc cag ctg      567
Ala Asn Ser Val Glu Glu Ala Gln Ile Trp Met Arg Gly Leu Gln Leu
                110                 115                 120
```

|   |   |
|---|---|
| ttg gtg gat ctt gtc acc agc atg gac cat cag gag cgc ctg gac caa<br>Leu Val Asp Leu Val Thr Ser Met Asp His Gln Glu Arg Leu Asp Gln<br>              125                     130                   135 | 615 |
| tgg ctg agc gat tgg ttt caa cgt gga gac aaa aat cag gat ggt aag<br>Trp Leu Ser Asp Trp Phe Gln Arg Gly Asp Lys Asn Gln Asp Gly Lys<br>         140                   145                   150 | 663 |
| atg agt ttc caa gaa gtt cag cgg tta ttg cac cta atg aat gtg gaa<br>Met Ser Phe Gln Glu Val Gln Arg Leu Leu His Leu Met Asn Val Glu<br>155                   160                   165 | 711 |
| atg gac caa gaa tat gcc ttc agt ctt ttt cag gca gca gac acg tcc<br>Met Asp Gln Glu Tyr Ala Phe Ser Leu Phe Gln Ala Ala Asp Thr Ser<br>170                   175                   180                   185 | 759 |
| cag tct gga acc ctg gaa gga gaa gaa ttc gta cag ttc tat aag gca<br>Gln Ser Gly Thr Leu Glu Gly Glu Glu Phe Val Gln Phe Tyr Lys Ala<br>              190                     195                   200 | 807 |
| ttg act aaa cgt gct gag gtg cag gaa ctg ttt gaa agt ttt tca gct<br>Leu Thr Lys Arg Ala Glu Val Gln Glu Leu Phe Glu Ser Phe Ser Ala<br>         205                   210                   215 | 855 |
| gat ggg cag aag ctg act ctg ctg gaa ttt ttg gat ttc ctc caa gag<br>Asp Gly Gln Lys Leu Thr Leu Leu Glu Phe Leu Asp Phe Leu Gln Glu<br>              220                   225                 230 | 903 |
| gag cag aag gag aga gac tgc acc tct gag ctt gct ctg gaa ctc att<br>Glu Gln Lys Glu Arg Asp Cys Thr Ser Glu Leu Ala Leu Glu Leu Ile<br>235                   240                   245 | 951 |
| gac cgc tat gaa cct tca gac agt ggc aaa ctg cgg cat gtg ctg agt<br>Asp Arg Tyr Glu Pro Ser Asp Ser Gly Lys Leu Arg His Val Leu Ser<br>250                   255                   260                   265 | 999 |
| atg gat ggc ttc ctc agc tac ctc tgc tct aag gat gga gac atc ttc<br>Met Asp Gly Phe Leu Ser Tyr Leu Cys Ser Lys Asp Gly Asp Ile Phe<br>              270                   275                 280 | 1047 |
| aac cca gcc tgc ctc ccc atc tat cag gat atg act caa ccc ctg aac<br>Asn Pro Ala Cys Leu Pro Ile Tyr Gln Asp Met Thr Gln Pro Leu Asn<br>285                   290                   295 | 1095 |
| cac tac ttc atc tgc tct tct cat aac acc tac cta gtg ggg gac cag<br>His Tyr Phe Ile Cys Ser Ser His Asn Thr Tyr Leu Val Gly Asp Gln<br>300                   305                   310 | 1143 |
| ctt tgc ggc cag agc agc gtc gag gga tat ata cgg gcc ctg aag cgg<br>Leu Cys Gly Gln Ser Ser Val Glu Gly Tyr Ile Arg Ala Leu Lys Arg<br>         315                   320                   325 | 1191 |
| ggg tgc cgc tgc gtg gag gtg gat gta tgg gat gga cct agc ggg gaa<br>Gly Cys Arg Cys Val Glu Val Asp Val Trp Asp Gly Pro Ser Gly Glu<br>330                   335                   340                 345 | 1239 |
| cct gtc gtt tac cac gga cac acc ctg acc tcc cgc atc ctg ttc aaa<br>Pro Val Val Tyr His Gly His Thr Leu Thr Ser Arg Ile Leu Phe Lys<br>              350                   355                 360 | 1287 |
| gat gtc gtg gcc aca gta gca cag tat gcc ttc cag aca tca gac tac<br>Asp Val Val Ala Thr Val Ala Gln Tyr Ala Phe Gln Thr Ser Asp Tyr<br>         365                   370                   375 | 1335 |
| cca gtc atc ttg tcc ctg gag acc cac tgc agc tgg gag cag cag cag<br>Pro Val Ile Leu Ser Leu Glu Thr His Cys Ser Trp Glu Gln Gln Gln<br>380                   385                   390 | 1383 |
| acc atg gcc cgt cat ctg act gag atc ctg ggg gag cag ctg ctg agc<br>Thr Met Ala Arg His Leu Thr Glu Ile Leu Gly Glu Gln Leu Leu Ser<br>         395                   400                   405 | 1431 |
| acc acc ttg gat ggg gtg ctg ccc act cag ctg ccc tcg cct gag gag<br>Thr Thr Leu Asp Gly Val Leu Pro Thr Gln Leu Pro Ser Pro Glu Glu<br>410                   415                   420                 425 | 1479 |
| ctt cgg agg aag atc ctg gtg aag ggg aag aag tta aca ctt gag gaa<br>Leu Arg Arg Lys Ile Leu Val Lys Gly Lys Lys Leu Thr Leu Glu Glu<br>              430                   435                 440 | 1527 |

```
                                                     -continued gac ctg gaa tat gag gaa gag gaa gca gaa cct gag ttg gaa gag tca       1575
Asp Leu Glu Tyr Glu Glu Glu Glu Ala Glu Pro Glu Leu Glu Glu Ser
            445                 450                 455 gaa ttg gcg ctg gag tcc cag ttt gag act gag cct gag ccc cag gag       1623
Glu Leu Ala Leu Glu Ser Gln Phe Glu Thr Glu Pro Glu Pro Gln Glu
        460                 465                 470 cag aac ctt cag aat aag gac aaa aag aag aaa tcc aag ccc atc ttg       1671
Gln Asn Leu Gln Asn Lys Asp Lys Lys Lys Lys Ser Lys Pro Ile Leu
475                 480                 485 tgt cca gcc ctc tct tcc ctg gtt atc tac ttg aag tct gtc tca ttc       1719
Cys Pro Ala Leu Ser Ser Leu Val Ile Tyr Leu Lys Ser Val Ser Phe
490                 495                 500                 505 cgc agc ttc aca cat tca aag gag cac tac cac ttc tac gag ata tca       1767
Arg Ser Phe Thr His Ser Lys Glu His Tyr His Phe Tyr Glu Ile Ser
                510                 515                 520 tct ttc tct gaa acc aag gcc aag cgc ctc atc aag gag gct ggc aat       1815
Ser Phe Ser Glu Thr Lys Ala Lys Arg Leu Ile Lys Glu Ala Gly Asn
            525                 530                 535 gag ttt gtg cag cac aat act tgg cag tta agc cgt gtg tat ccc agc       1863
Glu Phe Val Gln His Asn Thr Trp Gln Leu Ser Arg Val Tyr Pro Ser
        540                 545                 550 ggc ctg agg aca gac tct tcc aac tac aac ccc cag gaa ctc tgg aat       1911
Gly Leu Arg Thr Asp Ser Ser Asn Tyr Asn Pro Gln Glu Leu Trp Asn
    555                 560                 565 gca ggc tgc cag atg gtg gcc atg aat atg cag act gca ggg ctt gaa       1959
Ala Gly Cys Gln Met Val Ala Met Asn Met Gln Thr Ala Gly Leu Glu
570                 575                 580                 585 atg gac atc tgt gat ggg cat ttc cgc cag aat ggc ggc tgt ggc tat       2007
Met Asp Ile Cys Asp Gly His Phe Arg Gln Asn Gly Gly Cys Gly Tyr
                590                 595                 600 gtg ctg aag cca gac ttc ctg cgt gat atc cag agt tct ttc cac cct       2055
Val Leu Lys Pro Asp Phe Leu Arg Asp Ile Gln Ser Ser Phe His Pro
            605                 610                 615 gag aag ccc atc agc cct ttc aaa gcc cag act ctc tta atc cag gtg       2103
Glu Lys Pro Ile Ser Pro Phe Lys Ala Gln Thr Leu Leu Ile Gln Val
        620                 625                 630 atc agc ggt cag caa ctc ccc aaa gtg gac aag acc aaa gag ggg tcc       2151
Ile Ser Gly Gln Gln Leu Pro Lys Val Asp Lys Thr Lys Glu Gly Ser
    635                 640                 645 att gtg gat cca ctg gtg aaa gtg cag atc ttt ggc gtt cgt cta gac       2199
Ile Val Asp Pro Leu Val Lys Val Gln Ile Phe Gly Val Arg Leu Asp
650                 655                 660                 665 aca gca cgg cag gag acc aac tat gtg gag aac aat ggt ttt aat cca       2247
Thr Ala Arg Gln Glu Thr Asn Tyr Val Glu Asn Asn Gly Phe Asn Pro
                670                 675                 680 tac tgg ggg cag aca cta tgt ttc cgg gtg ctg gtg cct gaa ctt gcc       2295
Tyr Trp Gly Gln Thr Leu Cys Phe Arg Val Leu Val Pro Glu Leu Ala
            685                 690                 695 atg ctg cgt ttt gtg gta atg gat tat gac tgg aaa tcc cga aat gac       2343
Met Leu Arg Phe Val Val Met Asp Tyr Asp Trp Lys Ser Arg Asn Asp
        700                 705                 710 ttt att ggt cag tac acc ctg cct tgg acc tgc atg caa caa ggt tac       2391
Phe Ile Gly Gln Tyr Thr Leu Pro Trp Thr Cys Met Gln Gln Gly Tyr
    715                 720                 725 cgc cac att cac ctg ctg tcc aaa gat ggc atc agc ctc cgc cca gct       2439
Arg His Ile His Leu Leu Ser Lys Asp Gly Ile Ser Leu Arg Pro Ala
730                 735                 740                 745 tcc atc ttt gtg tat atc tgc atc cag gaa ggc ctg gag ggg gat gag       2487
Ser Ile Phe Val Tyr Ile Cys Ile Gln Glu Gly Leu Glu Gly Asp Glu
                750                 755                 760
```

```
tcc tga ggtgggcatt tcacgggaag ggttggtatg ctggctttag acggggagaa    2543
Ser * acatctggaa ggatgctcga gagaacaaat ggaggtggtg aaaatcaagc tttggattgt    2603
gcattcctag gcacaaaatt acctcattct tcctaacaag caatctggga cctgattttc    2663 caccttttt ctcttttctt cccttccttt gttttcataa gcctttggta tctttcctgc    2723
ccttttcctt tgtgtactct atactggagt tcccttcttc ctcttgctgt aggctcaatc    2783
ccataccgac atctacaact aatctttccc atcaactctg tgtgaaggca ggttgcaact    2843
agaaattcag aggggcttgg aatagagaaa cctaaagaag catcatcccc tccatcccca    2903
acttcctcaa agcccaaagc caagggaagg ataaatcaag gctcaaggct tccccagcaa    2963
agattaggga aagagacttg accccaggac tgtactacga ctcttaagag aacactgcac    3023
agcactcaaa gtcccccact ggactgcttc ctccttagcc ccactggtat aaatacatct    3083
ctctccaatt tggcaaaaaa aaaaaaaaaa aaa                                 3116
```

<210> SEQ ID NO 42
<211> LENGTH: 762
<212> TYPE: PRT
<213> ORGANISM: Homo Sapiens

<400> SEQUENCE: 42

```
Met Ala Ser Leu Leu Gln Asp Gln Leu Thr Thr Asp Gln Asp Leu Leu
 1               5                  10                  15

Leu Met Gln Glu Gly Met Pro Met Arg Lys Val Arg Ser Lys Ser Trp
            20                  25                  30

Lys Lys Leu Arg Tyr Phe Arg Leu Gln Asn Asp Gly Met Thr Val Trp
        35                  40                  45

His Ala Arg Gln Ala Arg Gly Ser Ala Lys Pro Ser Phe Ser Ile Ser
    50                  55                  60

Asp Val Glu Thr Ile Arg Asn Gly His Asp Ser Glu Leu Leu Arg Ser
65                  70                  75                  80

Leu Ala Glu Glu Leu Pro Leu Glu Gln Gly Phe Thr Ile Val Phe His
                85                  90                  95

Gly Arg Arg Ser Asn Leu Asp Leu Met Ala Asn Ser Val Glu Glu Ala
            100                 105                 110

Gln Ile Trp Met Arg Gly Leu Gln Leu Leu Val Asp Leu Val Thr Ser
        115                 120                 125

Met Asp His Gln Glu Arg Leu Asp Gln Trp Leu Ser Asp Trp Phe Gln
    130                 135                 140

Arg Gly Asp Lys Asn Gln Asp Gly Lys Met Ser Phe Gln Glu Val Gln
145                 150                 155                 160

Arg Leu Leu His Leu Met Asn Val Glu Met Asp Gln Glu Tyr Ala Phe
                165                 170                 175

Ser Leu Phe Gln Ala Ala Asp Thr Ser Gln Ser Gly Thr Leu Glu Gly
            180                 185                 190

Glu Glu Phe Val Gln Phe Tyr Lys Ala Leu Thr Lys Arg Ala Glu Val
        195                 200                 205

Gln Glu Leu Phe Glu Ser Phe Ser Ala Asp Gly Gln Lys Leu Thr Leu
    210                 215                 220

Leu Glu Phe Leu Asp Phe Leu Gln Glu Glu Lys Glu Arg Asp Cys
225                 230                 235                 240

Thr Ser Glu Leu Ala Leu Glu Leu Ile Asp Arg Tyr Glu Pro Ser Asp
                245                 250                 255
```

-continued

```
Ser Gly Lys Leu Arg His Val Leu Ser Met Asp Gly Phe Leu Ser Tyr
            260                 265                 270

Leu Cys Ser Lys Asp Gly Asp Ile Phe Asn Pro Ala Cys Leu Pro Ile
            275                 280             285

Tyr Gln Asp Met Thr Gln Pro Leu Asn His Tyr Phe Ile Cys Ser Ser
            290                 295                 300

His Asn Thr Tyr Leu Val Gly Asp Gln Leu Cys Gly Gln Ser Ser Val
305                 310                 315                 320

Glu Gly Tyr Ile Arg Ala Leu Lys Arg Gly Arg Cys Val Glu Val
                325                 330                 335

Asp Val Trp Asp Gly Pro Ser Gly Glu Pro Val Val Tyr His Gly His
            340                 345                 350

Thr Leu Thr Ser Arg Ile Leu Phe Lys Asp Val Val Ala Thr Val Ala
            355                 360                 365

Gln Tyr Ala Phe Gln Thr Ser Asp Tyr Pro Val Ile Leu Ser Leu Glu
    370                 375                 380

Thr His Cys Ser Trp Glu Gln Gln Thr Met Ala Arg His Leu Thr
385                 390                 395                 400

Glu Ile Leu Gly Glu Gln Leu Leu Ser Thr Thr Leu Asp Gly Val Leu
            405                 410                 415

Pro Thr Gln Leu Pro Ser Pro Glu Glu Leu Arg Arg Lys Ile Leu Val
            420                 425                 430

Lys Gly Lys Lys Leu Thr Leu Glu Glu Asp Leu Glu Tyr Glu Glu Glu
            435                 440                 445

Glu Ala Glu Pro Glu Leu Glu Glu Ser Glu Leu Ala Leu Glu Ser Gln
    450                 455                 460

Phe Glu Thr Glu Pro Glu Pro Gln Glu Gln Asn Leu Gln Asn Lys Asp
465                 470                 475                 480

Lys Lys Lys Lys Ser Lys Pro Ile Leu Cys Pro Ala Leu Ser Ser Leu
                485                 490                 495

Val Ile Tyr Leu Lys Ser Val Ser Phe Arg Ser Phe Thr His Ser Lys
            500                 505                 510

Glu His Tyr His Phe Tyr Glu Ile Ser Ser Phe Ser Glu Thr Lys Ala
            515                 520                 525

Lys Arg Leu Ile Lys Glu Ala Gly Asn Glu Phe Val Gln His Asn Thr
    530                 535                 540

Trp Gln Leu Ser Arg Val Tyr Pro Ser Gly Leu Arg Thr Asp Ser Ser
545                 550                 555                 560

Asn Tyr Asn Pro Gln Glu Leu Trp Asn Ala Gly Cys Gln Met Val Ala
                565                 570                 575

Met Asn Met Gln Thr Ala Gly Leu Glu Met Asp Ile Cys Asp Gly His
            580                 585                 590

Phe Arg Gln Asn Gly Gly Cys Gly Tyr Val Leu Lys Pro Asp Phe Leu
            595                 600                 605

Arg Asp Ile Gln Ser Ser Phe His Pro Glu Lys Pro Ile Ser Pro Phe
    610                 615                 620

Lys Ala Gln Thr Leu Leu Ile Gln Val Ile Ser Gly Gln Gln Leu Pro
625                 630                 635                 640

Lys Val Asp Lys Thr Lys Glu Gly Ser Ile Val Asp Pro Leu Val Lys
                645                 650                 655

Val Gln Ile Phe Gly Val Arg Leu Asp Thr Ala Arg Gln Glu Thr Asn
            660                 665                 670
```

```
                Tyr Val Glu Asn Asn Gly Phe Asn Pro Tyr Trp Gly Gln Thr Leu Cys
                            675                 680                 685

Phe Arg Val Leu Val Pro Glu Leu Ala Met Leu Arg Phe Val Val Met
                690                 695                 700

Asp Tyr Asp Trp Lys Ser Arg Asn Asp Phe Ile Gly Gln Tyr Thr Leu
                705                 710                 715                 720

Pro Trp Thr Cys Met Gln Gln Gly Tyr Arg His Ile His Leu Leu Ser
                                725                 730                 735

Lys Asp Gly Ile Ser Leu Arg Pro Ala Ser Ile Phe Val Tyr Ile Cys
                            740                 745                 750

Ile Gln Glu Gly Leu Glu Gly Asp Glu Ser
                        755                 760

<210> SEQ ID NO 43
<211> LENGTH: 1943
<212> TYPE: DNA
<213> ORGANISM: Homo Sapiens
<220> FEATURE:
<221> NAME/KEY: CDS
<222> LOCATION: (466)...(1758)

<400> SEQUENCE: 43
gggggctctc tccacgcctt gctgccgcgt cccggtccta ggcgcccggg atccacggcc      60
caccccgccc gcagcccgcg gcctgtctgg agaggagtat gaggcccggg gccccgcgga    120
cgccggccac cgggcggcag gggcctagct gcggagcccc gcgcccgaga gcggcgggta    180
aggagccgcg ggagccggcg aggcgtcggg gcgcgcagag gagcgcccct gcccgggcac    240
ccgctgggcc acgggactcg cgtgtggcct gagcgccggg gaggaggcgg aggcgcccct    300
ctgtccgggc tctgggaagg caacgagggg ctctgcgaag gcggcgaggg gctccgcggc    360
ggccccggac ccctggccac catcctcacg ctcctgctcc cgccgggggg atgtcgtggc    420
ccgggccccg agcgccgccc cggccccggg gctgagctcc ggacc atg tcc tcc cgc    477
                                              Met Ser Ser Arg
                                                1 agc ccc cgg ccc ccg ccc cgc cgt agc cgc cgc cgc ctg ccg cgc ccc       525
Ser Pro Arg Pro Pro Pro Arg Arg Ser Arg Arg Arg Leu Pro Arg Pro
 5                  10                  15                  20 tcc tgc tgc tgc tgc tgc tgc cgc cgt tcg cac ctc aac gag gac acc       573
Ser Cys Cys Cys Cys Cys Cys Arg Arg Ser His Leu Asn Glu Asp Thr
                25                  30                  35 ggc cgc ttc gtg ctg ctg gcg gcg ctc atc ggc ctc tac ctg gtg gcg       621
Gly Arg Phe Val Leu Leu Ala Ala Leu Ile Gly Leu Tyr Leu Val Ala
            40                  45                  50 ggt gcc aca gtc ttc tcg gcg ctc gag agc ccc ggc gag gcg gag gcg       669
Gly Ala Thr Val Phe Ser Ala Leu Glu Ser Pro Gly Glu Ala Glu Ala
        55                  60                  65 cgg gcg cgc tgg ggc gcc acg ctg cgc aac ttc agc gct gca cac ggc       717
Arg Ala Arg Trp Gly Ala Thr Leu Arg Asn Phe Ser Ala Ala His Gly
    70                  75                  80 gtg gcc gag cca gag ctg cgc gcc ttc ctc cgg cac tac gag gcc gcg       765
Val Ala Glu Pro Glu Leu Arg Ala Phe Leu Arg His Tyr Glu Ala Ala
85                  90                  95                 100 ctg gcc gcc ggc gtc cgc gcc gac gcg ctg cgc ccg cgc tgg gac ttc       813
Leu Ala Ala Gly Val Arg Ala Asp Ala Leu Arg Pro Arg Trp Asp Phe
                105                 110                 115 ccc ggc gcc ttc tac ttc gtg ggc acc gtg gtg tca acc ata ggt ttc       861
Pro Gly Ala Phe Tyr Phe Val Gly Thr Val Val Ser Thr Ile Gly Phe
            120                 125                 130
```

| | | |
|---|---|---|
| ggc atg acc acc ccc gcg acg gtg ggc ggg aag gcc ttc ctc atc gcc<br>Gly Met Thr Thr Pro Ala Thr Val Gly Gly Lys Ala Phe Leu Ile Ala<br>135                    140                    145 | 909 |
| tac ggg ctg ttc ggc tgc gct ggg acc atc ctg ttc ttc aac ctc ttc<br>Tyr Gly Leu Phe Gly Cys Ala Gly Thr Ile Leu Phe Phe Asn Leu Phe<br>150                    155                    160 | 957 |
| ctg gag cgc atc atc tcg ctg ctg gcc ttc atc atg cgc gcc tgc cgg<br>Leu Glu Arg Ile Ile Ser Leu Leu Ala Phe Ile Met Arg Ala Cys Arg<br>165                    170                    175                    180 | 1005 |
| gag cgc cag ctg cgc cgc agc ggc ctg ctg ccc gcc acc ttc cgc cgc<br>Glu Arg Gln Leu Arg Arg Ser Gly Leu Leu Pro Ala Thr Phe Arg Arg<br>                    185                    190                    195 | 1053 |
| ggc tcc gcg ctc tcg gag gcc gac agc ctg gcg ggc tgg aag ccc tcg<br>Gly Ser Ala Leu Ser Glu Ala Asp Ser Leu Ala Gly Trp Lys Pro Ser<br>              200                    205                    210 | 1101 |
| gtg tac cac gtg ctg ctc atc ctg ggc ctg ttc gcc gtg ctg ctg tcc<br>Val Tyr His Val Leu Leu Ile Leu Gly Leu Phe Ala Val Leu Leu Ser<br>              215                    220                    225 | 1149 |
| tgc tgc gcc tcg gcc atg tac acc agc gtg gag ggc tgg gac tac gtg<br>Cys Cys Ala Ser Ala Met Tyr Thr Ser Val Glu Gly Trp Asp Tyr Val<br>230                    235                    240 | 1197 |
| gac tcg ctc tac ttc tgc ttc gtc acc ttc agc acc atc ggc ttc ggg<br>Asp Ser Leu Tyr Phe Cys Phe Val Thr Phe Ser Thr Ile Gly Phe Gly<br>245                    250                    255                    260 | 1245 |
| gac ctg gtg agc agc cag cac gcc gcc tac cgg aac cag ggg ctc tac<br>Asp Leu Val Ser Ser Gln His Ala Ala Tyr Arg Asn Gln Gly Leu Tyr<br>                    265                    270                    275 | 1293 |
| cgc ctg ggc aac ttc ctc ttc atc ctc ctc ggc gtg tgc tgc att tac<br>Arg Leu Gly Asn Phe Leu Phe Ile Leu Leu Gly Val Cys Cys Ile Tyr<br>              280                    285                    290 | 1341 |
| tcg ctc ttc aac gtc atc tcc atc ctc atc aag cag gtg ctc aac tgg<br>Ser Leu Phe Asn Val Ile Ser Ile Leu Ile Lys Gln Val Leu Asn Trp<br>295                    300                    305 | 1389 |
| atg ctg cgc aag ctg agc tgc cgc tgc tgc gcg cgc tgc tgc ccg gct<br>Met Leu Arg Lys Leu Ser Cys Arg Cys Cys Ala Arg Cys Cys Pro Ala<br>310                    315                    320 | 1437 |
| cct ggc gcg ccc ctg gcc cgg cgc aat gcc atc acc cca ggc tcc cgg<br>Pro Gly Ala Pro Leu Ala Arg Arg Asn Ala Ile Thr Pro Gly Ser Arg<br>325                    330                    335                    340 | 1485 |
| ctg cgc cgc cgc ctg gcc gcg ctc ggc gcc gac ccc gcg gcc cgc gac<br>Leu Arg Arg Arg Leu Ala Ala Leu Gly Ala Asp Pro Ala Ala Arg Asp<br>                    345                    350                    355 | 1533 |
| agc gac gcc gag ggc cgc cgc ctc tcg ggc gag ctc atc tcc atg cgc<br>Ser Asp Ala Glu Gly Arg Arg Leu Ser Gly Glu Leu Ile Ser Met Arg<br>              360                    365                    370 | 1581 |
| gac ctc acg gcc tcc aac aag gtg tcg ctg gcg ctg ctg cag aag cag<br>Asp Leu Thr Ala Ser Asn Lys Val Ser Leu Ala Leu Leu Gln Lys Gln<br>375                    380                    385 | 1629 |
| ctg tcg gag acg gcc aac ggc tac ccg cgc agc gtg tgc gtc aac acg<br>Leu Ser Glu Thr Ala Asn Gly Tyr Pro Arg Ser Val Cys Val Asn Thr<br>390                    395                    400 | 1677 |
| cgc cag aac ggc ttc tcg ggc ggc gtg ggc gcg ctg ggc atc atg aac<br>Arg Gln Asn Gly Phe Ser Gly Gly Val Gly Ala Leu Gly Ile Met Asn<br>405                    410                    415                    420 | 1725 |
| aac cgg ctg gcc gag acc agc gcc tcc agg tag accgcccgtc cgcccgcgcc<br>Asn Arg Leu Ala Glu Thr Ser Ala Ser Arg  *<br>                    425                    430 | 1778 |

-continued

```
ggggaccctc tccaggccgc ggggccgccg ggcgtggttt gcttctctca gtcactgctg   1838
gcgctttctt aatctttatc caataaaatg aaacaaaaaa aattttttta aagaaaaaaa   1898
aaaaaaaaag ggcggatgtt atcaagggca ggttttgggg acgcc                   1943
```

<210> SEQ ID NO 44
<211> LENGTH: 430
<212> TYPE: PRT
<213> ORGANISM: Homo Sapiens

<400> SEQUENCE: 44

```
Met Ser Ser Arg Ser Pro Arg Pro Pro Arg Ser Arg Arg
 1               5                  10              15

Leu Pro Arg Pro Ser Cys Cys Cys Cys Cys Arg Arg Ser His Leu
              20                  25                  30

Asn Glu Asp Thr Gly Arg Phe Val Leu Ala Ala Leu Ile Gly Leu
              35                  40                  45

Tyr Leu Val Ala Gly Ala Thr Val Phe Ser Ala Glu Ser Pro Gly
 50                  55                  60

Glu Ala Glu Ala Arg Ala Arg Trp Gly Ala Thr Leu Arg Asn Phe Ser
65                   70                  75                  80

Ala Ala His Gly Val Ala Glu Pro Glu Leu Arg Ala Phe Leu Arg His
                     85                  90                  95

Tyr Glu Ala Ala Leu Ala Ala Gly Val Arg Ala Asp Ala Leu Arg Pro
                    100                 105                 110

Arg Trp Asp Phe Pro Gly Ala Phe Tyr Phe Val Gly Thr Val Val Ser
                    115                 120                 125

Thr Ile Gly Phe Gly Met Thr Thr Pro Ala Thr Val Gly Gly Lys Ala
130                 135                 140

Phe Leu Ile Ala Tyr Gly Leu Phe Gly Cys Ala Gly Thr Ile Leu Phe
145                 150                 155                 160

Phe Asn Leu Phe Leu Glu Arg Ile Ile Ser Leu Leu Ala Phe Ile Met
                    165                 170                 175

Arg Ala Cys Arg Glu Arg Gln Leu Arg Arg Ser Gly Leu Leu Pro Ala
                    180                 185                 190

Thr Phe Arg Arg Gly Ser Ala Leu Ser Glu Ala Asp Ser Leu Ala Gly
                    195                 200                 205

Trp Lys Pro Ser Val Tyr His Val Leu Leu Ile Leu Gly Leu Phe Ala
                    210                 215                 220

Val Leu Leu Ser Cys Cys Ala Ser Ala Met Tyr Thr Ser Val Glu Gly
225                 230                 235                 240

Trp Asp Tyr Val Asp Ser Leu Tyr Phe Cys Phe Val Thr Phe Ser Thr
                    245                 250                 255

Ile Gly Phe Gly Asp Leu Val Ser Ser Gln His Ala Ala Tyr Arg Asn
                    260                 265                 270

Gln Gly Leu Tyr Arg Leu Gly Asn Phe Leu Phe Ile Leu Leu Gly Val
                    275                 280                 285

Cys Cys Ile Tyr Ser Leu Phe Asn Val Ile Ser Ile Leu Ile Lys Gln
                    290                 295                 300

Val Leu Asn Trp Met Leu Arg Lys Leu Ser Cys Arg Cys Ala Arg
305                 310                 315                 320

Cys Cys Pro Ala Pro Gly Ala Pro Leu Ala Arg Arg Asn Ala Ile Thr
                    325                 330                 335

Pro Gly Ser Arg Leu Arg Arg Leu Ala Ala Leu Gly Ala Asp Pro
                    340                 345                 350
```

```
Ala Ala Arg Asp Ser Asp Ala Glu Gly Arg Arg Leu Ser Gly Glu Leu
            355                 360                 365

Ile Ser Met Arg Asp Leu Thr Ala Ser Asn Lys Val Ser Leu Ala Leu
    370                 375                 380

Leu Gln Lys Gln Leu Ser Glu Thr Ala Asn Gly Tyr Pro Arg Ser Val
385                 390                 395                 400

Cys Val Asn Thr Arg Gln Asn Gly Phe Ser Gly Val Gly Ala Leu
                405                 410                 415

Gly Ile Met Asn Asn Arg Leu Ala Glu Thr Ser Ala Ser Arg
            420                 425                 430

<210> SEQ ID NO 45
<211> LENGTH: 2384
<212> TYPE: DNA
<213> ORGANISM: Homo Sapiens
<220> FEATURE:
<221> NAME/KEY: CDS
<222> LOCATION: (233)...(2260)

<400> SEQUENCE: 45
```

| | |
|---|---|
| gctgaggctg gagtttggag tttgacccgc ttggaggctc tctcagcagc gggcatatag | 60 |
| gaggaagggt cactgctgtc tccggaagct cttggctgca agagagagg atcccgggta | 120 |
| tctccctcct tacaaccacc gccacctcct agtgccttag aagccactga cagcccccag | 180 |
| ggcaggtgag ccctgcatct ggaataagga tccagaggtc tcgttcagga cc atg gag | 238 |
|                                                                                                                                                       Met Glu<br>                            1 | |

```
agc ggc acc agc agc cct cag cct cca cag tta gat ccc ctg gat gcg    286
Ser Gly Thr Ser Ser Pro Gln Pro Pro Gln Leu Asp Pro Leu Asp Ala
        5                   10                  15 ttt ccc cag aag ggc ttg gag cct ggg gac atc gcg gtg cta gtt ctg    334
Phe Pro Gln Lys Gly Leu Glu Pro Gly Asp Ile Ala Val Leu Val Leu
    20                  25                  30 tac ttc ctc ttt gtc ctg gct gtt gga cta tgg tcc aca gtg aag acc    382
Tyr Phe Leu Phe Val Leu Ala Val Gly Leu Trp Ser Thr Val Lys Thr
35                  40                  45                  50 aaa aga gac aca gtg aaa ggc tac ttc ctg gct gga ggg gac atg gtg    430
Lys Arg Asp Thr Val Lys Gly Tyr Phe Leu Ala Gly Gly Asp Met Val
                55                  60                  65 tgg tgg cca gtg ggt gca tcc ttg ttt gcc agc aat gtt gga agt gga    478
Trp Trp Pro Val Gly Ala Ser Leu Phe Ala Ser Asn Val Gly Ser Gly
            70                  75                  80 cat ttc att ggc ctg gca ggg tca ggt gct gct acg ggc att tct gta    526
His Phe Ile Gly Leu Ala Gly Ser Gly Ala Ala Thr Gly Ile Ser Val
        85                  90                  95 tca gct tat gaa ctt aat ggc ttg ttt tct gtg ctg atg ttg gcc tgg    574
Ser Ala Tyr Glu Leu Asn Gly Leu Phe Ser Val Leu Met Leu Ala Trp
    100                 105                 110 atc ttc cta ccc atc tac att gct ggt cag gtc acc acg atg cca gaa    622
Ile Phe Leu Pro Ile Tyr Ile Ala Gly Gln Val Thr Thr Met Pro Glu
115                 120                 125                 130 tac cta cgg aag cgc ttc ggt ggc atc aga atc ccc atc atc ctg gct    670
Tyr Leu Arg Lys Arg Phe Gly Gly Ile Arg Ile Pro Ile Ile Leu Ala
                135                 140                 145 gta ctc tac cta ttt atc tac atc ttc acc aag atc tcg gta gac atg    718
Val Leu Tyr Leu Phe Ile Tyr Ile Phe Thr Lys Ile Ser Val Asp Met
            150                 155                 160 tat gca ggt gcc atc ttc atc cag cag tct ttg cac ctg gat ctg tac    766
Tyr Ala Gly Ala Ile Phe Ile Gln Gln Ser Leu His Leu Asp Leu Tyr
        165                 170                 175
```

| | | |
|---|---|---|
| ctg gcc ata gtt ggg cta ctg gcc atc act gct gta tac acg gtt gct<br>Leu Ala Ile Val Gly Leu Leu Ala Ile Thr Ala Val Tyr Thr Val Ala<br>180                          185                       190 | | 814 |
| ggt ggc ctg gct gct gtg atc tac acg gat gcc ctg cag acg ctg atc<br>Gly Gly Leu Ala Ala Val Ile Tyr Thr Asp Ala Leu Gln Thr Leu Ile<br>195                       200                     205              210 | | 862 |
| atg ctt ata gga gcg ctc acc ttg atg ggc tac agt ttt gcc gcg gtt<br>Met Leu Ile Gly Ala Leu Thr Leu Met Gly Tyr Ser Phe Ala Ala Val<br>                    215                     220                 225 | | 910 |
| ggt ggg atg gaa gga ctg aag gag aag tac ttc ttg gcc ctg gct agc<br>Gly Gly Met Glu Gly Leu Lys Glu Lys Tyr Phe Leu Ala Leu Ala Ser<br>              230                     235                 240 | | 958 |
| aac cgg agt gag aac agc agc tgc ggg ctg ccc cgg gaa gat gcc ttc<br>Asn Arg Ser Glu Asn Ser Ser Cys Gly Leu Pro Arg Glu Asp Ala Phe<br>245                         250                    255 | | 1006 |
| cat att ttc cga gat ccg ctg aca tct gat ctc ccg tgg ccg ggg gtc<br>His Ile Phe Arg Asp Pro Leu Thr Ser Asp Leu Pro Trp Pro Gly Val<br>      260                     265                    270 | | 1054 |
| cta ttt gga atg tcc atc cca tcc ctc tgg tac tgg tgc acg gat cag<br>Leu Phe Gly Met Ser Ile Pro Ser Leu Trp Tyr Trp Cys Thr Asp Gln<br>275                       280                    285              290 | | 1102 |
| gtg att gtc cag cgg act ctg gct gcc aag aac ctg tcc cat gcc aaa<br>Val Ile Val Gln Arg Thr Leu Ala Ala Lys Asn Leu Ser His Ala Lys<br>                    295                     300                 305 | | 1150 |
| gga ggt gct ctg atg gct gca tac ctg aag gtg ctg ccc ctc ttc ata<br>Gly Gly Ala Leu Met Ala Ala Tyr Leu Lys Val Leu Pro Leu Phe Ile<br>              310                     315                 320 | | 1198 |
| atg gtg ttc cct ggg atg gtc agc cgc atc ctc ttc cca gat caa gtg<br>Met Val Phe Pro Gly Met Val Ser Arg Ile Leu Phe Pro Asp Gln Val<br>            325                     330                 335 | | 1246 |
| gcc tgt gca gat cca gag atc tgc cag aag atc tgc agc aac ccc tca<br>Ala Cys Ala Asp Pro Glu Ile Cys Gln Lys Ile Cys Ser Asn Pro Ser<br>340                         345                    350 | | 1294 |
| ggc tgt tcg gac atc gcg tat ccc aaa ctc gtg ctg gaa ctc ctg ccc<br>Gly Cys Ser Asp Ile Ala Tyr Pro Lys Leu Val Leu Glu Leu Leu Pro<br>355                       360                    365              370 | | 1342 |
| aca ggg ctc cgt ggg ctg atg atg gct gtg atg gtg gcg gct ctc atg<br>Thr Gly Leu Arg Gly Leu Met Met Ala Val Met Val Ala Ala Leu Met<br>                    375                     380                 385 | | 1390 |
| tcc tcc ctc acc tcc atc ttt aac agt gcc agc acc atc ttc acc atg<br>Ser Ser Leu Thr Ser Ile Phe Asn Ser Ala Ser Thr Ile Phe Thr Met<br>              390                     395                 400 | | 1438 |
| gac ctc tgg aat cac ctc cgg cct cgg gca tct gag aag gag ctc atg<br>Asp Leu Trp Asn His Leu Arg Pro Arg Ala Ser Glu Lys Glu Leu Met<br>            405                     410                 415 | | 1486 |
| att gtg ggc agg gtg ttt gtg ctg ctg ctg gtc ctg gtc tcc atc ctc<br>Ile Val Gly Arg Val Phe Val Leu Leu Leu Val Leu Val Ser Ile Leu<br>420                         425                    430 | | 1534 |
| tgg atc cct gtg gtc cag gcc agc cag ggc ggc cag ctc ttc atc tat<br>Trp Ile Pro Val Val Gln Ala Ser Gln Gly Gly Gln Leu Phe Ile Tyr<br>435                         440                    445              450 | | 1582 |
| atc cag tcc atc agc tcc tac ctg cag ccg cct gtg gcg gtg gtc ttc<br>Ile Gln Ser Ile Ser Ser Tyr Leu Gln Pro Pro Val Ala Val Val Phe<br>                    455                     460                 465 | | 1630 |
| atc atg gga tgt ttc tgg aag agg acc aat gaa aag ggt gcc ttc tgg<br>Ile Met Gly Cys Phe Trp Lys Arg Thr Asn Glu Lys Gly Ala Phe Trp<br>              470                     475                 480 | | 1678 |
| ggc ctg atc tcg ggc ctg ctc ctg ggc ttg gtt agg ctg gtc ctg gac<br>Gly Leu Ile Ser Gly Leu Leu Leu Gly Leu Val Arg Leu Val Leu Asp<br>            485                     490                 495 | | 1726 |

-continued

| | | |
|---|---|---|
| ttt att tac gtg cag cct cga tgc gac cag cca gat gag cgc ccg gtc<br>Phe Ile Tyr Val Gln Pro Arg Cys Asp Gln Pro Asp Glu Arg Pro Val<br>500                      505                      510 | 1774 | |

```
ttt att tac gtg cag cct cga tgc gac cag cca gat gag cgc ccg gtc    1774
Phe Ile Tyr Val Gln Pro Arg Cys Asp Gln Pro Asp Glu Arg Pro Val
500                 505                 510 ctg gtg aag agc att cac tac ctc tac ttc tcc atg atc ctg tcc acg    1822
Leu Val Lys Ser Ile His Tyr Leu Tyr Phe Ser Met Ile Leu Ser Thr
515                 520                 525                 530 gtc acc ctc atc act gtc tcc acc gtg agc tgg ttc aca gag cca ccc    1870
Val Thr Leu Ile Thr Val Ser Thr Val Ser Trp Phe Thr Glu Pro Pro
        535                 540                 545 tcc aag gag atg gtc agc cac ctg acc tgg ttt act cgt cac gac ccc    1918
Ser Lys Glu Met Val Ser His Leu Thr Trp Phe Thr Arg His Asp Pro
    550                 555                 560 gtg gtc cag aag gaa caa gca cca cca gca gct ccc ttg tct ctt acc    1966
Val Val Gln Lys Glu Gln Ala Pro Pro Ala Ala Pro Leu Ser Leu Thr
565                 570                 575 ctc tct cag aac ggg atg cca gag gcc agc agc agc agc gtc cag        2014
Leu Ser Gln Asn Gly Met Pro Glu Ala Ser Ser Ser Ser Val Gln
580                 585                 590 ttc gag atg gtt caa gaa aac acg tct aaa acc cac agc tgt gac atg    2062
Phe Glu Met Val Gln Glu Asn Thr Ser Lys Thr His Ser Cys Asp Met
595                 600                 605                 610 acc cca aag cag tcc aaa gtg gtg aag gcc atc ctg tgg ctc tgt gga    2110
Thr Pro Lys Gln Ser Lys Val Val Lys Ala Ile Leu Trp Leu Cys Gly
        615                 620                 625 ata cag gag aag ggc aag gaa gag ctc ccg gcc aga gca gaa gcc atc    2158
Ile Gln Glu Lys Gly Lys Glu Glu Leu Pro Ala Arg Ala Glu Ala Ile
    630                 635                 640 ata gtt tcc ctg gaa gaa aac ccc ttg gtg aag acc ctc ctg gac gtc    2206
Ile Val Ser Leu Glu Glu Asn Pro Leu Val Lys Thr Leu Leu Asp Val
            645                 650                 655 aac ctc att ttc tgc gtg agc tgc gcc atc ttt atc tgg ggc tat ttt    2254
Asn Leu Ile Phe Cys Val Ser Cys Ala Ile Phe Ile Trp Gly Tyr Phe
660                 665                 670 gct tag tgtggggtga acccaggggt ccaaactctg tttctcttca gtgctccatt    2310
Ala *
675 tttttaatga agaaaaaat aataaagctt ttgtttacca aaaaaaaaaa aaaaaaaaa    2370 aaaaaaaaaa aaaa                                                    2384

<210> SEQ ID NO 46
<211> LENGTH: 675
<212> TYPE: PRT
<213> ORGANISM: Homo Sapiens

<400> SEQUENCE: 46

Met Glu Ser Gly Thr Ser Ser Pro Gln Pro Gln Leu Asp Pro Leu
1               5                   10                  15

Asp Ala Phe Pro Gln Lys Gly Leu Glu Pro Gly Asp Ile Ala Val Leu
                20                  25                  30

Val Leu Tyr Phe Leu Phe Val Leu Ala Val Gly Leu Trp Ser Thr Val
            35                  40                  45

Lys Thr Lys Arg Asp Thr Val Lys Gly Tyr Phe Leu Ala Gly Gly Asp
        50                  55                  60

Met Val Trp Trp Pro Val Gly Ala Ser Leu Phe Ala Ser Asn Val Gly
65                  70                  75                  80

Ser Gly His Phe Ile Gly Leu Ala Gly Ser Gly Ala Ala Thr Gly Ile
                85                  90                  95
```

```
Ser Val Ser Ala Tyr Glu Leu Asn Gly Leu Phe Ser Val Leu Met Leu
            100                 105                 110
Ala Trp Ile Phe Leu Pro Ile Tyr Ile Ala Gly Gln Val Thr Thr Met
        115                 120                 125
Pro Glu Tyr Leu Arg Lys Arg Phe Gly Ile Arg Ile Pro Ile Ile
    130                 135                 140
Leu Ala Val Leu Tyr Leu Phe Ile Tyr Ile Phe Thr Lys Ile Ser Val
145                 150                 155                 160
Asp Met Tyr Ala Gly Ala Ile Phe Ile Gln Gln Ser Leu His Leu Asp
                165                 170                 175
Leu Tyr Leu Ala Ile Val Gly Leu Leu Ala Ile Thr Ala Val Tyr Thr
            180                 185                 190
Val Ala Gly Gly Leu Ala Ala Val Ile Tyr Thr Asp Ala Leu Gln Thr
        195                 200                 205
Leu Ile Met Leu Ile Gly Ala Leu Thr Leu Met Gly Tyr Ser Phe Ala
    210                 215                 220
Ala Val Gly Gly Met Glu Gly Leu Lys Glu Lys Tyr Phe Leu Ala Leu
225                 230                 235                 240
Ala Ser Asn Arg Ser Glu Asn Ser Ser Cys Gly Leu Pro Arg Glu Asp
                245                 250                 255
Ala Phe His Ile Phe Arg Asp Pro Leu Thr Ser Asp Leu Pro Trp Pro
            260                 265                 270
Gly Val Leu Phe Gly Met Ser Ile Pro Ser Leu Trp Tyr Trp Cys Thr
        275                 280                 285
Asp Gln Val Ile Val Gln Arg Thr Leu Ala Ala Lys Asn Leu Ser His
    290                 295                 300
Ala Lys Gly Gly Ala Leu Met Ala Ala Tyr Leu Lys Val Leu Pro Leu
305                 310                 315                 320
Phe Ile Met Val Phe Pro Gly Met Val Ser Arg Ile Leu Phe Pro Asp
                325                 330                 335
Gln Val Ala Cys Ala Asp Pro Glu Ile Cys Gln Lys Ile Cys Ser Asn
            340                 345                 350
Pro Ser Gly Cys Ser Asp Ile Ala Tyr Pro Lys Leu Val Leu Glu Leu
        355                 360                 365
Leu Pro Thr Gly Leu Arg Gly Leu Met Met Ala Val Met Val Ala Ala
    370                 375                 380
Leu Met Ser Ser Leu Thr Ser Ile Phe Asn Ser Ala Ser Thr Ile Phe
385                 390                 395                 400
Thr Met Asp Leu Trp Asn His Leu Arg Pro Arg Ala Ser Glu Lys Glu
                405                 410                 415
Leu Met Ile Val Gly Arg Val Phe Val Leu Leu Leu Val Leu Val Ser
            420                 425                 430
Ile Leu Trp Ile Pro Val Val Gln Ala Ser Gln Gly Gly Gln Leu Phe
        435                 440                 445
Ile Tyr Ile Gln Ser Ile Ser Ser Tyr Leu Gln Pro Pro Val Ala Val
    450                 455                 460
Val Phe Ile Met Gly Cys Phe Trp Lys Arg Thr Asn Glu Lys Gly Ala
465                 470                 475                 480
Phe Trp Gly Leu Ile Ser Gly Leu Leu Leu Gly Leu Val Arg Leu Val
                485                 490                 495
Leu Asp Phe Ile Tyr Val Gln Pro Arg Cys Asp Gln Pro Asp Glu Arg
            500                 505                 510
```

```
Pro Val Leu Val Lys Ser Ile His Tyr Leu Tyr Phe Ser Met Ile Leu
        515             520             525
Ser Thr Val Thr Leu Ile Thr Val Ser Thr Val Ser Trp Phe Thr Glu
        530             535             540
Pro Pro Ser Lys Glu Met Val Ser His Leu Thr Trp Phe Thr Arg His
545             550             555             560
Asp Pro Val Val Gln Lys Glu Gln Ala Pro Pro Ala Ala Pro Leu Ser
                565             570             575
Leu Thr Leu Ser Gln Asn Gly Met Pro Glu Ala Ser Ser Ser Ser Ser
            580             585             590
Val Gln Phe Glu Met Val Gln Glu Asn Thr Ser Lys Thr His Ser Cys
        595             600             605
Asp Met Thr Pro Lys Gln Ser Lys Val Val Lys Ala Ile Leu Trp Leu
        610             615             620
Cys Gly Ile Gln Glu Lys Gly Lys Glu Glu Leu Pro Ala Arg Ala Glu
625             630             635             640
Ala Ile Ile Val Ser Leu Glu Glu Asn Pro Leu Val Lys Thr Leu Leu
                645             650             655
Asp Val Asn Leu Ile Phe Cys Val Ser Cys Ala Ile Phe Ile Trp Gly
            660             665             670
Tyr Phe Ala
        675
```

METHOD OF IDENTIFYING A COMPOUND CAPABLE OF TREATING A PAIN OR A PAINFUL DISORDER

RELATED APPLICATIONS

The present application claims the benefit of U.S. Provisional Application Ser. No. 60/444,781, filed on Feb. 4, 2003, of U.S. Provisional Application Ser. No. 60/452,291, filed on Mar. 5, 2003, of U.S. Provisional Application Ser. No. 60/454,540, filed on Mar. 13, 2003, of U.S. Provisional Application Ser. No. 60/478,805, filed on Jun. 16, 2003 and of U.S. Provisional Application Ser. No. 60/491,048, filed on Jul. 30, 2003. The entire contents of these provisional patent applications are hereby incorporated in their entirety by this reference.

BACKGROUND OF THE INVENTION

The sensation of pain can be categorized into two types, peripheral and central pain. Peripheral pain can be classified into three broad areas, nociceptive pain, inflammatory pain and neuropathic pain. Nociceptive pain is also referred to as physiological pain and serves as a defense mechanism throughout the animal kingdom. Inflammatory pain, arising from severe wounds and/or associated with inflammatory infiltrates, can be well controlled by non-steroidal anti-inflammatory drugs (NSAID)-like drugs, steroids and opiates. However, the etiology and management of neuropathic pain is not well understood. Neuropathic pain is thought to arise from inherent defects in sensory and as a consequence in sympathetic neurons and can be secondary to trauma.

Peripheral pain is mediated by two types of primary sensory neuron classes, the Ad- and C-fibers, whose cell bodies lie within the dorsal root ganglion. Although the mechanisms of generation of neuropathic pain are poorly understood it is clear that several factors influence the perception and transmission of the painful stimulus, namely, alterations in chemical environment, ectopic generation of sensory neuron firing and sympathetic discharge. Some of the most common syndromes associated with neuropathic pain arise from destruction of small sensory fibers (or possibly the alteration in ratios of small to large fibers) as it is common in post-traumatic situations. Other etiologies of pain arise from small fiber damage due to diabetic neuropathy, drug induced damage (chemotherapy drugs), alcoholism, damage due to cancer, and a variety of hereditary small- and large-fiber neuropathies. We rationalize that targets derived from the peripheral nervous system may be of strategic benefit in that candidate compounds do not need to cross the blood-brain barrier, they can act on the initiation site of pain without inducing central side effects.

It has long been established that central mechanisms are involved in the perception and modulation of pain. Electrical stimulation of the periaqueductal gray (PAG) area produces analgesia without loss of other sensory modalities. Descending pain pathways emanating from PAG and the nucleus raphe magnus impinge on dorsal spinal cord regions where primary nociceptive afferents terminate. Also, stimulation of regions such as the paragigantocellularis nucleus in the medulla oblongata result in analgesia. Finally, opiate receptors, when stimulated by opioid alkaloids and opioid peptides, mediate analgesia and these sites are located in key "pain centers" within the brain including PAG, thalamic nuclei and cortical regions. Identification of genes in these central nervous system (CNS) regions and the spinal thalamic tract from animal models of pain may elucidate important targets for pain modulation.

DETAILED DESCRIPTION OF THE INVENTION

The present invention provides methods and compositions for the diagnosis and treatment of a subject experiencing pain or suffering from a painful disorders. Preferably, the subject is a human, e.g., a patient with pain or a pain-associated disorder disclosed herein. For example, the subject can be a patient with pain elicited from tissue injury, e.g., inflammation, infection, ischemia; pain associated with musculoskeletal disorders, e.g., joint pain; tooth pain; headaches, e.g., migrane; pain associated with surgery; pain related to inflammation, e.g., irritable bowel syndrome; or chest pain. The subject can be a patient with complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia. The subject can be a cancer patient, e.g., a patient with brain cancer, bone cancer, or prostate cancer. In other embodiments, the subject is a non-human animal, e.g., an experimental animal, e.g., an arthritic rat model of chronic pain, a chronic constriction injury (CCI) rat model of neuropathic pain, or a rat model of unilateral inflammatory pain by intraplantar injection of Freund's complete adjuvant (FCA).

"Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, the small molecules, peptides, antibodies, ribozymes and antisense oligonucleotides described herein.

The present invention is based, at least in part, on the discovery that nucleic acid and protein molecules, (described infra), are differentially expressed in animal models of pain and in peripheral and central nervous system tissues known to be associated with pain (e.g. dorsal root ganglion (DRG)). The modulators of the molecules of the present invention, identified according to the methods of the invention can be used to modulate (e.g., inhibit, treat, or prevent) pain and painful conditions.

"Differential expression", as used herein, includes both quantitative as well as qualitative differences in the temporal and/or tissue expression pattern of a gene. Thus, a differentially expressed gene may have its expression activated or inactivated in normal versus painful disease conditions (for example, in an experimental pain model system such as in an animal model for pain). The degree to which expression differs in normal versus treated or control versus experimental states need only be large enough to be visualized via standard characterization techniques, e.g., quantitative PCR, Northern analysis, subtractive hybridization. The expression pattern of a differentially expressed gene may be used as part of a prognostic or diagnostic, evaluation, or may be used in methods for identifying compounds useful for the treatment of pain and painful disorders. In addition, a differentially expressed gene involved in pain or painful disorders may represent a target gene such that modulation of the level of target gene expression or of target gene product activity may act to ameliorate a painful disease condition. Compounds that modulate target gene expression or activity of the target gene product can be used in the treatment of pain or painful conditions. Although the genes described herein may be differentially expressed with respect to pain, and/or their products may interact with gene products important to pain, the genes may also be involved in mechanisms important to additional cell processes.

Molecules of the Present Invention

Molecules of the present invention include, but are not limited to ion channels (e.g. Potassium channels), transporters (e.g. amino acid transporters), receptors (e.g. G protein coupled receptors) and enzymes (e.g. kinases)

Transmembrane ion channel proteins that selectively mediate the conductance of sodium, potassium, calcium and chloride ions directly modulate the electrical activity of sensory neurons and are, thus, important in nociception. In particular, potassium channels are main players in regulating the frequency and pattern of neuronal firing. The expression and peak currents of potassium channels has been shown to be regulated after different models of inflammatory and chronic pain. Additionally, calcium ions serve important intracellular signaling roles including modulation of other ion channels and regulation of protein kinases and other enzymatic activity. As cell surface proteins with established three-dimensional structures and modes of action, the pore-forming alpha subunits of ion channels make ideal drug targets. In addition to alpha subunits, these channels may consist of beta subunits and other interacting proteins which modulate channel activity and are good targets for pharmacological manipulation of the channels. Therefore, ion channels are useful in treating pain and painful conditions.

Endogenous soluble factors mediate pain sensation by binding to specific transmembrane receptors either on the peripheral terminals of nociceptive neurons or on central neurons receiving input from these nociceptors. These soluble factors include, but are not limited to serotonine, histamine, bradykinin, tachykinins (substance P and neurokinin A), opioids, eicosanoids (leukotrienes, prostaglandins, thromboxanes), purines, excitatory amino acids and different proteins. In addition a growing body of evidence, including clinical trials in man, indicates that IL-1, TNFa, and members of the neurotrophin family are involved at several stages in the transmission of painful stimuli. Hydrogen ions (protons) may mediate pain associated with inflammation (and also acid taste) by activating vanilloid receptor calcium channels or amiloride-sensitive sodium channels. Additionally, numerous exogenous agents modulate pain by mimicking endogenous soluble factors. For instance the opiate drugs of abuse exert analgesic effects by binding to receptors for the endogenous opioids and capsaicin stimulates pain sensation by binding to vanilloid receptors. The receptors for these soluble factors are linked to several signal transduction mechanisms including tyrosine kinase activity (e.g. neurotrophin receptors), recruitment of cytoplasmic tyrosine kinases (e.g. cytokine receptors for TNFa and IL-1), ion channel opening, and G-protein coupled receptors. These cell surface receptors are ideal drug targets due to their transmembrane location, and the goal is to discover G-protein coupling receptors with known ligands or with surrogate ligands that may be important players in regulating pain mechanisms.

Intracellular kinases such as protein kinase A and protein kinase C are involved in the response to pain in sensory neurons. Similarly, enzymes such as cyclooxygenase(s) and thromboxane synthetase are know to be critical in the production of prostaglandins, leukotrienes and thromboxanes. Although these particular targets may be more important in inflammatory pain, the role of this gene family in long term or neuropathic pain is of importance.

Gene ID 16386

The human 16386 sequence (SEQ ID NO:1), known also as Brain sulfotransferase-like protein (hBR-STL), is approximately 2419 nucleotides long including untranslated regions. The coding sequence, located at about nucleic acid 21 to 875 of (SEQ ID NO:1), encodes a 284 amino acid protein (SEQ ID NO:2).

As assessed by TaqMan analysis, 16386 mRNA was primarily expressed in tissues of the central nervous system (CNS) in rat and human tissue samples. Additionally, 16386 mRNA was shown to be up-regulated in dorsal root ganglion (DRG) samples after chronic constriction injury (CCI). 16386 mRNA was also shown to be down-regulated in spinal cord samples after Rhizotomy. 16386 mRNA showed a 2 fold up-regulation in the DRG after Axotomy, Complete Freund's Adjuvant (CFA), Capsaicin, Spared Nerve Injury (SNI), or Tibial Nerve Injury (TNI). In addition, 16386 mRNA also showed a 2 fold up-regulation in spinal cord after Axotomy, CFA, capsaicin, SNI, TNI or CCI.

16386 is a sulfotransferase which acts on tyrosine derivative compounds. 16386 is potentially responsible for the inhibition and removal of dopamine by sulfation. Dopamine has analgesic effects in the spinal cord and central nervous system. Thus, inhibition of 16386 potentially has analgesic effects and thus is a novel inhibitor of pain. Due to 16386 expression in the dorsal root ganglion and spinal cord, along with its functional role, modulators of 16386 activity would be useful in treating disorders associated with the treatment of pain and painful disorders. 16386 polypeptides of the present invention are useful in screening for modulators of 16386 activity.

Gene ID 15402

The human 15402 sequence (SEQ ID NO:3), known also as HNK1 Sulfotransferase, is approximately 2877 nucleotides long including untranslated regions. The coding sequence, located at about nucleic acid 387 to 1457 of (SEQ ID NO:3), encodes a 356 amino acid protein (SEQ ID NO:4).

As assessed by TaqMan analysis, 15402 mRNA was primarily expressed in tissues of the central nervous system in both human and rat panels. 15402 MRNA was strongly up-regulated in the dorsal root ganglion (DRG) after Chronic Constriction Injury (CCI) and Axotomy. 15402 mRNA was down-regulated in the DRG after Rhizotomy and in the spinal cord after Tibial Nerve Injury (TNI).

15402 transfers a sulfate to the HNK-1 carbohydrate recognition site present in myelin-associated glycoprotein (MAG). Sulfated MAG is a major target for monoclonal IgM in patients with demyelinating neuropathy. Thus, inhibition of 15402 potentially blocks antibody interaction with MAG and thus could inhibit pain caused by demyelinating neuropathy. Due to the expression of 15402 in the spinal cord and dorsal root ganglion, along with its functional role, modulators of 15402 activity would be useful in treating disorders associated with the treatment of pain and painful disorders. 15402 polypeptides of the present invention are useful in screening for modulators of 15402 activity.

Gene ID 21165

The human 21165 sequence (SEQ ID NO:5), known also as lactosylceramide (LacCer) synthase, is approximately 3931 nucleotides long including untranslated regions. The coding sequence, located at about nucleic acid 298 to 1446 of (SEQ ID NO:5), encodes a 382 amino acid protein (SEQ ID NO:6).

As assessed by TaqMan analysis, 21165 mRNA was primarily expressed in tissues of the central nervous system in both human and rat panels. 21165 MRNA was strongly up-regulated in dorsal root ganglion (DRG) after Chronic Constriction Injury (CCI). 21165 mRNA was down-regulated in the DRG and spinal cord after Tibial Nerve Injury (TNI) and long-term Capsaicin treatment. 21165 mRNA was also down-regulated in DRG after Spared Nerve Injury (SNI), Complete Freund's Adjuvant (CFA) and Rhizotomy.

Inhibition of 21165 or lactosylceramide (LacCer) synthase, inhibits NGF pathways. In addition, inhibition of 21165 inhibits neuronal function. 21165 levels are markedly increased in a variety of peripheral neuropathies, and exogenous 21165 activates NF-Kappa-B pathways known to be involved in pain mediation. Exogenous 21165 also induces superoxide production and ERK-1, both of which have been demonstrated to be up-regulated in a variety of pain models. Finally, 21165 synthesis is up-regulated by TNF-alpha, a well established mediator of neuropathic pain, and this up-regulation results in an increase of ICAM-1, which has been shown to be up-regulated in a variety of painful conditions in both humans and animals. Thus, in a variety of manners, inhibitors of 21165 will likely be a novel mechanism for pain inhibition. Due to the expression of 21165 in the spinal cord and dorsal root ganglion, along with its functional role, modulators of 21165 activity would be useful in treating disorders associated with the treatment of pain and painful disorders. 21165 polypeptides of the present invention are useful in screening for modulators of 21165 activity.

Gene ID 1423

The human 1423 sequence (SEQ ID NO:7), known also as a N-Methyl-D-Aspartic Acid (NMDA) receptor, is approximately 3924 nucleotides long including untranslated regions. The coding sequence, located at about nucleic acid 1 to 3168 of (SEQ ID NO:7), encodes a 1055 amino acid protein (SEQ ID NO:8).

As assessed by TaqMan analysis, 1423 mRNA was primarily expressed in tissues of the central nervous system in both human and rat panels. 1423 mRNA was up-regulated in dorsal root ganglion (DRG) after chronic constriction injury (CCI) and in spinal cord after axotomy.

NMDA receptor activation is one of the basic mechanisms responsible for pain responses. Modulating the activity of NMDA receptors by antagonizing the activation of ephrin B2 (ephB2) may, not only block pain responses, but also block the synaptic plasticity involved in the maintenance of pain behaviors. Due to the expression of 1423 mRNA in the spinal cord and dorsal root ganglion, along with its functional role, modulators of 1423 activity would be useful in treating disorders associated with the treatment of pain and painful disorders. 1423 polypeptides of the present invention are useful in screening for modulators of 1423 activity.

Gene ID 636

The human 636 sequence (SEQ ID NO:9), known also as Potassium voltage-gated channel subfamily A member 6 (KCNA6); Potassium channel Kv1.6; or HBK2 potassium channel, is approximately 4234 nucleotides long including untranslated regions. The coding sequence, located at about nucleic acid 863 to 2452 of SEQ ID NO:9, encodes a 529 amino acid protein (SEQ ID NO:10).

As assessed by TaqMan analysis, 636 mRNA was primarily expressed in tissues of the central nervous system in rat and human panels. 636 mRNA was up-regulated in the dorsal root ganglion (DRG) and spinal cord (SC) after Tibial Nerve Injury (TNI). 636 mRNA was down-regulated in spinal cord (SC) after rhizotomy and in the dorsal root ganglion (DRG) after Capsaicin treatment. In situ hybridization experiments indicated that 636 mRNA was expressed in the spinal cord, brain, and a subpopulation of DRG neurons in both monkey and rat tissues.

Activation of potassium channels affects the frequency and the pattern of neuronal firing. Several voltage-gated potassium channels are expressed in sub-population of sensory neurons including those involved in nociception. In general, it has been shown that the expression of some voltage-gated potassium channels decreases in DRG neurons after axotomy and that the peak of potassium currents is reduced in sensory neurons during chronic inflammation. Furthermore, administration of potassium channel openers potentiated the antinociception produced by agonists of alpha-2-adrenoreceptors or by morphine. Due to 636 mRNA expression in the dorsal root ganglion and spinal cord, along with its functional role, modulators of 636 activity would be useful in treating disorders associated with the treatment of pain and painful disorders. 636 polypeptides of the present invention are useful in screening for modulators of 636 activity.

Gene ID 12303

The human 12303 sequence (SEQ ID NO:11), known also as Potassium channel KCNK4; TRAAK; or Two pore K+ channel KT4.1, is approximately 2747 nucleotides long including untranslated regions. The coding sequence, located at about nucleic acid 51 to 1310 of SEQ ID NO:11, encodes a 419 amino acid protein (SEQ ID NO:12).

As assessed by TaqMan analysis, 12303 MRNA was primarily expressed in tissues of the central nervous system (CNS) in both monkey and rat panels. 12303 mRNA was up-regulated in dorsal root ganglion (DRG) after Chronic Constriction Injury (CCI) and in the spinal cord after Capsaicin treatment. 12303 mRNA was down-regulated in spinal cord after Rhizotomy. In situ hybridization experiments indicated that 12303 mRNA was present in most neurons of monkey and rat DRG's and spinal cord tissues.

Activation of potassium channels affects the frequency and the pattern of neuronal firing. Several voltage-gated potassium channels are expressed in sub-population of sensory neurons including those involved in nociception. In general, it has been shown that the expression of some voltage-gated potassium channels decreases in DRG neurons after axotomy and that the peak of potassium currents is reduced in sensory neurons during chronic inflammation. Furthermore, administration of potassium channel openers potentiated the antinociception produced by agonists of alpha-2-adrenoreceptors or by morphine. The antinociception induced by intrathecal injection of morphine injection is blocked in a dose-dependent manner by glibenclamide (a blocker of ATP-sensitive K+ channels) and potentiated by nicorandil (a opener of ATP-sensitive K+ channels). 12303

(the potassium channel TRAAK) is important for the modulation of the firing pattern of nociceptive neurons. Drugs which open 12303 are potentially a novel mechanism for the inhibition of pain. Due to the expression of 12303 in the spinal cord and dorsal root ganglion, along with its functional role, modulators of 12303 activity would be useful in treating disorders associated with the treatment of pain and painful disorders. 12303 polypeptides of the present invention are useful in screening for modulators of 12303 activity.

Gene ID 21425

The human 21425 sequence (SEQ ID NO:13), known also as ELK2 potassium channel, is approximately 3985 nucleotides long including untranslated regions. The coding sequence, located at about nucleic acid 359 to 3610 of SEQ ID NO:13, encodes a 1083 amino acid protein (SEQ ID NO:14).

As assessed by TaqMan analysis, 21425 mRNA was expressed exclusively in tissues of the central nervous sytem (CNS) in both human and rat panels. 21425 MRNA was up-regulated in the dorsal root ganglion (DRG) after Chronic Constriction Injury (CCI), Tibial Nerve Injury (TNI) and Axotomy. 21425 mRNA was also up-regulated in spinal cord after Capsaicin, Spared Nerve Injury (SNI) and TNI. In situ hybridization experiments indicated that 21425 mRNA was highly expressed in monkey brain in a majority of neurons.

The human ELK2 K channel or 21425 is critical for hypersensitivity in different pain states and may therefore represent a unique target for pain. Due to the expression of 21425 in the spinal cord and dorsal root ganglion, along with its functional role, modulators of 21425 activity would be useful in treating disorders associated with the treatment of pain and painful disorders. 21425 polypeptides of the present invention are useful in screening for modulators of 21425 activity.

Gene ID 27410

The human 27410 sequence (SEQ ID NO:15), known also as Potassium channel subfamily K member 17 (KCNK17); TWIK-related alkaline pH activated K+ channel 2 (TALK-2); or TWIK-related acid-sensitive K+ channel 4 (TASK-4), is approximately 1764 nucleotides long including untranslated regions. The coding sequence, located at about nucleic acid 268 to 1266 of SEQ ID NO:15, encodes a 332 amino acid protein (SEQ ID NO:16).

As assessed by TaqMan analysis, 27410 mRNA was expressed at low levels in the lung, spinal cord, dorsal root ganglion (DRG) and liver. In situ hybridization experiments indicated that 27410 mRNA showed diffuse expression in human and rat brain, spinal cord and DRG tissues.

Activation of potassium channels affects the frequency and the pattern of neuronal firing. Several voltage-gated potassium channels are expressed in sub-population of sensory neurons including those involved in nociception. In general, it has been shown that the expression of some voltage-gated potassium channels decreases in DRG neurons after axotomy and that the peak of potassium currents is reduced in sensory neurons during chronic inflammation. Furthermore, administration of potassium channel openers potentiated the antinociception produced by agonists of alpha-2-adrenoreceptors or by morphine. The antinociception induced by intrathecal injection of morphine.injection is blocked in a dose-dependent manner by glibenclamide (a blocker of ATP-sensitive K+ channels) and potentiated by nicorandil (a opener of ATP-sensitive K+ channels). 27410 is important for the modulation of the firing pattern of nociceptive neurons. Drugs which open 27410 are novel mechanisms for the inhibition of pain. Due to the expression of 27410 in the spinal cord and dorsal root ganglion, along with its functional role, modulators of 27410 activity would be useful in treating disorders associated with the treatment of pain and painful disorders. 27410 polypeptides of the present invention are useful in screening for modulators of 27410 activity.

Gene ID 38554

The human 38554 sequence (SEQ ID NO:17), known also as Solute carrier family 21 member 14 (SLC21A14); Organic anion transporter F (OATP-F); Organic anion transporting polypeptide 14 (OATP14); or Organic anion transporter polypeptide related protein 5 (OATPRP5), is approximately 3227 nucleotides long including untranslated regions. The coding sequence, located at about nucleic acid 345 to 2483 of SEQ ID NO:17, encodes a 712 amino acid protein (SEQ ID NO:18).

As assessed by TaqMan analysis, 38554 mRNA was expressed predominantly in tissues of the central nervous system (CNS) in both rat and human panels. 38554 mRNA was up-regulated in dorsal root ganglion (DRG) after Axotomy and down-regulated in DRG after Spared Nerve Injury (SNI), Tibial Nerve Injury (TNI) and long term capsaicin treatment. 38554 mRNA was also down-regulated in spinal cord after SNI (8 weeks). In situ hybridization experiments indicated that 38554 mRNA was expressed throughout the brain, spinal cord, choroid plexus and DRG tissues, particularly in glial cells.

38554 is OATP-F, a member of the Organic Anion Transporter Polypeptide (OATP) family. OATP-F has been shown to transport estrone-3-sulfate and dihydroepiandrosterone sulfate. Other members of the OATP family, such as human OATP8, OATP-A and OATP-C, transport the opioid receptor agonists [D-penicillamine(2,5)]-enkephalin. OATP8 and OATP-A also transport the opioid receptor agonist deltorphin (*Gastroenterology* 120:525; *J Pharmacol Exp Ther* 294(1):73).

38554 is a critical gene in pain because it is a member of a family of transporters which transports opioid receptor agonists that are known to be involved in pain transmission. Blockers of 38554 could increase endogenous opioid receptor compounds and therefore be novel mechanisms for pain inhibition. Due to the expression of 38554 in the spinal cord and dorsal root ganglion, along with its functional role, modulators of 38554 activity would be useful in treating disorders associated with the treatment of pain and painful disorders. 38554 polypeptides of the present invention are useful in screening for modulators of 38554 activity.

Gene ID 38555

The human 38555 sequence (SEQ ID NO:19), known also as Solute carrier family 21 member 11 (SLC21A11); Organic anion transporting polypeptide D (OATP-D); Organic anion transporter polypeptide related protein 3 (OATPRP3); or PGE1 transporterOAPT-D, is approximately 2133 nucleotides long. The coding sequence, located at about nucleic acid 1 to 2133 of SEQ ID NO:19, encodes a 710 amino acid protein (SEQ ID NO:20).

As assessed by TaqMan analysis, 38555 mRNA was expressed at high levels in tissues of the central nervous sysytem (CNS) in both rat and human panels. 38555 mRNA was up-regulated in the dorsal root ganglion (DRG) after Axotomy and in the spinal cord after Chronic Constriction Injury (CCI) and Tibial Nerve Injury (TNI). 38555 MRNA was down-regulated in DRG after Spared Nerve Injury (SNI) or TNI. In situ hybridization experiments indicated that 38555 mRNA was expressed in brain, spinal cord, heart, small and medium sized neurons in DRG and sympathetic neurons.

38555 is OAPT-D, a member of the Organic Anion Transporter Polypeptide (OATP) family. OATP-D has been shown to transport estrone-3-sulfate, benzylpenicillin, and Prostaglandin E2 (*Biochem Biophys Res Commun* 273:251). Prostaglandin E2 has been shown to mediate bradykinin-induced hyperalgesia caused by intradermal injection of adenosine in the hindpaw of the rat (*Neuroscience* 1990;38 (3):757–62). Other members of the OATP family (human OATP8, OATP-A and OATP-C) transport the opioid receptor agonists [D-penicillamine(2,5)]-enkephalin. OATP8 and OATP-A also transport the opioid receptor agonist deltorphin (*Gastroenterology* 120:525; *J Pharmacol Exp Ther* 294(1):73).

38555 is a critical gene in pain because it transports Prostaglandin E2 and may additionally transport several other molecules that are known to be involved in pain transmission. Furthermore, 38555 is localized in nociceptive neurons of the DRG. Blockers of 38555 would therefore be novel mechanisms for pain inhibition. Due to the expression of 38555 in the spinal cord and dorsal root ganglion, along with its functional role, modulators of 38555 activity would be useful in treating disorders associated with the treatment of pain and painful disorders. 38555 polypeptides of the present invention are useful in screening for modulators of 38555 activity.

Gene ID 55063

The human 55063 sequence (SEQ ID NO:21), known also as NMDA receptor subunit 3A (NR3A) or (NMDAR-L), is approximately 4197 nucleotides long including untranslated regions. The coding sequence, located at about nucleic acid 1 to 3348 of SEQ ID NO:21, encodes a 1115 amino acid protein (SEQ ID NO:22).

As assessed by TaqMan analysis, 55063 mRNA was expressed predominantly in tissues of the central nervous system (CNS) in human and rat panels. 55063 MRNA was also down-regulated in the dorsal root ganglion (DRG) after Axotomy, Rhizotomy, Capsaicin, Spared Nerve Injury (SNI) and Tibial Nerve Injury (TNI) pain models. In situ hybridization experiments indicated that 55063 MRNA was restricted to a sub-population of neurons in the spinal cord, laminae and a sub-population of neurons in the cortex.

55063 is NR3A (a.k.a. NMDAR-L). This NMDA receptor subunit is not functional by itself, but forms functional subunits when co-expressed with either the NR1 or NR2 subunits (*J Neurosci* 15(10):6498; *J Neurosci* 15(10):6509; *J Neurosci* 21(4):1128). NMDA receptors are well known mediators of pain transmission. In addition, many of the downstream effects of NMDA receptor are thought to be responsibe for NMDA receptor mediated pain transmission (for recent reviews, see *Ann N Y Acad Sci*. 933:142–56; *Curr Pharm Des*. 8(10):887–912; *Z Rheumatol*. 60(6):404–15; *Trends Pharmacol Sci*. 22(12):636–42). However, NMDA receptor blockers are well known to have a number of negative side effects due to their primary role in the central nervous system. Therefore, a drug which could increase the function of NR3A could decrease the NMDA receptor-mediated pain transmission by decreasing NMDA function and by decreasing calcium influx via NMDA receptors. In addition, since NR3A does not abolish NMDA receptor activity, side effects could be less than those caused by NMDA receptor antagonists.

55063 plays a critical role in pain because it is localized to a subpopulation of neurons in the regions of the spinal cord where nociceptive neurons terminate and because it is down-regulated in the DRG of several models of pain. Furthermore, 55063 is known to decrease NMDA receptor mediated currents and calcium influx. Since NMDA receptor function and calcium influx are clearly linked to pain, a decrease in 55063 expression would therefore increase pain transmission. Therefore, drugs which increase 55063 function would be novel mechanisms to decrease pain transmission without the side effects commonly seen with antagonists which completely abolish NMDA receptor function. Due to the expression of 55063 in the spinal cord and dorsal root ganglion, along with its functional role, modulators of 55063 activity would be useful in treating disorders associated with the treatment of pain and painful disorders. 55063 polypeptides of the present invention are useful in screening for modulators of 55063 activity.

Gene ID 57145

The human 57145 sequence (SEQ ID NO:23), known also Organic cation transporter 5 (OCT5), is approximately 2561 nucleotides long including untranslated regions. The coding sequence, located at about nucleic acid 184 to 1830 of SEQ ID NO:23, encodes a 548 amino acid protein (SEQ ID NO:24).

As assessed by TaqMan analysis, 57145 mRNA was primarily expressed in tissues of the central nervous system in human and rat panels. 57145 mRNA was up-regulated in the dorsal root ganglion (DRG) after Chronic Constriction Injury (CCI) and Complete Freund's Adjuvant (CFA). 57145 MRNA was also down-regulated in DRG and spinal cord after Rhizotomy and in spinal cord after CCI, CFA, and Axotomy. In situ hybridization experiments performed on 57145 mRNA showed diffuse expression in monkey brain, spinal cord and DRG neurons. It is also expressed in TRG, SCG neurons.

57145 is a novel member of the organic cation family. Organic transporter activity is increased by PKC, Calmodulin (CaM), Protein Kinase A and CaM kinase II (J Am Soc Nephrol 11:1216; Am J Physiol Renal Physiol 284:F293) which are known to be critical mediators of pain transmission. (for recent review, see Eur J Pharmacol 429:23–37; Ann N Y Acad Sci 933:142–56). Furthermore, CCI and formalin injection models of pain cause a movement of PKC from the cytosol to the membrane in spinal cord nociceptive neurons, an effect known to be associated with an increase in PKC activity. This PKC translocation correlates well with an increase in hyperalgesia (*J Neurophysiol* 70:470; *Neurosci Lett* 198:75; Pain 94:17). In addition, PKC activation mediates the increase in NMDA receptor activity in the CFA model of pain, since PKC inhibitors block this NMDA receptor increase (*J Physiol* 537:115). Since CCI and CFA models of pain increase PKC levels which increase organic cation transport activity, small molecule inhibitors of 57145 may be a novel mechanism for the inhibition of pain.

57145 plays an important role in pain transmission because it is up-regulated in DRG after CCI and CFA models of pain. Since CCI and CFA increase the activity of PKC, (known to be an important pain mediator) which in turn increases organic cation transport activity, small molecule inhibitors of 57145 could be a novel mechanism for the inhibition of pain. Due to the expression of 57145 in the spinal cord and dorsal root ganglion, along with its functional role, modulators of 57145 activity would be useful in treating disorders associated with the treatment of pain and painful disorders. 57145 polypeptides of the present invention are useful in screening for modulators of 57145 activity.

Gene ID 59914

The human 59914 sequence (SEQ ID NO:25), known also as Choline transporter-like 3 (CTL3), is approximately 2500 nucleotides long including untranslated regions. The coding sequence, located at about nucleic acid 105 to 2258 of SEQ ID NO:25, encodes a 717 amino acid protein (SEQ ID NO:26).

As assessed by TaqMan analysis, 59914 mRNA was primarily expressed in human brain, muscle and spinal cord samples. In situ hybrization experiments indicated that 59914 MRNA was expressed in both human and rat brain, spinal cord and majority of dorsal root ganglion (DRG) neurons.

Many studies have demonstrated that cholinergic receptor (AChR) agonists inhibit pain whereas antagonists increase pain (for review, see *Annu Rev Physiol* 59:457–82). However, a recent study has demonstrated that mecamylamine, a non-subtype selective nAChR antagonist, can produce an inhibition of pain after formalin injection at early times, and an increase in pain at late times, suggesting that nAChRs may exert opposing effects on acute versus tonic pain (*Brain Res* 888(1):102–106). 59914 is a novel choline transporter that may serve to transport choline back into cholinergic nerve terminals following acetylcholine release and breakdown by acetylcholinesterase. Thus, inhibition of 59914 may serve to deplete DRG neurons of acetylcholine, thus inhibiting acute forms of pain transmission.

59914 plays an important role in pain because it is localized in DRG and spinal cord neurons. Inhibition of 59914 potentially prevents the re-uptake of choline into cholinergic neurons, thereby depleting cholinergic cells of acetylcholine. Because of the importance of acetylcholine in pain transmission, such 59914 inhibitors may be a novel mechanism for the inhibition of acute pain. Due to the expression of 59914 in the spinal cord, along with its functional role, modulators of 59914 activity would be useful in treating disorders associated with the treatment of pain and painful disorders. 59914 polypeptides of the present invention are useful in screening for modulators of 59914 activity.

Gene ID 94921

The human 94921 sequence (SEQ ID NO:27), known also as Equilibrative nucleoside transporter 4 (ENT4), is approximately 2763 nucleotides long including untranslated regions. The coding sequence, located at about nucleic acid 34 to 1626 of SEQ ID NO:27, encodes a 530 amino acid protein (SEQ ID NO:28).

As assessed by TaqMan analysis, 94921 mRNA was primarily expressed in the human brain, pancreas, spinal cord and in rat nervous system tissue samples. 94921 mRNA was up-regulated in dorsal root ganglion (DRG) after Chronic constriction Injury (CCI) and Axotomy. In situ hybridization experiments indicated that 94921 mRNA was expressed in mouse brain, spinal cord and in a subpopulation (small and medium size) of the DRG neurons.

94921 is a novel member of the equilibrative nucleoside transporter (ENT) family, which transports both purines and pyrimidines. Since this family is equilibrative, it can take up or release nucleosides, depending on the concentration gradient. Extracellular purines stimulate the synthesis and release of trophic factors such as nerve growth factor (NGF), S100beta protein and transforming growth factor beta from astrocytes (for review, see *Int J Dev Neurosci* 19(4):395–414). Many studies indicate that growth factors such as NGF are mediators of neuropathic pain such as that produced in chronic constriction injury (CCI) models (for review, see *Curr Opin Pharmacol* 1(1):66–72). The levels of both NGF and 94921 increase in DRG after CCI, suggest that 94921 may be a primary cause of the increase in NGF. Therefore, blockade of 94921 could prevent the increase in NGF levels following CCI and could therefore be a novel mechanism for the inhibition of pain associated with neuropathy.

94921 plays an important role in pain transmission during painful neuropathy, because levels of 94921 and NGF increase in DRG after CCI. Since 94921 transports adenosine, a known player in pain transmission, drugs which inhibit 94921 could be a novel way of inhibiting NGF levels after neuropathy, and could therefore be a novel mechanism for the inhibition of pain. Due to the expression of 94921 in the spinal cord and dorsal root ganglion, along with its functional role, modulators of 94921 activity would be useful in treating disorders associated with the treatment of pain and painful disorders. 94921 polypeptides of the present invention are useful in screening for modulators of 94921 activity.

Gene ID 16852

The human 16852 sequence (SEQ ID NO:29), known also as large-conductance calcium-activated potassium channel (slowpoke) beta subunit KCNMB4, is approximately 1107 nucleotides long including untranslated regions. The coding sequence, located at about nucleic acid 56 to 688 of SEQ ID NO:29, encodes a 210 amino acid protein (SEQ ID NO:30).

As assessed by TaqMan analysis, 16852 MRNA was primarily expressed in tissues of the central nervous system in human and rat panels. 16852 mRNA was up-regulated in the dorsal root ganglion (DRG) after Axotomy, Chronic Constriction Injury (CCI) and Spared Nerve Injury (SNI) and in the in spinal cord after CCI and Axotomy. In situ hybridization experiments indicated that 16852 MRNA was expressed in both human, monkey and rat brains and in monkey spinal cord and small and medium size of the DRG neurons.

Activation of potassium channels affects the frequency and the pattern of neuronal firing. Several voltage-gated potassium channels are expressed in sub-population of sensory neurons including those involved in nociception. In general, it has been shown that the expression of some voltage-gated potassium channels decreases in DRG neurons after axotomy and that the peak of potassium currents is reduced in sensory neurons during chronic inflammation. Furthermore, administration of potassium channel openers potentiated the antinociception produced by agonists of alpha-2-adrenoreceptors or by morphine. The antinociception induced by intrathecal injection of morphine.injection is blocked in a dose-dependent manner by glibenclamide (a blocker of ATP-sensitive K+ channels) and potentiated by nicorandil (a opener of ATP-sensitive K+ channels).

16852 is a b subunit of the large conductance, calcium-dependent K+ channel, Slowpoke. When co-expressed with Slowpoke, 16852 down-regulates Slowpoke channel activity by shifting its activation range to more depolarized voltages and slowing its activation kinetics. 16852 may play an important role in pain transmission because it is up-regulated in several pain models. Inhibitors of 16852 will increase large conductance, calcium-dependent potassium channel activity and thus decrease neuronal firing. Thus, drugs which inhibit 16852 may be novel methods for the inhibition of pain. Due to the expression of 16852 in the spinal cord and dorsal root ganglion, along with its functional role, modulators of 16852 activity would be useful in treating disorders associated with the treatment of pain and painful disorders. 16852 polypeptides of the present invention are useful in screening for modulators of 16852 activity.

Gene ID 33260

The human 33260 sequence (SEQ ID NO:31), known also as Potassium voltage-gated channel subfamily H member 1 (KCNH1); or as Ether-a-go-go potassium channel 1 (hEAG1), is approximately 3083 nucleotides long including untranslated regions. The coding sequence, located at about nucleic acid 37 to 3006 of SEQ ID NO:31, encodes a 989 amino acid protein (SEQ ID NO:32).

As assessed by TaqMan analysis, 33260 mRNA was primarily expressed in tissues of the central nervous system (CNS) in both monkey and rat panels. 33260 mRNA was up-regulated in the dorsal root ganglion (DRG) after Chronic Constriction Injury (CCI) and in the spinal cord after Capsaicin treatment. In situ hybridization experiments indicated that 33260 mRNA was expressed in a sub-population of DRG neurons in monkey and rat and in the spinal cord, with highest levels in the superficial laminae of the dorsal horn, in both monkey and rat. 33260 was also shown to be expressed in a sub-population of cortical neurons in both monkey and rat.

Activation of potassium channels affects the frequency and the pattern of neuronal firing. Several voltage-gated potassium channels are expressed in sub-population of sensory neurons including those involved in nociception. In general, it has been shown that the expression of some voltage-gated potassium channels decreases in DRG neurons after axotomy and that the peak of potassium currents is reduced in sensory neurons during chronic inflammation. Furthermore, administration of potassium channel openers potentiated the antinociception produced by agonists of alpha-2-adrenoreceptors or by morphine. The antinociception induced by intrathecal injection of morphine.injection is blocked in a dose-dependent manner by glibenclamide (a blocker of ATP-sensitive K+ channels) and potentiated by nicorandil (a opener of ATP-sensitive K+ channels).

33260 (the potassium channel EAG-1) is important for the modulation of the firing pattern of nociceptive neurons. Drugs which open 33260 may therefore be a novel mechanism for the inhibition of pain. Due to the expression of 33260 in the spinal cord and dorsal root ganglion, along with its functional role, modulators of 33260 activity would be useful in treating disorders associated with the treatment of pain and painful disorders. 33260 polypeptides of the present invention are useful in screening for modulators of 33260 activity.

Gene ID 58573

The human 58573 sequence (SEQ ID NO:33), known also as a sodium-bicarbonate co-transporter NBC4, is approximately 6313 nucleotides long including untranslated regions. The coding sequence, located at about nucleic acid 348 to 3713 of SEQ ID NO:33, encodes a 1121 amino acid protein (SEQ ID NO:34).

As assessed by TaqMan analysis, 58573 mRNA was expressed in tissues of the central nervous system (CNS) and in kidney tissue samples in both monkey and rat panels. 58573 MRNA was up-regulated in the dorsal root ganglion (DRG) after Chronic Constriction Injury (CCI) and in C5-T1 DRG 4 weeks post-Rhizotomy. 58573 mRNA was up-regulated in spinal cord after Axotomy. 58573 mRNA was down-regulated in DRG after Complete Freund's Adjuvant (CFA) and in C3 DRG 4 weeks post-Rhizotomy. 58573 mRNA was down-regulated in the DRG and spinal cord after Spared Nerve Injury (SNI), Tibial Nerve Injury (TNI) and long-term Capsaicin treatment. In situ hybridization experiments indicated that 58573 mRNA was expressed in a sub-population of small neurons in the DRG and in a sub-population of thalamic neurons in the monkey.

58573 is an important gene in the sensation of pain because it is present in nociceptive neurons of the DRG and in sensory thalamic neurons and it is up-regulated in DRG and spinal cord in some models of pain. 58573 is a member of the sodium-bicarbonate cotransporter (NBC) family. NBC's are known to transport bicarbonate into cells and are thought to be at least partially responsible for extracellular acidification after neuronal activity. Since protons are known mediators of pain, inhibition of 58573 will be a novel mechanism for the inhibition of pain. Due to the expression of 58573 in the spinal cord and dorsal root ganglion, along with its functional role, modulators of 58573 activity would be useful in treating disorders associated with the treatment of pain and painful disorders. 58573 polypeptides of the present invention are useful in screening for modulators of 58573 activity.

Gene ID 30911

The human 30911 sequence (SEQ ID NO:35), known also a sodium-proton exchanger (NHE5), is approximately 3761 nucleotides long including untranslated regions. The coding sequence, located at about nucleic acid 70 to 2760 of SEQ ID NO:35, encodes a 896 amino acid protein (SEQ ID NO:36).

As assessed by TaqMan analysis, 30911 mRNA was expressed at highest levels in tissues of the central nervous system (CNS) of human and rat models. 30911 mRNA was up-regulated at multiple time points in dorsal root ganglion (DRG) after Chronic Constriction Injury (CCI). 30911 mRNA was down-regulated in early time points in the DRG after Spared Nerve Injury (SNI) and after long-term Capsaicin treatment.

30911 is an important gene in the sensation of pain because it is up-regulated in DRG in a neuropathic model of pain. 30911 is a member of the sodium-proton exchanger (NHE) family. NHE play an important role in pH regulation, since they pump protons out of the cell. Since protons are known mediators of pain, inhibiting 30911 will be a novel mechanism for the inhibition of pain. Due to 30911 mRNA expression in the dorsal root ganglion, along with its functional role, modulators of 30911 activity would be useful in treating disorders associated with the treatment of pain and painful disorders. 30911 polypeptides of the present invention are useful in screening for modulators of 30911 activity.

Gene ID 85913

The human 85913 sequence (SEQ ID NO:37), a member of the hyperpolarization activated cyclic nucleotide-gated potassium channel family (HCN1), is approximately 4069 nucleotides long including untranslated regions. The coding sequence, located at about nucleic acid 43 to 2691 of SEQ ID NO:37, encodes a 882 amino acid protein (SEQ ID NO:38).

As assessed by TaqMan analysis, 85913 mRNA was expressed at highest levels in tissues of the central nervous system (CNS) of human and rat models. 85913 was also shown to be highly expressed in rat bladder tissue samples. Additionally, 85913 was shown to be up-regulated in dorsal root ganglion (DRG) samples after Axotomy, Tibial Nerve Injury (TNI) and Spared Nerve Injury (SNI). 85913 was also shown to be down-regulated in spinal cord samples after Axotomy, Complete Freund's Adjuvant (CFA), SNI and Rhizotomy. 85913 was additionally shown to be downregulated in DRG after chronic constriction injury (CCI), CFA and Rhizotomy. No regulation was observed in DRG and spinal cord samples after capsaicin treatment. In situ hybridization experiments demonstrated that 85913 was expressed in both human and rat brains, dorsal horn or the spinal cord and subpopulations of the DRG neurons.

85913, known also as HCN1, is a member of the hyperpolarization activated cyclic nucleotide-gated potassium channel family. HCN channels are permeate to both Na+ and K+ and open upon hyperpolarization. Since they depolarize the cell at negative potentials, they act as "pacemaker" channels, providing a mechanism for increasing the action potential firing rate (for review, see *News Physiol Sci* 17:32–7). Since 85913 is localized in the dorsal horn of the spinal cord and in a subpopulation of DRG neurons, and since 85913 may be important for increasing the action potential rate from nociceptive neurons, 85913 may play a critical role in the transmission of pain information. Therefore, without being bound by theory, inhibiting 85913 may be a novel mechanism for the inhibition of pain. Due to 85913 mRNA expression in the dorsal root ganglion, along with its functional role, modulators of 85913 activity would be useful in treating disorders associated with the treatment of pain and painful disorders. 85913 polypeptides of the present invention are useful in screening for modulators of 85913 activity.

Gene ID 14303

The human 14303 sequence (SEQ ID NO:39), a sodium-proton exchanger (NHE6), is approximately 4452 nucleotides long including untranslated regions. The coding sequence, located at about nucleic acid 36 to 2045 of SEQ ID NO:39, encodes a 669 amino acid protein (SEQ ID NO:40)

As assessed by TaqMan analysis, 14303 mRNA was expressed at highest levels in tissues of the central nervous system (CNS) of human and rat models. Additionally, 14303 was shown to be up-regulated in dorsal root ganglion (DRG) samples after chronic constriction injury (CCI). 14303 was also shown to be down-regulated in DRG and spinal cord samples after Tibial Nerve Injury (TNI) and it was shown to be down-regulated in DRG after Spared Nerve Injury (SNI). 14303 was additionally shown to be down-regulated in C3 DRG after Rhizotomy and it was shown to be down-regulated in long term DRG after capsaicin treatment.

In situ hybridization experiments demonstrated that 14303 was expressed in all neurons of DRG, spinal cord and cortex. 14303 was also demonstrated to be expressed in monkey prostate muscle cells.

14303 is also known as a sodium-proton exchanger (NHEs), which are thought to be important regulators of pH in and around neurons by pumping protons out of cells following neuronal activity (see, for example, *J Clin Invest* 104(5):637–45; *J Neurosci Res* 56(4):358–70; *J Neurosci Res* 1998 Feb. 15;51(4):431–41). Extracellular acidification has been shown to mediate pain. Continuous administration of low pH solutions in humans causes pain and hyperalgesia (*Neurosci Lett* 154:113–116). In addition, protons selectively induce lasting excitation and sensitization to mechanical stimulation of nociceptors in rat skin, in vitro (*J Neurosci* 12(1):86–95). Most importantly, protons directly activate VR-1 receptors present in nociceptive neurons in the DRG (*J Physiol* 433:145–61; TIPS 20:(3):112–8). VR-1 receptors are important players in pathways involved in pain. Therefore, 14303 may be an important gene in the sensation of pain because it is up-regulated in DRG in a neuropathic model of pain. 14303 is a member of the sodium-proton exchanger (NHE) family. NHE's are thought to play an important role in pH regulation, since they pump protons out of the cell. Since protons are known mediators of pain, inhibition of 14303 may be a novel mechanism for the inhibition of pain. Due to 14303 mRNA expression in the dorsal root ganglion, along with its functional role, modulators of 14303 activity would be useful in treating disorders associated with the treatment of pain and painful disorders. 14303 polypeptides of the present invention are useful in screening for modulators of 14303 activity.

Gene ID 16816

The human 16816 sequence (SEQ ID NO:41), a Phospholipase C Delta 4, is approximately 3116 nucleotides long including untranslated regions. The coding sequence, located at about nucleic acid 205 to 2493 of SEQ ID NO:41, encodes a 762 amino acid protein (SEQ ID NO:42)

As assessed by TaqMan analysis using a human tissue panel, 16816 mRNA was expressed at highest levels in skeletal muscle tissues, followed by bladder tissue samples and tissues of the central nervous system (CNS). Additional TaqMan experiments on a rat tissue panel demonstrated expression in skeletal muscle, bladder and CNS tissue samples. Additionally, 16816 was shown to be up-regulated as well as down-regulated in dorsal root ganglion (DRG) samples after chronic constriction injury (CCI). 16816 was also shown to be down-regulated in DRG and up-regulated in spinal cord samples after Spared Nerve Injury (SNI).

In situ hybridization experiments demonstrated that 16816 was expressed in nociceptive neurons in both monkey and rat DRG samples. 16816 was also demonstrated to be expressed in monkey brain (thalamus) and muscle tissue samples.

16816 is also known as a phatidylinositol-specific phospholipase C (PLC), which plays an important role in receptor-mediated signal transduction by generating 2 second messenger molecules, inositol 1,4,5-triphosphate (IP3) and diacylglycerol, from phosphatidylinositol 4,5-bisphosphate (PIP2). PLC is well known to be involved in nociceptive pathways. It is well established, for example, that bradykinin and nerve growth factor (NGF), two pro-algesic agents, activate G-protein-coupled (BK2) and tyrosine kinase (TrkA) receptors, respectively, to stimulate phospholipase C (PLC) signalling pathways in primary afferent neurons. It has been shown that bradykinin- or NGF-mediated potentiation of thermal sensitivity in vivo requires expression of VR1, a well established receptor involved in pain. Diminution of plasma membrane phosphatidylinositol-4,5-bisphosphate (PtdIns(4,5)P2) levels through antibody sequestration or PLC-mediated hydrolysis mimics the potentiating effects of bradykinin or NGF at the cellular level. Moreover, recruitment of PLC-gamma to TrkA is essential for NGF-mediated potentiation of channel activity, and biochemical studies suggest that VR1 associates with this complex (*Nature*. 2001 411(6840):957–62). Given the importance of PLC in pain pathways, drugs which modulate 16816 may be important for the treatment of pain. Due to 16816 MRNA expression in the dorsal root ganglion, along with its functional role, modulators of 16816 activity would be useful in treating disorders associated with the treatment of pain and painful disorders. 16816 polypeptides of the present invention are useful in screening for modulators of 16816 activity.

Gene ID 17827

The human 17827 sequence (SEQ ID NO:43), a potassium channel KCNK12 (THIK2), is approximately 1943 nucleotides long including untranslated regions. The coding sequence, located at about nucleic acid 466 to 1758 of SEQ ID NO:43, encodes a 430 amino acid protein (SEQ ID NO:44)

As assessed by TaqMan analysis, 17827 mRNA was expressed at highest levels in tissues of the central nervous system (CNS) of human and rat models. Expression of 17827 was additionally observed in lung, prostate and trachea tissue samples in the rat panel. Additionally, 17827 was shown to be up-regulated in dorsal root ganglion (DRG) samples after chronic constriction injury (CCI). 17827 was also shown to be up-regulated in spinal cord samples after Spared Nerve Injury (SNI). 17827 was additionally shown to be down-regulated in L5, L6 DRG samples after Spinal Nerve Ligation (SNL) after 84 days.

In situ hybridization experiments demonstrated that 17827 was expressed in both monkey and rat DRG neurons of all sizes, TRG. 17827 was also demonstrated to be expressed in monkey and rat spinal cord and brain samples.

17827 is a potassium channel present in DRG neurons. Activation of potassium channels affect the frequency and the pattern of neuronal firing. Modulation of potassium channels may be important for the firing pattern of nociceptive neurons. Therefore drugs which interact with 17827 could be a novel mechanism for the inhibition of pain. Due to 17827 mRNA expression in the dorsal root ganglion and spinal cord, along with its functional role, modulators of 17827 activity would be useful in treating disorders associated with the treatment of pain and painful disorders. 17827 polypeptides of the present invention are useful in screening for modulators of 17827 activity.

Gene ID 32620

The human 32620 sequence (SEQ ID NO:45), a sodium-glucose cotransporter SMIT2, is approximately 2384 nucleotides long including untranslated regions. The coding sequence, located at about nucleic acid 233 to 2260 of SEQ ID NO:45, encodes a 675 amino acid protein (SEQ ID NO:46)

As assessed by TaqMan analysis, 32620 mRNA was expressed at highest levels in tissues of the central nervous system (CNS) of human and rat models. Expression of 32620 was additionally observed in colon and small intestine tissue samples in the human panel and in the kidney, prostate and duodenum samples in the rat panel. Additionally, 32620 was shown to be down-regulated in dorsal root ganglion (DRG) samples after chronic constriction injury (CCI). 32620 was also shown to be up-regulated in DRG and spinal cord samples after axotomy. 32620 was additionally shown to be down-regulated in DRG after Spared Nerve Injury (SNI).

In situ hybridization experiments demonstrated that 32620 was mainly expressed in small diameter neurons of DRG. 32620 was also shown to be expressed in glial cells of the spinal cord and cortex of monkey tissues.

32620 transports myo-inositol in a sodium-dependent manner. Intrathecal injection of myo-inositol (2.5 mg) significantly reversed both the anti-hyperalgesic and anti-allodynic effect of intrathecal injection of lithium (*Pain* 2000 85:59–64). Thus, drugs which interact with 32620 may be important for the treatment of pain. Due to 32620 MRNA expression in the dorsal root ganglion and spinal cord, along with its functional role, modulators of 32620 activity would be useful in treating disorders associated with the treatment of pain and painful disorders. 32620 polypeptides of the present invention are useful in screening for modulators of 32620 activity.

Various aspects of the invention are described in further detail in the following subsections:

Screening Assays:

The invention provides a method (also referred to herein as a "screening assay") for identifying modulators, i.e., candidate or test compounds or agents (e.g., peptides, peptidomimetics, small molecules (organic or inorganic) or other drugs) which bind to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins, have a stimulatory or inhibitory effect on, for example, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity, or have a stimulatory or inhibitory effect on, for example, the expression or activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate. Compounds identified using the assays described herein may be useful for treating pain and painful conditions.

These assays are designed to identify compounds that bind to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, bind to other intracellular or extracellular proteins that interact with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, and interfere with the interaction of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein with other intercellular or extracellular proteins. For example, in the case of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, which is a transmembrane receptor-type protein, such techniques can identify ligands for such a receptor. A 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein ligand or substrate can, for example, be used to ameliorate pain and painful conditions. Such compounds may include, but are not limited to peptides, antibodies, or small organic or inorganic compounds. Such compounds may also include other cellular proteins.

Compounds identified via assays such as those described herein may be useful, for example, for treating pain and painful conditions. In instances whereby a painful condition results from an overall lower level of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression and/or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein in a cell or tissue, compounds that interact with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein may include compounds which accentuate or amplify the activity of the bound 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Such compounds would bring about an effective increase in the level of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein activity, thus ameliorating symptoms.

In other instances, mutations within the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene may cause aberrant types or excessive amounts of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins to be made which have a deleterious effect that leads to a pain. Similarly, physiological conditions may cause an excessive increase in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression leading pain. In such cases, compounds that bind to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein may be identified that inhibit the activity of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Assays for testing the effectiveness of compounds identified by techniques such as those described in this section are discussed herein.

In one embodiment, the invention provides assays for screening candidate or test compounds which are substrates of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or polypeptide or biologically active portion thereof. In another embodiment, the invention provides assays for screening candidate or test compounds which bind to or modulate the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or biologically active portion thereof is contacted with a test compound and the ability of the test compound to modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is determined. Determining the ability of the test compound to modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity can be accomplished by monitoring, for example, intracellular calcium, $IP_3$, cAMP, or diacylglycerol concentration, the phosphorylation profile of intracellular proteins, cell proliferation and/or migration, gene expression of, for example, cell surface adhesion molecules or genes associated with analgesia, or the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-regulated transcription factor. The cell can be of mammalian origin, e.g., a neural cell. In one embodiment, compounds that interact with a receptor domain can be screened for their ability to function as ligands, i.e., to bind to the receptor and modulate a signal transduction pathway. Identification of ligands, and measuring the activity of the ligand-receptor complex, leads to the identification of modulators (e.g., antagonists) of this interaction. Such modulators may be useful in the treatment of pain and painful conditions.

The ability of the test compound to modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 binding to a substrate or to bind to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can also be determined. Determining the ability of the test compound to modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 binding to a substrate can be accomplished, for example, by coupling the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate with a radioisotope or enzymatic label such that binding of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be determined by detecting the labeled 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate in a complex. 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 could also be coupled with a radioisotope or enzymatic label to monitor the ability of a test compound to modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 binding to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate in a complex. Determining the ability of the test compound to bind 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be accomplished, for example, by coupling the compound with a radioisotope or enzymatic label such that binding of the compound to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be determined by detecting the labeled 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 compound in a complex. For example, compounds (e.g., 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 ligands or substrates) can be labeled with $^{125}$I, $^{35}$S, $^{14}$C, or $^{3}$H, either directly or indirectly, and the radioisotope detected by direct counting of radioemmission or by scintillation counting. Compounds can further be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 ligand or substrate) to interact with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 without the labeling of any of the interactants. For example, a microphysiometer can be used to detect the interaction of a compound with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 without the labeling of either the compound or the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 (McConnell, H. M. et al. (1992) *Science* 257: 1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620.

In another embodiment, an assay is a cell-based assay comprising contacting a cell expressing a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule (e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate) with a test compound and determining the ability of the test compound to modulate (e.g., stimulate or inhibit) the activity of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule. Determining the ability of the test compound to modulate the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule can be accomplished, for example, by determining the ability of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to bind to or interact with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule.

Determining the ability of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or a biologically active fragment thereof, to bind to or interact with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule can be accomplished by one of the methods described above for determining direct binding. In a preferred embodiment, determining the ability of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to bind to or interact with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, cAMP), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response (e.g., gene expression).

In yet another embodiment, an assay of the present invention is a cell-free assay in which a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or biologically active portion thereof, is contacted with a test compound and the ability of the test compound to bind to the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or biologically active portion thereof is determined. Preferred biologically active portions of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins to be used in assays of the present invention include fragments which participate in interactions with non-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 molecules, e.g., fragments with high surface probability scores. Binding of the test compound to the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be determined either directly or indirectly as described above. In a preferred embodiment, the assay includes contacting the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or biologically active portion thereof with a known compound which binds 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 to form an assay mixture, contacting the assay mixture with a test compound, and determining the ability of the test compound to interact with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, wherein determining the ability of the test compound to interact with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein comprises determining the ability of the test compound to preferentially bind to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 or biologically active portion thereof as compared to the known compound. Compounds that modulate the interaction of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 with a known target protein may be useful in regulating the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, especially a mutant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein.

In another embodiment, the assay is a cell-free assay in which a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or biologically active portion thereof is contacted with a test compound and the ability of the test compound to modulate (e.g., stimulate or inhibit) the activity of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or biologically active portion thereof is determined. Determining the ability of the test compound to modulate the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be accomplished, for example, by determining the ability of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to bind to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule by one of the methods described above for determining direct binding. Determining the ability of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to bind to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule can also be accomplished using a technology such as real-time Biomolecular Interaction Analysis (BIA) (Sjolander, S. and Urbaniczky, C. (1991) *Anal. Chem.* 63:2338–2345 and Szabo et al. (1995) *Curr. Opin. Struct. Biol.* 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another embodiment, determining the ability of the test compound to modulate the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be accomplished by determining the ability of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to further modulate the activity of a downstream effector of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule. For example, the activity of the effector molecule on an appropriate target can be determined or the binding of the effector to an appropriate target can be determined as previously described.

In yet another embodiment, the cell-free assay involves contacting a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or biologically active portion thereof with a known compound which binds the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to form an assay mixture, contacting the assay mixture with a test compound, and determining the ability of the test compound to interact with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, wherein determining the ability of the test compound to interact with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein comprises determining the ability of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to preferentially bind to or modulate the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule.

In more than one embodiment of the above assay methods of the present invention, it may be desirable to immobilize either 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 or its target molecule to facilitate separation of complexed from uncomplexed forms of one or both of the proteins, as well as to accommodate automation of the assay. Binding of a test compound to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, or interaction of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 binding or activity determined using standard techniques.

Other techniques for immobilizing proteins on matrices can also be used in the screening assays of the invention. For example, either a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 target molecule can be immobilized utilizing conjugation of biotin and streptavidin. Biotinylated 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or target molecules but which do not interfere with binding of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to its target molecule can be derivatized to the wells of the plate, and unbound target or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein trapped in the wells by antibody conjugation. Methods for detecting such complexes, in addition to those described above for the GST-immobilized complexes, include immunodetection of complexes using antibodies reactive with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or target molecule, as well as enzyme-linked assays which rely on detecting an enzymatic activity associated with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or target molecule.

In another embodiment, modulators of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression are identified in a method wherein a cell is contacted with a candidate compound and the expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or protein in the cell is determined. The level of expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 MRNA or protein in the presence of the candidate compound is compared to the level of expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or protein in the absence of the candidate compound. The candidate compound can then be identified as a modulator of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression based on this comparison. For example, when expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or protein is greater (statistically significantly greater) in the presence of the candidate compound than in its absence, the candidate compound is identified as a stimulator of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or protein expression. Alternatively, when expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or protein is less (statistically significantly less) in the presence of the candidate compound than in its absence, the candidate compound is identified as an inhibitor of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or protein expression. The level of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or protein expression in the cells can be determined by methods described herein for detecting 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 MRNA or protein.

In yet another aspect of the invention, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 ("16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-binding proteins" or "16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-bp") and are involved in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. Such 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-binding proteins are also likely to be involved in the propagation of signals by the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 targets as, for example, downstream elements of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-mediated signaling pathway. Alternatively, such 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-binding proteins are likely to be 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 inhibitors.

The two-hybrid system is based on the modular nature of most transcription factors, which consist of separable DNA-binding and activation domains. Briefly, the assay utilizes two different DNA constructs. In one construct, the gene that codes for a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein.

In another aspect, the invention pertains to a combination of two or more of the assays described herein. For example, a modulating agent can be identified using a cell-based or a cell free assay, and the ability of the agent to modulate the activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be confirmed in vivo, e.g., in an animal such as an animal model for pain, as described herein.

This invention further pertains to novel agents identified by the above-described screening assays. Accordingly, it is within the scope of this invention to further use an agent identified as described herein in an appropriate animal model. For example, an agent identified as described herein (e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulating agent, an antisense 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecule, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-specific antibody, or a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate pain. Cell-based and animal model-based assays for the identification of compounds exhibiting such an ability to ameliorate pain are described herein.

In addition, animal-based models of pain, such as those described herein, may be used to identify compounds capable of treating pain and painful conditions. Such animal models may be used as test substrates for the identification of drugs, pharmaceuticals, therapies, and interventions which may be effective in treating pain. For example, animal models may be exposed to a compound, suspected of exhibiting an ability to treat pain, at a sufficient concentration and for a time sufficient to elicit such an amelioration of pain in the exposed animals. The response of the animals to the exposure may be monitored by assessing the reversal of the symptoms of pain before and after treatment.

With regard to intervention, any treatments which reverse any aspect of pain (i.e. have an analgesic effect) should be considered as candidates for human pain therapeutic intervention. Dosages of test agents may be determined by deriving dose-response curves.

Additionally, gene expression patterns may be utilized to assess the ability of a compound to ameliorate pain. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Gene expression profiles may be generated, for example, by utilizing a differential display procedure, Northern analysis and/or RT-PCR. In one embodiment, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences may be used as probes and/or PCR primers for the generation and corroboration of such gene expression profiles.

Gene expression profiles may be characterized for known states, either pain or painful disorders or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a pain disease model system to more closely resemble the control system. Administration of a compound may, alternatively, cause the gene expression profile of a control system to begin to mimic pain or a painful disease state. Such a compound may, for example, be used in further characterizing the compound of interest, or may be used in the generation of additional animal models.

Cell- and Animal-Based Model Systems

Described herein are cell- and animal-based systems which act as models for pain. These systems may be used in a variety of applications. For example, the cell- and animal-based model systems may be used to further characterize differentially expressed genes associated with pain or painful disorders, e.g., 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620. In addition, animal- and cell-based assays may be used as part of screening strategies designed to identify compounds which are capable of ameliorating pain, as described, below. Thus, the animal- and cell-based models may be used to identify drugs, pharmaceuticals, therapies and interventions which may be effective in treating pain or painful disorders. Furthermore, such animal models may be used to determine the LD50 and the ED50 in animal subjects, and such data can be used to determine the in vivo efficacy of potential pain treatments.

Animal-Based Systems

Animal-based model systems of pain may include, but are not limited to, non-recombinant and engineered transgenic animals.

Non-recombinant animal models for pain may include, for example, genetic models.

Additionally, animal models exhibiting pain may be engineered by using, for example, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences described above, in conjunction with techniques for producing transgenic animals that are well known to those of skill in the art. For example, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences may be introduced into, and overexpressed in, the genome of the animal of interest, or, if endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences are present, they may either be overexpressed or, alternatively, be disrupted in order to underexpress or inactivate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression.

The host cells of the invention can also be used to produce non-human transgenic animals. For example, in one embodiment, a host cell of the invention is a fertilized oocyte or an embryonic stem cell into which 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-coding sequences have been introduced. Such host cells can then be used to create non-human transgenic animals in which exogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequences have been introduced into their genome or homologous recombinant animals in which endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequences have been altered. Such animals are useful for studying the function and/or activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 and for identifying and/or evaluating modulators of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene has been altered by homologous recombination between the endogenous gene and an exogenous DNA molecule introduced into a cell of the animal, e.g., an embryonic cell of the animal, prior to development of the animal.

A transgenic animal used in the methods of the invention can be created by introducing a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-encoding nucleic acid into the male pronuclei of a fertilized oocyte, e.g., by microinjection, retroviral infection, and allowing the oocyte to develop in a pseudopregnant female foster animal. The 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 cDNA sequence can be introduced as a transgene into the genome of a non-human animal. Alternatively, a nonhuman homologue of a human 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, such as a mouse or rat 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, can be used as a transgene. Alternatively, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene homologue, such as another 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 family member, can be isolated based on hybridization to the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 cDNA sequences and used as a transgene. Intronic sequences and polyadenylation signals can also be included in the transgene to increase the efficiency of expression of the transgene. A tissue-specific regulatory sequence(s) can be operably linked to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 transgene to direct expression of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 transgene in its genome and/or expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA in tissues or cells of the animals. A transgenic founder animal can then be used to breed additional animals carrying the transgene. Moreover, transgenic animals carrying a transgene encoding a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can further be bred to other transgenic animals carrying other transgenes.

To create a homologous recombinant animal, a vector is prepared which contains at least a portion of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene into which a deletion, addition or substitution has been introduced to thereby alter, e.g., functionally disrupt, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene. The 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene can be a human gene but more preferably, is a non-human homologue of a human 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene. For example, a rat 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene can be used to construct a homologous recombination nucleic acid molecule, e.g., a vector, suitable for altering an endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene in the mouse genome. In a preferred embodiment, the homologous recombination nucleic acid molecule is designed such that, upon homologous recombination, the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene is functionally disrupted (i.e., no longer encodes a functional protein; also referred to as a "knock out" vector). Alternatively, the homologous recombination nucleic acid molecule can be designed such that, upon homologous recombination, the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene is mutated or otherwise altered but still encodes functional protein (e.g., the upstream regulatory region can be altered to thereby alter the expression of the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein). In the homologous recombination nucleic acid molecule, the altered portion of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene is flanked at its 5' and 3' ends by additional nucleic acid sequence of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene to allow for homologous recombination to occur between the exogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene carried by the homologous recombination nucleic acid molecule and an endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene in a cell, e.g., an embryonic stem cell. The additional flanking 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene has homologously recombined with the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene are selected (see e.g., Li, E. et al. (1992) Cell 69:915). The selected cells can then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) Current Opinion in Biotechnology 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals for use in the methods of the invention can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

The 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 transgenic animals that express 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 peptide (detected immunocytochemically, using antibodies directed against 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 epitopes) at easily detectable levels should then be further evaluated to identify those animals which display characteristic pain.

Cell-Based Systems

Cells that contain and express 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences which encode a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, and, further, exhibit cellular phenotypes associated with nociception, may be used to identify compounds that exhibit analgesic effect. Such cells may include non-recombinant monocyte cell lines, such as U937 (ATCC# CRL-1593), THP-1 (ATCC#TIB-202), and P388D1 (ATCC# TIB-63); endothelial cells such as human umbilical vein endothelial cells (HUVECs), human microvascular endothelial cells (HMVEC), and bovine aortic endothelial cells (BAECs); as well as generic mammalian cell lines such as HeLa cells and COS cells, e.g., COS-7 (ATCC# CRL-1651), and neural cell lines. Further, such cells may include recombinant, transgenic cell lines. For example, the pain animal models of the invention, discussed above, may be used to generate cell lines, containing one or more cell types involved in nociception, that can be used as cell culture models for this disorder. While primary cultures derived from the pain model transgenic animals of the invention may be utilized, the generation of continuous cell lines is preferred. For examples of techniques which may be used to derive a continuous cell line from the transgenic animals, see Small et al., (1985) Mol. Cell Biol. 5:642–648.

Alternatively, cells of a cell type known to be involved in nociception may be transfected with sequences capable of increasing or decreasing the amount of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression within the cell. For example, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences may be introduced into, and overexpressed in, the genome of the cell of interest, or, if endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences are present, they may be either overexpressed or, alternatively disrupted in order to underexpress or inactivate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression.

In order to overexpress a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, the coding portion of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene may be ligated to a regulatory sequence which is capable of driving gene expression in the cell type of interest, e.g., an endothelial cell. Such regulatory regions will be well known to those of skill in the art, and may be utilized in the absence of undue experimentation. Recombinant methods for expressing target genes are described above.

For underexpression of an endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequence, such a sequence may be isolated and engineered such that when reintroduced into the genome of the cell type of interest, the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 alleles will be inactivated. Preferably, the engineered 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequence is introduced via gene targeting such that the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequence is disrupted upon integration of the engineered 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequence into the cell's genome. Transfection of host cells with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 genes is discussed, above.

Cells treated with compounds or transfected with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 genes can be examined for phenotypes associated with nociception.

Transfection of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid may be accomplished by using standard techniques (described in, for example, Ausubel (1989) supra). Transfected cells should be evaluated for the presence of the recombinant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences, for expression and accumulation of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 MRNA, and for the presence of recombinant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein production. In instances wherein a decrease in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression is desired, standard techniques may be used to demonstrate whether a decrease in endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression and/or in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein production is achieved.

Also provided are cells or a purified preparation thereof, e.g., human cells, in which an endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 is under the control of a regulatory sequence that does not normally control the expression of the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene. For example, an endogenous 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published on May 16, 1991.

Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein and/or nucleic acid expression as well as 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity, in the context of a biological sample (e.g., blood, serum, cells, e.g., endothelial cells, or tissue, e.g., vascular tissue) to thereby determine whether an individual is afflicted with a predisposition or is experiencing pain. The invention also provides for prognostic (or predictive) assays for determining whether an individual is at risk of developing a painful disorder. For example, mutations in a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene can be assayed for in a biological sample. Such assays can be used for prognostic or predictive purpose to thereby phophylactically treat an individual prior to the onset of a painful disorder.

Another aspect of the invention pertains to monitoring the influence of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulators (e.g., anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 ribozymes) on the expression or activity of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 in clinical trials.

These and other agents are described in further detail in the following sections.

Diagnostic Assays

To determine whether a subject is afflicted with a disease, a biological sample may be obtained from a subject and the biological sample may be contacted with a compound or an agent capable of detecting a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or nucleic acid (e.g., mRNA or genomic DNA) that encodes a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, in the biological sample. A preferred agent for detecting 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or genomic DNA is a labeled nucleic acid probe capable of hybridizing to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 MRNA or genomic DNA. The nucleic acid probe can be, for example, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid set forth in SEQ ID NO:1, 3, 5, 7, 9, 11, 13, 15, 17, 19, 21, 23, 25, 27, 29, 31, 33, 35, 37, 39, 41, 43 or 45, or a portion thereof, such as an oligonucleotide of at least 15, 20, 25, 30, 25, 40, 45, 50, 100, 250 or 500 nucleotides in length and sufficient to specifically hybridize under stringent conditions to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA or genomic DNA. Other suitable probes for use in the diagnostic assays of the invention are described herein.

A preferred agent for detecting 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein in a sample is an antibody capable of binding to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA, protein, or genomic DNA in a biological sample in vitro as well as in vivo. For example, in vitro techniques for detection of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 MRNA include Northern hybridizations and in situ hybridizations. In vitro techniques for detection of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein include enzyme linked immunosorbent assays (ELISAs), Western blots, immunoprecipitations and immunofluorescence. In vitro techniques for detection of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 genomic DNA include Southern hybridizations. Furthermore, in vivo techniques for detection of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein include introducing into a subject a labeled anti- 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, MRNA, or genomic DNA, such that the presence of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, mRNA or genomic DNA is detected in the biological sample, and comparing the presence of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, mRNA or genomic DNA in the control sample with the presence of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, mRNA or genomic DNA in the test sample.

Prognostic Assays

The present invention further pertains to methods for identifying subjects having or at risk of developing a disease associated with aberrant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity.

As used herein, the term "aberrant" includes a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity which deviates from the wild type 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity. Aberrant expression or activity includes increased or decreased expression or activity, as well as expression or activity which does not follow the wild type developmental pattern of expression or the subcellular pattern of expression. For example, aberrant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity is intended to include the cases in which a mutation in the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene causes the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene to be under-expressed or over-expressed and situations in which such mutations result in a non-functional 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or a protein which does not function in a wild-type fashion, e.g., a protein which does not interact with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate, or one which interacts with a non-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate.

The assays described herein, such as the preceding diagnostic assays or the following assays, can be used to identify a subject having or at risk of developing a disease. A biological sample may be obtained from a subject and tested for the presence or absence of a genetic alteration. For example, such genetic alterations can be detected by ascertaining the existence of at least one of 1) a deletion of one or more nucleotides from a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, 2) an addition of one or more nucleotides to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, 3) a substitution of one or more nucleotides of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, 4) a chromosomal rearrangement of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, 5) an alteration in the level of a messenger RNA transcript of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, 6) aberrant modification of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, such as of the methylation pattern of the genomic DNA, 7) the presence of a non-wild type splicing pattern of a messenger RNA transcript of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, 8) a non-wild type level of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-protein, 9) allelic loss of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, and 10) inappropriate post-translational modification of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-protein.

As described herein, there are a large number of assays known in the art which can be used for detecting genetic alterations in a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene. For example, a genetic alteration in a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene (see Abravaya et al. (1995) *Nucleic Acids Res.* 23:675–682). This method includes collecting a biological sample from a subject, isolating nucleic acid (e.g., genomic DNA, mRNA or both) from the sample, contacting the nucleic acid sample with one or more primers which specifically hybridize to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene under conditions such that hybridization and amplification of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be identified by hybridizing biological sample derived and control nucleic acids, e.g., DNA or RNA, to high density arrays containing hundreds or thousands of oligonucleotide probes (Cronin, M. T. et al. (1996) *Human Mutation* 7:244–255; Kozal, M. J. et al. (1996) *Nature Medicine* 2:753–759). For example, genetic mutations in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene in a biological sample and detect mutations by comparing the sequence of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 in the biological sample with the corresponding wild-type (control) sequence. Examples of sequencing reactions include those based on techniques developed by Maxam and Gilbert (1977) *Proc. Natl. Acad. Sci. USA* 74:560) or Sanger (1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448–53), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397 and Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequence, e.g., a wild-type 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766; see also Cotton (1993) *Mutat. Res.* 285:125–144 and Hayashi (1992) *Genet. Anal. Tech. Appl.* 9:73–79). Single-stranded DNA fragments of sample and control 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acids will be denatured and allowed to renature. The secondary structure of single-stranded nucleic acids varies according to sequence, the resulting alteration in electrophoretic mobility enables the detection of even a single base change The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulator (e.g., an agonist, antagonist, peptidomimetic, protein, peptide, nucleic acid, or small molecule) to effectively treat a disease.

Monitoring of Effects During Clinical Trials

The present invention further provides methods for determining the effectiveness of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulator (e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulator identified herein) in treating a disease. For example, the effectiveness of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulator in increasing 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression, protein levels, or in upregulating 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity, can be monitored in clinical trials of subjects exhibiting decreased 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression, protein levels, or downregulated 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. Alternatively, the effectiveness of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulator in decreasing 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression, protein levels, or in downregulating 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity, can be monitored in clinical trials of subjects exhibiting increased 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression, protein levels, or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. In such clinical trials, the expression or activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, and preferably, other genes that have been implicated in nociception can be used as a "read out" or marker of the phenotype of a particular cell.

For example, and not by way of limitation, genes, including 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620, that are modulated in cells by treatment with an agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity (e.g., identified in a screening assay as described herein) can be identified. Thus, to study the effect of agents which modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity on subjects suffering from a painful disorder in, for example, a clinical trial, cells can be isolated and RNA prepared and analyzed for the levels of expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 and other genes implicated in the painful disorder. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 or other genes. In this way, the gene expression pattern can serve as a marker, indicative of the physiological response of the cells to the agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. This response state may be determined before, and at various points during treatment of the individual with the agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity.

In a preferred embodiment, the present invention provides a method for monitoring the effectiveness of treatment of a subject with an agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, mRNA, or genomic DNA in the pre-administration sample; (iii) obtaining one or more post-administration samples from the subject; (iv) detecting the level of expression or activity of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, mRNA, or genomic DNA in the post-administration samples; (v) comparing the level of expression or activity of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, mRNA, or genomic DNA in the pre-administration sample with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, mRNA, or genomic DNA in the post administration sample or samples; and (vi) altering the administration of the agent to the subject accordingly. For example, increased administration of the agent may be desirable to increase the expression or activity of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 to higher levels than detected, i.e., to increase the effectiveness of the agent. Alternatively, decreased administration of the agent may be desirable to decrease expression or activity of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 to lower levels than detected, i.e. to decrease the effectiveness of the agent. According to such an embodiment, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity may be used as an indicator of the effectiveness of an agent, even in the absence of an observable phenotypic response.

Methods of Treatment:

The present invention provides for both prophylactic and therapeutic methods of treating a subject, e.g., a human, at risk of (or susceptible to) a disease. With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring an subject's prophylactic or therapeutic treatment with either the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 molecules of the present invention or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Prophylactic Methods

In one aspect, the invention provides a method for preventing in a subject, a disease by administering to the subject an agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. Subjects at risk for a pain or painful disorder can be identified by, for example, any or a combination of the diagnostic or prognostic assays described herein. Administration of a prophylactic agent can occur prior to the manifestation of symptoms characteristic of aberrant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity, such that a disease is prevented or, alternatively, delayed in its progression. Depending on the type of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 aberrancy, for example, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 agonist or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antagonist agent can be used for treating the subject. The appropriate agent can be determined based on screening assays described herein.

Therapeutic Methods

Described herein are methods and compositions whereby pain may be ameliorated. Certain painful disorders are brought about, at least in part, by an excessive level of a gene product, or by the presence of a gene product exhibiting an abnormal or excessive activity. As such, the reduction in the level and/or activity of such gene products would bring about the amelioration of pain. Techniques for the reduction of gene expression levels or the activity of a protein are discussed below.

Alternatively, certain other painful disorders are brought about, at least in part, by the absence or reduction of the level of gene expression, or a reduction in the level of a protein's activity. As such, an increase in the level of gene expression and/or the activity of such proteins would bring about the amelioration of pain.

In some cases, the up-regulation of a gene in a disease state reflects a protective role for that gene product in responding to the disease condition. Enhancement of such a gene's expression, or the activity of the gene product, will reinforce the protective effect it exerts. Some pain states may result from an abnormally low level of activity of such a protective gene. In these cases also, an increase in the level of gene expression and/or the activity of such gene products would bring about the amelioration of pain. Techniques for increasing target gene expression levels or target gene product activity levels are discussed herein.

Accordingly, another aspect of the invention pertains to methods of modulating 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity for therapeutic purposes. Accordingly, in an exemplary embodiment, the modulatory method of the invention involves contacting a cell with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 or agent that modulates one or more of the activities of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein activity associated with the cell (e.g., an endothelial cell or an ovarian cell). An agent that modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein activity can be an agent as described herein, such as a nucleic acid or a protein, a naturally-occurring target molecule of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein (e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 ligand or substrate), a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 agonist or antagonist, a peptidomimetic of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 agonist or antagonist, or other small molecule. In one embodiment, the agent stimulates one or more 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activities. Examples of such stimulatory agents include active 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein and a nucleic acid molecule encoding 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 that has been introduced into the cell. In another embodiment, the agent inhibits one or more 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activities. Examples of such inhibitory agents include antisense 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecules, anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies, and 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or nucleic acid molecule. In one embodiment, the method involves administering an agent (e.g., an agent identified by a screening assay described herein), or combination of agents that modulates (e.g., upregulates or downregulates) 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity. In another embodiment, the method involves administering a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or nucleic acid molecule as therapy to compensate for reduced, aberrant, or unwanted 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity.

Stimulation of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is desirable in situations in which 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 is abnormally down-regulated and/or in which increased 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is likely to have a beneficial effect. Likewise, inhibition of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is desirable in situations in which 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 is abnormally upregulated and/or in which decreased 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is likely to have a beneficial effect.

Methods for Inhibiting Target Gene Expression, Synthesis, or Activity

As discussed above, genes involved in pain or painful disorders may cause such disorders via an increased level of gene activity. In some cases, such up-regulation may have a causative or exacerbating effect on the disease state. A variety of techniques may be used to inhibit the expression, synthesis, or activity of such genes and/or proteins.

For example, compounds such as those identified through assays described above, which exhibit inhibitory activity, may be used in accordance with the invention to ameliorate pain. Such molecules may include, but are not limited to, small organic molecules, peptides, antibodies, and the like.

For example, compounds can be administered that compete with endogenous ligand for the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. The resulting reduction in the amount of ligand-bound 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein will modulate endothelial cell physiology. Compounds that can be particularly useful for this purpose include, for example, soluble proteins or peptides, such as peptides comprising one or more of the extracellular domains, or portions and/or analogs thereof, of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 receptor site, but do not activate the protein, (e.g., receptor-ligand antagonists) can be effective in inhibiting 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein activity.

Further, antisense and ribozyme molecules which inhibit expression of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene may also be used in accordance with the invention to inhibit aberrant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene activity. Still further, triple helix molecules may be utilized in inhibiting aberrant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene activity.

The antisense nucleic acid molecules used in the methods of the invention are typically administered to a subject or generated in situ such that they hybridize with or bind to cellular mRNA and/or genomic DNA encoding a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, an antisense nucleic acid molecule used in the methods of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA transcripts to thereby inhibit translation of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA. A ribozyme having specificity for a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-encoding nucleic acid can be designed based upon the nucleotide sequence of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 cDNA disclosed herein (i.e., SEQ ID NO:1, 3, 5, 7, 9, 11, 13, 15, 17, 19, 21, 23, 25, 27, 29, 31, 33, 35, 37, 39, 41, 43 or 45). For example, a derivative of a *Tetrahymena* L-19 IVS RNA can be constructed in which the nucleotide sequence of the active site is complementary to the nucleotide sequence to be cleaved in a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-encoding mRNA (see, for example, Cech et al. U.S. Pat. No. 4,987,071; and Cech et al. U.S. Pat. No. 5,116,742). Alternatively, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA can be used to select a catalytic RNA having a specific ribonuclease activity from a pool of RNA molecules (see, for example, Bartel, D. and Szostak, J. W. (1993) *Science* 261:1411–1418).

16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression can also be inhibited by targeting nucleotide sequences complementary to the regulatory region of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 (e.g., the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 promoter and/or enhancers) to form triple helical structures that prevent transcription of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene in target cells (see, for example, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15).

Antibodies that are both specific for the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein and interfere with its activity may also be used to modulate or inhibit 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein function. Such antibodies may be generated using standard techniques described herein, against the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889–7893).

In some instances, the target gene protein is extracellular, or is a transmembrane protein, such as the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Antibodies that are specific for one or more extracellular domains of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, for example, and that interfere with its activity, are particularly useful in treating pain or a painful disorder. Such antibodies are especially efficient because they can access the target domains directly from the bloodstream. Any of the administration techniques described below which are appropriate for peptide administration may be utilized to effectively administer inhibitory target gene antibodies to their site of action.

Methods for Restoring or Enhancing Target Gene Activity

Genes that cause pain may be underexpressed within pain or painful disorders. Alternatively, the activity of the protein products of such genes may be decreased, leading to the development of pain. Such down-regulation of gene expression or decrease of protein activity might have a causative or exacerbating effect on the disease state.

In some cases, genes that are up-regulated in the disease state might be exerting a protective effect. A variety of techniques may be used to increase the expression, synthesis, or activity of genes and/or proteins that exert a protective effect in response to pain conditions.

Described in this section are methods whereby the level 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity may be increased to levels wherein pain are ameliorated. The level of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity may be increased, for example, by either increasing the level of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene expression or by increasing the level of active 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein which is present.

For example, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, at a level sufficient to ameliorate pain may be administered to a patient exhibiting such symptoms. Any of the techniques discussed below may be used for such administration. One of skill in the art will readily know how to determine the concentration of effective, non-toxic doses of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, utilizing techniques such as those described below.

Additionally, RNA sequences encoding a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein may be directly administered to a patient exhibiting pain, at a concentration sufficient to produce a level of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein such that pain are ameliorated. Any of the techniques discussed below, which achieve intracellular administration of compounds, such as, for example, liposome administration, may be used for the administration of such RNA molecules. The RNA molecules may be produced, for example, by recombinant techniques such as those described herein.

Further, subjects may be treated by gene replacement therapy. One or more copies of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene, or a portion thereof, that directs the production of a normal 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene sequences into human cells.

Cells, preferably, autologous cells, containing 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expressing gene sequences may then be introduced or reintroduced into the subject at positions which allow for the amelioration of pain. Such cell replacement techniques may be preferred, for example, when the gene product is a secreted, extracellular gene product.

Pharmaceutical Compositions

Another aspect of the invention pertains to methods for treating a subject suffering from a disease. These methods involve administering to a subject an agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity (e.g., an agent identified by a screening assay described herein), or a combination of such agents. In another embodiment, the method involves administering to a subject a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or nucleic acid molecule as therapy to compensate for reduced, aberrant, or unwanted 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 expression or activity.

Stimulation of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is desirable in situations in which 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 is abnormally downregulated and/or in which increased 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is likely to have a beneficial effect. Likewise, inhibition of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is desirable in situations in which 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 is abnormally upregulated and/or in which decreased 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity is likely to have a beneficial effect.

The agents which modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity (e.g., a fragment of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or an anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity can also be prepared in the form of suppositories (e.g., with conventional suppository bases such as cocoa butter and other glycerides) or retention enemas for rectal delivery.

In one embodiment, the agents that modulate 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity, as well as tailoring the dosage and/or therapeutic regimen of treatment with an agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity.

Pharmacogenomics deals with clinically significant hereditary variations in the response to drugs due to altered drug disposition and abnormal action in affected persons. See, for example, Eichelbaum, M. et al. (1996) Clin. Exp-.Pharmacol. Physiol. 23(10–11): 983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein used in the methods of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 molecule or 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 modulator used in the methods of the present invention) can give an indication whether gene pathways related to toxicity have been turned on.

Information generated from more than one of the above pharmacogenomics approaches can be used to determine appropriate dosage and treatment regimens for prophylactic or therapeutic treatment of a subject. This knowledge, when applied to dosing or drug selection, can avoid adverse reactions or therapeutic failure and, thus, enhance therapeutic or prophylactic efficiency when treating a subject suffering from pain or painful disorders with an agent which modulates 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity.

Recombinant Expression Vectors and Host Cells Used in the Methods of the Invention The methods of the invention (e.g., the screening assays described herein) include the use of vectors, preferably expression vectors, containing a nucleic acid encoding a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins, mutant forms of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins, fusion proteins, and the like).

The recombinant expression vectors to be used in the methods of the invention can be designed for expression of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins in prokaryotic or eukaryotic cells. For example, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity assays, (e.g., direct assays or competitive assays described in detail below), or to generate antibodies specific for 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins. In a preferred embodiment, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual. 2nd ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to the use of host cells into which a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecule of the invention is introduced, e.g., a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecule within a recombinant expression vector or a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Accordingly, the invention further provides methods for producing a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein using the host cells of the invention. In one embodiment, the method comprises culturing the host cell of the invention (into which a recombinant expression vector encoding a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein has been introduced) in a suitable medium such that a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein is produced. In another embodiment, the method further comprises isolating a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein from the medium or the host cell.

Isolated Nucleic Acid Molecules Used in the Methods of the Invention

The methods of the invention include the use of isolated nucleic acid molecules that encode 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins or biologically active portions thereof, as well as nucleic acid fragments sufficient for use as hybridization probes to identify 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-encoding nucleic acid molecules (e.g., 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA) and fragments for use as PCR primers for the amplification or mutation of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:1, 3, 5, 7, 9, 11, 13, 15, 17, 19, 21, 23, 25, 27, 29, 31, 33, 35, 37, 39, 41, 43 or 45, or a portion thereof, can be isolated using standard molecular biology techniques and the sequence information provided herein. Using all or portion of the nucleic acid sequence of SEQ ID NO:1, 3, 5, 7, 9, 11, 13, 15, 17, 19, 21, 23, 25, 27, 29, 31, 33, 35, 37, 39, 41, 43 or 45, as a hybridization probe, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, 3, 5, 7, 9, 11, 13, 15, 17, 19, 21, 23, 25, 27, 29, 31, 33, 35, 37, 39, 41, 43 or 45 can be isolated by the polymerase chain reaction (PCR) using synthetic oligonucleotide primers designed based upon the sequence of SEQ ID NO:1, 3, 5, 7, 9, 11, 13, 15, 17, 19, 21, 23, 25, 27, 29, 31, 33, 35, 37, 39, 41, 43 or 45.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:1, 3, 5, 7, 9, 11, 13, 15, 17, 19, 21, 23, 25, 27, 29, 31, 33, 35, 37, 39, 41, 43 or 45, a complement of the nucleotide sequence shown in SEQ ID NO:1, 3, 5, 7, 9, 11, 13, 15, 17, 19, 21, 23, 25, 27, 29, 31, 33, 35, 37, 39, 41, 43 or 45, or a portion of any of these nucleotide sequences. A nucleic acid molecule which is complementary to the nucleotide sequence shown in SEQ ID NO:1, 3, 5, 7, 9, 11, 13, 15, 17, 19, 21, 23, 25, 27, 29, 31, 33, 35, 37, 39, 41, 43 or 45, is one which is sufficiently complementary to the nucleotide sequence shown in SEQ ID NO:1, 3, 5, 7, 9, 11, 13, 15, 17, 19, 21, 23, 25, 27, 29, 31, 33, 35, 37, 39, 41, 43 or 45, such that it can hybridize to the nucleotide sequence shown in SEQ ID NO:1, 3, 5, 7, 9, 11, 13, 15, 17, 19, 21, 23, 25, 27, 29, 31, 33, 35, 37, 39, 41, 43 or 45, thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO:1, 3, 5, 7, 9, 11, 13, 15, 17, 19, 21, 23, 25, 27, 29, 31, 33, 35, 37, 39, 41, 43 or 45, or a portion of any of this nucleotide sequence.

Moreover, the nucleic acid molecules used in the methods of the invention can comprise only a portion of the nucleic acid sequence of SEQ ID NO:1, 3, 5, 7, 9, 11, 13, 15, 17, 19, 21, 23, 25, 27, 29, 31, 33, 35, 37, 39, 41, 43 or 45, for example, a fragment which can be used as a probe or primer or a fragment encoding a portion of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, e.g., a biologically active portion of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 5, 7, 9, 11, 13, 15, 17, 19, 21, 23, 25, 27, 29, 31, 33, 35, 37, 39, 41, 43 or 45, of an anti-sense sequence of SEQ ID NO:1, 3, 5, 7, 9, 11, 13, 15, 17, 19, 21, 23, 25, 27, 29, 31, 33, 35, 37, 39, 41, 43 or 45, or of a naturally occurring allelic variant or mutant of SEQ ID NO:1, 3, 5, 7, 9, 11, 13, 15, 17, 19, 21, 23, 25, 27, 29, 31, 33, 35, 37, 39, 41, 43 or 45. In one embodiment, a nucleic acid molecule used in the methods of the present invention comprises a nucleotide sequence which is greater than 100, 100–200, 200–300, 300–400, 400–500, 500–600, 600–700, 700–800, 800–900, 900–1000, 1000–1100, 1100–1200, 1200–1300, or more nucleotides in length and hybridizes under stringent hybridization conditions to a nucleic acid molecule of SEQ ID NO:1, 3, 5, 7, 9, 11, 13, 15, 17, 19, 21, 23, 25, 27, 29, 31, 33, 35, 37, 39, 41, 43 or 45.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(°C.)=2(\# \text{ of A+T bases})+4(\# \text{ of G+C bases})$. For hybrids between 18 and 49 base pairs in length, $T_m(°C.)=81.5+16.6(\log_{10}[Na^+])+0.41(\% \text{ G+C})-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991–1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, such as by measuring a level of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-encoding nucleic acid in a sample of cells from a subject e.g., detecting 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA levels or determining whether a genomic 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene has been mutated or deleted.

The methods of the invention further encompass the use of nucleic acid molecules that differ from the nucleotide sequence shown in SEQ ID NO:1, 3, 5, 7, 9, 11, 13, 15, 17, 19, 21, 23, 25, 27, 29, 31, 33, 35, 37, 39, 41, 43 or 45, due to degeneracy of the genetic code and thus encode the same 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins as those encoded by the nucleotide sequence shown in SEQ ID NO:1, 3, 5, 7, 9, 11, 13, 15, 17, 19, 21, 23, 25, 27, 29, 31, 33, 35, 37, 39, 41, 43 or 45. In another embodiment, an isolated nucleic acid molecule included in the methods of the invention has a nucleotide sequence encoding a protein having an amino acid sequence shown in SEQ ID NO:2, 4, 6, 8, 10, 12, 14, 16, 18, 20, 22, 24, 26, 28, 30, 32, 34, 36, 38, 40, 42, 44 or 46.

The methods of the invention further include the use of allelic variants of human 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620, e.g., functional and non-functional allelic variants. Functional allelic variants are naturally occurring amino acid sequence variants of the human 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein that maintain a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. Functional allelic variants will typically contain only conservative substitution of one or more amino acids of SEQ ID NO:2, 4, 6, 8, 10, 12, 14, 16, 18, 20, 22, 24, 26, 28, 30, 32, 34, 36, 38, 40, 42, 44 or 46, or substitution, deletion or insertion of non-critical residues in non-critical regions of the protein.

Non-functional allelic variants are naturally occurring amino acid sequence variants of the human 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein that do not have a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. Non-functional allelic variants will typically contain a non-conservative substitution, deletion, or insertion or premature truncation of the amino acid sequence of SEQ ID NO:2, 4, 6, 8, 10, 12, 14, 16, 18, 20, 22, 24, 26, 28, 30, 32, 34, 36, 38, 40, 42, 44 or 46, or a substitution, insertion or deletion in critical residues or critical regions of the protein.

The methods of the present invention may further use non-human orthologues of the human 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Orthologues of the human 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein are proteins that are isolated from non-human organisms and possess the same 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity.

The methods of the present invention further include the use of nucleic acid molecules comprising the nucleotide sequence of SEQ ID NO:1, 3, 5, 7, 9, 11, 13, 15, 17, 19, 21, 23, 25, 27, 29, 31, 33, 35, 37, 39, 41, 43 or 45, or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 (e.g., the sequence of SEQ ID NO:2, 4, 6, 8, 10, 12, 14, 16, 18, 20, 22, 24, 26, 28, 30, 32, 34, 36, 38, 40, 42, 44 or 46) without altering the biological activity, whereas an "essential" amino acid residue is required for biological activity. For example, amino acid residues that are conserved among the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins of the present invention are not likely to be amenable to alteration.

Mutations can be introduced into SEQ ID NO:1, 3, 5, 7, 9, 11, 13, 15, 17, 19, 21, 23, 25, 27, 29, 31, 33, 35, 37, 39, 41, 43 or 45, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein is preferably replaced with another amino acid residue from the same side chain family. Alternatively, in another embodiment, mutations can be introduced randomly along all or part of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 coding sequence, such as by saturation mutagenesis, and the resultant mutants can be screened for 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 biological activity to identify mutants that retain activity. Following mutagenesis of SEQ ID NO:1, 3, 5, 7, 9, 11, 13, 15, 17, 19, 21, 23, 25, 27, 29, 31, 33, 35, 37, 39, 41, 43 or 45, the encoded protein can be expressed recombinantly and the activity of the protein can be determined using the assay described herein.

Another aspect of the invention pertains to the use of isolated nucleic acid molecules which are antisense to the nucleotide sequence of SEQ ID NO:1, 3, 5, 7, 9, 11, 13, 15, 17, 19, 21, 23, 25, 27, 29, 31, 33, 35, 37, 39, 41, 43 or 45. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 coding strand, or to only a portion thereof. In one embodiment, an antisense nucleic acid molecule is antisense to a "coding region" of the coding strand of a nucleotide sequence encoding a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620. The term "noncoding region" refers to 5' and 3' sequences which flank the coding region that are not translated into amino acids (also referred to as 5' and 3' untranslated regions).

Given the coding strand sequences encoding 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 disclosed herein, antisense nucleic acids of the invention can be designed according to the rules of Watson and Crick base pairing. The antisense nucleic acid molecule can be complementary to the entire coding region of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA, but more preferably is an oligonucleotide which is antisense to only a portion of the coding or noncoding region of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA. For example, the antisense oligonucleotide can be complementary to the region surrounding the translation start site of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). Antisense nucleic acid molecules used in the methods of the invention are further described above, in section IV.

In yet another embodiment, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci.* 93:14670–675.

PNAs of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-OKeefe et al. (1996) supra).

In another embodiment, PNAs of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Isolated 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 Proteins and Anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 Antibodies Used in the Methods of the Invention The methods of the invention include the use of isolated 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins, and biologically active portions thereof, as well as polypeptide fragments suitable for use as immunogens to raise anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies. In one embodiment, native 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins can be isolated from cells or tissue sources by an appropriate purification scheme using standard protein purification techniques. In another embodiment, 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins are produced by recombinant DNA techniques. Alternative to recombinant expression, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or polypeptide can be synthesized chemically using standard peptide synthesis techniques.

As used herein, a "biologically active portion" of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein includes a fragment of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein having a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity. Biologically active portions of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein include peptides comprising amino acid sequences sufficiently identical to or derived from the amino acid sequence of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, e.g., the amino acid sequence shown in SEQ ID NO:2, 4, 6, 8, 10, 12, 14, 16, 18, 20, 22, 24, 26, 28, 30, 32, 34, 36, 38, 40, 42, 44 or 46, which include fewer amino acids than the full length 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins, and exhibit at least one activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Typically, biologically active portions comprise a domain or motif with at least one activity of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein (e.g., the N-terminal region of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein that is believed to be involved in the regulation of apoptotic activity). A biologically active portion of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be a polypeptide which is, for example, 25, 50, 75, 100, 125, 150, 175, 200, 250, 300 or more amino acids in length. Biologically active portions of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be used as targets for developing agents which modulate a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 activity.

In a preferred embodiment, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein used in the methods of the invention has an amino acid sequence shown in SEQ ID NO:2, 4, 6, 8, 10, 12, 14, 16, 18, 20, 22, 24, 26, 28, 30, 32, 34, 36, 38, 40, 42, 44 or 46. In other embodiments, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein is substantially identical to SEQ ID NO:2, 4, 6, 8, 10, 12, 14, 16, 18, 20, 22, 24, 26, 28, 30, 32, 34, 36, 38, 40, 42, 44 or 46, and retains the functional activity of the protein of SEQ ID NO:2, 4, 6, 8, 10, 12, 14, 16, 18, 20, 22, 24, 26, 28, 30, 32, 34, 36, 38, 40, 42, 44 or 46, yet differs in amino acid sequence due to natural allelic variation or mutagenesis, as described in detail in subsection V above. Accordingly, in another embodiment, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO:2, 4, 6, 8, 10, 12, 14, 16, 18, 20, 22, 24, 26, 28, 30, 32, 34, 36, 38, 40, 42, 44 or 46.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 amino acid sequence of SEQ ID NO:2, 4, 6, 8, 10, 12, 14, 16, 18, 20, 22, 24, 26, 28, 30, 32, 34, 36, 38, 40, 42, 44 or 46 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444–453 (1970)) algorithm which has been incorporated into the GAP program in the GCG software package using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11–17 (1988)) which has been incorporated into the ALIGN program (version 2.0 or 2.0U), using a PAM120 weight residue table, a gap length penalty of 12 and a gap penalty of 4.

The methods of the invention may also use 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 chimeric or fusion proteins. As used herein, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 "chimeric protein" or "fusion protein" comprises a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide operatively linked to a non-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide. An "16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide" refers to a polypeptide having an amino acid sequence corresponding to a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 molecule, whereas a "non-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide" refers to a polypeptide having an amino acid sequence corresponding to a protein which is not substantially homologous to the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, e.g., a protein which is different from the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein and which is derived from the same or a different organism. Within a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion protein the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide can correspond to all or a portion of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. In a preferred embodiment, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion protein comprises at least one biologically active portion of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. In another preferred embodiment, a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion protein comprises at least two biologically active portions of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Within the fusion protein, the term "operatively linked" is intended to indicate that the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide and the non-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide are fused in-frame to each other. The non-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide can be fused to the N-terminus or C-terminus of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide.

For example, in one embodiment, the fusion protein is a GST-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion protein in which the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequences are fused to the C-terminus of the GST sequences. Such fusion proteins can facilitate the purification of recombinant 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620.

In another embodiment, this fusion protein is a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein containing a heterologous signal sequence at its N-terminus. In certain host cells (e.g., mammalian host cells), expression and/or secretion of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be increased through use of a heterologous signal sequence.

The 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion proteins used in the methods of the invention can be incorporated into pharmaceutical compositions and administered to a subject in vivo. The 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion proteins can be used to affect the bioavailability of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate. Use of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fusion proteins may be useful therapeutically for the treatment of disorders caused by, for example, (i) aberrant modification or mutation of a gene encoding a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein; (ii) mis-regulation of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 gene; and (iii) aberrant post-translational modification of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein.

Moreover, the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-fusion proteins used in the methods of the invention can be used as immunogens to produce anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies in a subject, to purify 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 ligands and in screening assays to identify molecules which inhibit the interaction of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 substrate.

Preferably, a 16386, 15402, 21165, 1423, 636, 12303, 21425, 27410, 38554, 38555, 55063, 57145, 59914, 94921, 16852, 33260, 58573, 30911; 85913, 14303, 16816, 17827 or 32620 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-encoding nucleic acid can be cloned into such an expression vector such that the fusion moiety is linked in-frame to the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein.

The present invention also pertains to the use of variants of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins which function as either 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 agonists (mimetics) or as 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antagonists. Variants of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins can be generated by mutagenesis, e.g., discrete point mutation or truncation of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. An agonist of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins can retain substantially the same, or a subset, of the biological activities of the naturally occurring form of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. An antagonist of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can inhibit one or more of the activities of the naturally occurring form of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein by, for example, competitively modulating a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620-mediated activity of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein.

In one embodiment, variants of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein which function as either 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 agonists (mimetics) or as 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antagonists can be identified by screening combinatorial libraries of mutants, e.g., truncation mutants, of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein for 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein agonist or antagonist activity. In one embodiment, a variegated library of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 variants is generated by combinatorial mutagenesis at the nucleic acid level and is encoded by a variegated gene library. A variegated library of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 variants can be produced by, for example, enzymatically ligating a mixture of synthetic oligonucleotides into gene sequences such that a degenerate set of potential 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequences is expressible as individual polypeptides, or alternatively, as a set of larger fusion proteins (e.g., for phage display) containing the set of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequences therein. There are a variety of methods which can be used to produce libraries of potential 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein coding sequence can be used to generate a variegated population of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 fragments for screening and subsequent selection of variants of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. In one embodiment, a library of coding sequence fragments can be generated by treating a double stranded PCR fragment of a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 variants (Arkin and Yourvan (1992) *Proc. Natl. Acad. Sci. USA* 89:7811–7815; Delgrave et al. (1993) *Protein Engineering* 6(3):327–331).

The methods of the present invention further include the use of anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies. An isolated 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein, or a portion or fragment thereof, can be used as an immunogen to generate antibodies that bind 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 using standard techniques for polyclonal and monoclonal antibody preparation. A full-length 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein can be used or, alternatively, antigenic peptide fragments of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be used as immunogens. The antigenic peptide of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 comprises at least 8 amino acid residues of the amino acid sequence shown in SEQ ID NO:2, 4, 6, 8, 10, 12, 14, 16, 18, 20, 22, 24, 26, 28, 30, 32, 34, 36, 38, 40, 42, 44 or 46 and encompasses an epitope of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 such that an antibody raised against the peptide forms a specific immune complex with the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 that are located on the surface of the protein, e.g., hydrophilic regions, as well as regions with high antigenicity.

A 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 immunogen is typically used to prepare antibodies by immunizing a suitable subject, (e.g., rabbit, goat, mouse, or other mammal) with the immunogen. An appropriate immunogenic preparation can contain, for example, recombinantly expressed 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein or a chemically synthesized 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 polypeptide. The preparation can further include an adjuvant, such as Freund's complete or incomplete adjuvant, or similar immunostimulatory agent. Immunization of a suitable subject with an immunogenic 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 preparation induces a polyclonal anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 molecules. The term "monoclonal antibody" or "monoclonal antibody composition", as used herein, refers to a population of antibody molecules that contain only one species of an antigen binding site capable of immunoreacting with a particular epitope of 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620. A monoclonal antibody composition thus typically displays a single binding affinity for a particular 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein with which it immunoreacts.

Polyclonal anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies can be prepared as described above by immunizing a suitable subject with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 immunogen. The anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody titer in the immunized subject can be monitored over time by standard techniques, such as with an enzyme linked immunosorbent assay (ELISA) using immobilized 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620. If desired, the antibody molecules directed against 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 can be isolated from the mammal (e.g., from the blood) and further purified by well known techniques, such as protein A chromatography to obtain the IgG fraction. At an appropriate time after immunization, e.g., when the anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 immunogen as described above, and the culture supernatants of the resulting hybridoma cells are screened to identify a hybridoma producing a monoclonal antibody that binds 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620.

Any of the many well known protocols used for fusing lymphocytes and immortalized cell lines can be applied for the purpose of generating an anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 monoclonal antibody (see, e.g., G. Galfre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620, e.g., using a standard ELISA assay.

Alternative to preparing monoclonal antibody-secreting hybridomas, a monoclonal anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody can be identified and isolated by screening a recombinant combinatorial immunoglobulin library (e.g., an antibody phage display library) with 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 to thereby isolate immunoglobulin library members that bind 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999-1005; Wood et al. (1985) *Nature* 314:446–449; Shaw et al. (1988) *J. Natl. Cancer Inst.* 80:1553–1559; Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141: 4053–4060.

An anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibody can be used to detect 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein (e.g., in a cellular lysate or cell supernatant) in order to evaluate the abundance and pattern of expression of the 16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 protein. Anti-16386, 15402, 21165, 1423, 636, 12303, 21425, 27410, 38554, 38555, 55063, 57145, 59914, 94921, 16852, 33260, 58573, 30911, 85913, 14303, 16816, 17827 or 32620 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

This invention is further illustrated by the following examples which should not be construed as limiting. The contents of all references, patents and published patent applications cited throughout this application, as well as the Figure and the Sequence Listing is incorporated herein by reference.

EXAMPLES

Example 1

Tissue Distribution of Using Taqman™ Analysis

This example describes the TaqMan™ procedure. The TaqMan™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., heart, kidney, liver, skeletal muscle, and various vessels, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Example 2

Tissue Distribution of Using In Situ Analysis

For in situ analysis, various tissues, e.g., tissues obtained from normal colon, breast, lung, and ovarian normal tissue, as well as colon, breast, lung, and ovarian tumors, colon metastatic to the liver, and angiogenic tissues were first frozen on dry ice. Ten-micrometer-thick sections of the tissues were post-fixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for identifying a compound capable of treating a pain or a painful disorder, comprising:
   a) combining a compound to be tested with a polypeptide selected from the group consisting of:
      i) a polypeptide comprising the amino acid sequence of SEQ ID NO:2; and
      ii) a polypeptide which is encoded by a nucleic acid molecule comprising the nucleotide sequence of SEQ ID NO:1;
   under conditions suitable for binding of the test compound to the polypeptide; and
   b) detecting binding of the test compound to the polypeptide to thereby identify a compound which binds to the polypeptide,
thereby identifying a compound capable of treating a pain or a painful disorder.

2. The method of claim 1, wherein the compound is selected from the group consisting of a small molecule, a peptide or an antibody.

3. The method of claim 1, wherein the polypeptide further comprises heterologous sequences.

4. The method of claim 1, wherein the polypeptide is an isolated polypeptide, a membrane-bound form of an isolated polypeptide or an intracellular polypeptide.

5. The method of claim 1, wherein the disorder is a disorder associated with aberrant nociception.

6. The method of claim 1, wherein the disorder is pain.

7. The method of claim 1, wherein the binding of the test compound to the polypeptide is detected by a method selected from the group consisting of: a) a competition binding assay; b) an immunoassay; and c) a yeast two-hybrid assay.

* * * * *